United States Patent
Yonekubo et al.

(10) Patent No.: US 8,217,069 B2
(45) Date of Patent: Jul. 10, 2012

(54) NITROGENATED FUSED RING DERIVATIVE, PHARMACEUTICAL COMPOSITION COMPRISING THE SAME, AND USE OF THE SAME FOR MEDICAL PURPOSES

(75) Inventors: Shigeru Yonekubo, Azumino (JP); Takashi Miyagi, Azumino (JP); Kohsuke Ohno, Azumino (JP); Mikie Kambara, Azumino (JP); Nobuhiko Fushimi, Azumino (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 292 days.

(21) Appl. No.: 12/596,313

(22) PCT Filed: Apr. 16, 2008

(86) PCT No.: PCT/JP2008/057390
§ 371 (c)(1),
(2), (4) Date: Oct. 16, 2009

(87) PCT Pub. No.: WO2008/129994
PCT Pub. Date: Oct. 30, 2008

(65) Prior Publication Data
US 2010/0112090 A1 May 6, 2010

(30) Foreign Application Priority Data
Apr. 18, 2007 (JP) .................... 2007-108926

(51) Int. Cl.
*A61K 31/415* (2006.01)
*C07D 233/00* (2006.01)

(52) U.S. Cl. ............................. 514/392; 548/316.4

(58) Field of Classification Search ............ 514/392; 548/316.4
See application file for complete search history.

(56) References Cited

U.S. PATENT DOCUMENTS

| | | | |
|---|---|---|---|
| 4,144,341 A | 3/1979 | Clark et al. | |
| 5,200,422 A | 4/1993 | Olsen et al. | |
| 2004/0116388 A1 | 6/2004 | Armistead et al. | |
| 2006/0019965 A1 | 1/2006 | Garrick et al. | |
| 2006/0106022 A1 | 5/2006 | Liu et al. | |
| 2006/0111391 A1 | 5/2006 | Jiang et al. | |
| 2007/0037804 A1 | 2/2007 | Stappenbeck et al. | |
| 2007/0167435 A1* | 7/2007 | Mutahi et al. | 514/218 |
| 2009/0023723 A1* | 1/2009 | Cole et al. | 514/234.2 |
| 2009/0069341 A1 | 3/2009 | Chene et al. | |
| 2009/0118263 A1 | 5/2009 | Hashimoto et al. | |

FOREIGN PATENT DOCUMENTS

| | | |
|---|---|---|
| JP | 51-143696 A | 12/1976 |
| JP | 04-305568 A | 10/1992 |
| JP | 11-292720 A | 10/1999 |
| JP | 2003-511378 A | 3/2003 |
| WO | 97/21704 A1 | 6/1997 |
| WO | 99/57103 A | 11/1999 |
| WO | 2006/009734 A | 1/2006 |
| WO | 2006/010594 A1 | 2/2006 |
| WO | 2006/036883 A2 | 4/2006 |
| WO | 2006/049890 A1 | 5/2006 |
| WO | 2006/127584 A1 | 11/2006 |
| WO | 2007/034817 A1 | 3/2007 |

OTHER PUBLICATIONS

Joanne M. Smallheer, et al., "SAR and factor IXa crystal structure of a dual inhibitor of factors IXa and Xa", Bioorganic & Medicinal Chemistry Letters, 2004, pp. 5263-5267, vol. 14, No. 21.
Robert L. Clark, et al., "Synthesis and Analgesic Activity of 1,3-Dihydro-3-(substituted phenyl)imidazo[4,5-b]pyridin-2-ones and 3-(Substituted phenyl)-1,2,3-triazolo[4,5-b]pyridines", Journal of Medicinal Chemistry, 1978, pp. 965-978, vol. 21, No. 9.
Extended European Search Report dated Aug. 17, 2011, issued in European Application No. 08740471.1.-2117.
Bianchi, Mario, et al., "Compounds with antiulcer and antisecretory activity", Eur. J. Med. Chem.-Chimica Therapeutica, (1981), 16, No. 4, pp. 321-326.

* cited by examiner

*Primary Examiner* — Paul Zarek
(74) *Attorney, Agent, or Firm* — Sughrue Mion, PLLC

(57) ABSTRACT

[Purpose] The present invention provides compounds useful as agents for the prevention or treatment of a sex hormone-dependent disease or the like.
[Solution] The present invention provides nitrogen-containing fused ring derivatives represented by the following general formula (I) which has a GnRH antagonistic activity, prodrugs, salts, pharmaceutical compositions containing the same, medicinal uses thereof and the like. In the formula (I), rings A and B are independently aryl or heteroaryl; $R^A$ and $R^B$ are independently halogen, cyano, alkyl, alkylsulfonyl, —$OW^1$, —$SW^1$, —$COW^2$, —$NW^3W^4$, —$SO_2NW^3W^4$, aryl, etc.; $R^C$ is H or alkyl; E is oxygen atom, etc.; U is single bond or alkylene; and X is Y, —CO—Y, —$SO_2$—Y, —S-(alkylene)-Y, —O-(alkylene)-Y, —$SO_2$-(alkylene)-Y, etc.; Y is Z or amino, etc.; and Z is cycloalkyl, heterocycloalkyl, aryl, heteroaryl, etc.

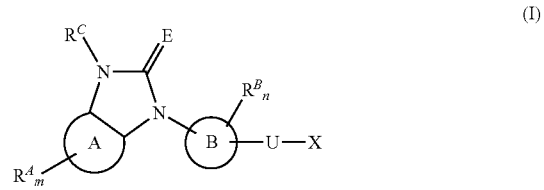

(I)

24 Claims, No Drawings

NITROGENATED FUSED RING DERIVATIVE, PHARMACEUTICAL COMPOSITION COMPRISING THE SAME, AND USE OF THE SAME FOR MEDICAL PURPOSES

CROSS REFERENCE TO RELATED APPLICATIONS

This application is a National Stage of International Application No. PCT/JP2008/057390 filed Apr. 16, 2008, claiming priority based on Japanese Patent Application No. 2007-108926, filed Apr. 18, 2007, the contents of all of which are incorporated herein by reference in their entirety.

TECHNICAL FIELD

The present invention relates to nitrogen-containing fused ring derivatives.

More particularly, the present invention relates to nitrogen-containing fused ring derivatives which have an antagonistic activity against gonadotropin releasing hormone and can be used for the prevention or treatment of a sex hormone-dependent disease such as benign prostatic hypertrophy, hysteromyoma, endometriosis, metrofibroma, precocious puberty, amenorrhea, premenstrual syndrome, dysmenorrhea or the like, or prodrugs thereof, or pharmaceutically acceptable salts thereof, and pharmaceutical compositions containing the same and the like.

BACKGROUND ART

Gonadotropin Releasing Hormone (GnRH, or it is also called Luteinizing Hormone Releasing Hormone: LHRH, hereinafter referred to as "GnRH") is a peptide consisting of 10 amino acids: pGlu-His-Trp-Ser-Tyr-Gly-Leu-Arg-Pro-Gly-$NH_2$), which is secreted from the hypothalamus. GnRH secreted into hypophyseal portal vein promotes the production and secretion of gonadotropin of anterior pituitary hormones, Luteinizing Hormone: LH and Follicle Stimulating Hormone: FSH, via the receptors which are considered to exist in the anterior lobe of the pituitary, GnRH receptor. These gonadotropins affect gonad, ovary and testis, to promote the follicular growth, ovulation and luteinization and spermatogenesis and also promote the production and secretion of sex hormones such as estrogen, progesterone and androgen (see Non-patent reference 1). Accordingly, antagonists specifically and selectively acting on the GnRH receptors should control the activities of GnRH and control the production and secretion of gonadotropin and sex hormones, and therefore, are expected to be useful as an agent for the prevention or treatment of sex hormone-dependent diseases.

As an agent inhibiting the function of GnRH receptor, GnRH receptor superagonists (hereinafter referred to as "GnRH superagonist") have been used as agents for the treatment of sex hormone-dependent diseases such as prostatic cancer, breast cancer and endometriosis and the like. The GnRH superagonists bind GnRH receptors and exert an initial temporary gonadotropin secretion-stimulating effect so-called "flare-up phenomenon", and then suppress the function by causing gonadotropin depletion and GnRH receptor down-regulation to suppress. Therefore, the GnRH receptor superagonists have a problem that the disease becomes exacerbated transiently by the initially promoted secretion of gonadotropin. On the other hand, the suppression mechanism of GnRH receptor antagonists (hereinafter referred to as "GnRH antagonist") is an inhibition of the binding to GnRH receptors, and therefore, are expected to exert promptly suppressive effects without secretion of gonadotropin. In these years, as GnRH antagonists, peptidic GnRH antagonists such as abarelix and cetrorelix have been developed and used for the treatment of prostatic cancer, infertility and the like. However, since these peptidic GnRH antagonists have bad oral absorbability, they have to be subcutaneously or intramuscularly administered. Thus, development of a non-peptidic GnRH antagonist which can be orally administered wherein local reactivity at injected sites can be reduced and the dosages can be flexibly adjusted is desired (see Non-patent reference 2).

As fused imidazolidine derivatives, various compounds are illustrated as anticancer agents in Patent reference 1, feeding control agents in Patent reference 2, antigastric ulcers in Non-patent reference 3 and antimicrobials in Non-patent reference 4, respectively. However, in any of these references, there are no description or suggestion about that a fused imidazolidine derivative of the present invention has a GnRH antagonistic activity.

Non-patent reference 1: *Hyojun Seirigaku* (Standard Physiology), Edition 5, Igakusyoin, pp. 882-891.

Non-patent reference 2: *Sanka to Fujinka* (Obstetrics and Gynecology), 2004, Vol. 71, No. 3, pp. 280-285 and 301-307.

Non-patent reference 3: Mario Bianch et. al. and 4 persons, Eur. J. Med. Chem., Chimica Therapeitica, 1981, Vol. 16, No. 4, pp. 321-326.

Non-patent reference 4: V. K. Agrawal et. al. and 2 persons, Indian Journal of Chemistry, May 1981, Vol. 20B, pp. 398-400.

Patent reference 1: International publication No. WO2006/10594 pamphlet.

Patent reference 2: International publication No. WO2005/35498 pamphlet.

DISCLOSURE OF THE INVENTION

Objects to be Solved by the Invention

The present invention aims to provide a compound which has a GnRH antagonistic activity.

Means for Solving the Problems

The present inventors have studied earnestly to solve the above problems. As a result, it was found that a nitrogen-containing fused ring derivative represented by the following general formula (I) exerts an excellent GnRH antagonistic activity, thereby forming the basis of the present invention.

That is, the present invention relates to:

[1] a nitrogen-containing fused ring derivative represented by the general formula (I):

[Chem. 1]

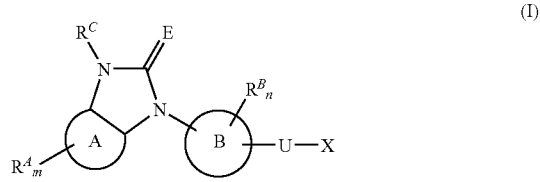

(I)

wherein ring A and ring B independently represent aryl or heteroaryl;

$R^A$ and $R^B$ independently represent a halogen atom, a cyano group, a nitro group, an optionally substituted lower alkyl group, an optionally substituted lower alkenyl group, an optionally substituted lower alkynyl group, a hydroxyiminomethyl group, an optionally substituted (lower alkyl)sulfonyl group, an optionally substituted (lower alkyl)sulfinyl group, $-OW^1$, $-SW^1$, $-COW^2$, $-NW^3W^4$, $-SO_2NW^3W^4$, an optionally substituted aryl group, an optionally substituted heteroaryl group, an optionally substituted cycloalkyl group, an optionally substituted heterocycloalkyl group or a hydroxycarbamimidoyl group with the proviso that $R^B$ does not represent a hydroxycarbamimidoyl group;

$R^C$ represents a hydrogen atom or an optionally substituted lower alkyl group;

m represents an integer number 0 to 3 with the proviso that when m is 2 or more, these $R^A$ may be the same or different from each other;

n represents an integer number 0 to 2 with the proviso that when n is 2, these $R^B$ may be the same or different from each other;

E represents an oxygen atom or a sulfur atom;

U represents a single bond or an optionally substituted lower alkylene group;

X represents a group represented by Y, $-CO-Y$, $-S-L-Y$, $-O-L-Y$, $-CO-L-Y$, $-COO-L-Y$, $-SO-L-Y$, $-SO_2-L-Y$, $-S-Z$, $-O-Z$, $COO-Z$, $-N(Q)-L-Y$, $-N(Q)-CO-Y$, $-N(Q)-SO_2-Y$, $-N(Q)-L-CO-Y$, $-N(Q)-L-SO_2-Y$, $-N(Q)-CO-L-Y$ or $-N(Q)-SO_2-L-Y$;

in which $W^1$ represents a hydrogen atom, an optionally substituted lower alkyl group, an optionally substituted aryl group, an optionally substituted heteroaryl group, an optionally substituted cycloalkyl group or an optionally substituted heterocycloalkyl group;

$W^2$ represents a hydrogen atom, a hydroxyl group, an optionally substituted lower alkyl group, an optionally substituted lower alkoxy group, $-NW^5W^6$, an optionally substituted aryl group, an optionally substituted heteroaryl group, an optionally substituted cycloalkyl group or an optionally substituted heterocycloalkyl group;

$W^3$ and $W^4$ independently represent a hydrogen atom, an optionally substituted lower alkyl group, $-COW^7$, $-SO_2W^8$, an optionally substituted aryl group, an optionally substituted heteroaryl group, an optionally substituted cycloalkyl group or an optionally substituted heterocycloalkyl group, or $W^3$ and $W^4$ optionally bind together to form an optionally substituted cyclic amino group with the neighboring nitrogen atom;

$W^5$ and $W^6$ independently represent a hydrogen atom, an optionally substituted lower alkyl group, an optionally substituted lower alkoxy group, an optionally substituted aryl group, an optionally substituted heteroaryl group, an optionally substituted cycloalkyl group or an optionally substituted heterocycloalkyl group with the proviso that both are not optionally substituted lower alkoxy groups at the same time, or $W^5$ and $W^6$ optionally bind together to form an optionally substituted cyclic amino group with the neighboring nitrogen atom;

$W^7$ represents a hydrogen atom, an optionally substituted lower alkyl group, an optionally substituted lower alkoxy group, $-NW^9W^{10}$, an optionally substituted aryl group, an optionally substituted heteroaryl group, an optionally substituted cycloalkyl group or an optionally substituted heterocycloalkyl group;

$W^8$ represents an optionally substituted lower alkyl group, $-NW^9W^{10}$, an optionally substituted aryl group, an optionally substituted heteroaryl group, an optionally substituted cycloalkyl group or an optionally substituted heterocycloalkyl group;

$W^9$ and $W^{10}$ independently represent a hydrogen atom, an optionally substituted lower alkyl group, an optionally substituted lower alkoxy group, an optionally substituted aryl group, an optionally substituted heteroaryl group, an optionally substituted cycloalkyl group or an optionally substituted heterocycloalkyl group with the proviso that both are not optionally substituted lower alkoxy groups at the same time, or $W^9$ and $W^{10}$ optionally bind together to form an optionally substituted cyclic amino group with the neighboring nitrogen atom;

L represents an optionally substituted lower alkylene group;

Y represents a group represented by Z or $NW^{11}W^{12}$, wherein $W^{11}$ and $W^{12}$ independently represent a hydrogen atom, an optionally substituted lower alkyl group or Z with the proviso that $W^{11}$ and $W^{12}$ are not hydrogen atoms at the same time, or $W^{11}$ and $W^{12}$ optionally bind together to form an optionally substituted cyclic amino group with the neighboring nitrogen atom;

Z represents an optionally fused and optionally substituted cycloalkyl group, an optionally fused and optionally substituted heterocycloalkyl group, an optionally fused and optionally substituted aryl group or an optionally fused and optionally substituted heteroaryl group;

Q has the same meaning with $W^3$ and $W^4$ but independently of $W^3$ and $W^4$ and with the proviso that Q optionally forms an optionally substituted heteroaryl group or an optionally substituted heterocycloalkyl group with $R^B$;

or a prodrug thereof, or a pharmaceutically acceptable salt thereof;

[2] a nitrogen-containing fused ring derivative as described in the above [1], wherein $R^A$ is a hydroxycarbamimidoyl group, or a prodrug thereof, or a pharmaceutically acceptable salt thereof;

[3] a nitrogen-containing fused ring derivative as described in the above [1], wherein $R^A$ and $R^B$ independently are a halogen atom, a cyano group, a nitro group, an optionally substituted lower alkyl group, an optionally substituted lower alkenyl group, an optionally substituted lower alkynyl group, a hydroxyiminomethyl group, an optionally substituted (lower alkyl)sulfonyl group, an optionally substituted (lower alkyl)sulfinyl group, $-OW^1$, $-SW^1$, $-COW^2$, $-NW^3W^4$, $-SO_2NW^3W^4$, an optionally substituted aryl group, an optionally substituted heteroaryl group, an optionally substituted cycloalkyl group or an optionally substituted heterocycloalkyl group in which $W^1$ to $W^4$ have the same meanings as defined in claim 1, or a prodrug thereof, or a pharmaceutically acceptable salt thereof;

[4] a nitrogen-containing fused ring derivative as described in the above [3], wherein $R^A$ is a halogen atom, a cyano group, an optionally substituted lower alkyl group, an optionally substituted (lower alkyl)sulfonyl group, $-OW^1$, $-SW^1$, $-COW^2$, $-NW^3W^4$ or an optionally substituted heteroaryl group in which $W^1$ to $W^4$ have the same meanings as defined in claim 1, or a prodrug thereof or a pharmaceutically acceptable salt thereof;

[5] a nitrogen-containing fused ring derivative as described in any of the above [1]-[4], wherein ring A is a 6-membered heteroaryl ring containing one or two nitrogen atoms, or a prodrug thereof, or a pharmaceutically acceptable salt thereof;

[6] a nitrogen-containing fused ring derivative as described in the above [5], wherein ring A is a pyridine ring or a pyrimidine ring, or a prodrug thereof, or a pharmaceutically acceptable salt thereof;

[7] a nitrogen-containing fused ring derivative as described in any of the above [1]-[6], wherein ring B is a benzene ring, a pyridine ring or a thiophene ring, or a prodrug thereof, or a pharmaceutically acceptable salt thereof;

[8] a nitrogen-containing fused ring derivative as described in the above [7], wherein ring B is any of rings represented by the formula:

[Chem. 2]

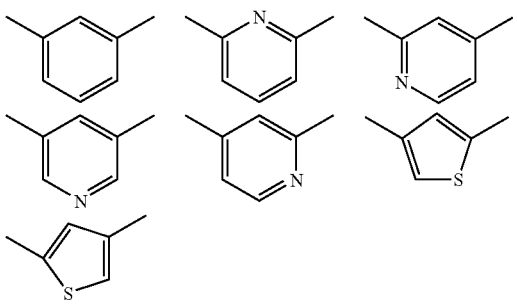

or a prodrug thereof, or a pharmaceutically acceptable salt thereof;

[9] a nitrogen-containing fused ring derivative as described in the above [8], wherein n is 1 or 2 and ring B is any of rings in which $R^B$ binds to the position of ring B represented by the following formula:

[Chem.3]

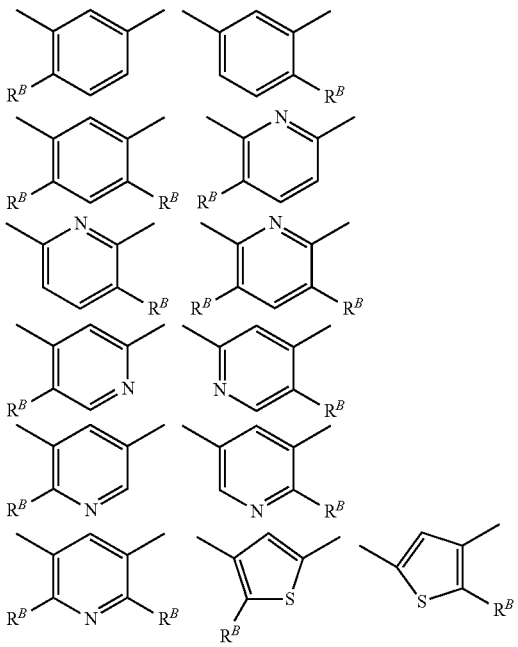

or a prodrug thereof, or a pharmaceutically acceptable salt thereof;

[10] a nitrogen-containing fused ring derivative as described in any of the above [1]-[9], wherein $R^C$ is a hydrogen atom, or a prodrug thereof, or a pharmaceutically acceptable salt thereof;

[11] a nitrogen-containing fused ring derivative as described in any of the above [1]-[10], wherein U is a single bond, a methylene group or an ethylene group, or a prodrug thereof, or a pharmaceutically acceptable salt thereof;

[12] a nitrogen-containing fused ring derivative as described in the above [11], wherein U is a single bond and X is a group represented by —CO—Y, —SO$_2$—Y, —S-L-Y, —O-L-Y, —CO-L-Y, —SO$_2$-L-Y, —N(Q)-L-Y, —N(Q)-CO—Y or —N(Q)-SO$_2$—Y in which L, Y and Q have the same meanings as defined in claim 1, or a prodrug thereof, or a pharmaceutically acceptable salt thereof;

[13] a nitrogen-containing fused ring derivative as described in the above [11], wherein U is a methylene group and X is a group represented by —Y, —S—Z or —O—Z with proviso that Y is —NW$^{11}$W$^{12}$ in which W$^{11}$W$^{12}$ and Z have the same meanings as defined in claim 1, or a prodrug thereof, or a pharmaceutically acceptable salt thereof;

[14] a nitrogen-containing fused ring derivative as described in the above [11], wherein U is an ethylene group and X is —Y with the proviso that Y is Z in which Z has the same meaning as defined in claim 1, or a prodrug thereof, or a pharmaceutically acceptable salt thereof;

[15] a nitrogen-containing fused ring derivative as described in any of the above [1]-[12], wherein L is a C$_{1-3}$ alkylene group, or a prodrug thereof, or a pharmaceutically acceptable salt thereof;

[16] a nitrogen-containing fused ring derivative as described in any of the above [1]-[15], wherein Z is an optionally fused and optionally substituted aryl group or an optionally fused and optionally substituted heteroaryl group, or a prodrug thereof, or a pharmaceutically acceptable salt thereof;

[17] a pharmaceutical composition comprising as an active ingredient a nitrogen-containing fused ring derivative as described in any of the above [1]-[16], or a prodrug thereof, or a pharmaceutically acceptable salt thereof;

[18] a pharmaceutical composition as described in the above [17], which is a gonadotropin releasing hormone antagonist;

[19] a pharmaceutical composition as described in the above [17], which is an agent for the prevention or treatment of a sex hormone-dependent disease, a reproduction regulator, a contraceptive, an ovulation inducing agent or an agent for the prevention of post-operative recurrence of sex hormone-dependent cancers;

[20] a pharmaceutical composition as described in the above [19], wherein the sex hormone-dependent disease is selected from the group consisting of benign prostatic hypertrophy, hysteromyoma, endometriosis, metrofibroma, precocious puberty, amenorrhea, premenstrual syndrome, dysmenorrhea, polycystic ovary syndrome, lupus erythematosis, hirsutism, short stature, sleep disorders, acne, baldness, Alzheimer's disease, infertility, irritable bowel syndrome, pro static cancer, uterine cancer, ovary cancer, breast cancer and pituitary tumor;

[21] a pharmaceutical composition as described in the above [17], wherein the composition is an oral formulation;

[22] a method for the prevention or treatment of a sex hormone-dependent disease, which comprises administering an effective amount of a nitrogen-containing fused ring derivative as described in any of the above [1]-[16] or a prodrug thereof, or a pharmaceutically acceptable salt thereof;

[23] a method as described in the above [22], wherein the sex hormone-dependent disease is selected from the group consisting of benign prostatic hypertrophy, hysteromyoma, endometriosis, metrofibroma, precocious puberty, amenorrhea, premenstrual syndrome, dysmenorrhea, polycystic ovary syndrome, lupus erythematosis, hirsutism, short stature, sleep disorders, acne, baldness, Alzheimer's disease, infertility, irritable bowel syndrome, prostatic cancer, uterine cancer, ovary cancer, breast cancer and pituitary tumor;

[24] a method for the reproduction regulation, contraception, ovulation induction or prevention of post-operative recurrence of sex hormone-dependent cancers, which comprises administering an effective amount of a nitrogen-containing fused ring derivative as described in any of the above [1]-[16] or a prodrug thereof, or a pharmaceutically acceptable salt thereof;

[25] a use of a nitrogen-containing fused ring derivative as described in any of the above [1]-[16] or a prodrug thereof, or a pharmaceutically acceptable salt thereof for the manufacture of a pharmaceutical composition for the prevention or treatment of a sex hormone-dependent disease;

[26] a use of a nitrogen-containing fused ring derivative as described in any of the above [1]-[16] or a prodrug thereof, or a pharmaceutically acceptable salt thereof for the manufacture of a pharmaceutical composition for the reproduction regulation, contraception, ovulation induction or prevention of post-operative recurrence of sex hormone-dependent cancers;

[27] a pharmaceutical composition as described in the above [17], which comprises a combination with at least one drug selected from the group consisting of a GnRH superagonist, a chemotherapeutic agent, a peptidic GnRH antagonist, a 5α-reductase inhibitor, an α-adrenoceptor inhibitor, an aromatase inhibitor, an adrenal androgen production inhibitor and a hormonotherapeutic agent;

[28] a pharmaceutical composition as described in the above [27], wherein the GnRH superagonist is selected from the group consisting of leuprorelin acetate, gonadorelin, buserelin, triptorelin, goserelin, nafarelin, histrelin, deslorelin, meterelin and lecirelin;

[29] a pharmaceutical composition as described in the above [27], wherein the chemotherapeutic agent is selected from the group consisting of ifosfamide, adriamycin, peplomycin, cisplatin, cyclophosphamide, 5-FU, UFT, methotrexate, mitomycin C, mitoxantrone, paclitaxel and dotaxel;

[30] a pharmaceutical composition as described in the above [27], wherein the peptidic GnRH antagonist is selected from the group consisting of cetrorelix, ganirelix, abarelix, ozarelix, iturelix, degarelix and teverelix;

[31] a pharmaceutical composition as described in the above [27], wherein the 5α-reductase inhibitor is selected from the group consisting of finasteride and dutasteride;

[32] a pharmaceutical composition as described in the above [27], wherein the α-adrenoceptor inhibitor is selected from the group consisting of tamsulosin, silodosin and urapidil;

[33] a pharmaceutical composition as described in the above [27], wherein the aromatase inhibitor is selected from the group consisting of fadrozole, letrozole, anastrozole and formestane;

[34] a pharmaceutical composition as described in the above [27], wherein the adrenal androgen production inhibitor is liarozole;

[35] a pharmaceutical composition as described in the above [27], wherein the hormonotherapeutic agent is selected from the group consisting of an antiestrogenic agent, a progestational agent, an androgenic agent, an estrogeninc agent and an antiandrogenic agent;

[36] a method for the prevention or treatment of a sex hormone-dependent disease as described in the above [22] or [23], which comprises a combination administration with at least one drug selected from the group consisting of a GnRH superagonist, a chemotherapeutic agent, a peptidic GnRH antagonist, a 5α-reductase inhibitor, an α-adrenoceptor inhibitor, an aromatase inhibitor, an adrenal androgen production inhibitor and a hormonotherapeutic agent;

[37] a method for the reproduction regulation, contraception, ovulation induction or prevention of post-operative recurrence of sex hormone-dependent cancers as described in the above [24], which comprises a combination administration with at least one drug selected from the group consisting of a GnRH superagonist, a chemotherapeutic agent, a peptidic GnRH antagonist, a 5α-reductase inhibitor, an α-adrenoceptor inhibitor, an aromatase inhibitor, an adrenal androgen production inhibitor and a hormonotherapeutic agent;

[38] a use of (A) a nitrogen-containing fused ring derivative as described in any of the above [1]-[16] or a prodrug thereof, or a pharmaceutically acceptable salt thereof, and (B) at least one drug selected from the group consisting of a GnRH superagonist, a chemotherapeutic agent, a peptidic GnRH antagonist, a 5α-reductase inhibitor, an α-adrenoceptor inhibitor, an aromatase inhibitor, an adrenal androgen production inhibitor and a hormonotherapeutic agent for the manufacture of a pharmaceutical composition for the prevention or treatment of a sex hormone-dependent disease;

[39] a use of (A) a nitrogen-containing fused ring derivative as described in any of the above [1]-[16] or a prodrug thereof, or a pharmaceutically acceptable salt thereof, and (B) at least one drug selected from the group consisting of a GnRH superagonist, a chemotherapeutic agent, a peptidic GnRH antagonist, a 5α-reductase inhibitor, an α-adrenoceptor inhibitor, an aromatase inhibitor, an adrenal androgen production inhibitor and a hormonotherapeutic agent for the manufacture of a pharmaceutical composition for the reproduction regulation, contraception, ovulation induction or prevention of post-operative recurrence of sex hormone-dependent cancers; and the like.

Effects of the Invention

Since a nitrogen-containing fused ring derivative (I) of the present invention or a prodrug thereof, or a pharmaceutically acceptable salt thereof, has an excellent GnRH antagonistic activity, it can control the effect of gonadotropin releasing hormone and control the production and secretion of gonadotropin and sex hormones, and as a result, it can be used as an agent for the prevention or treatment of sex hormone-dependent diseases.

BEST MODE TO PUT THE INVENTION TO PRACTICE

Meanings of terms used in this description are as follows.

The term "aryl" means phenyl or naphthyl.

The term "heteroaryl" means monocyclic heteroaryl having 1 or more hetero atoms selected from the group consisting of a nitrogen atom, an oxygen atom and a sulfur atom such as thiazole, oxazole, isothiazole, isoxazole, pyridine, pyrimidine, pyrazine, pyridazine, pyrrole, furan, thiophene, imidazole, pyrazole, oxadiazole, thiadiazole, triazole, tetrazole, furazan or the like, including an isomer formed when a hydroxyl group exists on a carbon atom adjacent to the nitrogen atom such as 1H-pyridin-2-on, 1H-pyrimidin-2-on and 4H-[1,2,4]oxadiazol-5-on.

The term "6-membered heteroaryl ring containing one or two nitrogen atoms" means 6-membered monocyclic heteroaryl as mentioned above having 1 or 2 nitrogen atoms in the ring, and for example, pyridine, pyrimidine, pyrazine and pyridazine can be illustrated.

The term "optionally substituted" means which may have a substituent.

The term "halogen atom" means a fluorine atom, a chlorine atom, a bromine atom or a iodine atom.

The term "lower alkyl" means optionally branched alkyl having 1 to 6 carbon atoms such as methyl, ethyl, propyl, isopropyl, butyl, isobutyl, sec-butyl, tert-butyl, pentyl, isopentyl, neopentyl, tert-pentyl, hexyl or the like.

The term "lower alkenyl" means optionally branched alkenyl having 2 to 6 carbon atoms such as vinyl, allyl, 1-propenyl, isopropenyl, 1-butenyl, 2-butenyl, 2-methylallyl or the like.

The term "lower alkynyl" means optionally branched alkynyl having 2 to 6 carbon atoms such as ethynyl, 2-propynyl or the like.

The term "(lower alkyl)sulfonyl" means sulfonyl substituted by the above lower alkyl.

The term "(lower alkyl)sulfinyl" means sulfinyl substituted by the above lower alkyl.

The term "lower alkylene" means optionally branched alkylene having 1 to 6 carbon atoms such as methylene, ethylene, methylmethylene, trimethylene, dimethylmethylene, ethylmethylene, methylethylene, propylmethylene, isopropylmethylene, dimethylethylene, butylmethylene, ethylmethylmethylene, pentamethylene, diethylmethylene, dimethyltrimethylene, hexamethylene, diethylethylene or the like.

The term "$C_{1-3}$ alkylene" means the above lower alkylene having 1 to 3 carbon atoms.

The term "lower alkoxy" means optionally branched alkoxy having 1 to 6 carbon atoms such as methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy or the like.

The term "cycloalkyl" means monocyclic cycloalkyl having 3 to 8 carbon atoms, for example, monocyclic cycloalkyl such as cyclopropyl, cyclobutyl, cyclopentyl, cyclohexyl, cycloheptyl, cyclooctyl and the like can be illustrated.

The term "heterocycloalkyl" means 3 to 8-membered heterocycloalkyl having 1 or more hetero atoms selected from the group consisting of a nitrogen atom, an oxygen atom and a sulfur atom and optionally having 1 or 2 oxo groups such as pyrrolidinyl, piperidinyl, oxopiperidinyl, morpholinyl, piperazinyl, oxopiperazinyl, thiomorpholinyl, azepanyl, diazepanyl, oxazepanyl, thiazepanyl, dioxothiazepanyl, azokanyl, tetrahydropyranyl, tetrahydropyranyl, oxazolidinyl, dioxanyl, dioxolanyl or the like. In case of having a sulfur atom in the ring, the sulfur atom may be oxidized.

The term "optionally fused" means which may be fused with a ring selected from the group consisting of the above cycloalkyl, the above heterocycloalkyl, the above aryl and the above heteroaryl. As "fused cycloalkyl", "fused heterocycloalkyl", "fused aryl" and "fused heteroaryl", for example, indolyl, isoindolyl, benzofuranyl, isobenzofuranyl, benzothiophenyl, benzoxazolyl, benzothiazolyl, benzoisoxazolyl, benzoisothiazolyl, indazolyl, benzimidazolyl, quinolinyl, isoquinolinyl, phthalazinyl, quinoxalinyl, quinazolinyl, cinnolinyl, indolizinyl, naphthyridinyl, pteridinyl, indanyl, 1,2,3,4-tetrahydronaphthyl, indolinyl, isoindolinyl, 2,3,4,5-tetrahydrobenzo[b]oxepinyl, 6,7,8,9-tetrahydro-5H-benzocycloheptenyl, chromanyl and the like can be illustrated, and the free valency may be on either ring.

The term "cyclic amino" means a group having at least a nitrogen atom which is a binding site in the ring among the above optionally fused heterocycloalkyl. For example, 1-pyrrolidinyl, 1-piperidinyl, 1-piperazinyl, 4-morpholinyl, 4-thiomorpholinyl, pyrrolidin-2-on-1-yl, oxazolidin-2-on-3-yl, morpholin-3-on-4-yl, 2,3,4,5,6,7-hexahydro-1H-azepin-1-yl, 1-indolinyl, 2-isoindolinyl, 3,4-dihydro-1,5-naphthyridin-1(2H)-yl, 1,2,3,4-tetrahydro-quinolin-1-yl, 3,4-dihydroquinolin-1(2H)-yl, 3,4-dihydroisoquinolin-2(1H)-yl, octahydroquinolin-1(2H)-yl, octahydroisoquinolin-2(1H)-yl, perhydroquinolin-1-yl, 2,3-dihydro-4H-1,4-benzoxazin-4-yl, 2,3-dihydro-4H-1,4-benzothiazin-4-yl, 3,4-dihydroquinoxalin-1(2H)-yl, 2,3-dihydro-4H-pyrid[3,2-b][1,4]oxazin-4-yl, 2,3,4,5-tetrahydro-1H-1-benzoazepin-1-yl, 1,3,4,5-tetrahydro-2H-2-benzoazepin-2-yl, 3,4-dihydro-1,5-benzoxazepin-5(2H)-yl, 2,3-dihydro-4,1-benzothiazepin-1(5H)-yl, 3,4-dihydro-1,5-benzothiazepin-5(2H)-yl, 2,3-dihydro-4,1-benzoxazepin-1(5H)-yl, 2,3,4,5-tetrahydro-1H-1,5-benzodiazepin-1-yl, 2,3,4,5-tetrahydro-1H-1,4-benzodiazepin-1-yl, 5,6,7,8-tetrahydro-4H-thieno[3,2-b]-azepin-4-yl, 3,4,5,6-tetrahydro-1-benzazocin-1(2H)-yl and the like can be illustrated.

The term "halo(lower alkyl)" means the above lower alkyl substituted by the above halogen atom(s).

The term "(lower alkyl)thio" means optionally branched alkylthio having 1 to 6 carbon atoms such as a methylthio group, an ethylthio group, a propylthio group, an isopropylthio group, a butylthio group, an isobutylthio group, a sec-butylthio group, a tert-butylthio group, a pentylthio group, an isopentylthio group, a neopentylthio group, a tert-pentylthio group, a hexylthio group or the like.

The term "(lower alkoxy)carbonyl" means an optionally branched alkoxycarbonyl group having 2 to 7 carbon atoms such as a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, an isopentyloxycarbonyl group, a neopentyloxycarbonyl group, a tert-pentyloxycarbonyl group, a hexyloxycarbonyl group or the like.

The term "lower acyl" means optionally branched aliphatic carboxylic acyl having 2 to 7 carbon atoms, cycloalkylcarboxylic acyl, heterocycloalkylcarboxylic acyl, arylcarboxylic acyl, or heteroarylcarboxylic acyl.

The term "(di)(lower alkyl)carbamoyl" means carbamoyl mono- or di-substituted by the above lower alkyl. Two lower alkyl groups in di-substituted amino may be different and the two lower alkyl groups may bind together to form a cyclic amino group with the neighboring nitrogen atom.

The term "(di)(lower alkyl)amino" means amino mono- or di-substituted by the above lower alkyl. Two lower alkyl groups in di-substituted amino may be different and the two lower alkyl groups may bind together to form a cyclic amino group with the neighboring nitrogen atom.

In the general formula (I), as ring A, 6-membered heteroaryl ring containing one or two nitrogen atoms such as a pyridine ring, a pyrimidine ring, a pyrazine ring or a pyridazine ring is preferable, a pyridine ring, a pyrimidine ring or a pyrazine ring is more preferable. In this case, a nitrogen atom of ring A preferably exists at the position wherein the part of (A1) in the following formula (A) is represented by any of (A2):

[Chem. 4]

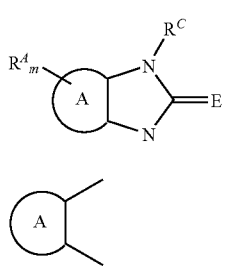

(A)

(A1)

(A2)

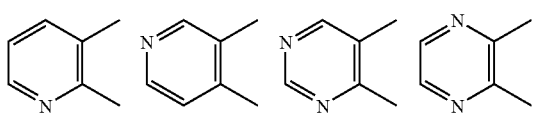

wherein in case that m is 2 or more, these $R^A$ may be the same or different. In case that m is 1 or 2, ring A wherein $R^A$ exists at the position on ring A represented by the following formula is preferable:

[Chem.5]

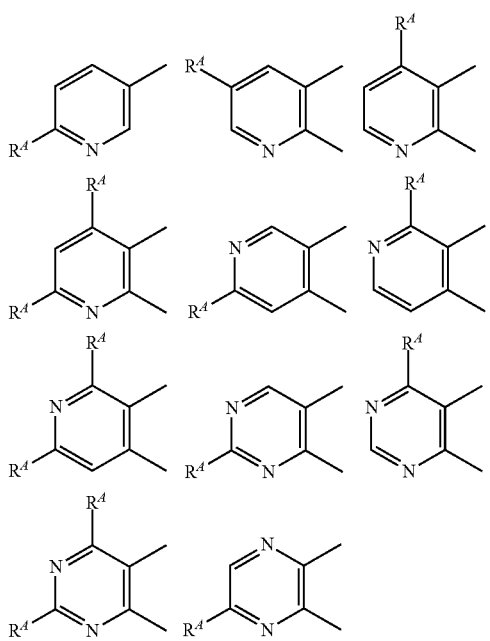

As $R^A$, a halogen atom, a cyano group, an optionally substituted lower alkyl group, an optionally substituted (lower alkyl)sulfonyl group, —$SW^1$, —$COW^2$, —$NW^3W^4$, an optionally substituted heteroaryl group or a hydroxycarbamimidoyl group in which $W^1$ to $W^4$ have the same meanings as defined in above [1] is preferable.

As ring B, a benzene ring, a pyridine ring or a thiophene ring is preferable. In this case, ring B preferably binds at the position represented by the following formula:

[Chem. 6]

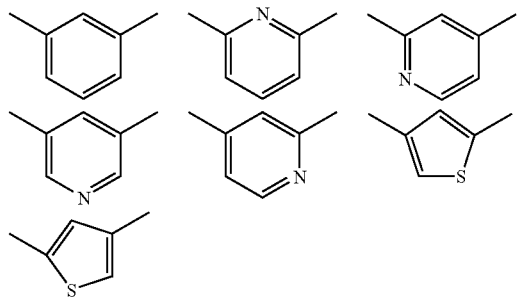

wherein the left bond represents a bond with the nitrogen atom of the fused imidazoline ring and the right bond represents a bond with U. In case that n is 1 or 2, ring B wherein $R^B$ exists at the position on ring B represented by the following formula is preferable.

[Chem. 7]

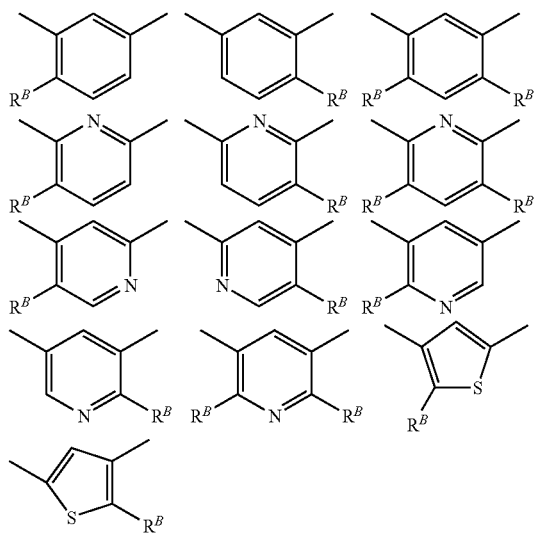

As $R^B$, a halogen atom, an optionally substituted lower alkyl group, —$OW^1$, —$COW^2$ in which $W^1$ and $W^2$ have the same meanings as defined in the above [1] and the like are preferable. In case that n is 2, two $R^B$ may be the same or different. In addition, in case that ring B is a benzene ring, a pyridine ring or a thiophene ring wherein $R^B$ binds at the position of ring B represented by the following formula:

[Chem.8]

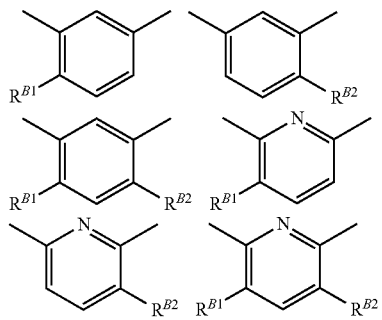

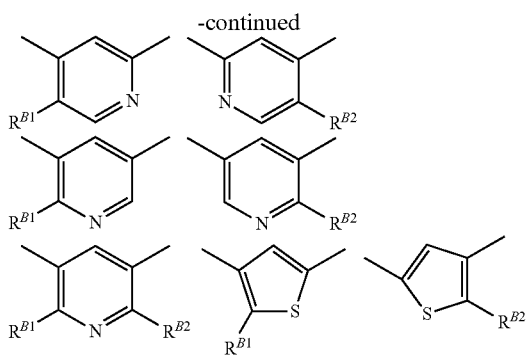

wherein the left bond of the bonds not bound to any of $R^{B1}$ and $R^{B2}$ represents a bond with the nitrogen atom of the fused imidazoline ring and the right bond represents a bond with U, as $R^{B1}$, a fluorine atom or a chlorine atom is preferable, and as $R^{B2}$, a halogen atom, an optionally substituted lower alkyl group, —$OW^1$ or —$COW^2$ in which $W^1$ and $W^2$ have the same meanings as defined in the above [1] is preferable.

As $R^C$, a hydrogen atom is preferable.

In the general formula (I), U is preferably a single bond, a methylene group or an ethylene group.

Especially, (i) when U is a single bond, as X, a group represented by —CO—Y, —$SO_2$—Y, —S-L-Y, —O-L-Y, —CO-L-Y, $SO_2$-L-Y, —N(Q)-L-Y, —N(Q)-CO—Y or —N(Q)-$SO_2$—Y wherein L, Y and Q have the same meanings as defined in the above [1]; (ii) when U is a methylene group, as X, a group represented by —Y, —S—Z or —O—Z with the proviso that Y represents $NW^{11}W^{12}$ and $W^{11}$, $W^{12}$ and Z have the same meanings as defined in the above [1]; and (iii) when U is an ethylene group, as X, —Y with the proviso that Y is Z and Z has the same meaning as defined in the above [1]; are preferable, respectively.

As L, a $C_{1-3}$ lower alkylene group is preferable.

As Z, an optionally fused and optionally substituted aryl group or an optionally fused and optionally substituted heteroaryl group is preferable. In this case, as a substituent which an optionally substituted aryl group or an optionally substituted heteroaryl group may have, a halogen atom, an optionally substituted lower alkyl group or —$OW^{13}$ in which $W^{13}$ has the same meanings as defined below is preferable.

As a substituent which an optionally substituted cyclic amino group, an optionally substituted cycloalkyl group or an optionally substituted heterocycloalkyl group may have, for example, an oxo group, a halogen atom, a cyano group, an optionally substituted lower alkyl group, an optionally substituted lower alkenyl group, an optionally substituted lower alkynyl group, an optionally substituted (lower alkyl)sulfonyl group, an optionally substituted (lower alkyl)sulfinyl group, —$OW^{13}$, —$SW^{13}$, —$COW^{14}$, —$NW^{15}W^{16}$, —$SO_2NW^{15}W^{16}$ an aryl group which may have a substituent selected from substituent group A, a heteroaryl group which may have a substituent selected from substituent group A, a cycloalkyl group which may have a substituent selected from substituent group B, a heterocycloalkyl group which may have a substituent selected from substituent group B and the like can be illustrated, and the same or different two or more groups selected from these groups may exist.

As a substituent which an optionally substituted aryl or an optionally substituted heteroaryl group may have, for example, a halogen atom, a nitro group, a cyano group, an optionally substituted lower alkyl group, an optionally substituted lower alkenyl group, an optionally substituted lower alkynyl group, an optionally substituted (lower alkyl)sulfonyl group, an optionally substituted (lower alkyl)sulfinyl group, —$OW^{13}$, —$SW^{13}$, —$COW^{14}$, —$NW^{15}W^{16}$, —$SO_2NW^{15}W^{16}$, an aryl group which may have a substituent selected from substituent group A, a heteroaryl group which may have a substituent selected from substituent group A, a cycloalkyl group which may have a substituent selected from substituent group B, a heterocycloalkyl group which may have a substituent selected from substituent group B and the like can be illustrated, and the same or different two or more groups selected from these groups may exist.

In an optionally fused and optionally substituted cycloalkyl group, an optionally fused and optionally substituted heterocycloalkyl group, an optionally fused and optionally substituted aryl group and an optionally fused and optionally substituted heteroaryl group, the above substituents optionally exist on the same or different rings in the fused ring:

The above $W^{13}$ represents a hydrogen atom, an optionally substituted lower alkyl group, an aryl group which may have a substituent selected from substituent group A, a heteroaryl group which may have a substituent selected from substituent group A, a cycloalkyl group which may have a substituent selected from substituent group B or a heterocycloalkyl group which may have a substituent selected from substituent group B;

$W^{14}$ represents a hydrogen atom, a hydroxyl group, an optionally substituted lower alkyl group, an optionally substituted lower alkoxy group, —$NW^{17}W^{18}$, an aryl group which may have a substituent selected from substituent group A, a heteroaryl group which may have a substituent selected from substituent group A, a cycloalkyl group which may have a substituent selected from substituent group B or a heterocycloalkyl group which may have a substituent selected from substituent group B;

$W^{15}$ and $W^{16}$ independently represent a hydrogen atom, an optionally substituted lower alkyl group, —$COW^{19}$, —$SO_2W^{20}$, an aryl group which may have a substituent selected from substituent group A, a heteroaryl group which may have a substituent selected from substituent group A, a cycloalkyl group which may have a substituent selected from substituent group B or a heterocycloalkyl group which may have a substituent selected from substituent group B, or $W^{15}$ and $W^{16}$ may bind together with the neighboring nitrogen atom to form a cyclic amino group which may have a substituent selected from substituent group B;

$W^{17}$ and $W^{18}$ independently represent a hydrogen atom, an optionally substituted lower alkyl group, an optionally substituted lower alkoxy group, an aryl group which may have a substituent selected from substituent group A, a heteroaryl group which may have a substituent selected from substituent group A, a cycloalkyl group which may have a substituent selected from substituent group B or a heterocycloalkyl group which may have a substituent selected from substituent group B and with the proviso that $W^{17}$ and $W^{18}$ are not an optionally substituted lower alkoxy group at the same time, or $W^{17}$ and $W^{18}$ may bind together with the neighboring nitrogen atom to form a cyclic amino group which may have a substituent selected from substituent group B;

$W^{19}$ represents a hydrogen atom, an optionally substituted lower alkyl group, an optionally substituted lower alkoxy group, —$NW^{21}W^{22}$, an aryl group which may have a substituent selected from substituent group A, a heteroaryl group which may have a substituent selected from substituent group A, a cycloalkyl group which may have a substituent selected from substituent group B or a heterocycloalkyl group which may have a substituent selected from substituent group B;

$W^{20}$ represents an optionally substituted lower alkyl group, $-NW^{21}W^{22}$, aryl group which may have a substituent selected from substituent group A, a heteroaryl group which may have a substituent selected from substituent group A, a cycloalkyl group which may have a substituent selected from substituent group B or a heterocycloalkyl group which may have a substituent selected from substituent group B; and $W^{21}$ and $W^{22}$ independently represent a hydrogen atom, an optionally substituted lower alkyl group, an optionally substituted lower alkoxy group, an aryl group which may have a substituent selected from substituent group A, a heteroaryl group which may have a substituent selected from substituent group A, a cycloalkyl group which may have a substituent selected from substituent group B or a heterocycloalkyl group which may have a substituent selected from substituent group B and with the proviso that $W^{21}$ and $W^{22}$ are not an optionally substituted lower alkoxy group at the same time, or $W^{21}$ and $W^{22}$ may bind together with the neighboring nitrogen atom to form a cyclic amino group which may have a substituent selected from substituent group B.

As a substituent which an optionally substituted lower alkyl, an optionally substituted lower alkylene, an optionally substituted lower alkenyl, an optionally substituted lower alkynyl, an optionally substituted (lower alkyl)sulfonyl, an optionally substituted (lower alkyl)sulfinyl or an optionally substituted lower alkoxy may have, a halogen atom, a cyano group, a (lower alkyl)sulfonyl group which may have a substituent selected from substituent group C, a (lower alkyl)sulfinyl group which may have a substituent selected from substituent group C, $-OW^{23}$, $-SW^{23}$, $-COW^{24}$, $-NW^{25}W^{26}$, $-SO_2NW^{25}$ an aryl group which may have a substituent selected from substituent group A, a heteroaryl group which may have a substituent selected from substituent group A, a cycloalkyl group which may have a substituent selected from substituent group B, a heterocycloalkyl group which may have a substituent selected from substituent group B and the like can be illustrated, and the same or different two or more groups selected from these groups may exist.

The above $W^{23}$ represents a hydrogen atom, a lower alkyl group which may have a substituent selected from substituent group C, an aryl group which may have a substituent selected from substituent group A, a heteroaryl group which may have a substituent selected from substituent group A, a cycloalkyl group which may have a substituent selected from substituent group B or a heterocycloalkyl group which may have a substituent selected from substituent group B;

$W^{24}$ represents a hydrogen atom, a hydroxyl group, a lower alkyl group which may have a substituent selected from substituent group C, a lower alkoxy group which may have a substituent selected from substituent group C, $-NW^{27}W^{28}$, an aryl group which may have a substituent selected from substituent group A, a heteroaryl group which may have a substituent selected from substituent group A, a cycloalkyl group which may have a substituent selected from substituent group B or a heterocycloalkyl group which may have a substituent selected from substituent group B;

$W^{25}$ and $W^{26}$ independently represent a hydrogen atom, a lower alkyl group which may have a substituent selected from substituent group C, $-COW^{29}$, $-SO_2W^{30}$, an aryl group which may have a substituent selected from substituent group A, a heteroaryl group which may have a substituent selected from substituent group A, a cycloalkyl group which may have a substituent selected from substituent group B or a heterocycloalkyl group which may have a substituent selected from substituent group B, or $W^{25}$ and $W^{26}$ may bind together with the neighboring nitrogen atom to form a cyclic amino group which may have a substituent selected from substituent group B;

$W^{27}$ and $W^{28}$ independently represent a hydrogen atom, a lower alkyl group which may have a substituent selected from substituent group C, a lower alkoxy group which may have a substituent selected from substituent group C, an aryl group which may have a substituent selected from substituent group A, a heteroaryl group which may have a substituent selected from substituent group A, a cycloalkyl group which may have a substituent selected from substituent group B or a heterocycloalkyl group which may have a substituent selected from substituent group B and with the proviso that $W^{27}$ and $W^{28}$ are not a lower alkoxy group which may have a substituent selected from substituent group C at the same time, or $W^{27}$ and $W^{28}$ may bind together with the neighboring nitrogen atom to form a cyclic amino group which may have a substituent selected from substituent group B;

$W^{29}$ represents a hydrogen atom, a lower alkyl group which may have a substituent selected from substituent group C, a lower alkoxy group which may have a substituent selected from substituent group C, $-NW^{31}W^{32}$, an aryl group which may have a substituent selected from substituent group A, a heteroaryl group which may have a substituent selected from substituent group A, a cycloalkyl group which may have a substituent selected from substituent group B or a heterocycloalkyl group which may have a substituent selected from substituent group B;

$W^{30}$ represents a lower alkyl group which may have a substituent selected from substituent group C, $-NW^{31}W^{32}$, an aryl group which may have a substituent selected from substituent group A, a heteroaryl group which may have a substituent selected from substituent group A, a cycloalkyl group which may have a substituent selected from substituent group B or a heterocycloalkyl group which may have a substituent selected from substituent group B; and $W^{31}$ and $W^{32}$ independently represent a hydrogen atom, a lower alkyl group which may have a substituent selected from substituent group C, a lower alkoxy group which may have a substituent selected from substituent group C, an aryl group which may have a substituent selected from substituent group A, a heteroaryl group which may have a substituent selected from substituent group A, a cycloalkyl group which may have a substituent selected from substituent group B or a heterocycloalkyl group which may have a substituent selected from substituent group B and with the proviso that $W^{31}$ and $W^{32}$ are not a lower alkoxy group which may have a substituent selected from substituent group C at the same time, or $W^{31}$ and $W^{32}$ may bind together with the neighboring nitrogen atom to form a cyclic amino group which may have a substituent selected from substituent group B.

[Substituent Group A]

a halogen atom, a cyano group, a nitro group, a hydroxyl group, a lower alkyl group, a halo(lower alkyl) group, a lower alkoxy group, a lower alkenyl group, a lower alkynyl group, a (lower alkyl)thio group, a (lower alkyl)sulfonyl group, a (lower alkyl)sulfinyl group, a carboxy group, a (lower alkoxy)carbonyl group, a lower acyl group, a carbamoyl group, a (di)(lower alkyl)carbamoyl group, an amino group, a (di)(lower alkyl)amino group, an aryl group, a heteroaryl group, a cycloalkyl group and a heterocycloalkyl group.

[Substituent Group B]

an oxo group, a halogen atom, a cyano group, a hydroxyl group, a lower alkyl group, a halo(lower alkyl) group, a lower alkoxy group, a lower alkenyl group, a lower alkynyl group, a (lower alkyl)thio group, a (lower alkyl)sulfonyl group, a (lower alkyl)sulfinyl group, a carboxy group, a (lower alkoxy) carbonyl group, a lower acyl group, a carbamoyl group, a (di)(lower alkyl)carbamoyl group, an amino group, a (di) (lower alkyl)amino group, an aryl group, a heteroaryl group, a cycloalkyl group and a heterocycloalkyl group.

[Substituent Group C]

a halogen atom, a cyano group, a hydroxyl group, a lower alkoxy group, a (lower alkyl)thio group, a (lower alkyl)sulfonyl group, a (lower alkyl)sulfinyl group, a carboxy group, a (lower alkoxy)carbonyl group, a lower acyl group, a carbamoyl group, a (di)(lower alkyl)carbamoyl group, an amino group, a (di)(lower alkyl)amino group, an aryl group, a heteroaryl group, a cycloalkyl group and a heterocycloalkyl group.

An example of the methods for preparing a nitrogen-containing fused ring derivative represented by the general formula (I) of the present invention is shown below.

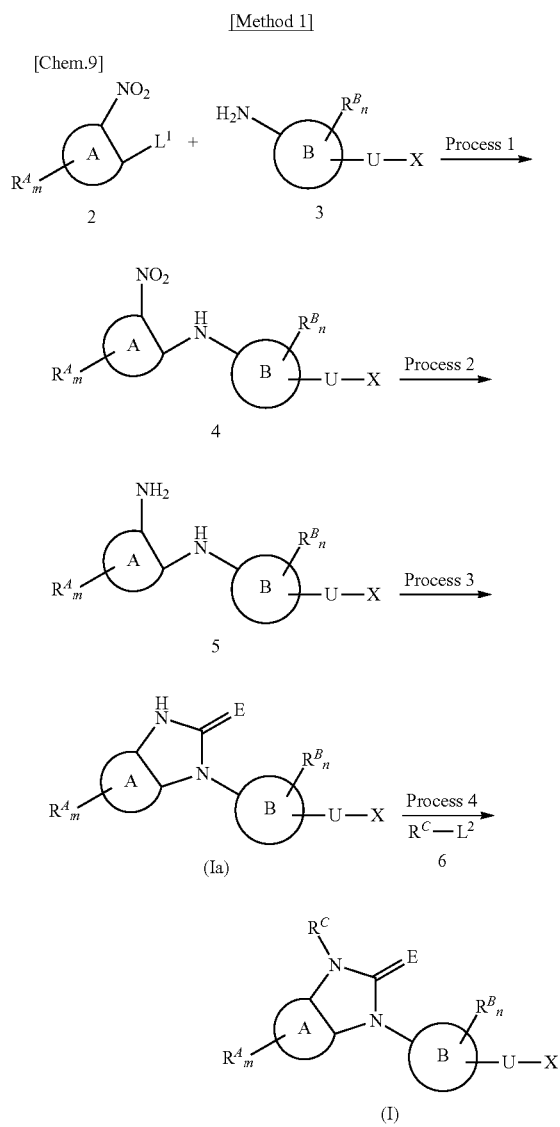

In the formula, $L^1$ represents a halogen atom or trifluoromethanesulfonyloxy; $L^2$ represents a chlorine atom, a bromine atom, a iodine atom, methanesulfonyloxy, p-toluenesulfonyloxy or trifluoromethanesulfonyloxy; ring A, ring B, $R^A$, $R^B$, m, n, E, U and X have the same meanings as defined above.

Process 1

Nitro compound (2) can be converted by allowing to react with Amine compound (3) in an inert solvent such as acetonitrile, tetrahydrofuran, N,N-dimethylformamide, N,N-dimethylacetamide, 1-methyl-2-pyrolidone, a mixed solvent thereof or the like, or without any solvent in the presence or absence of an additive agent such as copper powder or the like in the presence of a base such as triethylamine, N,N-diisopropylethylamine, pyridine, 4-dimethylaminopyridine, sodium hydride, potassium hydride, sodium hexamethyldisilazide, lithium hexamethyldisilazide, potassium hexamethyldisilazide, potassium carbonate, cesium carbonate, cesium fluoride, potassium tert-butoxide, sodium tert-butoxide or the like usually at from −78° C. to reflux temperature for 30 minutes to 3 days into Nitro compound (4).

Nitro compound (2) also can be converted by allowing to react with Amine compound (3) in an inert solvent such as 1,4-dioxane, 2-propanol, tert-butanol, 1,2-dimethoxyethane, toluene, tetrahydrofuran, N,N-dimethylformamide, N,N-dimethylacetamide, 1-methyl-2-pyrolidone, water, a mixed solvent thereof or the like, using a catalyst such as tris(dibenzylideneacetone)dipalladium(0), palladium(II) acetate, tetrakis(triphenylphosphine)palladium(0) or the like in the presence or absence of a ligand such as 4,5-bis(diphenylphosphino)-9,9-dimethylxanthene, tri(tert-butyl)phosphine, 2-(dicyclohexylphosphino)-2'-methylbiphenyl, bis(2-diphenylphosphinophenyl)ether or the like in the presence of a base such as cesium carbonate, potassium carbonate, cesium fluoride, potassium tert-butoxide, sodium tert-butoxide or the like usually at from room temperature to reflux temperature for 1 hour to 3 days into Nitro compound (4).

Process 2

Diamine compound (5) can be prepared by reducing the nitro group of Nitro compound (4) by a general catalytic reduction method, a reducing agent method or the like. A catalytic reduction method can be conducted, for example, by allowing Nitro compound (4) to react under a hydrogen atmosphere in an inert solvent such as methanol, ethanol, ethyl acetate, tetrahydrofuran, acetic acid, water, a mixed solvent thereof or the like in the presence of a catalyst such as palladium-carbon powder, platinum-carbon powder or the like usually at from room temperature to reflux temperature for 30 minutes to 1 day. A reducing agent method can be conducted, for example, by allowing Nitro compound (4) to react in an inert solvent such as methanol, ethanol, tetrahydrofuran, acetonitrile, water, a mixed solvent thereof or the like in the presence of a reducing agent such as sodium borohydride, sodium hydrosulfite or the like in the presence or absence of an additive such as nickel(II) bromide, sodium hydroxide, potassium hydroxide or the like usually under ice-cooling to at reflux temperature for 30 minutes to 1 day.

Process 3

A nitrogen-containing fused ring derivative of the present invention (Ia) can be prepared by cyclizing Diamine compound (5) by a general cyclization method to form an imidazolone ring or the like. A cyclization reaction can be conducted by allowing Diamine compound (5) to react in an inert solvent such as tetrahydrofuran, N,N-dimethylformamide, methanol, ethanol, methylene chloride, a mixed solvent thereof or the like using, for example, phosgene, diphosgene, triphosgene, 1,1'-carbonyldiimidazole or the like when E is an oxygen atom; carbon disulfide, thiophosgene or the like when E is a sulfur atom, in the presence or absence of a base such as triethylamine, N,N-diisopropylethylamine, pyridine, 4-dimethylaminopyridine, sodium hydride, sodium methoxide, sodium ethoxide, sodium hydroxide, potassium hydroxide or the like usually under ice-cooling to at reflux temperature for 30 minutes to 1 day.

Process 4

A nitrogen-containing fused ring derivative of the present invention (I) can be prepared by alkylating a nitrogen-containing fused ring derivative of the present invention (Ia) by a general method. An alkylating reaction can be conducted, for example, by allowing a nitrogen-containing fused ring derivative (Ia) of the present invention to react with Alkylating agent (6) in an inert solvent such as tetrahydrofuran, N,N-dimethylformamide, acetone, a mixed solvent thereof or the like in the presence of a base such as potassium carbonate, cesium carbonate, sodium hydride or the like occasionally using an additive such as sodium iodide or the like usually under ice-cooling to at reflux temperature for 30 minutes to 1 day.

Among the nitrogen-containing fused ring derivatives represented by the general formula (I) of the present invention, a compound wherein E is an oxygen atom also can be prepared, for example, by Methods 2 to 5.

[Method 2]

[Chem. 10]

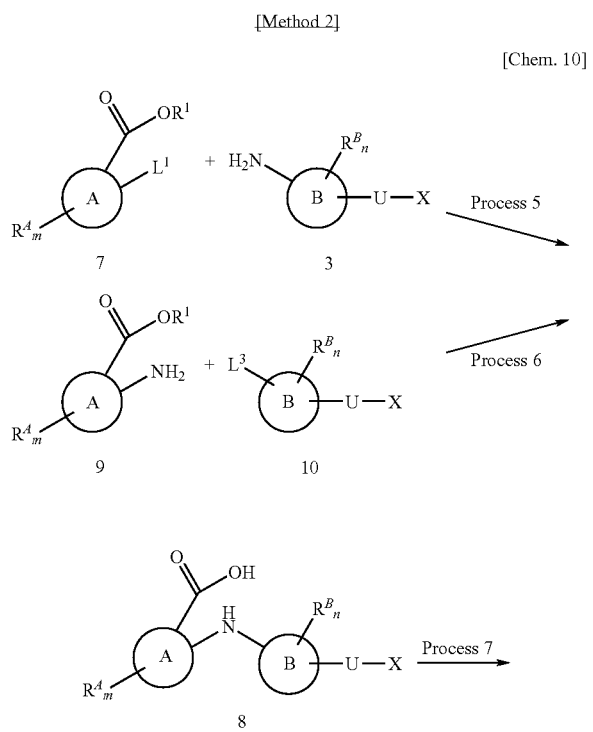

In the formula, $R^1$ represents a hydrogen atom, a lower alkyl group or an aryl group; $L^3$ represents a chlorine atom, a bromine atom, a iodine atom or trifluoromethanesulfonyloxy; $L^1$, ring A, ring B, $R^A$, $R^B$, m, n, U and X have the same meanings as defined above.

Process 5

Compound (8) can be prepared by subjecting a compound having a leaving group and an amine compound to condensation by a general coupling method under basic condition, under the presence of palladium or the like. A coupling method under basic condition can be conducted by allowing Compound having a leaving group (7) to react with Amine compound (3), for example, in an inert solvent such as acetonitrile, tetrahydrofuran, N,N-dimethylformamide, N,N-dimethylacetamide, 1-methyl-2-pyrolidone, a mixed solvent thereof or without any solvent in the presence of a base such as triethylamine, N,N-diisopropylethylamine, pyridine, 4-dimethylaminopyridine, sodium hydride, potassium hydride, sodium hexamethyldisilazide, lithium hexamethyldisilazide, potassium hexamethyldisilazide, potassium carbonate, cesium carbonate, cesium fluoride, potassium tert-butoxide, sodium tert-butoxide or the like optionally using an additive such as copper powder or the like usually at from −78° C. to reflux temperature for 30 minutes to 1 day.

A coupling method under the presence of palladium can be conducted by allowing Compound having a leaving group (7) to react with Amine compound (3), for example, in an inert solvent such as 1,4-dioxane, 2-propanol, tert-butanol, 1,2-dimethoxyethane, toluene, tetrahydrofuran, N,N-dimethylformamide, N,N-dimethylacetamide, 1-methyl-2-pyrolidone, water, a mixed solvent thereof or the like using a catalyst such as tris(dibenzylideneacetone)-dipalladium(0), palladium(II) acetate, tetrakis(triphenylphosphine)palladium (0) or the like in the presence or absence of a ligand such as 4,5-bis(diphenylphosphino)-9,9-dimethylxanthene, tri(tert-butyl)phosphine, 2-(dicyclohexylphosphino)-2'-methylbiphenyl, bis(2-diphenylphosphinophenyl)ether or the like in the presence of a base such as cesium carbonate, potassium carbonate, cesium fluoride, potassium tert-butoxide, sodium tert-butoxide or the like usually at from room temperature to reflux temperature for 1 hour to 3 days.

Process 6

Compound (8) also can be prepared by condensing Amine compound (9) and Compound having a leaving group (10) by a method similar to the coupling method under the presence of palladium as described in the above Process 5.

In the above Processes 5 and 6, when $R^1$ is a lower alkyl group or an aryl group, the compound can be hydrolyzed by allowing to react in an inert solvent such as methanol, ethanol, 2-propanol, tetrahydrofuran, water, a mixed solvent thereof or the like using a base such as sodium hydroxide, lithium hydroxide, potassium hydroxide or the like usually at from room temperature to reflux temperature for 1 hour to 3 days to derive into a carboxy group.

Process 7

A nitrogen-containing fused ring derivative of the present invention (Ib) can be prepared by conducting Curtius transfer reaction using Compound (8). Curtius transfer reaction can be conducted by treating Compound (8) in an inert solvent such as 1,4-dioxane, 1,2-dimethoxyethane, tetrahydrofuran, a mixed solvent thereof or the like using a reagent such as diphenylphosphoryl azide or the like in the presence of a base such as triethylamine, N,N-diisopropylethylamine, pyridine, 4-dimethylaminopyridine or the like usually at from 0° C. to reflux temperature for 1 hour to 1 day.

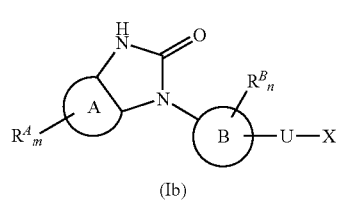

(Ib)

[Method 3]

[Chem.11]

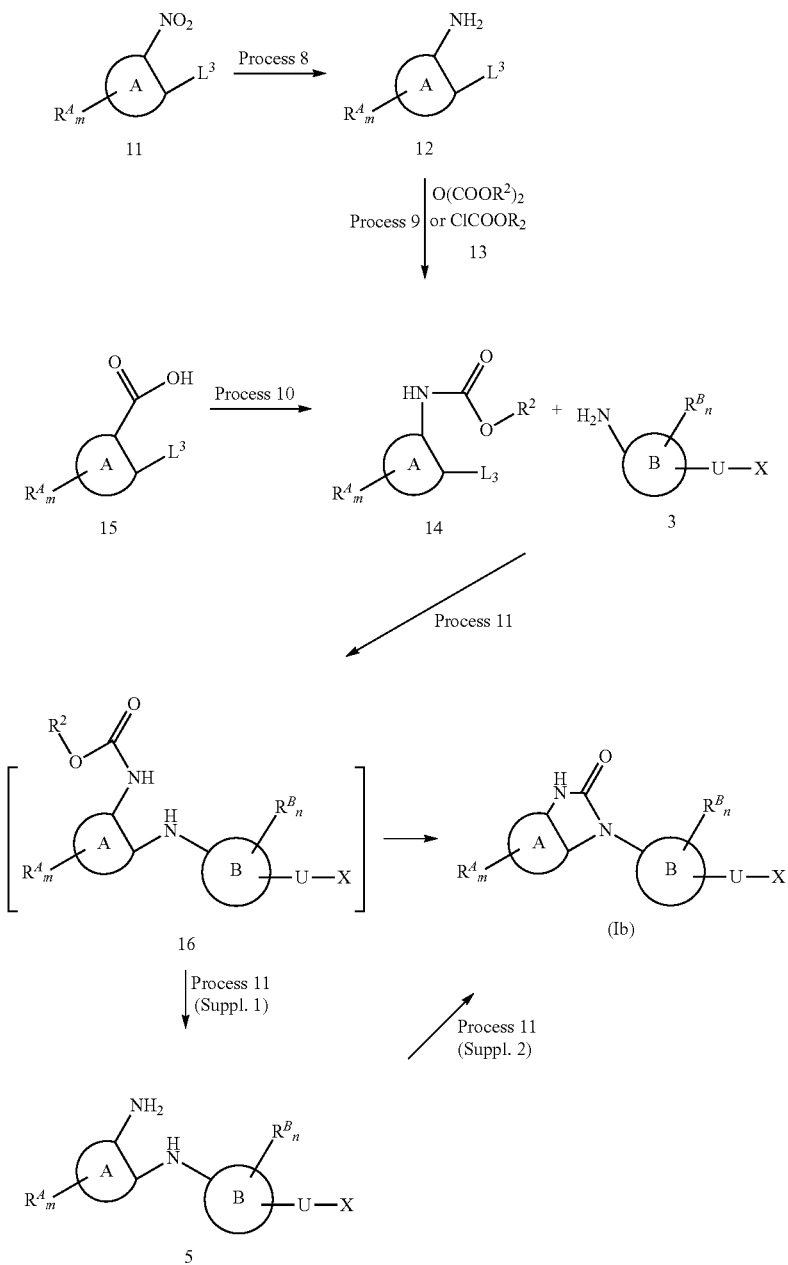

In the formula, $R^2$ represents a lower alkyl group and ring A, ring B, $R^A$, $R^B$, m, U, X and $L^3$ have the same meanings as defined above.

Process 8

Amine compound (12) can be prepared by reducing Nitro compound (11) by a general catalytic reduction method, a reducing agent method or the like. A catalytic reduction method can be conducted, for example, by treating Nitro compound (11) under a hydrogen atmosphere in an inert solvent such as methanol, ethanol, ethyl acetate, tetrahydrofuran, acetic acid, water, a mixed solvent thereof or the like in the presence of a catalyst such as palladium-carbon powder, platinum-carbon powder or the like usually at from room temperature to reflux temperature for 30 minutes to 1 day. A reducing agent method can be conducted, for example, by treating Nitro compound (11) in an inert solvent such as methanol, ethanol, tetrahydrofuran, acetonitrile, water, a mixed solvent thereof or the like using a reducing agent such as sodium borohydride, sodium hydrosulfite or the like in the presence or absence of an additive such as nickel(II) bromide, sodium hydroxide, potassium hydroxide or the like usually under ice-cooling to at reflux temperature for 30 minutes to 1 day.

Process 9

Carbamate compound (14) can be prepared by subjecting Amine compound (12) to carbamating reaction. Carbamating reaction can be conducted, for example, by allowing Amine compound (12) to react with Dicarbonate ester or Chloroformate ester (13) in an inert solvent such as tetrahydrofuran, methylene chloride, N,N-dimethylformamide, 1,4-dioxane, water, a mixed solvent thereof or the like in the presence or absence of a base such as sodium hexamethyldisilazide, lithium hexamethyldisilazide, triethylamine, N,N-diisopropylethylamine, pyridine, 4-dimethylaminopyridine, sodium hydride or the like usually at from −78° C. to reflux temperature for 30 minutes to 1 day. In addition, when the amino group is dicarbamated, monocarbamate can be obtained by allowing the obtained dicarbamate to react in an inert solvent such as methanol, ethanol, 2-propanol, a mixed solvent thereof or the like in the presence of a base such as sodium carbonate, potassium carbonate, sodium hydrogen carbonate, potassium hydrogen carbonate or the like usually at from room temperature to reflux temperature for 1 hour to 1 day.

Process 10

Carbamate compound (14) also can be prepared by conducting Curtius transfer reaction using Compound (15). Curtius transfer reaction can be conducted by treating Compound (15) in an inert solvent such as 1,4-dioxane, 1,2-dimethoxyethane, tetrahydrofuran, a mixed solvent thereof or the like using a reagent such as diphenylphosphoryl azide or the like in the presence of a base such as triethylamine, N,N-diisopropylethylamine, pyridine, 4-dimethylaminopyridine or the like and an alcohol, for example, a lower alcohol such as methanol, ethanol, tert-butanol or the like usually at from 0° C. to reflux temperature for 1 hour to 1 day.

Process 11

A nitrogen-containing fused ring derivative of the present invention (Ib) can be prepared by allowing Carbamate compound (14) to react with Amine compound (3) in an inert solvent such as 1,4-dioxane, 2-propanol, tert-butanol, 1,2-dimethoxyethane, toluene, tetrahydrofuran, N,N-dimethylformamide, N,N-dimethylacetamide, 1-methyl-2-pyrolidone, water, a mixed solvent thereof or the like using a catalyst such as tris(dibenzylideneacetone)-dipalladium(0), palladium(II) acetate, tetrakis(triphenylphosphine)palladium (0) or the like in the presence or absence of a ligand such as 4,5-bis(diphenylphosphino)-9,9-dimethylxanthene, tri(tert-butyl)phosphine, 2-(dicyclohexylphosphino)-2'-methylbiphenyl, bis(2-diphenylphosphinophenyl)ether or the like in the presence of a base such as cesium carbonate, potassium carbonate, cesium fluoride, potassium tert-butoxide, sodium tert-butoxide or the like usually at from room temperature to reflux temperature for 1 hour to 3 days.

Process 11, Supplement 1

In Process 11, when Intermediate (16) is obtained, Diamine compound (5) can be prepared occasionally by deprotecting by a general method. Deprotection reaction can be conducted, for example, by allowing Intermediate (16) to react in an inert solvent such as methanol, ethanol, ethyl acetate, tetrahydrofuran, 1,4-dioxane, methylene chloride, water, a mixed solvent thereof or the like using an reagent such as hydrochloric acid, trifluoroacetic acid or the like when $R^2$ is tert-butyl in Intermediate (16), usually at from 0° C. to reflux temperature for 30 minutes to 1 day.

Process 11, Supplement 2

A nitrogen-containing fused ring derivative of the present invention (Ib) also can be prepared by cyclizing Diamine compound (5) by a method similar to that as described in the above Process 3.

[Method 4]

[Chem.12]

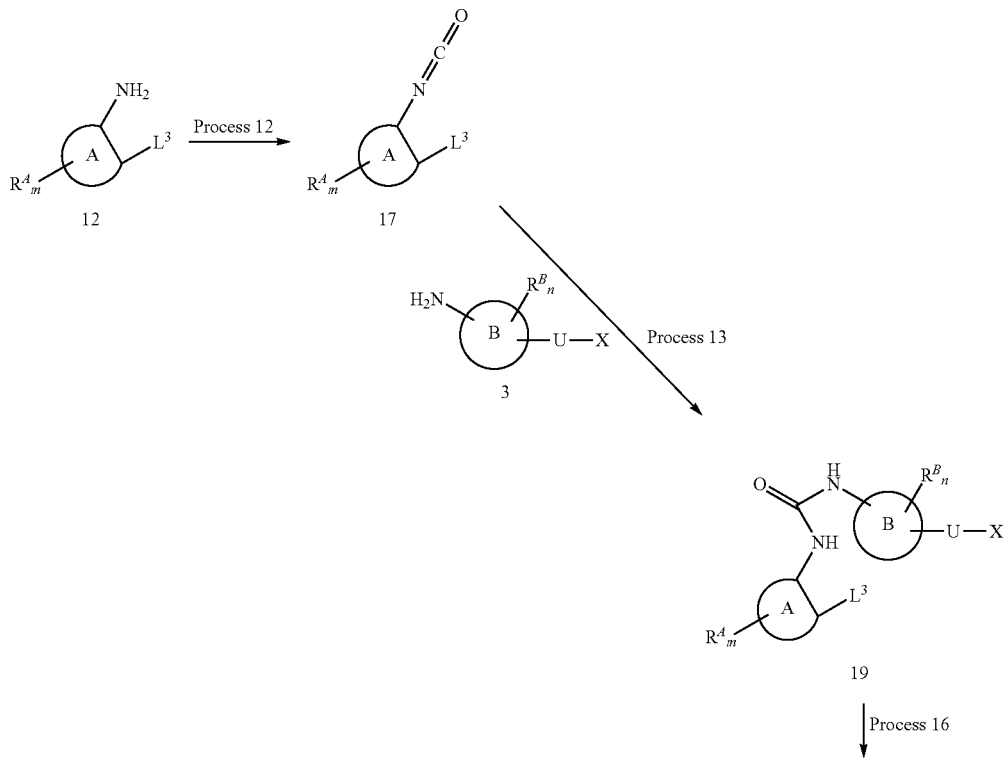

-continued

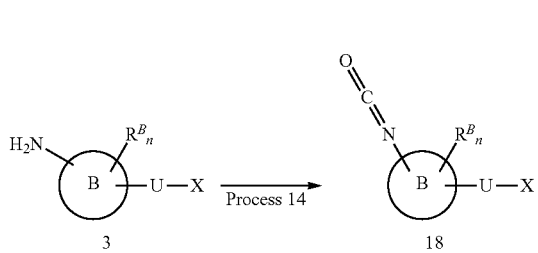
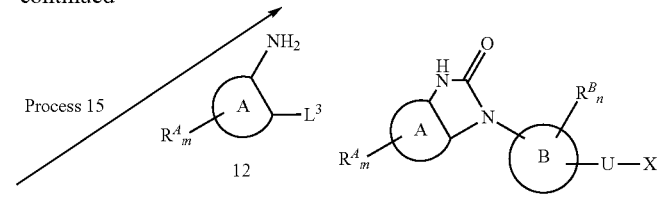

In the formula, ring A, ring B, $R^A$, $R^B$, m, n, U, X and $L^3$ have the same meanings as defined above.

Process 12

Amine compound (12) can be converted by allowing to react in an inert solvent such as tetrahydrofuran, ethyl acetate, methylene chloride, a mixed solvent thereof or the like using a reagent such as phosgene, diphosgene, triphosgene or the like in the presence of a base such as triethylamine, N,N-diisopropylethylamine, pyridine or the like usually under ice-cooling to at reflux temperature for 30 minutes to 1 day into Isocyanate compound (17).

Process 13

Urea compound (19) can be prepared by subjecting Isocyanate compound (17) to addition reaction with Amine compound (3). Addition reaction can be conducted, for example, in an inert solvent such as tetrahydrofuran, methylene chloride, ethyl acetate, a mixed solvent thereof or the like in the presence or absence of a base such as triethylamine, N,N-diisopropylethylamine, pyridine, 4-dimethylaminopyridine or the like usually under ice-cooling to at reflux temperature for 1 hour to 3 days.

Process 14

Isocyanate compound (18) can be prepared by allowing Amine compound (3) to react in an inert solvent such as tetrahydrofuran, ethyl acetate, methylene chloride, a mixed solvent thereof or the like using a reagent such as phosgene, diphosgene, triphosgene or the like in the presence of a base such as triethylamine, N,N-diisopropylethylamine, pyridine or the like usually under ice-cooling to at reflux temperature for 30 minutes to 1 day.

Process 15

Urea compound (19) also can be prepared by subjecting Isocyanate compound (18) to addition reaction with Amine compound (12). Addition reaction can be conducted, for example, in an inert solvent such as tetrahydrofuran, methylene chloride, ethyl acetate, a mixed solvent thereof or the like in the presence or absence of a base such as triethylamine, N,N-diisopropylethylamine, pyridine, 4-dimethylaminopyridine or the like usually under ice-cooling to at reflux temperature for 1 hour to 3 days.

Process 16

A nitrogen-containing fused ring derivative of the present invention (Ib) also can be prepared by subjecting Urea compound (19) to cyclization reaction. A cyclization reaction can be conducted in an inert solvent such as 1,4-dioxane, 2-propanol, tert-butanol, 1,2-dimethoxyethane, toluene, tetrahydrofuran, N,N-dimethylformamide, N,N-dimethyl-acetamide, 1-methyl-2-pyrrolidone, water, a mixed solvent thereof or the like using a catalyst such as tris(dibenzylideneacetone) dipalladium (0), palladium (II) acetate, tetrakis(triphenylphosphine)palladium (0) or the like in the presence or absence or a ligand such as 4,5-bis(diphenylphosphino)-9,9-dimethylxanthene, tri(tert-butyl)phosphine, 2-(dicyclohexylphosphino)-2'-methylbiphenyl, bis(2-diphenylphosphinophenyl)ether or the like and in the presence of a base such as cesium carbonate, potassium carbonate, cesium fluoride, potassium tert-butoxide, sodium tert-butoxide or the like usually at from room temperature to reflux temperature for 1 hour to 3 days.

[Method 5]

[Chem.3]

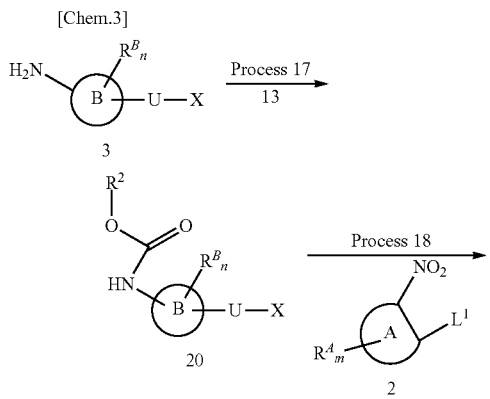
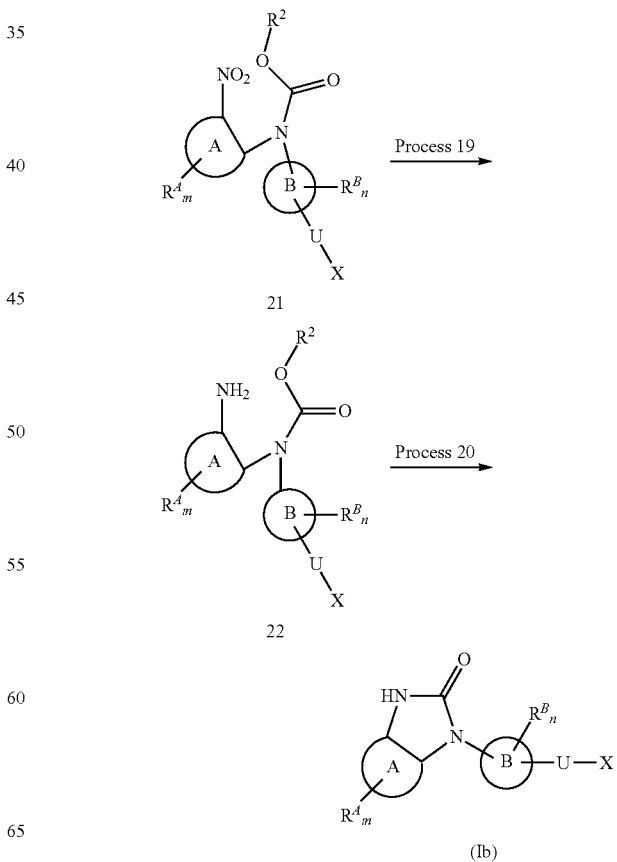

In the formula, ring A, ring B, $R^A$, $R^B$, m, n, U, X, $R^2$ and $L^1$ have the same meanings as defined above.

Process 17

Carbamate compound (20) can be prepared by converting the amino group of Amine compound (3) into carbamate by a method similar to that as described in the above Process 9.

Process 18

Nitro compound (21) can be prepared by condensing Carbamate compound (20) with Nitro compound (2) by a general coupling method under the basic condition, under the presence of palladium or the like as described in the above Process 5.

Process 19

Amine compound (22) can be prepared by reducing the nitro group of Nitro compound (21) by a general reduction method such as a catalytic reduction method, a reducing agent method or the like as described in the above Process 2.

Process 20

A nitrogen-containing fused ring derivative of the present invention (Ib) also can be prepared by allowing Amine compound (22) to react for cyclization in an inert solvent such as acetonitrile, tetrahydrofuran, N,N-dimethylformamide, N,N-dimethylacetamide, 1-methyl-2-pyrolidone, diglyme, a mixed solvent thereof or the like or without any solvent in the presence or absence of a base such as triethylamine, N,N-diisopropylethylamine, pyridine, 4-dimethylaminopyridine, sodium hydride, potassium hydride, sodium hexamethyldisilazide, lithium hexamethyldisilazide, potassium hexamethyldisilazide, potassium carbonate, Cesium carbonate, cesium fluoride, potassium tert-butoxide, sodium tert-butoxide or the like usually under ice-cooling to at reflux temperature for 30 minutes to 1 day.

Amine compound (3) used as a starting material in the above Methods also can be obtained, for example, by reducing Nitro compound (23), which is commercially available or synthesized by a method described in literatures, combining general synthetic methods or the like, by a general reduction method or the like. For example, it can be prepared by the following Method 6.

[Method 6]

[Chem.14]

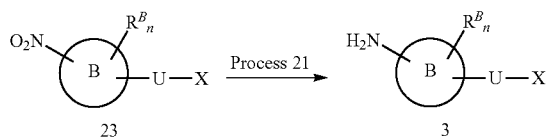

In the formula, ring B, $R^B$, n, U and X have the same meaning as defined above.

Process 21

Amine compound (3) can be prepared by reducing Nitro compound (23) by a general reduction method such as a catalytic reduction method, a reducing agent method or the like as described in the above Process 2.

In addition, when a compound used or prepared in the above Methods has a functional group which changes under the reaction conditions or inhibits the reaction progression, needless to say, the group may be protected by an appropriate protective group a commonly used by a skilled person in the art and the protective group may be removed in an appropriate step.

A nitrogen-containing fused ring derivative represented by the general formula (I) of the present invention can be converted into a prodrug wherein its carboxyl group, hydroxy group and/or amino group is converted, by allowing to react with a reagent to produce a prodrug. In addition, a prodrug of a nitrogen-containing fused ring derivative represented by the general formula (I) of the present invention may be a compound to be converted into a compound (1) of the present invention under physiological conditions described in "*Iyakuhin no Kaihatsu*" (Development of medicines), Vol. 7, Molecular design, pp. 163-198, issued by *Hirokawa syoten* (Hirokawa Book Store). As such a prodrug, as for a hydroxyl group, a lower acyl group such as an acetyl group, a pivaloyl group or the like, a lower alkoxycarbobyl group such as a methoxycarbonyl group, an ethoxycarbonyl group or the like can be illustrated; and as for a carboxy group, a (lower alkoxycarbonyloxy) lower alkyl group such as a 1-(methoxycarbonyloxy)ethyl group, a 1-(ethoxycarbonyloxy)ethyl group or the like, a (cycloalkyloxycarbonyloxy)lower alkyl group such as a 1-(cyclopentyloxycarbonyloxy)ethyl group, 1-(cyclohexyloxycarbonyloxy)ethyl group or the like can be illustrated. In the above, the term "lower alkoxycarbonyloxy" means oxy substituted by the above lower alkoxycarbonyl, the term "(lower alkoxycarbonyloxy)lower alkyl" means the above lower alkyl substituted by the above lower alkoxycarbonyloxy, the term "cycloalkyloxy" means oxy substituted by the above cycloalkyl, the term "cycloalkyloxycarbonyl" means carbonyl substituted by the above cycloalkyloxy, a term "cycloalkyloxycarbonyloxy" means oxy substituted by the above cycloalkyloxycarbonyl, and the term "(cycloalkyloxycarbonyloxy)lower alkyl" means the above lower alkyl substituted by the above cycloalkyloxycarbonyloxy.

A nitrogen-containing fused ring derivative represented by the general formula (I) or a prodrug thereof can be converted into a pharmaceutically acceptable salt thereof in the usual way. As such a salt, for example, a salt with an inorganic acid such as hydrochloric acid, nitric acid or the like; a salt with an organic acid such as acetic acid, methanesulfonic acid or the like; and a sodium salt and a potassium salt; an additive salt with an organic base such as N,N'-dibenzylethylenediamine, 2-aminoethanol or the like can be illustrated.

A nitrogen-containing fused ring derivative represented by the general formula (I) or a prodrug thereof, or a pharmaceutically acceptable salt thereof sometimes can be obtained as a hydrate or solvate in the course of purification or preparing salts thereof. A nitrogen-containing fused ring derivative represented by the general formula (I) of the present invention or a prodrug thereof, or a pharmaceutically acceptable salt thereof includes a hydrate thereof or a solvate thereof with a pharmaceutically acceptable solvent. As the pharmaceutically acceptable solvent, ethanol or the like can be illustrated.

Furthermore, in a nitrogen-containing fused ring derivative represented by the general formula (I) or a prodrug thereof, there can be tautomers, geometrical isomers and/or optical isomers. For a pharmaceutical composition of the present invention, any of the isomers and a mixture thereof can be employed.

A nitrogen-containing fused ring derivative (I) of the present invention has an excellent GnRH antagonistic activity and can control the effect of gonadotropin releasing hormone and control the production and secretion of gonadotropin and sex hormones. As a result, a nitrogen-containing fused ring derivative (I) of the present invention or a prodrug thereof, or a pharmaceutically acceptable salt thereof is extremely useful as an agent for the prevention or treatment of sex hormone-dependent diseases such as benign prostatic hypertrophy, hysteromyoma, endometriosis, metrofibroma, precocious puberty, amenorrhea, premenstrual syndrome, dysmenorrhea, polycystic ovary syndrome, lupus erythematosis, hirsutism, short stature, sleep disorders, acne, baldness, Alzheimer's disease, infertility, irritable bowel syndrome, prostatic cancer, uterine cancer, ovary cancer, breast cancer and pituitary tumor; a reproduction regulator, a contraceptive, an ovulation inducing agent or an agent for the prevention of postoperative recurrence of sex hormone-dependent cancers or the like.

A Pharmaceutical composition may be prepared by mixing a nitrogen-containing fused ring derivative (I) of the present invention or a prodrug thereof, or a pharmaceutically acceptable salt thereof, and a conventional pharmaceutical carrier.

The pharmaceutical carrier may be used optionally in combination according to a dosage form as described below. As the pharmaceutical carrier, for example, excipients such as lactose or the like; lubricants such as magnesium stearate or the like; disintegrators such as carboxymethylcellulose or the like; binders such as hydroxypropylmethylcellulose or the like; surfactants such as macrogol or the like; foamings such as sodium hydrogen carbonate or the like; dissolving aids such as cyclodextrin or the like; acidities such as citric acid or the like; stabilizers such as sodium edetate or the like; pH adjusters such as phosphoric acid salt or the like can be illustrated.

As the dosage form of the pharmaceutical composition of the present invention, for example, formulations for oral administration such as powders, granules, fine granules, dry syrups, tablets, capsules and the like; formulations for parenteral administration such as injections, poultices, suppositories and the like are illustrated, and a formulation for oral administration is preferable.

It is preferable to manufacture the above formulations in such a way that the dosage of the compound represented by the general formula (I) of the present invention or a pharmaceutically acceptable salt thereof is appropriately within the range of from 0.1 to 1,000 mg per day per adult human in case of oral administration and approximately within the range of from 0.01 to 100 mg per day per adult human in the case of parenteral injection in the formulation.

Furthermore, a pharmaceutical composition of the present invention can include other drug(s). Examples of such other drugs include a GnRH superagonist (for example, leuprorelin acetate, gonadorelin, buserelin, triptorelin, goserelin, nafarelin, histrelin, deslorelin, meterelin, lecirelin and the like), a chemotherapeutic agent (for example, ifosfamide, adriamycin, peplomycin, cisplatin, cyclophosphamide, 5-FU, UFT, methotrexate, mitomycin C, mitoxantrone, paclitaxel, dotaxel and the like), a peptidic GnRH antagonist (for example, cetrorelix, ganirelix, abarelix, ozarelix, iturelix, degarelix, teverelix and the like), a 5α-reductase inhibitor (for example, finasteride, dutasteride and the like), an α-adrenoceptor inhibitor (for example, tamsulosin, silodosin, urapidil and the like), an aromatase inhibitor (for example, fadrozole, letrozole, anastrozole, formestane and the like), an adrenal androgen production inhibitor (for example, liarozole and the like), a hormonotherapeutic agent (for example, an antiestrogenic agent such as tamoxifen, fulvestrant and the like, a progestational agent such as medroxyprogesterone and the like, an androgenic agent, an estrogeninc agent and an antiandrogenic agent such as oxendolone, flutamide, nilutamide, bicalutamide and the like) and the like can be illustrated.

EXAMPLES

The present invention is further illustrated in more detail by way of the following Reference Examples, Examples and Test Examples. However, the present invention is not limited thereto.

Reference Example 1

2,3-Difluoro-6-methoxybenzyl Chloride

To a solution of 2,3-difluoro-6-methoxybenzyl alcohol (6.97 g) in toluene (100 mL) was added thionyl chloride (4.4 mL) in a dropwise manner at room temperature, and the mixture was stirred at room temperature for 1 hour. The reaction mixture was poured into water, and the resulting mixture was extracted with ethyl acetate. The extract was washed with water and brine twice, and dried over anhydrous sodium sulfate. The solvent was removed under reduced pressure to give the title compound (7.65 g).

Reference Example 2

5-Chloro-2-(2,3-difluoro-6-methoxybenzyloxy)anisole

A mixture of 2,3-difluoro-6-methoxybenzyl chloride (7.65 g), 4-chloro-2-methoxyphenol (6.34 g), potassium carbonate (8.29 g) and sodium iodide (1.2 g) in N,N-dimethylformamide (20 mL) was stirred at 80° C. for 2 hours. The reaction mixture was poured into water, and the resulting mixture was extracted with diethyl ether. The extract was washed with 1 mol/L aqueous sodium hydroxide solution, water and brine successively, and dried over anhydrous magnesium sulfate, and the solvent was removed under reduced pressure. The residual solids were suspended in a mixed solvent (n-hexane/diethyl ether=5/1), and collected by filtration. The collected solids were washed with the same solvent, and dried under reduced pressure to give the title compound (8.6 g).

Reference Example 3

The compound of Reference Example 3 was prepared in a similar manner to that described in Reference Example 2 using the corresponding starting materials.

Reference Example 4

5-Chloro-2-(2,3-difluoro-6-methoxybenzyloxy)-4-nitroanisole

To a suspension of 5-chloro-2-(2,3-difluoro-6-methoxybenzyloxy)anisole (8.6 g) in acetic anhydride (54 mL) was added 60% nitric acid (2.9 mL) in a dropwise manner under ice-cooling, and the mixture was stirred under ice-cooling for 30 minutes. To the reaction mixture was added water (54 mL) in a dropwise manner, and the resulting mixture was stirred under ice-cooling for 30 minutes. The precipitated crystals were collected by filtration. The collected crystals were washed with water and a mixed solvent (n-hexane/ethanol=4/1), and dried under reduced pressure to give the title compound (9.41 g).

Reference Example 5

The compound of Reference Example 5 was prepared in a similar manner to that described in Reference Example 4 using the corresponding starting materials.

Reference Example 6

2-Chloro-5-(2,3-difluoro-6-methoxybenzyloxy)-4-methoxyaniline

To a mixture of 5-chloro-2-(2,3-difluoro-6-methoxybenzyloxy)-4-nitroanisole (9.41 g), nickel(II) bromide (0.29 g), tetrahydrofuran (100 mL) and methanol (100 mL) was added sodium borohydride (2.97 g) under ice-cooling, and the mixture was stirred under ice-cooling for 30 minutes, and then stirred at room temperature for 30 minutes. To the reaction mixture was added a saturated aqueous sodium hydrogen carbonate solution, and the resulting mixture was extracted with ethyl acetate. The extract was washed with brine twice, and dried over anhydrous magnesium sulfate. The solvent was removed under reduced pressure, and the residue was purified by column chromatography on silica gel (eluent: n-hexane/ethyl acetate=4/1-3/2) to give the title compound (7.77 g).

Reference Example 7

The compound of Reference Example 7 was prepared in a similar manner to that described in Reference Example 6 using the corresponding starting materials.

Reference Example 8

2-Chloro-5-(2,3-difluoro-6-methoxybenzyloxy)-4-methoxyaniline Hydrochloride

To a mixture of 5-chloro-2-(2,3-difluoro-6-methoxybenzyloxy)-4-nitroanisole (7.04 g), nickel(II) bromide (0.21 g), tetrahydrofuran (100 mL) and methanol (100 mL) was added sodium borohydride (2.22 g) under ice-cooling, and the mixture was stirred under ice-cooling for 30 minutes, and then stirred at room temperature for 30 minutes. To the reaction mixture was added a saturated aqueous sodium hydrogen carbonate solution, and the resulting mixture was extracted with ethyl acetate. The extract was washed with brine twice, and dried over anhydrous magnesium sulfate. The solvent was removed under reduced pressure, and the residue was dissolved in ethyl acetate (20 mL). To the solution was added hydrochloric acid (4 mol/L ethyl acetate solution, 10 mL) in a dropwise manner under ice-cooling, and the mixture was stirred for 5 minutes. To the mixture was added diisopropyl ether (30 mL), and the mixture was stirred under ice-cooling for 30 minutes. The precipitated crystals were collected by filtration. The collected crystals were washed with diisopropyl ether, and dried under reduced pressure to give the title compound (6.54 g).

Reference Example 9

The compound of Reference Example 9 was prepared in a similar manner to that described in Reference Example 8 using the corresponding starting materials.

Reference Example 10

2-Chloro-5-mercapto Aniline

To a mixture of concentrated hydrochloric acid (30 mL) and ice (25 g) was added tin (29.7 g) under ice-cooling, followed by adding 4-chloro-3-nitrobenzenesulfonyl chloride (6.4 g), and the mixture was stirred under ice-cooling for 1.5 hours, and then stirred at 90° C. for 2 hours. The insoluble material was removed by filtration, and the filtrate was stirred at room temperature overnight. The precipitated crystals were collected by filtration. The collected crystals were washed with water, and dried under reduced pressure to give the title compound (2.95 g).

Reference Example 11

2-Chloro-5-(1-methyl-1-phenylethylthio)aniline

To a mixture of water (10 mL) and concentrated sulfuric acid (10 mL) was added 2-chloro-5-mercaptoaniline (1.6 g) at room temperature, and the mixture was stirred for 15 minutes. To the mixture was added a solution of 2-phenyl-2-propanol (1.36 g) in tetrahydrofuran (10 mL) in a dropwise manner, and the mixture was stirred at room temperature for 30 minutes. The reaction mixture was poured into ice water, and the resulting mixture was extracted with ethyl acetate. The extract was washed with water, a saturated aqueous sodium hydrogen carbonate solution and brine successively, and dried over anhydrous magnesium sulfate. The solvent was removed under reduced pressure, and the residue was purified by column chromatography on silica gel (eluent: n-hexane–n-hexane/ethyl acetate=4/1) to give the title compound (1.62 g).

Reference Example 12

2-Chloro-5-(3,4-dihydroquinolin-1(2H)-ylsulfonyl)aniline

To a suspension of 1,2,3,4-tetrahydroquinoline (3.12 g) and sodium hydrogen carbonate (2.66 g) in tetrahydrofuran (60 mL) were added water (6 mL) and a solution of 4-chloro-3-nitrobenzenesulfonyl chloride (5.4 g) in tetrahydrofuran (30 mL) successively, and the mixture was stirred at room temperature overnight. The reaction mixture was diluted with ethyl acetate, and the resulting mixture was washed with water, 1 mol/L hydrochloric acid, water and brine successively, and dried over anhydrous magnesium sulfate. The solvent was removed under reduced pressure to give 1-[(4-chloro-3-nitrophenyl)-sulfonyl]-1,2,3,4-tetrahydroquinoline (5.0 g). This material was dissolved in tetrahydrofuran (45 mL). To the solution were added methanol (45 mL), nickel(II) bromide (0.15 g) and sodium borohydride (1.61 g) under ice-cooling, and the mixture was stirred at the same temperature for 30 minutes, and then stirred at room temperature for 30 minutes. The reaction mixture was diluted with ethyl acetate, and the resulting mixture was washed with a saturated aqueous sodium hydrogen carbonate solution, water and brine successively, and dried over anhydrous magnesium sulfate. The solvent was removed under reduced pressure, and the residue was purified by column chromatography on silica gel (eluent: n-hexane/ethyl acetate=3/1) to give the title compound (4.33 g).

Reference Example 13

4-(tert-Butoxycarbonylamino)-5-chloro-2-(2,3-difluoro-6-methoxybenzyloxy)anisole To a solution of 2-chloro-5-(2,3-difluoro-6-methoxybenzyloxy)-4-methoxyaniline (0.66 g) in tetrahydrofuran (10 mL) were added 4-dimethylaminopyridine (73 mg) and di(tert-butyl)dicarbonate (0.87 g), and the mixture was heated at reflux overnight. The reaction mixture was poured into 0.5 mol/L hydrochloric acid, and the resulting mixture was extracted with ethyl acetate. The extract was washed with water and brine, and dried over anhydrous sodium sulfate, and the solvent was removed under reduced pressure. To the residue were added methanol (10 mL) and potassium carbonate (0.83 g), and the mixture was heated at reflux for 2 hours. To the reaction mixture was added water, and then the mixture was poured into brine, and the resulting mixture was extracted with ethyl acetate. The extract was dried over anhydrous sodium sulfate, and the solvent was removed under reduced pressure. The residue was purified by column chromatography on silica gel (eluent: n-hexane/ethyl acetate=3/1) to give the title compound (0.79 g).

Reference Example 14

2,6-Dichloro-4-methoxynicotinic Acid

To a solution of diisopropylamine (1.83 mL) in tetrahydrofuran (40 mL) was added n-butyllithium (2.64 mol/L n-hexane solution, 4.52 mL) at −78° C., and the mixture was stirred at the same temperature for 5 minutes. To the reaction mixture was added a solution of 2,6-dichloro-4-methoxypyridine (1.93 g) in tetrahydrofuran (10 mL) in a dropwise manner, and the mixture was stirred at the same temperature for 30 minutes. To the reaction mixture was added dry ice (5 g), and the mixture was stirred at the same temperature for 30 minutes. To the reaction mixture were added a saturated aqueous ammonium chloride solution and 2 mol/L hydrochloric acid, and the resulting mixture was extracted with ethyl acetate. The extract was washed with brine, and dried over anhydrous magnesium sulfate. The solvent was removed under reduced pressure, and the residue was purified by column chromatography on silica gel (eluent: ethyl acetate) to give the title compound (1.2 g).

Reference Example 15

2,6-Dibromonicotinic Acid

To a solution of 2,6-dibromo-3-formylpyridine (0.3 g) in tert-butanol (12 mL)-water (1 mL) were added sodium dihydrogen phosphate (0.14 g), 2-methyl-2-butene (0.32 g) and a solution of sodium chlorite (0.36 g) in water (2 mL) successively at room temperature, and the mixture was stirred for 2 hours. The reaction mixture was poured into water. The mixture was acidified by adding 1 mol/L hydrochloric acid, and the resulting mixture was extracted with ethyl acetate. The extract was washed with water, and dried over anhydrous magnesium sulfate. The solvent was removed under reduced pressure to give the title compound (0.28 g).

Reference Example 16

The compound of Reference Example 16 was prepared in a similar manner to that described in Reference Example 11 using the corresponding starting materials.

Reference Example 17

Methyl 5-(tert-butoxycarbonylamino)-6-iodopyridine-2-carboxylate

A mixture of methyl 5-aminopyridine-2-carboxylate (2.92 g), iodine (3.9 g) and sodium periodate (1.64 g) in N,N-dimethylformamide (24 mL) was stirred at 60° C. for 2 days. The reaction mixture was cooled to room temperature. To the reaction mixture was added 10% aqueous sodium sulfite solution, and the resulting mixture was stirred for 10 minutes. The crystals were collected by filtration. The collected crystals were washed with water, and dried under reduced pressure to give methyl 5-amino-6-iodopyridine-2-carboxylate (3.26 g). To sodium hexamethyldisilazide (1.03 mol/L tetrahydrofuran solution, 7.68 mL) was added a solution of methyl 5-amino-6-iodopyridine-2-carboxylate (1 g) in tetrahydrofuran (5 mL) in a dropwise manner at −14° C., and the mixture was stirred at the same temperature for 10 minutes. To the mixture was added a solution of di(tert-butyl)dicarbonate (0.82 g) in tetrahydrofuran (3 mL) in a dropwise manner, and the mixture was stirred at the same temperature for 30 minutes. To the reaction mixture was added 1 mol/L hydrochloric acid (13.6 mL), and the resulting mixture was extracted with ethyl acetate. The extract was washed with water and brine, and dried over anhydrous magnesium sulfate, and the solvent was removed under reduced pressure. To the residue were added 2-propanol (2.8 mL) and water (3.4 mL), and the mixture was stirred at 80° C. for 30 minutes, and then stirred at room temperature for 30 minutes. The crystals were collected by filtration. The collected crystals were washed with a mixed solvent (2-propanol/water=5/6), and dried under reduced pressure to give the title compound (0.82 g).

Reference Example 18

The compound of Reference Example 18 was prepared in a similar manner to that described in Reference Example 12 using the corresponding starting materials.

Reference Example 19

2-Cyano-4-methyl-5-nitropyridine

To a solution of 2-hydroxy-4-methyl-5-nitropyridine (5 g) and triethylamine (12.2 mL) in methylene chloride (150 mL) was added trifluoromethanesulfonic anhydride (7.1 mL) under ice-cooling over 10 minutes, and the mixture was stirred at room temperature overnight. The reaction mixture was poured into a saturated aqueous sodium hydrogen carbonate solution, and the resulting mixture was extracted with methylene chloride. The extract was concentrated under reduced pressure, and the residue was purified by column chromatography on silica gel (eluent: n-hexane/ethyl acetate=6/1) to give 2-trifluoromethanesulfonyloxy-4-methyl-5-nitropyridine (7.9 g). To this material were added N,N-dimethylformamide (200 mL), zinc cyanide (3.24 g) and tetrakis(triphenylphosphine)palladium(0) (1.85 g), and the mixture was stirred at 80° C. under an argon atmosphere for 5 hours. The reaction mixture was cooled to room temperature, and the insoluble material was removed by filtration. To the filtrate were added water and ethyl acetate, and the organic layer was separated. The organic layer was washed with water and brine, and dried over anhydrous magnesium sulfate. The solvent was removed under reduced pressure, and the residue was purified by column chromatography on silica gel (eluent: n-hexane/ethyl acetate=5/1) to give the title compound (3.54 g).

Reference Example 20

Ethyl 4-methyl-5-nitropyridine-2-carboxylate

To concentrated sulfuric acid (45 mL) was added ethanol (100 mL) under ice-cooling, followed by adding 2-cyano-4-methyl-5-nitropyridine (3.54 g), and the reaction vessel was equipped with a reflux condenser, and the mixture was stirred at 120° C. for 2 hours. The reaction mixture was cooled to room temperature. The reaction mixture was poured into ice, and the resulting mixture was extracted with diethyl ether. The water layer was extracted with methylene chloride. The extracts were combined, and dried over anhydrous magnesium sulfate. The solvent was removed under reduced pressure, and the residue was purified by column chromatography on silica gel (eluent: n-hexane/ethyl acetate=3/1) to give the title compound (3.23 g).

Reference Example 21

5-Amino-2-cyano-4-methylpyridine

To a suspension of 2-cyano-4-methyl-5-nitropyridine (1.86 g) and ammonium chloride (3.05 g) in water (50 mL) was added zinc (7.46 g) under ice-cooling over 10 minutes, and the mixture was stirred at the same temperature for 1 hour. To the reaction mixture was added ethyl acetate (50 mL), and the resulting mixture was stirred at room temperature for 30 minutes. The insoluble material was removed by filtration, and the organic layer of the filtrate was separated. The organic layer was washed with brine, and dried over anhydrous magnesium sulfate, and the solvent was removed under reduced pressure. The residual solids were suspended in a mixed solvent (n-hexane/ethyl acetate=1/1), and collected by filtration. The collected solids were dried under reduced pressure to give the title compound (0.7 g).

Reference Example 22

Ethyl 5-amino-4-methylpyridine-2-carboxylate

A mixture of ethyl 4-methyl-5-nitropyridine-2-carboxylate (3.23 g) and 10% palladium-carbon powder (0.65 g) in ethanol (50 mL) was stirred at room temperature under a hydrogen atmosphere overnight. The insoluble material was removed by filtration, and the filtrate was concentrated under reduced pressure to give the title compound (2.74 g).

Reference Example 23

Ethyl 5-(tert-butoxycarbonylamino)-6-iodo-4-methylpyridine-2-carboxylate

A mixture of ethyl 5-amino-4-methylpyridine-2-carboxylate (2.58 g), iodine (2.91 g) and sodium periodate (1.22 g) in N,N-dimethylformamide (20 mL) was stirred at 60° C. for 6 days. The reaction mixture was cooled to room temperature. To the reaction mixture was added 1 mol/L aqueous sodium thiosulfate solution, and the resulting mixture was extracted with ethyl acetate twice. The extracts were washed with water and brine, and dried over anhydrous magnesium sulfate. The solvent was removed under reduced pressure, and the residue was purified by column chromatography on silica gel (eluent: n-hexane/ethyl acetate=2/1–1/1) to give ethyl 5-amino-6-iodo-4-methylpyridine-2-carboxylate (2.31 g). To sodium hexamethyldisilazide (1.03 mol/L tetrahydrofuran solution, 10.5 mL) was added a solution of ethyl 5-amino-6-iodo-4-methylpyridine-2-carboxylate (1.51 g) in tetrahydrofuran (9 mL) in a dropwise manner at −10° C., and the mixture was stirred at the same temperature for 10 minutes. To the mixture was added a solution of di(tert-butyl)dicarbonate (1.18 g) in tetrahydrofuran (4 mL) in a dropwise manner, and the mixture was stirred at the same temperature for 30 minutes. To the reaction mixture was added 1 mol/L hydrochloric acid, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: n-hexane/ethyl acetate=3/1–2/1) to give the title compound (1.11 g).

Reference Example 24

The compound of Reference Example 24 was prepared in a similar manner to that described in Reference Example 23 using the corresponding starting materials.

Reference Example 25

The compound of Reference Example 25 was prepared in a similar manner to that described in Reference Example 23 using 2-amino-3,5-dibromopyrazine instead of ethyl 5-amino-6-iodo-4-methylpyridine-2-carboxylate.

Reference Example 26

6-(tert-Butyldimethylsilyloxy)methyl-2-chloro-4-methoxynicotinic acid

To a solution of 6-chloro-2-hydroxymethyl-4-methoxypyridine (1.85 g), which was prepared by a method mentioned in Tokkaihei 10-59942 (JP1998-59942A), and imidazole (0.87 g) in N,N-dimethylformamide (30 mL) was added tert-butyldimethylchlorosilane (1.77 g), and the mixture was stirred at room temperature overnight. The reaction mixture was poured into water, and the resulting mixture was extracted with diethyl ether. The extract was washed with water twice, and dried over anhydrous magnesium sulfate. The solvent was removed under reduced pressure, and the residue was purified by column chromatography on silica gel (eluent: n-hexane–n-hexane/ethyl acetate=85/15) to give 2-(tert-butyldimethylsilyloxy)methyl-6-chloro-4-methoxypyridine (2.83 g). To a solution of N,N-diisopropylamine (0.54 mL) in tetrahydrofuran (20 mL) was added n-butyllithium (2.77 mol/L n-hexane solution, 1.25 mL) at −78° C., and the mixture was stirred at the same temperature for 5 minutes. To the reaction mixture was added a solution of 2-(tert-butyldimethylsilyloxy)methyl-6-chloro-4-methoxypyridine (1 g) in tetrahydrofuran (5 mL), and the mixture was stirred at the same temperature for 20 minutes. To the reaction mixture was added N,N-dimethylformamide (0.32 mL), and the mixture was stirred at the same temperature for 10 minutes. To the reaction mixture was added a saturated aqueous ammonium chloride solution, and the resulting mixture was stirred at room temperature for 5 minutes. The mixture was poured into water, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: n-hexane–n-hexane/ethyl acetate=3/1) to give 6-(tert-butyldimethylsilyloxy)methyl-2-chloro-4-methoxy-3-formylpyridine (0.28 g). The title compound was prepared in a similar manner to that described in Reference Example 15 using 6-(tert-butyldimethylsilyloxy)methyl-2-chloro-4-methoxy-3-formylpyridine instead of 2,6-dibromo-3-formylpyridine.

Reference Example 27

4-Fluoro-5-(1,3-dioxo-1,3-dihydroisoindol-2-yl)-2-methoxybenzenesulfonyl chloride A suspension of 2-fluoro-4-methoxyaniline (2.22 g) and phthalic anhydride (2.33 g) in N,N-dimethylformamide (16 mL) was stirred at 120° C. for 1 hour. The reaction mixture was cooled to room temperature. To the reaction mixture was added water, and the resulting mixture was extracted with ethyl acetate. The extract was washed with water and brine, and dried over anhydrous magnesium sulfate. The solvent was removed under reduced pressure. The residual crystals were suspended in ethyl acetate (5 mL), and the suspension was stirred at room temperature for 10 minutes. To the suspension was added n-hexane (25 mL), and the crystals were collected by filtration. The collected crystals were dried under reduced pressure to give 3-fluoro-4-(1,3-dioxo-1,3-dihydroisoindol-2-yl)anisole (3.35 g). This material was suspended in 1,2-dichloroethane (12.4 mL). To the suspension was added chlorosulfonic acid (1.81 mL) in a dropwise manner under ice-cooling, and the mixture was heated at reflux for 1 hour. The reaction mixture was cooled to room temperature. To the reaction mixture were added thionyl chloride (4.5 mL) and N,N-dimethylformamide (0.048 mL), and the mixture was heated at reflux for 2 hours. The reaction mixture was cooled to room temperature, and diluted with ethyl acetate. To the mixture was added water, and the organic layer was separated. The organic layer was washed with brine, and dried over anhydrous magnesium sulfate, and the solvent was removed under reduced pressure. The residual crystals were suspended in ethyl acetate (10 mL). To the suspension was added n-hexane (30 mL), and the crystals were collected by filtration. The collected crystals were washed with n-hexane, and dried under reduced pressure to give the title compound (3.6 g).

Reference Examples 28 to 30

The compounds of Reference Examples 28 to 30 were prepared in a similar manner to that described in Reference Example 27 using the corresponding starting materials.

Reference Example 31

4-Fluoro-3-nitrobenzenesulfonyl Chloride

To 2-fluoronitrobenzene (2.33 g) was added fuming sulfuric acid (20 mL), and the mixture was stirred at 60° C. for 30 minutes. The reaction mixture was cooled to room temperature. The reaction mixture was poured into ice and potassium chloride (10 g), and the resulting mixture was stirred at room temperature for 30 minutes. The precipitated crystals were collected by filtration. The collected crystals were washed with water, and dried under reduced pressure to give 4-fluoro-3-nitrobenzenesulfonic acid (3.15 g). To phosphoryl chloride (85 mL) were added 4-fluoro-3-nitrobenzenesulfonic acid (3.15 g) and phosphorus pentachloride (2.82 g) under ice-cooling, and the mixture was heated at reflux overnight. The reaction mixture was cooled to room temperature, and concentrated under reduced pressure. To the residue was added ice water, and the resulting mixture was extracted with diethyl ether. The extract was washed with brine, and dried over anhydrous magnesium sulfate. The solvent was removed under reduced pressure, and the residue was purified by column chromatography on silica gel (eluent: n-hexane–n-hexane/ethyl acetate=3/1) to give the title compound (2.65 g).

Reference Example 32

5-Chloro-4-(1,3-dioxo-1,3-dihydroisoindol-2-yl)-2-mercaptoanisole

To a suspension of 4-chloro-5-(1,3-dioxo-1,3-dihydroisoindol-2-yl)-2-methoxy-benzenesulfonyl chloride (0.83 g) in tetrahydrofuran (10 mL) were added triphenylphosphine (1.98 g) and water (1.5 mL), and the mixture was stirred at room temperature overnight. To the reaction mixture were added water and ethyl acetate, and the organic layer was separated. The organic layer was washed with brine, and dried over anhydrous magnesium sulfate. The solvent was removed under reduced pressure, and the residue was purified by column chromatography on silica gel (eluent: n-hexane–n-hexane/ethyl acetate=1/1) to give the title compound (0.62 g).

Reference Example 33

The compound of Reference Example 33 was prepared in a similar manner to that described in Reference Example 32 using the corresponding starting materials.

Reference Example 34

2-Chloro-5-mercapto-4-methoxyaniline

To a solution of 5-chloro-4-(1,3-dioxo-1,3-dihydroisoindol-2-yl)-2-mercaptoanisole (0.65 g) in tetrahydrofuran (20 mL) was added hydrazine monohydrate (0.5 mL), and the mixture was heated at reflux for 1.5 hours. The insoluble material was removed by filtration, and the filtrate was concentrated under reduced pressure. The residue was purified by column chromatography on silica gel (eluent: n-hexane–n-hexane/ethyl acetate=1/1) to give the title compound (0.3 g).

Reference Example 35

The compound of Reference Example 35 was prepared in a similar manner to that described in Reference Example 34 using the corresponding starting materials.

Reference Example 36

The compound of Reference Example 36 was prepared in a similar manner to that described in Reference Example 10 using the corresponding starting materials.

Reference Examples 37 and 38

The compounds of Reference Examples 37 and 38 were prepared in a similar manner to that described in Reference Example 32 and Reference Example 34 using the corresponding starting materials.

Reference Example 39

2-Fluoro-5-mercaptoaniline

To a mixture of 5-bromo-2-fluoroaniline (4.15 g), methyl 3-mercaptopropionate (2.62 g), 4,5-bis(diphenylphosphino)-9,9-dimethylxanthene (0.63 g) and N,N-diisopropylethylamine (5.64 g) in 1,4-dioxane (80 mL) was added tris(dibenzylideneacetone)-dipalladium(0) (0.3 g), and the mixture was heated at reflux under an argon atmosphere overnight. The insoluble material was removed by filtration, and the filtrate was concentrated under reduced pressure. The residue was purified by column chromatography on silica gel (eluent: n-hexane/ethyl acetate=20/1–5/1–2/1) to give 2-fluoro-5-(2-methoxy-carbonylethylthio)aniline (4.62 g). This material was dissolved in tetrahydrofuran (120 mL). To the solution was added potassium tert-butoxide (1 mol/L tetrahydrofuran solution, 80.6 mL) at −78° C., and the mixture was stirred at the same temperature for 15 minutes. To the reaction mixture was added 1 mol/L hydrochloric acid (81 mL), and the reaction mixture was allowed to warm to room temperature, and stirred for 5 minutes. The mixture was poured into ethyl acetate, and the organic layer was separated. The organic layer was washed with brine, and dried over anhydrous magnesium sulfate. The solvent was removed under reduced pressure, and the residue was purified by column chromatography on silica gel (eluent: n-hexane/ethyl acetate=4/1) to give the title compound (1.85 g).

Reference Example 40

4-Chloro-2-methoxy-5-nitroaniline

To a suspension of 4-chloro-2-methoxyaniline (1.88 g) in concentrated sulfuric acid (18 mL) was added guanidine nitrate (1.46 g) under ice-cooling over 15 minutes, and the mixture was stirred at the same temperature for 15 minutes. The reaction mixture was poured into a saturated aqueous sodium carbonate solution cooled in ice, and the precipitated crystals were collected by filtration. The crystals were dissolved in ethyl acetate, and the solution was dried over anhydrous magnesium sulfate. The solvent was removed under reduced pressure to give the title compound (1.94 g).

Reference Example 41

2-Fluoro-6-methoxybenzyl Bromide

To a solution of 2-fluoro-6-methoxybenzyl alcohol (0.78 g) and triethylamine (0.91 mL) in ethyl acetate (12 mL) was added methanesulfonyl chloride (0.43 mL) under ice-cooling, and the mixture was stirred at the same temperature for 30 minutes. The insoluble material was removed by filtration, and the insoluble material was washed with ethyl acetate (4 mL). The filtrate and washing were combined. To the solution was added lithium bromide monohydrate (2.62 g), and the mixture was stirred at 55° C. for 2 hours. The reaction mixture was poured into water, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: n-hexane–n-hexane/ethyl acetate=7/3) to give the title compound (0.82 g).

Reference Examples 42 and 43

The compounds of Reference Examples 42 and 43 were prepared in a similar manner to that described in Reference Example 41 using the corresponding starting materials.

Reference Example 44

2-Chloro-6-methoxybenzyl bromide

A mixture of 3-chloro-2-methylanisole (2 g), N-bromosuccinimide (2.39 g) and 2,2'-azobis(2-methylpropionitrile) (32 mg) in carbon tetrachloride (15 mL) was heated at reflux for 3 hours. The insoluble material was removed by filtration, and the filtrate was concentrated under reduced pressure. The residue was purified by column chromatography on silica gel (eluent: n-hexane–n-hexane/ethyl acetate=4/1) to give the title compound (2.9 g).

Reference Example 45

2-(2-Fluoro-6-methoxyphenyl)-2-propanol

To a solution of methyl 2-fluoro-6-methoxybenzoate (0.92 g) in tetrahydrofuran (12.5 mL) was added methylmagnesium iodide (3.0 mol/L diethyl ether solution, 5 mL) under ice-cooling, and the mixture was stirred at room temperature overnight. To the reaction mixture was added a saturated aqueous ammonium chloride solution, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: n-hexane–n-hexane/ethyl acetate=1/1) to give the title compound (0.8 g).

Reference Examples 46 to 51

The compounds of Reference Examples 46 to 51 were prepared in a similar manner to that described in Reference Example 45 using the corresponding starting materials.

Reference Example 52

2-Chloro-4-methoxy-5-[1-(2-methoxyphenyl)-1-methylethylthio]aniline

To concentrated sulfuric acid (6 mL) was added water (6 mL) under ice-cooling, and the mixture was stirred at the same temperature for 10 minutes. To the mixture was added a solution of 2-chloro-5-mercapto-4-methoxyaniline (0.5 g) and 2-(2-methoxyphenyl)-2-propanol (0.88 g) in tetrahydrofuran (6 mL), and the mixture was stirred at room temperature for 3 hours. The reaction mixture was poured into ice water, and the resulting mixture was extracted with ethyl acetate. The extract was washed with water, a saturated aqueous sodium hydrogen carbonate solution and brine successively, and dried over anhydrous magnesium sulfate. The solvent was removed under reduced pressure, and the residue was purified by column chromatography on silica gel (eluent: n-hexane–n-hexane/ethyl acetate=4/1) to give the title compound (0.3 g).

Reference Examples 53 to 73

The compounds of Reference Examples 53 to 73 were prepared in a similar manner to that described in Reference Example 52 using the corresponding starting materials.

Reference Example 74

2-Chloro-4-methoxy-5-(1-methyl-1-phenylethylthio) aniline

To a solution of 2-phenyl-2-propanol (0.45 g) in 1,2-dichloroethane (5 mL) were added zinc iodide (0.53 g) and a solution of 5-chloro-4-(1,3-dioxo-1,3-dihydroisoindol-2-yl)-2-mercaptoanisole (1 g) in 1,2-dichloroethane (5 mL) successively, and the mixture was stirred at room temperature for 1 hour. The reaction mixture was poured into water, and the resulting mixture was extracted with ethyl acetate. The extract was washed with brine, and dried over anhydrous magnesium sulfate. The solvent was removed under reduced pressure, and the residue was purified by column chromatography on silica gel (eluent: n-hexane/ethyl acetate=3/1) to give 5-chloro-4-(1,3-dioxo-1,3-dihydroisoindol-2-yl)-2-(1-methyl-1-phenylethylthio)anisole (1.32 g). This material was dissolved in tetrahydrofuran (20 mL). To the solution was added hydrazine monohydrate (0.73 mL), and the mixture was heated at reflux for 2 hours. The reaction mixture was cooled to room temperature, and the insoluble material was removed by filtration. To the filtrate were added water and ethyl acetate, and the organic layer was separated. The organic layer was dried over anhydrous magnesium sulfate, and the solvent was removed under reduced pressure. The residue was purified by column chromatography on silica gel (eluent: n-hexane/ethyl acetate=4/1) to give the title compound (0.74 g).

Reference Examples 75 to 85

The compounds of Reference Examples 75 to 85 were prepared in a similar manner to that described in Reference Example 74 using the corresponding starting materials.

Reference Example 86

2-Fluoro-5-(2,3,4,5-tetrahydro-1H-1-benzoazepin-1-ylsulfonyl)aniline

To a solution of 2,3,4,5-tetrahydro-1H-benzo[B]azepine (0.37 g), triethylamine (0.35 mL) and 4-dimethylaminopyridine (26 mg) in methylene chloride (8 mL) was added 4-fluoro-3-nitrobenzenesulfonyl chloride (0.5 g), and the mixture was stirred at room temperature for 5 hours. The reaction mixture was poured into water, and the resulting mixture was extracted with ethyl acetate. The extract was washed with 1 mol/L hydrochloric acid, water and brine successively, and dried over anhydrous magnesium sulfate. The solvent was removed under reduced pressure, and the residue was dissolved in tetrahydrofuran (7 mL). To the solution were added methanol (7 mL) and nickel(II) bromide (23 mg). To the mixture was added sodium borohydride (0.24 g) under ice-cooling, and the mixture was stirred at the same temperature for 30 minutes, and then stirred at room temperature for 30 minutes. To the reaction mixture was added a saturated aqueous sodium hydrogen carbonate solution, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: n-hexane–n-hexane/ethyl acetate=1/1) to give the title compound (0.26 g).

Reference Examples 87 to 97

The compounds of Reference Examples 87 to 97 were prepared in a similar manner to that described in Reference Example 86 using the corresponding starting materials.

Reference Example 98

3-Amino-4-chloro-N-(2-fluoro-6-methoxyphenyl)-N-methylbenzenesulfonamide

To a mixture of 2-fluoro-6-methoxyaniline (0.56 g), sodium hydrogen carbonate (0.67 g) and water (2 mL) in tetrahydrofuran (20 mL) was added a solution of 4-chloro-3-nitrobenzenesulfonyl chloride (1.0 g) in tetrahydrofuran (10 mL), and the mixture was stirred at room temperature overnight. The reaction mixture was diluted with ethyl acetate, and the resulting mixture was washed with 1 mol/L hydrochloric acid, water and brine successively, and dried over anhydrous magnesium sulfate. The solvent was removed under reduced pressure, and the residue was purified by column chromatography on silica gel (eluent: n-hexane/ethyl acetate=2/3) to give 4-chloro-N-(2-fluoro-6-methoxyphenyl)-3-nitrobenzenesulfonamide (0.56 g). This material was dissolved in N,N-dimethylformamide (15 mL).

To the solution were added methyl iodide (0.15 mL) and sodium hydride (55%, 75 mg) under ice-cooling, and the mixture was stirred at room temperature for 2 hours. The reaction mixture was poured into water, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: n-hexane–n-hexane/ethyl acetate=1/1) to give 4-chloro-N-(2-fluoro-6-methoxyphenyl)-N-methyl-3-nitrobenzenesulfonamide (0.4 g). This material was dissolved in tetrahydrofuran (3 mL). To the solution were added methanol (3 mL) and nickel(II) bromide (12 mg). To the mixture was added sodium borohydride (0.12 g) under ice-cooling, and the mixture was stirred at the same temperature for 30 minutes, and then stirred at room temperature for 1 hour. To the reaction mixture was added a saturated aqueous sodium hydrogen carbonate solution, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: n-hexane–n-hexane/ethyl acetate=1/4) to give the title compound (0.3 g).

Reference Examples 99 to 106

The compounds of Reference Examples 99 to 106 were prepared in a similar manner to that described in Reference Example 98 using the corresponding starting materials.

Reference Example 107

2-Fluoro-5-(2,3,4,5-tetrahydro-1H-1-benzoazepin-1-ylsulfonyl)-4-methoxyaniline

To a solution of 2,3,4,5-tetrahydro-1H-benzo[B]azepine (0.24 g), triethylamine (0.23 mL) and 4-dimethylaminopyridine (17 mg) in methylene chloride (8 mL) was added 4-fluoro-5-(1,3-dioxo-1,3-dihydroisoindol-2-yl)-2-methoxybenzenesulfonyl chloride (0.5 g), and the mixture was stirred at room temperature for 5 hours. The reaction mixture was poured into water, and the resulting mixture was extracted with ethyl acetate. The extract was washed with 1 mol/L hydrochloric acid, water and brine successively, and dried over anhydrous magnesium sulfate, and the solvent was removed under reduced pressure to give 5-fluoro-2-(2,3,4,5-tetrahydro-1H-1-benzoazepin-1-ylsulfonyl)-4-(1,3-dioxo-1,3-dihydroisoindol-2-yl)anisole (0.57 g). This material was dissolved in tetrahydrofuran (11 mL). To the solution was added hydrazine monohydrate (0.29 mL), and the mixture was heated at reflux for 2 hours. The reaction mixture was cooled to room temperature, and diluted with ethyl acetate. The insoluble material was removed by filtration, and the filtrate was concentrated under reduced pressure, and the residue was purified by column chromatography on silica gel (eluent: n-hexane–n-hexane/ethyl acetate=2/3) to give the title compound (0.32 g).

Reference Examples 108 to 121

The compounds of Reference Examples 108 to 121 were prepared in a similar manner to that described in Reference Example 107 using the corresponding starting materials.

Reference Example 122

5-Amino-4-chloro-2-methoxy-N-methyl-N-(1-methyl-1-phenylethyl)benzenesulfonamide

To a solution of 4-chloro-5-(1,3-dioxo-1,3-dihydroisoindol-2-yl)-2-methoxybenzene-sulfonyl chloride (0.2 g) in methylene chloride (6 mL) were added 2-amino-2-phenylpropane (70 mg), triethylamine (0.11 mL) and 4-dimethylaminopyridine (6 mg), and the mixture was stirred at room temperature for 2 hours. The reaction mixture was poured into 1 mol/L hydrochloric acid, and the resulting mixture was extracted with ethyl acetate. The extract was washed with water and brine, and dried over anhydrous magnesium sulfate, and the solvent was removed under reduced pressure. The residue was dissolved in N,N-dimethylformamide (6 mL). To the solution were added methyl iodide (0.057 mL) and sodium hydride (55%, 22 mg) under ice-cooling, and the mixture was stirred at room temperature for 1 hour. The reaction mixture was poured into 1 mol/L hydrochloric acid, and the resulting mixture was extracted with ethyl acetate. The extract was washed with water and brine, and dried over anhydrous magnesium sulfate. The solvent was removed under reduced pressure, and the residue was dissolved in tetrahydrofuran (10 mL). To the solution was added hydrazine monohydrate (0.11 mL), and the mixture was heated at reflux for 2 hours. The reaction mixture was cooled to room temperature, and the insoluble material was removed by filtration. To the filtrate were added water and ethyl acetate, and the organic layer was separated. The organic layer was dried over anhydrous magnesium sulfate, and the solvent was removed under reduced pressure. The residue was purified by column chromatography on silica gel (eluent: n-hexane/ethyl acetate=2/1) to give the title compound (97 mg).

Reference Examples 123 to 126

The compounds of Reference Examples 123 to 126 were prepared in a similar manner to that described in Reference Example 122 using the corresponding starting materials.

Reference Example 127

The compound of Reference Example 127 was prepared in a similar manner to that described in Reference Example 27 and Reference Example 122 using the corresponding starting materials.

Reference Example 128

5-Benzylthio-2-chloroaniline

To a solution of 2-chloro-5-mercaptoaniline (0.64 g) and benzyl bromide (0.52 mL) in N,N-dimethylformamide (10 mL) was added potassium carbonate (0.61 g), and the mixture was stirred at room temperature for 1 hour. The reaction mixture was poured into water, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: n-hexane–n-hexane/ethyl acetate=7/3) to give the title compound (0.37 g).

Reference Examples 129 to 131

The compounds of Reference Examples 129 to 131 were prepared in a similar manner to that described in Reference Example 128 using the corresponding starting materials.

Reference Example 132

N-(5-Amino-4-chloro-2-methoxyphenyl)-N-(2,3-difluoro-6-methoxybenzyl)acetamide

To a mixture of 4-chloro-2-methoxy-5-nitroaniline (0.3 g) and sodium hydrogen carbonate (0.37 g) in tetrahydrofuran (4.5 mL) was added acetyl chloride (0.12 mL), and the mixture was stirred at room temperature for 5 hours. The reaction mixture was poured into water, and the resulting mixture was extracted with ethyl acetate. The extract was washed with 1 mol/L hydrochloric acid, water and brine successively, and dried over anhydrous magnesium sulfate. The solvent was removed under reduced pressure, and the residue was purified by column chromatography on silica gel (eluent: n-hexane–n-hexane/ethyl acetate=3/7) to give N-(4-chloro-2-methoxy-5-nitrophenyl)acetamide (0.24 g). This material was dissolved in N,N-dimethylformamide (5 mL). To the solution were added 2,3-difluoro-6-methoxybenzyl bromide (0.28 g) and sodium hydride (55%, 48 mg) under ice-cooling, and the mixture was stirred at room temperature for 30 minutes. The reaction mixture was poured into water, and the resulting mixture was extracted with ethyl acetate. The extract was washed with water and brine, and dried over anhydrous magnesium sulfate. The solvent was removed under reduced pressure, and the residue was dissolved in tetrahydrofuran (4 mL). To the solution were added methanol (4 mL) and nickel(II) bromide (11 mg). To the mixture was added sodium borohydride (0.11 g) under ice-cooling, and the mixture was stirred at the same temperature for 30 minutes, and then stirred at room temperature for 30 minutes. To the reaction mixture was added a saturated aqueous sodium hydrogen carbonate solution, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: n-hexane–n-hexane/ethyl acetate=3/7) to give the title compound (0.27 g).

Reference Example 133

The compound of Reference Example 133 was prepared in a similar manner to that described in Reference Example 132 using the corresponding starting materials.

Reference Example 134

5-Fluoro-2-(2,3,4,5-tetrahydro-1H-1-benzoazepin-1-ylsulfonyl)-4-(1,3-dioxo-1,3-dihydroisoindol-2-yl) phenol

To a solution of 5-fluoro-2-(2,3,4,5-tetrahydro-1H-1-benzoazepin-1-yl-sulfonyl)-4-(1,3-dioxo-1,3-dihydroisoindol-2-yl)anisole (0.57 g) in methylene chloride (12 mL) was added boron tribromide (1 mol/L methylene chloride solution, 3.53 mL) under ice-cooling, and the mixture was stirred at room temperature for 3 hours. To the reaction mixture was added 1 mol/L hydrochloric acid, and the resulting mixture was extracted with ethyl acetate. The extract was washed with brine, and dried over anhydrous magnesium sulfate. The solvent was removed under reduced pressure, and the residue was purified by column chromatography on silica gel (eluent: n-hexane–n-hexane/ethyl acetate=1/1) to give the title compound (0.46 g).

Reference Example 135

The compound of Reference Example 135 was prepared in a similar manner to that described in Reference Example 134 using the corresponding starting materials.

Reference Example 136

4-Amino-5-chloro-2-(2,3,4,5-tetrahydro-1H-1-benzoazepin-1-ylsulfonyl)phenol

5-Chloro-2-(2,3,4,5-tetrahydro-1H-1-benzoazepin-1-ylsulfonyl)-4-(1,3-dioxo-1,3-dihydroisoindol-2-yl)phenol (0.49 g) was dissolved in tetrahydrofuran (10 mL). To the solution was added hydrazine monohydrate (0.25 mL), and the mixture was heated at reflux for 2 hours. The reaction mixture was cooled to room temperature, and diluted with ethyl acetate. The insoluble material was removed by filtration, and the filtrate was concentrated under reduced pressure, and the residue was purified by column chromatography on silica gel (eluent: n-hexane–n-hexane/ethyl acetate=1/1) to give the title compound (0.27 g).

Reference Example 137

4-[2-(tert-Butyldimethylsilyloxy)ethoxy]-2-fluoro-5-(2,3,4,5-tetrahydro-1H-1-benzoazepin-1-ylsulfonyl)aniline To a suspension of 5-fluoro-2-(2,3,4,5-tetrahydro-1H-1-benzoazepin-1-yl-sulfonyl)-4-(1,3-dioxo-1,3-dihydroisoindol-2-yl)phenol (0.46 g) and cesium carbonate (0.48 g) in N,N-dimethylformamide (5 mL) was added 1-bromo-2-(tert-butyl-dimethylsilyloxy)ethane (0.25 mL), and the mixture was stirred at room temperature overnight. The reaction mixture was poured into water, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: n-hexane n-hexane/ethyl acetate=1/1) to give 5-fluoro-2-(2,3,4,5-tetrahydro-1H-1-benzoazepin-1-yl-sulfonyl)-4-(1,3-dioxo-1,3-dihydroisoindol-2-yl)-1-[2-(tert-butyldimethylsilyloxy)ethoxy]-benzene (66 mg). This material was dissolved in tetrahydrofuran (3 mL). To the solution was added hydrazine monohydrate (0.026 mL), and the mixture was heated at reflux for 2 hours. The reaction mixture was cooled to room temperature, and diluted with ethyl acetate. The insoluble material was removed by filtration, and the filtrate was concentrated under reduced pressure, and the residue was purified by column chromatography on silica gel (eluent: n-hexane–n-hexane/ethyl acetate=1/1) to give the title compound (52 mg).

Reference Example 138

The compound of Reference Example 138 was prepared in a similar manner to that described in Reference Example 137 using the corresponding starting materials.

Reference Example 139

2-[4-Amino-5-chloro-2-(2,3,4,5-tetrahydro-1H-1-benzoazepin-1-ylsulfonyl)phenoxy]-N-methylacetamide To a suspension of 5-chloro-2-(2,3,4,5-tetrahydro-1H-1-benzoazepin-1-yl-sulfonyl)-4-(1,3-dioxo-1,3-dihydroisoindol-2-yl)phenol (0.26 g) and potassium carbonate (0.11 g) in N,N-dimethylformamide (3 mL) was added ethyl bromoacetate (0.078 mL), and the mixture was stirred at room temperature for 2 hours. The reaction mixture was diluted with ethyl acetate, and the resulting mixture was washed with water and brine, and dried over anhydrous magnesium sulfate. The solvent was removed under reduced pressure, and the residue was purified by column chromatography on silica gel (eluent: n-hexane/ethyl acetate=9/1–1/9) to give ethyl 2-[5-chloro-2-(2,3,4,5-tetrahydro-1H-1-benzoazepin-1-yl-sulfonyl)-4-(1,3-dioxo-1,3-dihydroisoindol-2-yl)phenoxy]acetate (0.29 g). To this material were added tetrahydrofuran (10 mL), methanol (5 mL), water (5 mL) and lithium hydroxide monohydrate (0.21 g), and the mixture was stirred at room temperature for 1 hour. The reaction mixture was poured into 1 mol/L hydrochloric acid, and the resulting mixture was extracted with ethyl acetate. The extract was washed with water and brine, and dried over anhydrous magnesium sulfate. The solvent was removed under reduced pressure, and the residue was dissolved in tetrahydrofuran (5 mL). To the solution was added 1,1'-carbonyldiimidazole (0.16 g), and the mixture was stirred at room temperature for 30 minutes. To the reaction mixture was added methylamine (40% methanol solution, 2.5 mL), and the mixture was stirred at room temperature for 5 hours, and then stirred at 50° C. for 1 hour. The reaction mixture was poured into 2 mol/L hydrochloric acid, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: n-hexane/ethyl acetate=1/1–ethyl acetate) to give the title compound (0.14 g).

Reference Example 140

5-(1-{2-[2-(tert-Butyldimethylsilyloxy)ethoxy]phenyl}-1-methylethylthio)-2-chloroaniline 2-Chloro-5-{1-[2-(2-hydroxyethoxy)phenyl]-1-methylethylthio}aniline was prepared in a similar manner to that described in Reference Example 52 using 2-chloro-5-mercaptoaniline and 2-{2-[2-(tert-butyldimethyl silyloxy)ethoxy]phenyl}-2-propanol instead of 2-chloro-5-mercapto-4-methoxyaniline and 2-(2-methoxyphenyl)-2-propanol, respectively. To the solution of the obtained 2-chloro-5-{1-[2-(2-hydroxyethoxy)-phenyl]-1-methylethylthio}aniline (0.55 g) and imidazole (0.14 g) in N,N-dimethylformamide (3 mL) was added tert-butyldimethylsilyl chloride (0.24 g), and the mixture was stirred at room temperature for 2 hours. To the reaction mixture was added water, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: n-hexane–n-hexane/ethyl acetate=4/1) to give the title compound (0.66 g).

Reference Example 141

3-Amino-4-chloro-N-methyl-N-phenylbenzamide

To a solution of 4-chloro-3-nitrobenzoic acid (1 g) and N,N-dimethylformamide (2 drops) in tetrahydrofuran (5 mL) was added oxalyl chloride (0.64 mL), and the mixture was stirred at room temperature for 30 minutes. The reaction mixture was concentrated under reduced pressure. To a mixture of N-methylaniline (0.58 g) and sodium hydrogen carbonate (0.63 g) in tetrahydrofuran (5 mL) was added the solution of the residue in tetrahydrofuran (5 mL), and the mixture was stirred at room temperature overnight. The reaction mixture was poured into water, and the resulting mixture was extracted with ethyl acetate. The extract was washed with brine, and dried over anhydrous magnesium sulfate. The solvent was removed under reduced pressure, and the residue was purified by column chromatography on silica gel (eluent: n-hexane–n-hexane/ethyl acetate=2/1) to give 4-chloro-3-nitro-N-methyl-N-phenylbenzamide (1.3 g). This material was dissolved in tetrahydrofuran (20 mL). To the solution were added methanol (20 mL) and nickel(II) bromide (54 mg). To the mixture was added sodium borohydride (0.56 g) under ice-cooling, and the mixture was stirred at the same temperature for 30 minutes, and then stirred at room temperature for 30 minutes. The reaction mixture was poured into a saturated aqueous sodium hydrogen carbonate solution, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: n-hexane–n-hexane/ethyl acetate=1/1) to give the title compound (1.15 g).

Reference Example 142

The compound of Reference Example 142 was prepared in a similar manner to that described in Example 1 using the corresponding starting materials.

Reference Example 143

4-Chloro-5-nitrocatechol

To a solution of 4-chloro-2-methoxyphenol (26.6 g) in N,N-dimethylformamide (85 mL) were added potassium carbonate (46.3 g) and methyl iodide (15.6 mL) under ice-cooling, and the mixture was stirred at the same temperature for 1 hour, and then stirred at room temperature overnight. The reaction mixture was poured into water, and the resulting mixture was extracted with diethyl ether. The extract was washed with 1 mol/L aqueous sodium hydroxide solution, water and brine successively, and dried over anhydrous magnesium sulfate. The solvent was removed under reduced pressure, and the residue was dissolved in acetic anhydride (160 mL). To the solution was added 60% nitric acid (13.5 mL) in a dropwise manner at around 15° C., and the mixture was stirred at the same temperature for 30 minutes. To the reaction mixture was added water (0.3 L), and the mixture was stirred under ice-cooling for 30 minutes. The precipitated crystals were collected by filtration. The collected crystals were washed with water, and dried under reduced pressure to give 2-chloro-4,5-dimethoxy-1-nitrobenzene (32.2 g). To this material were added acetic acid (133 mL) and 47% hydrobromic acid (167 mL), and the reaction vessel was equipped with a reflux condenser, and the reaction mixture was stirred at 140° C. for 62 hours. The reaction mixture was cooled to room temperature, and concentrated under reduced pressure. To the residue was added water, and the resulting mixture was extracted with ethyl acetate. The extract was washed with water and brine, and dried over anhydrous sodium sulfate, and the solvent was removed under reduced pressure. To the residue were added toluene (100 mL) and n-hexane (100 mL), and the mixture was stirred at room temperature for 30 minutes. The precipitated crystals were collected by filtration. The collected crystals were washed with n-hexane, and dried under reduced pressure to give the title compound (19.6 g).

Reference Example 144

5-Chloro-2-(2,3-difluoro-6-methoxybenzyloxy)-4-nitrophenol

To a solution of 4-chloro-5-nitrocatechol (10.4 g) in N,N-dimethylformamide (55 mL) was added sodium hydride (55%, 5.04 g) under ice-cooling, and the mixture was stirred at the same temperature for 10 minutes. To the reaction mixture was added N,N-dimethylformamide (11 mL), followed by adding a solution of 2,3-difluoro-6-methoxy-benzyl bromide (14.3 g) in N,N-dimethylformamide (22 mL) under ice-cooling, and the mixture was stirred at the same temperature for 10 minutes, and then stirred at room temperature for 1.5 hours. The reaction mixture was diluted with water. The mixture was poured into 1 mol/L hydrochloric acid, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=7/3–1/1) to give the title compound (18.5 g).

Reference Example 145

The compound of Reference Example 145 was prepared in a similar manner to that described in Reference Example 144 using the corresponding starting materials.

Reference Example 146

4-Chloro-2-methoxy-5-nitrophenol

To a suspension of 4-chloro-2-methoxyphenol (14.0 g) and potassium carbonate (16.6 g) in N,N-dimethylformamide (80 mL) was added benzyl bromide (9.52 mL), and the mixture was stirred at room temperature overnight. The reaction mixture was poured into water, and the resulting mixture was extracted with diethyl ether. The extract was washed with 1 mol/L aqueous sodium hydroxide solution, water and brine, and dried over anhydrous magnesium sulfate. The solvent was removed under reduced pressure, and the residue was dissolved in acetic anhydride (160 mL). To the solution was added 60% nitric acid (8.53 mL) in a dropwise manner at around 16° C., and the mixture was stirred at the same temperature for 30 minutes. The reaction mixture was cooled in ice. To the reaction mixture was added water (160 mL) in a dropwise manner, and the mixture was stirred at the same temperature for 30 minutes. The precipitated crystals were collected by filtration. The collected crystals were washed with water and a mixed solvent (ethanol/n-hexane=1/4), and dried under reduced pressure to give 2-benzyloxy-5-chloro-4-nitroanisole (21.7 g). To this material was added trifluoroacetic acid (100 mL), and the reaction vessel was equipped with a reflux condenser, and the reaction mixture was stirred at 75° C. for 3 hours. The reaction mixture was poured into a mixed solvent (ethyl acetate/water), and the insoluble material was removed by filtration. The organic layer of the filtrate was separated. The organic layer was washed with water and brine, and dried over anhydrous sodium sulfate, and the solvent was removed under reduced pressure. To the residue was added n-hexane (500 mL), and the insoluble material was collected by filtration. The collected material was washed with a mixed solvent (n-hexane/ethyl acetate=5/1), and dried under reduced pressure to give the title compound (7.7 g).

Reference Example 147

2-Bromo-4-chloro-5-nitrophenol

To a solution of 2-bromo-4-chlorophenol (20.7 g) and triethylamine (16.7 mL) ethyl acetate (200 mL) was added ethyl chloroformate (10.5 mL) under ice-cooling, and the mixture was stirred at the same temperature for 1 hour. The reaction mixture was washed with 0.5 mol/L hydrochloric acid, water, a saturated aqueous sodium hydrogen carbonate solution and brine successively, and dried over anhydrous sodium sulfate, and the solvent was removed under reduced pressure. To the residue was added concentrated sulfuric acid (70 mL) under ice-cooling, and the mixture was stirred at the same temperature for 15 minutes. To the mixture was added fuming nitric acid (7 mL) in a dropwise manner under ice-cooling, and the mixture was stirred at the same temperature for 30 minutes. The reaction mixture was allowed to warm to room temperature, and poured into ice, and the resulting mixture was stirred at room temperature for 30 minutes. The precipitated crystals were collected by filtration. The collected crystals were washed with water, and dried under reduced pressure to give 4-bromo-2-chloro-5-ethoxycarbonyloxy-1-nitrobenzene (32.1 g). To this material were added methanol (250 mL) and sodium hydrogen carbonate (24.9 g), and the mixture was stirred at room temperature for 24 hours. To the mixture was added potassium carbonate (6.84 g), and the mixture was stirred at room temperature for 30 minutes. The reaction mixture was poured into water (500 mL). To the mixture was added 1 mol/L hydrochloric acid slowly until the pH became 3 with stirring, and the mixture was extracted with ethyl acetate. The extract was washed with brine, and dried over anhydrous sodium sulfate. The solvent was removed under reduced pressure, and the residue was purified by column chromatography on silica gel (eluent: n-hexane/ethyl acetate=2/1-1/1) to give the title compound (22.6 g).

Reference Example 148

2,3-Difluoro-6-[2-(methoxymethyloxy)ethoxy]benzyl Alcohol

A mixture of 2,3-difluoro-6-hydroxybenzaldehyde (2.17 g), 2-(methoxymethyloxy)-ethyl bromide (1.92 mL), potassium carbonate (2.85 g) and sodium iodide (0.41 g) in N,N-dimethylformamide (20 mL) was stirred at room temperature overnight. The reaction mixture was poured into water, and the resulting mixture was extracted with diethyl ether. The extract was washed with water and brine, and dried over anhydrous sodium sulfate. The solvent was removed under reduced pressure, and the residue was purified by column chromatography on silica gel (eluent: n-hexane/ethyl acetate=4/1-1/1) to give 2,3-difluoro-6-[2-(methoxymethyloxy)ethoxy]benzaldehyde (1.02 g). This material was dissolved in tetrahydrofuran (15 mL). To the solution were added water (1.5 mL) and sodium borohydride (92 mg), and the mixture was stirred at room temperature for 1 hour. The reaction mixture was poured into 10% aqueous sodium chloride solution, and the resulting mixture was extracted with ethyl acetate. The extract was washed with brine, and dried over anhydrous sodium sulfate. The solvent was removed under reduced pressure to give the title compound (1.0 g).

Reference Example 149

The compound of Reference Example 149 was prepared in a similar manner to that described in Reference Example 148 using the corresponding starting materials.

Reference Examples 150 and 151

The compounds of Reference Examples 150 and 151 were prepared in a similar manner to that described in Reference Example 41 using the corresponding starting materials.

Reference Example 152

2-Chloro-5-(2-fluoro-6-methoxybenzyloxy)-4-methoxyaniline

To a solution of 4-chloro-2-methoxy-5-nitrophenol (0.67 g) and 2-fluoro-6-methoxy-benzyl bromide (0.66 g) in N,N-dimethylformamide (3 mL) was added potassium carbonate (0.54 g), and the mixture was stirred at room temperature for 3 days. The reaction mixture was poured into water, and the resulting mixture was stirred at room temperature for 30 minutes. The precipitated crystals were collected by filtration. The collected crystals were washed with water and a mixed solvent (diethyl ether/n-hexane=1/3), and dried under reduced pressure to give 5-chloro-2-(2-fluoro-6-methoxybenzyloxy)-4-nitroanisole (0.97 g). This material was dissolved in tetrahydrofuran (15 mL). To the solution were added methanol (15 mL) and nickel(II) bromide (31 mg). To the mixture was added sodium borohydride (0.32 g) under ice-cooling, and the mixture was stirred at the same temperature for 30 minutes, and then stirred at room temperature for 30 minutes. The reaction mixture was poured into a saturated aqueous sodium hydrogen carbonate solution, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=4/1–3/2) to give the title compound (0.79 g).

Reference Examples 153 to 156

The compounds of Reference Examples 153 to 156 were prepared in a similar manner to that described in Reference Example 152 using the corresponding starting materials.

Reference Example 157

5-{6-[2-(tert-Butoxycarbonylamino)ethoxy]-2,3-difluorobenzyloxy}-2-chloroaniline To a solution of 6-[2-(tert-butoxycarbonylamino)ethoxy]-2,3-difluorobenzyl alcohol (0.54 g), 4-chloro-3-nitrophenol (0.31 g) and triphenylphosphine (0.54 g) in tetrahydrofuran (4 mL) was added diisopropyl azodicarboxylate (40% toluene solution, 1.03 mL), and the mixture was stirred at room temperature overnight. The reaction mixture was poured into a saturated aqueous sodium hydrogen carbonate solution, and the resulting mixture was extracted with ethyl acetate. The extract was washed with water and brine, and dried over anhydrous sodium sulfate. The solvent was removed under reduced pressure, and the residue was dissolved in tetrahydrofuran (6 mL). To the solution were added methanol (6 mL) and nickel(II) bromide (20 mg). To the mixture was added sodium borohydride (0.2 g) under ice-cooling, and the mixture was stirred at the same temperature for 30 minutes, and then stirred at room temperature for 30 minutes. The reaction mixture was poured into a saturated aqueous sodium hydrogen carbonate solution, and the resulting mixture was extracted with ethyl acetate. The extract was washed with brine twice, and dried over anhydrous magnesium sulfate. The solvent was removed under reduced pressure, and the residue was purified by column chromatography on silica gel (eluent: n-hexane/ethyl acetate=3/1–1/1) and column chromatography on amino-propylated silica gel (eluent: n-hexane/ethyl acetate=3/1–2/3) successively to give the title compound (0.75 g).

Reference Example 158

Ethyl 2-[4-amino-5-chloro-2-(2-fluoro-6-methoxybenzyloxy)phenoxy]acetate

To a suspension of 5-chloro-2-(2-fluoro-6-methoxybenzyloxy)-4-nitrophenol (5 g) and potassium carbonate (3.16 g) in N,N-dimethylformamide (15 mL) was added ethyl bromoacetate (2.2 mL), and the mixture was stirred at room temperature for 3 days. The reaction mixture was poured into water, and the resulting mixture was extracted with ethyl acetate. The extract was washed with brine, and dried over anhydrous sodium sulfate. The solvent was removed under reduced pressure, and the residue was dissolved in tetrahydrofuran (75 mL). To the solution were added methanol (75 mL) and nickel(II) bromide (0.17 g). To the mixture was added sodium borohydride (1.73 g) under ice-cooling, and the mixture was stirred at the same temperature for 30 minutes, and then stirred at room temperature for 30 minutes. The reaction mixture was poured into a saturated aqueous sodium hydrogen carbonate solution, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=3/1–2/1) to give the title compound (4.11 g).

Reference Examples 159 to 166

The compounds of Reference Examples 159 to 166 were prepared in a similar manner to that described in Reference Example 158 using the corresponding starting materials.

Reference Example 167

2-Chloro-5-(2,3-difluoro-6-methoxybenzyloxy)-4-methoxymethyloxyaniline

To a solution of 5-chloro-2-(2,3-difluoro-6-methoxybenzyloxy)-4-nitrophenol (0.52 g) and N,N-diisopropylethylamine (0.52 mL) in methylene chloride (5 mL) was added (chloromethyl)methyl ether (0.17 mL) under ice-cooling, and the mixture was stirred at room temperature for 3 days. The reaction mixture was poured into 1 mol/L hydrochloric acid, and the resulting mixture was extracted with ethyl acetate. The extract was washed with water and brine, and dried over anhydrous sodium sulfate. The solvent was removed under reduced pressure, and the residue was dissolved in tetrahydrofuran (7.5 mL). To the solution were added methanol (7.5 mL) and nickel(II) bromide (17 mg). To the mixture was added sodium borohydride (0.17 g) under ice-cooling, and the mixture was stirred at the same temperature for 30 minutes, and then stirred at room temperature for 30 minutes. The reaction mixture was poured into a saturated aqueous sodium hydrogen carbonate solution, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=4/1–1/1) to give the title compound (0.4 g).

Reference Example 168

2-Chloro-4-(2-fluoroethoxy)-5-(2,3-difluoro-6-methoxybenzyloxy)aniline

To a solution of 5-chloro-2-(2,3-difluoro-6-methoxybenzyloxy)-4-nitrophenol (0.35 g), 2-fluoroethanol (71 mg) and triphenylphosphine (0.31 g) in tetrahydrofuran (1.5 mL) was added diisopropyl azodicarboxylate (40% toluene solution, 0.68 mL), and the mixture was stirred at room temperature for 1 hour. The reaction mixture was purified by column chromatography on silica gel (eluent: n-hexane/ethyl acetate=9/1–1/1) to give 2-chloro-4-(2-fluoroethoxy)-5-(2,3-difluoro-6-methoxybenzyloxy)-1-nitrobenzene (0.24 g). This material was dissolved in tetrahydrofuran (5 mL). To the solution were added methanol (3 mL) and nickel(II) bromide (7 mg). To the mixture was added sodium borohydride (70 mg) under ice-cooling, and the mixture was stirred at the same temperature for 30 minutes, and then stirred at room temperature for 30 minutes. The reaction mixture was poured into a saturated aqueous sodium hydrogen carbonate solution, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=3/1–1/1) to give the title compound (0.2 g).

Reference Example 169

The compound of Reference Example 169 was prepared in a similar manner to that described in Reference Example 168 using the corresponding starting materials.

Reference Example 170

2-Chloro-5-(2,3-difluoro-6-methoxybenzyloxy)-4-(2,2-dimethyl-1,3-dioxan-5-yloxy)aniline To a suspension of 5-chloro-2-(2,3-difluoro-6-methoxybenzyloxy)-4-nitrophenol (1.38 g) and potassium carbonate (0.83 g) in acetone (10 mL) was added diethyl 2-bromomalonate (0.89 mL), and the mixture was stirred at room temperature for 3 days. The reaction mixture was poured into 1 mol/L hydrochloric acid, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=4/1–3/2) to give diethyl 2-[5-chloro-2-(2,3-difluoro-6-methoxybenzyloxy)-4-nitro-phenoxy]malonate (1.35 g). This material was dissolved in tetrahydrofuran (53 mL). To the solution was added diisobutylaluminium hydride (1.02 mol/L n-hexane solution, 26.3 mL) at −10° C., and the mixture was stirred under ice-cooling for 3 hours. The reaction mixture was poured into 1 mol/L hydrochloric acid, and the resulting mixture was extracted with ethyl acetate. The insoluble material was removed by filtration, and the filtrate was washed with water and brine, and dried over anhydrous sodium sulfate. The solvent was removed under reduced pressure, and the residue was purified by column chromatography on silica gel (eluent: n-hexane/ethyl acetate=1/1–1/9) to give 2-chloro-5-(2,3-difluoro-6-methoxy-benzyloxy)-4-(1,3-dihydroxy-2-propoxy)-1-nitrobenzene (0.47 g). To this material were added 2,2-dimethoxypropane (10 mL), p-toluenesulfonic acid monohydrate (43 mg) and molecular sieves 4A, and the mixture was heated at reflux for 1 hour. The insoluble material was removed by filtration, and the filtrate was concentrated under reduced pressure. The residue was purified by column chromatography on silica gel (eluent: n-hexane/ethyl acetate=7/1–3/2) to give 2-chloro-5-(2,3-difluoro-6-methoxybenzyloxy)-4-(2,2-dimethyl-1,3-dioxan-5-yloxy)-1-nitrobenzene (0.37 g). This material was dissolved in tetrahydrofuran (4 mL). To the solution were added methanol (4 mL) and nickel(II) bromide (9 mg). To the mixture was added sodium borohydride (91 mg) under ice-cooling, and the mixture was stirred at the same temperature for 30 minutes, and then stirred at room temperature for 30 minutes. The reaction mixture was poured into a saturated aqueous sodium hydrogen carbonate solution, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=4/1–1/1) to give the title compound (0.24 g).

Reference Example 171

4-Bromo-2-chloro-difluoro-6-methoxybenzyloxy)-1-nitrobenzene

To a solution of 2-bromo-4-chloro-5-nitrophenol (22.6 g) and 2,3-difluoro-6-methoxybenzyl bromide (20.1 g) in N,N-dimethylformamide (85 mL) was added potassium carbonate (17.6 g), and the mixture was stirred at room temperature overnight. To the reaction mixture was added water (400 mL), and the resulting mixture was stirred at room temperature for 30 minutes. The precipitated crystals were collected by filtration. The collected crystals were washed with water, and dried under reduced pressure. The crystals were suspended in a mixed solvent (n-hexane/ethyl acetate=20/1), and collected by filtration. The collected crystals were dried under reduced pressure to give the title compound (29.7 g).

Reference Example 172

2-Chloro-5-(2,3-difluoro-6-methoxybenzyloxy)-4-(2,2-dimethyl-1,3-dioxolan-4-ylmethyl)-aniline To a solution of 4-bromo-2-chloro-5-(2,3-difluoro-6-methoxybenzyloxy)-1-nitrobenzene (0.82 g) in 1,4-dioxane (40 mL) were added allyltri(n-butyl)tin (0.74 mL) and tetrakis(triphenylphosphine)palladium(0) (0.46 g), and the reaction vessel was equipped with a reflux condenser, and the reaction mixture was stirred at 120° C. under an argon atmosphere overnight. The reaction mixture was cooled to room temperature, and concentrated under reduced pressure. The residue was purified by column chromatography on silica gel (eluent: n-hexane/ethyl acetate=9/1–3/1) to give 4-allyl-2-chloro-5-(2,3-difluoro-6-methoxybenzyl-oxy)-1-nitrobenzene (0.68 g). This material was dissolved in tetrahydrofuran (20 mL). To the solution were added water (10 mL), 50% aqueous N-methylmorpholine-N-oxide solution (0.96 mL) and osmium(VIII) oxide, microencapsulated (about 10%, 0.23 g), and the mixture was stirred at room temperature for 4 days. The reaction mixture was poured into water, and the resulting mixture was extracted with ethyl acetate. The extract was washed with brine, and dried over anhydrous sodium sulfate. The solvent was removed under reduced pressure, and the residue was purified by column chromatography on silica gel (eluent: n-hexane/ethyl acetate=2/1–1/4) to give 2-chloro-5-(2,3-difluoro-6-methoxybenzyloxy)-4-(2,3-dihydroxy-propyl)-1-nitrobenzene (0.29 g). The title compound was prepared in a similar manner to that described in Reference Example 170 using this material instead of 2-chloro-5-(2,3-difluoro-6-methoxybenzyloxy)-4-(1,3-dihydroxy-2-propoxy)-1-nitrobenzene.

Reference Example 173

Ethyl 3-[4-amino-5-chloro-2-(2,3-difluoro-6-methoxybenzyloxy)phenyl]propionate

A mixture of 4-bromo-2-chloro-5-(2,3-difluoro-6-methoxybenzyloxy)-1-nitrobenzene (3.06 g), ethyl acrylate (1.64 mL), palladium(II) acetate (84 mg), tris(2-methylphenyl)phosphine (0.23 g) and triethylamine (5.2 mL) in acetonitrile (30 mL) was heated at reflux overnight. The reaction mixture was cooled to room temperature, and poured into 1 mol/L hydrochloric acid, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=4/1–2/1) to give ethyl 5-chloro-2-(2,3-difluoro-6-methoxybenzyloxy)-4-nitrocinnamate (2.46 g). This material was dissolved in tetrahydrofuran (30 mL). To the solution were added methanol (30 mL) and nickel(II) bromide (63 mg). To the mixture was added sodium borohydride (0.65 g) under ice-cooling, and the mixture was stirred at the same temperature for 30 minutes, and then stirred at room temperature for 30 minutes. The reaction mixture was poured into a saturated aqueous sodium hydrogen carbonate solution, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=4/1–1/1) to give the title compound (0.69 g).

Reference Example 174

2-Chloro-5-(2,3-difluoro-6-methoxybenzyloxy)-4-(2-hydroxyethyl)aniline

To a solution of 4-bromo-2-chloro-5-(2,3-difluoro-6-methoxybenzyloxy)-1-nitrobenzene (3.06 g) in toluene (120 mL) were added vinyltri(n-butyl)tin (2.4 mL) and tetrakis(triphenylphosphine)palladium(0) (0.87 g), and the reaction mixture was heated at reflux under an argon atmosphere overnight. The reaction mixture was cooled to room temperature, and concentrated under reduced pressure. To the residue were added tetrahydrofuran (30 mL), water (30 mL) and 0.5 mol/L aqueous potassium fluoride solution (30 mL), and the mixture was stirred at room temperature for 1 hour. The insoluble material was removed by filtration, and then the insoluble material was washed with ethyl acetate. The filtrate and washing were combined, and the organic layer was separated. The organic layer was washed with brine, and dried over anhydrous sodium sulfate. The solvent was removed under reduced pressure, and the residual crystals were suspended in a mixed solvent (n-hexane/ethyl acetate=5/1), and collected by filtration. The collected crystals were dried under reduced pressure to give 2-chloro-5-(2,3-difluoro-6-methoxybenzyloxy)-1-nitro-4-vinylbenzene (2.32 g). This material was dissolved in tetrahydrofuran (65 mL). To the solution was added borane-tetrahydrofuran complex (1.2 mol/L tetrahydrofuran solution, 9 mL) in a dropwise manner under ice-cooling, and the mixture was stirred at the same temperature for 30 minutes, and then stirred at room temperature overnight. To the reaction mixture were added 1 mol/L aqueous sodium hydroxide solution (30 mL) and 30% aqueous hydrogen peroxide solution (30 mL) under ice-cooling, and the mixture was stirred at the same temperature for 30 minutes. The reaction mixture was stirred at room temperature for 1 hour, and then stirred at 90° C. for 1 hour. The reaction mixture was poured into water, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=4/1–1/1) to give the title compound (0.38 g).

Reference Example 175

Ethyl 4-[4-amino-5-chloro-2-(2,3-difluoro-6-methoxybenzyloxy)phenyl]butyrate

To a suspension of 4-bromo-2-chloro-5-(2,3-difluoro-6-methoxybenzyloxy)-1-nitrobenzene (2.04 g) in tetrahydrofuran (10 mL) were added 4-ethoxy-4-oxobutylzinc bromide (0.5 mol/L tetrahydrofuran solution, 12 mL) and tetrakis(triphenylphosphine)palladium(0) (0.2 g), and the mixture was stirred at room temperature under an argon atmosphere overnight. The reaction mixture was poured into 1 mol/L hydrochloric acid, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=4/1–3/2) to give ethyl 4-[5-chloro-2-(2,3-difluoro-6-methoxybenzyloxy)-4-nitro-phenyl]butyrate (0.72 g). This material was dissolved in tetrahydrofuran (5 mL). To the solution were added methanol (5 mL) and nickel (II) bromide (11 mg). To the mixture was added sodium borohydride (0.12 g) under ice-cooling, and the mixture was stirred at the same temperature for 30 minutes, and then stirred at room temperature for 30 minutes. The reaction mixture was poured into a saturated aqueous sodium hydrogen carbonate solution, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=4/1–3/2) to give the title compound (0.41 g).

Reference Example 176

4-(tert-Butyldimethylsilyloxy)methyl-2-chloro-difluoro-6-methoxybenzyloxy)aniline To a solution of 4-chloro-2-hydroxymethylphenol (1.01 g) and triethylamine (2.67 mL) in tetrahydrofuran (13 mL) was added triphosgene (0.95 g) under ice-cooling, and the mixture was stirred at the same temperature for 30 minutes, and then stirred at room temperature for 30 minutes. To the reaction mixture was added 1 mol/L hydrochloric acid, and the resulting mixture was extracted with ethyl acetate. The extract was washed with water and brine, and dried over anhydrous sodium sulfate. The solvent was removed under reduced pressure. To the residue was added concentrated sulfuric acid (9.7 mL) under ice-cooling, and the mixture was stirred at the same temperature for 15 minutes. To the mixture was added fuming nitric acid (0.44 mL) in a dropwise manner under ice-cooling, and the mixture was stirred at the same temperature for 30 minutes. The reaction mixture was allowed to warm to room temperature, and poured into ice, and the resulting mixture was stirred at room temperature for 30 minutes. The mixture was extracted with ethyl acetate. The extract was washed with water twice and brine twice, and dried over anhydrous sodium sulfate. The solvent was removed under reduced pressure, and the residue was purified by column chromatography on silica gel (eluent: n-hexane/ethyl acetate=2/1–1/2) to give 4-chloro-2-hydroxymethyl-5-nitrophenol (0.34 g). This material was dissolved in N,N-dimethylformamide (5 mL). To the solution were added potassium carbonate (0.51 g) and 2,3-difluoro-6-methoxybenzyl bromide (0.44 g), and the mixture was stirred at room temperature overnight. To the reaction mixture were added water and 1 mol/L hydrochloric acid, and the resulting mixture was extracted with ethyl acetate. The extract was washed with water and brine, and dried over anhydrous sodium sulfate, and the solvent was removed under reduced pressure. The residual crystals were suspended in a mixed solvent (n-hexane/ethyl acetate=4/1), and collected by filtration. The collected crystals were dried under reduced pressure to give 5-chloro-2-(2,3-difluoro-6-methoxybenzyloxy)-4-nitrobenzyl alcohol (0.24 g). This material was dissolved in N,N-dimethylformamide (4 mL). To the solution was added imidazole (89 mg), followed by adding a solution of tert-butyldimethylchlorosilane (0.15 g) in N,N-dimethylformamide (2 mL), and the mixture was stirred at room temperature overnight. The reaction mixture was poured into water, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=7/1–2/1) to give 4-(tert-butyldimethylsilyloxy)-methyl-2-chloro-5-(2,3-difluoro-6-methoxybenzyloxy)-1-nitrobenzene (0.25 g). This material was dissolved in tetrahydrofuran (2.5 mL). To the solution were added methanol (2.5 mL) and nickel(II) bromide (6 mg). To the mixture was added sodium borohydride (60 mg) under ice-cooling, and the mixture was stirred at the same temperature for 30 minutes, and then stirred at room temperature for 30 minutes. The reaction mixture was poured into a saturated aqueous sodium hydrogen carbonate solution, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=4/1–2/1) to give the title compound (0.19 g).

Reference Example 177

4,6-Dihydroxy-2-methyl-5-nitropyrimidine

To fuming nitric acid (50 mL) was added 4,6-dihydroxy-2-methylpyrimidine (25 g) slowly under ice-cooling, and the mixture was stirred at the same temperature for 15 minutes. To the reaction mixture was added ice water (500 mL), and the resulting mixture was stirred at room temperature until the ice melted. The precipitated crystals were collected by filtration. The collected crystals were washed with water, and dried under reduced pressure to give the title compound (26.6 g).

Reference Example 178

4,6-Dichloro-2-methyl-5-nitropyrimidine

To 4,6-dihydroxy-2-methyl-5-nitropyrimidine were added phosphoryl chloride (160 mL) and N,N-diethylaniline (49.4 mL), and the reaction vessel was equipped with a reflux condenser, and the mixture was stirred at 110° C. for 1.5 hours. The reaction mixture was cooled to room temperature, and poured into ice, and the resulting mixture was stirred at room temperature until the ice melted. To the mixture was added diethyl ether, and the mixture was stirred at the same temperature for 10 minutes. The insoluble material was removed by filtration, and the organic layer of the filtrate was separated. The organic layer was washed with water and brine, and dried over anhydrous magnesium sulfate. The solvent was removed under reduced pressure, and the residue was purified by column chromatography on silica gel (eluent: n-hexane/ethyl acetate=20/1–9/1) to give the title compound (24.7 g).

Reference Example 179

4-Chloro-6-methoxy-2-methyl-5-nitropyrimidine

To a solution of 4,6-dichloro-2-methyl-5-nitropyrimidine (6.54 g) in methanol (31.5 mL) was added sodium methoxide (28% methanol solution, 6.05 mL) in a dropwise manner under ice-cooling, and the mixture was stirred at the same temperature for 1 hour, and then stirred at room temperature for 1.5 days. The reaction mixture was poured into water, and the resulting mixture was extracted with diethyl ether. The extract was washed with water and brine, and dried over anhydrous magnesium sulfate. The solvent was removed under reduced pressure, and the residue was purified by column chromatography on silica gel (eluent: n-hexane–n-hexane/ethyl acetate=9/1) to give the title compound (5.7 g).

Reference Example 180

The compound of Reference Example 180 was prepared in a similar manner to that described in Reference Example 179 using the corresponding starting materials.

Reference Example 181

4-Acetyl-6-chloro-2-methyl-5-nitropyrimidine

A mixture of 4,6-dichloro-2-methyl-5-nitropyrimidine (3.12 g), tributyl(1-ethoxy-vinyl)tin (5.3 mL) and dichlorobis(triphenylphosphine)palladium(II) (0.53 g) in tetrahydrofuran (60 mL) was stirred at 85° C. under an argon atmosphere in a reaction vessel equipped with a reflux condenser for 4 hours. The reaction mixture was cooled to room temperature. To the mixture was added 0.5 mol/L aqueous potassium fluoride solution (20 mL), and the resulting mixture was stirred at room temperature for 1 hour. The insoluble material was removed by filtration, and the insoluble material was washed with ethyl acetate. The filtrate and washing were combined, and the organic layer was separated. The organic layer was washed with water and brine, and dried over anhydrous sodium sulfate. The solvent was removed under reduced pressure, and the residue was purified by column chromatography on silica gel (eluent: n-hexane/ethyl acetate=20/1–4/1). The product was dissolved in ethyl acetate. To the solution were added 0.5 mol/L aqueous potassium fluoride solution (20 mL) and water (20 mL), and the mixture was stirred at room temperature for 30 minutes. The insoluble material was removed by filtration, and the filtrate was extracted with ethyl acetate. The extract was washed with brine, and dried over anhydrous sodium sulfate, and the solvent was removed under reduced pressure to give 4-chloro-6-(1-ethoxyvinyl)-2-methyl-5-nitropyrimidine (3.65 g). This material was dissolved in acetone (30 mL). To the solution was added p-toluenesulfonic acid monohydrate (2.28 g), and the mixture was heated at reflux for 4 hours. The reaction mixture was cooled to room temperature, and concentrated under reduced pressure. The residue was purified by column chromatography on silica gel (eluent: n-hexane/ethyl acetate=20/1–4/1) to give the title compound (2.32 g).

Reference Example 182

2-Fluoromethyl-4,6-dihydroxy-5-nitropyrimidine

A solution of fluoroacetonitrile (11 g) in ethanol (10.9 mL)-diethyl ether (186 mL) was bubbled with hydrogen chloride under ice-cooling until the solution was saturated with hydrogen chloride with stirring, and the mixture was stirred at the same temperature for 4 hours. The precipitated crystals were collected by filtration. The collected crystals were washed with diethyl ether, and dried under reduced pressure to give ethyl 2-fluoroacetimidate hydrochloride (24.9 g). This material was suspended in ethanol (50 mL). To the suspension was added ethanol (130 mL) containing ammonia (about 5 g), and the mixture was stirred at room temperature overnight. The crystals were collected by filtration. The collected crystals were washed with diethyl ether, and dried under reduced pressure to give 2-fluoroacetamidine hydrochloride (16.3 g). To a mixture of sodium methoxide (28% methanol solution, 83.6 mL) and methanol (145 mL) was added 2-fluoroacetamidine hydrochloride (16.3 g), followed by adding diethyl malonate (22.0 mL), and the mixture was heated at reflux for 11 hours. The reaction mixture was concentrated under reduced pressure. To the residue was added water (145 mL). The mixture was acidified by adding concentrated hydrochloric acid (18 mL), and the mixture was stirred at room temperature for 30 minutes. The precipitated crystals were collected by filtration. The collected crystals were washed with water and diethyl ether, and dried under reduced pressure to give 2-fluoromethyl-4,6-dihydroxypyrimidine (20.1 g). To a mixture of fuming nitric acid (36 mL) and acetic acid (18 mL) was added 2-fluoromethyl-4,6-dihydroxypyrimidine (20.1 g) slowly under ice-cooling, and the mixture was stirred at room temperature for 30 minutes. The reaction mixture was cooled in ice. To the mixture was added cold water, and the mixture was stirred at room temperature for 1 hour. The precipitated crystals were collected by filtration. The collected crystals were washed with water and diethyl ether, and dried under reduced pressure to give the title compound (16.8 g).

Reference Example 183

The compound of Reference Example 183 was prepared in a similar manner to that described in Reference Example 182 using the corresponding starting materials.

Reference Example 184

The compound of Reference Example 184 was prepared in a similar manner to that described in Reference. Example 182 using O-methylisourea hemisulfate instead of 2-fluoroacetamidine hydrochloride.

Reference Example 185

2-Difluoromethyl-4,6-dihydroxy-5-nitropyrimidine

A mixture of malonamide (5.1 g) and sodium ethoxide (20% ethanol solution, 34.3 g) in methanol (125 mL) was stirred at room temperature for 1 hour. To the mixture was added ethyl 2,2-difluoroacetate (6.31 mL), and the mixture was heated at reflux for 10 hours, and then stirred at room temperature overnight. To the mixture was added 1 mol/L hydrochloric acid until the pH became 3. The mixture was poured into a saturated aqueous ammonium chloride solution, and the resulting mixture was extracted with ethyl acetate thrice. The extracts were washed with brine, and dried over anhydrous sodium sulfate, and the solvent was removed under reduced pressure. The residual solids were suspended in a mixed solvent (n-hexane/ethyl acetate=2/1), and collected by filtration. The collected solids were dried under reduced pressure to give 2-difluoromethyl-4,6-dihydroxypyrimidine (2.36 g). The title compound was prepared in a similar manner to that described in Reference Example 177 using this material instead of 4,6-dihydroxy-2-methylpyrimidine.

Reference Example 186

2-Acetyloxymethyl-4,6-dihydroxy-5-nitropyrimidine

A mixture of 52% aqueous hydroxyacetonitrile solution (50 g) in ethanol (26.6 mL)-diethyl ether (460 mL) was bubbled with hydrogen chloride under ice-cooling until the mixture was saturated with hydrogen chloride with stirring, and the mixture was stirred at the same temperature for 4 hours. The supernatant solution was removed by decantation, and the crystals were suspended in 2-propanol, and collected by filtration. The collected crystals were washed with diethyl ether, and dried under reduced pressure to give ethyl 2-hydroxyacetimidate hydrochloride (29.2 g). This material was suspended in ethanol (50 mL). To the suspension was added ethanol (210 mL) containing ammonia (about 15 g), and the mixture was stirred at room temperature overnight. The reaction mixture was concentrated under reduced pressure, and the residual crystals were suspended in diethyl ether, and collected by filtration. The crystals were washed with diethyl ether, and dried under reduced pressure to give 2-hydroxyacetamidine hydrochloride (22.7 g). To a mixture of sodium ethoxide (20% ethanol solution, 209.8 g) and ethanol (100 mL) was added 2-hydroxyacetamidine hydrochloride (22.7 g), followed by adding diethyl malonate (31.2 mL), and the mixture was heated at reflux for 7 hours. The reaction mixture was concentrated under reduced pressure. To the residue was added water (150 mL). The mixture was acidified by adding concentrated hydrochloric acid (40 mL), and the mixture was stirred at room temperature for 30 minutes. The precipitated crystals were collected by filtration. The collected crystals were washed with water, ethanol and diethyl ether successively, and dried under reduced pressure to give 2-hydroxymethyl-4,6-dihydroxy-pyrimidine (19 g). To a mixture of fuming nitric acid (35 mL) and acetic acid (17.5 mL) was added 2-hydroxymethyl-4,6-dihydroxypyrimidine (19 g) slowly at 10-15° C. of internal temperature, and the mixture was stirred at room temperature for 30 minutes. The reaction mixture was cooled in ice. To the mixture was added cold water, and stirred at room temperature for 30 minutes, and the precipitated crystals were collected by filtration. The collected crystals were washed with water, ethanol and diethyl ether successively, and dried under reduced pressure to give 2-hydroxymethyl-4,6-dihydroxy-5-nitropyrimidine (23.3 g). The suspension of the obtained 2-hydroxymethyl-4,6-dihydroxy-5-nitropyrimidine (10.3 g) in acetic acid (66 mL)-acetic anhydride (66 mL) was stirred at 105° C. for 3 hours. The reaction mixture was cooled to room temperature, and concentrated under reduced pressure. The residual solids were suspended in water, and collected by filtration. The collected solids were washed with water and diethyl ether, and dried under reduced pressure to give the title compound (7.35 g).

Reference Examples 187 and 188

The compounds of Reference Examples 187 and 188 were prepared in a similar manner to that described in Reference Example 186 using the corresponding starting materials.

Reference Examples 189 to 195

The compounds of Reference Examples 189 to 195 were prepared in a similar manner to that described in Reference Example 178 and Reference Example 179 using the corresponding starting materials. When a similar manner to that described in Reference Example 179 was operated, tetrahydrofuran was added as solvent, as occasion demands.

Reference Example 196

Ethyl 4-hydroxy-6-methylpyrimidine-5-carboxylate

A mixture of diethyl malonate (4.8 mL), triethyl orthoacetate (17 mL), acetic anhydride (0.11 mL) and zinc chloride (1.2 g) was stirred at 140° C. To the mixture was added acetic anhydride (0.11 mL) each after 30, 90 and 120 minutes, and then stirred at the same temperature overnight. The reaction mixture was cooled to room temperature, and the insoluble material was removed by filtration. The filtrate was concentrated under reduced pressure, and the residue was purified by column chromatography on silica gel (eluent: n-hexane/ethyl acetate=4/1–7/3) to give diethyl 2-(1-ethoxyethylidene)malonate (5.02 g). To a solution of diethyl 2-(1-ethoxyethylidene)malonate (4.13 g) in ethanol (15 mL) were added formamidine hydrochloride (1.73 g) and a solution of potassium hydroxide (2.21 g) in water (7.5 mL), and the mixture was stirred at room temperature for 2 days. The reaction mixture was neutralized by adding acetic acid. To the mixture was added ethyl acetate (30 mL), and the mixture was stirred at room temperature for 30 minutes. The insoluble material was removed by filtration, and the filtrate was concentrated under reduced pressure. The residue was purified by column chromatography on silica gel (eluent: ethyl acetate–ethyl acetate/methanol=9/1) to give the title compound (1.5 g).

Reference Example 197

Methyl 2,4-dihydroxy-6-methylpyrimidine-5-carboxylate

To a suspension of methyl 3-aminocrotonate (2.0 g) in diethyl ether (15 mL) was added a solution of ethoxycarbonylisocyanate (2 g) in diethyl ether (5 mL) in a dropwise manner under ice-cooling, and the mixture was stirred at the same temperature for 4 hours. The insoluble material was collected by filtration, and the collected material was washed with diethyl ether, and dried under reduced pressure. To this material was added 25% aqueous triethylamine solution (20 mL), and the mixture was stirred at 50° C. overnight, and then stirred at 60° C. for 4 hours. The reaction mixture was concentrated under reduced pressure. The residual crystals were suspended in methylene chloride, and collected by filtration. The collected crystals were washed with methylene chloride, and dried under reduced pressure to give the title compound (1.59 g).

Reference Example 198

2,4-Dihydroxy-6-methoxy-5-nitropyrimidine

To a suspension of barbituric acid (51.2 g) in methanol (1 L) was added concentrated sulfuric acid (80 mL) in a dropwise manner over 20 minutes, and the mixture was stirred at room temperature for 22 hours. The crystals were collected by filtration. The collected crystals were washed with methanol, cold water and diethyl ether successively, and dried under reduced pressure to give 2,4-dihydroxy-6-methoxypyrimidine (52.9 g). To a mixture of fuming nitric acid (20 mL) and concentrated sulfuric acid (10 mL) was added 2,4-dihydroxy-6-methoxypyrimidine (14.2 g) slowly at around 15° C., and the mixture was stirred at room temperature for 1 hour. To the reaction mixture was added ice water (150 mL), and the mixture was stirred at room temperature for 30 minutes. The crystals were collected by filtration. The collected crystals were washed with water, and dried under reduced pressure to give the title compound (7.4 g).

Reference Examples 199 to 201

The compounds of Reference Examples 199 to 201 were prepared in a similar manner to that described in Reference Example 178 using the corresponding starting materials.

Reference Examples 202 and 203

The compounds of Reference Examples 202 and 203 were prepared in a similar manner to that described in Reference Example 178 and Reference Example 181 using the corresponding starting materials.

Reference Examples 204 to 206

The compounds of Reference Examples 204 to 206 were prepared in a similar manner to that described in Reference Example 158 using the corresponding starting materials.

Reference Example 207

The compound of Reference Example 207 was prepared in a similar manner to that described in Reference Example 182 using the corresponding starting materials.

Reference Example 208

The compound of Reference Example 208 was prepared in a similar manner to that described in Reference Example 178 and Reference Example 179 using the corresponding starting materials.

Reference Example 209

The compound of Reference Example 209 was prepared in a similar manner to that described in Reference Example 158 using the corresponding starting materials.

Reference Example 210

3-(tert-Butoxycarbonylamino)-6-(tert-butyldimethylsilyloxy)methyl-2-iodo-4-methylpyridine To a solution of ethyl 5-(tert-butoxycarbonylamino)-6-iodo-4-methylpyridine-2-carboxylate (1.94 g) in toluene (48 mL) was added diisobutylaluminium hydride (0.99 mol/L toluene solution, 25 mL) at −78° C., and the mixture was stirred under ice-cooling for 2 hours, and then stirred at room temperature overnight. The reaction mixture was poured into 1 mol/L hydrochloric acid, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: n-hexane/ethyl acetate=9/1–1/9) to give 3-(tert-butoxycarbonylamino)-6-hydroxymethyl-2-iodo-4-methylpyridine (1 g). This material was dissolved in N,N-dimethylformamide (5 mL). To the solution were added imidazole (0.24 g) and tert-butyldimethylchlorosilane (0.46 g), and the mixture was stirred at room temperature for 2 hours. The reaction mixture was poured into water, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: n-hexane–n-hexane/ethyl acetate=7/3) to give the title compound (1.3 g).

Reference Example 211

The compound of Reference Example 211 was prepared in a similar manner to that described in Example 40 using the corresponding starting materials.

Example 1

3-[2-Chloro-5-(2,3-difluoro-6-methoxybenzyloxy)-4-methoxyphenyl]-dihydro-2H-imidazo[4,5-b]pyridin-2-one To a mixture of 2-chloronicotinic acid (0.47 g) and 2-chloro-5-(2,3-difluoro-6-methoxybenzyloxy)-4-methoxyaniline (0.99 g) in tetrahydrofuran (5 mL) was added lithium hexamethyldisilazide (1.05 mol/L n-hexane solution, 8.57 mL) at −78° C., and the mixture was stirred at the same temperature for 10 minutes. To the reaction mixture was added tetrahydrofuran (4 mL), and the mixture was allowed to warm slowly to room temperature, and the mixture was stirred at room temperature overnight. To the reaction mixture was added 1 mol/L hydrochloric acid, and the resulting mixture was extracted with ethyl acetate twice. The extracts were washed with water and brine, and dried over anhydrous magnesium sulfate, and the solvent was removed under reduced pressure. To the mixture of the residue and triethylamine (1.25 mL) in 1,4-dioxane (10 mL) was added diphenylphosphoryl azide (0.71 mL), and the mixture was stirred at room temperature for 1 hour, and then heated at reflux for 2 hours. The reaction mixture was concentrated under reduced pressure, and the residue was purified by column chromatography on silica gel (eluent: n-hexane/ethyl acetate=3/2–1/4) to give the title compound (0.94 g).

Example 2

The compound of Example 2 was prepared in a similar manner to that described in Example 1 using the corresponding starting materials.

Example 3

3-[2-Chloro-5-(2,3-difluoro-6-methoxybenzyloxy)-4-methoxyphenyl]-1-(2-hydroxyethyl)-1-dihydro-2H-imidazo[4,5-b]pyri din-2-one To a solution of 3-[2-chloro-5-(2,3-difluoro-6-methoxybenzyloxy)-4-methoxyphenyl]-1,3-dihydro-2H-imidazo[4,5-b]pyridin-2-one (33 mg) in N,N-dimethylformamide (1 mL) was added sodium hydride (55%, 10 mg), and the mixture was stirred at room temperature for 10 minutes. To the reaction mixture were added 2-bromoethyl acetate (0.04 mL) and a catalytic amount of sodium iodide, and the mixture was stirred at room temperature for 1 hour. The reaction mixture was poured into 1 mol/L hydrochloric acid, and the resulting mixture was extracted with ethyl acetate. The extract was washed with brine, and dried over anhydrous sodium sulfate. The solvent was removed under reduced pressure, and the residue was dissolved in tetrahydrofuran (3 mL)-methanol (2 mL). To the solution was added sodium methoxide (28% methanol solution, 0.02 mL), and the mixture was stirred at room temperature for 1 hour. The reaction mixture was poured into 1 mol/L hydrochloric acid, and the resulting mixture was extracted with ethyl acetate. The extract was washed with brine, and dried over anhydrous sodium sulfate, and the solvent was removed under reduced pressure. The residual solids were suspended in diethyl ether, and collected by filtration. The collected solids were washed with diethyl ether, and dried under reduced pressure to give the title compound (21 mg).

Example 4

5-Chloro-3-[2-fluoro-5-(2,3-difluoro-6-methoxybenzyloxy)-4-methoxyphenyl]-1,3-dihydro-2H-imidazo[4,5-b]pyridin-2-one To a mixture of 2,6-dichloronicotinic acid (0.58 g) and 2-fluoro-5-(2,3-difluoro-6-methoxybenzyloxy)-4-methoxyaniline hydrochloride (0.7 g) in 1-methyl-2-pyrrolidone (4 mL) was added sodium hydride (55%, 0.35 g), and the mixture was stirred at 120° C. overnight. The reaction mixture was poured into 1 mol/L hydrochloric acid, and the resulting mixture was extracted with ethyl acetate. The extract was washed with water and brine, and dried over anhydrous sodium sulfate, and the solvent was removed under reduced pressure. The residual solids were suspended in a mixed solvent (n-hexane/ethyl acetate=2/1), and collected by filtration. The collected solids were washed with the same solvent, and dried under reduced pressure. To the obtained solids were added 1,4-dioxane (5 mL), triethylamine (0.31 mL) and diphenylphosphoryl azide (0.24 mL), and the mixture was stirred at room temperature for 1 hour, and then heated at reflux for 4 hours. The reaction mixture was concentrated under reduced pressure, and the residue was purified by column chromatography on silica gel (eluent: n-hexane/ethyl acetate=1/1–1/3) to give the title compound (0.16 g).

Examples 5 and 6

The compounds of Examples 5 and 6 were prepared in a similar manner to that described in Example 4 using the corresponding starting materials.

Example 7

5-(n-Butoxycarbonyl)-3-[2-fluoro-5-(2,3-difluoro-6-methoxybenzyloxy)-4-methoxyphenyl]-1,3-dihydro-2H-imidazo[4,5-b]pyridin-2-one A mixture of 5-chloro-3-[2-fluoro-5-(2,3-difluoro-6-methoxybenzyloxy)-4-methoxyphenyl]-1,3-dihydro-2H-imidazo[4,5-b]pyridin-2-one (0.14 g), palladium(II) acetate (7 mg), 1,3-bis(diphenylphosphino)propane (12 mg), triethylamine (0.13 mL) and n-butanol (2 mL) in dimethyl sulfoxide (3 mL) was stirred at 130° C. under a carbon monoxide atmosphere in a reaction vessel equipped with a reflux condenser overnight. The reaction mixture was diluted with ethyl acetate, and the resulting mixture was washed with 1 mol/L hydrochloric acid, water and brine successively, and dried over anhydrous sodium sulfate. The solvent was removed under reduced pressure, and the residue was purified by column chromatography on silica gel (eluent: n-hexane/ethyl acetate=1/1–1/2) to give the title compound (0.13 g).

Example 8

5-Carboxy-3-[2-fluoro-5-(2,3-difluoro-6-methoxybenzyloxy)-4-methoxyphenyl]-1,3-dihydro-2H-imidazo[4,5-b]pyridin-2-one To a mixture of 5-(n-butoxycarbonyl)-3-[2-fluoro-5-(2,3-difluoro-6-methoxy-benzyloxy)-4-methoxyphenyl]-1,3-dihydro-2H-imidazo[4,5-b]pyridin-2-one (0.11 g), tetrahydrofuran (2 mL), methanol (1 mL) and water (1 mL) was added lithium hydroxide monohydrate (43 mg), and the mixture was stirred at room temperature for 30 minutes. The reaction mixture was acidified by adding 1 mol/L hydrochloric acid, and the resulting mixture was extracted with ethyl acetate. The extract was washed with 10% aqueous sodium chloride solution and brine, and dried over anhydrous magnesium sulfate. The solvent was removed under reduced pressure, and the residue was purified by column chromatography on silica gel (eluent: n-hexane/ethyl acetate=1/2–ethyl acetate) to give the title compound (23 mg).

Example 9

5-Chloro-3-[2-chloro-5-(2,3-difluoro-6-methoxybenzyloxy)-4-methoxyphenyl]-1,3-dihydro-2H-imidazo[4,5-b]pyridin-2-one A mixture of 2,6-dichloro-3-nitropyridine (0.97 g), 2-chloro-5-(2,3-difluoro-6-methoxybenzyloxy)-4-methoxyaniline (1.81 g) and N,N-diisopropylethylamine (0.87 mL) in acetonitrile (15 mL) was heated at reflux for 12 hours. The reaction mixture was poured into 1 mol/L hydrochloric acid, and the resulting mixture was extracted with ethyl acetate. The extract was washed with water and brine, and dried over anhydrous magnesium sulfate, and the solvent was removed under reduced pressure. The residual solids were suspended in a mixed solvent (n-hexane/ethyl acetate=2/1), and collected by filtration. The collected solids were washed with the same solvent, and dried under reduced pressure to give 6-chloro-2-[2-chloro-5-(2,3-difluoro-6-methoxybenzyloxy)-4-methoxyphenylamino]-3-nitropyridine (1.24 g). To the suspension of the obtained 6-chloro-2-[2-chloro-5-(2,3-difluoro-6-methoxybenzyloxy)-4-methoxyphenylamino]-3-nitropyridine (0.6 g) and nickel(II) bromide (13 mg) in tetrahydrofuran (4 mL)-methanol (4 mL) was added sodium borohydride (0.14 g) under ice-cooling, and the mixture was stirred under ice-cooling for 10 minutes, and then stirred at room temperature for 20 minutes. The reaction mixture was poured into a saturated aqueous sodium hydrogen carbonate solution, and the resulting mixture was extracted with ethyl acetate. The extract was washed with brine, and dried over anhydrous sodium sulfate. The solvent was removed under reduced pressure, and the residue was purified by column chromatography on silica gel (eluent: n-hexane/ethyl acetate=7/3–2/3) to give 3-amino-6-chloro-2-[2-chloro-5-(2,3-difluoro-6-methoxybenzyloxy)-4-methoxyphenylamino]pyridine (0.48 g). The obtained 3-amino-6-chloro-2-[2-chloro-5-(2,3-difluoro-6-methoxybenzyloxy)-4-methoxyphenylamino]pyridine (0.28 g) was dissolved in tetrahydrofuran (6 mL). To the solution was added sodium hydride (55%, 66 mg) at room temperature, and the mixture was stirred at room temperature for 10 minutes. To the reaction mixture was added triphosgene (59 mg), and the mixture was stirred at room temperature for 30 minutes. The reaction mixture was acidified by adding 1 mol/L hydrochloric acid, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=1/1–1/3) to give the title compound (0.18 g).

Examples 10 and 11

The compounds of Examples 10 and 11 were prepared in a similar manner to that described in Example 9 using the corresponding starting materials.

Examples 12 and 13

The compounds of Examples 12 and 13 were prepared in a similar manner to that described in Example 7 and Example 8 using the corresponding starting materials.

Example 14

The compound of Example 14 was prepared in a similar manner to that described in Example 1, Example 7 and Example 8 using the corresponding starting materials.

Example 15

9-[2-Chloro-5-(2,3-difluoro-6-methoxybenzyloxy)-4-methoxyphenyl]-2-methoxy-7,9-dihydro-8H-purin-8-one A mixture of ethyl 4-chloro-2-methoxypyrimidine-5-carboxylate (0.22 g), 2-chloro-5-(2,3-difluoro-6-methoxybenzyloxy)-4-methoxyaniline hydrochloride (0.4 g) and N,N-diisopropylethylamine (0.37 mL) in acetonitrile (3 mL) was heated at reflux for 1.5 hours. The reaction mixture was poured into water. To the mixture was added ethyl acetate, and the insoluble material was collected by filtration. The collected solids were washed with water and ethyl acetate, and dried under reduced pressure to give ethyl 4-[2-chloro-5-(2,3-difluoro-6-methoxybenzyloxy)-4-methoxyphenylamino]-2-methoxypyrimidine-5-carboxylate (91 mg). To this material were added methanol (2 mL) and 1 mol/L aqueous sodium hydroxide solution (0.9 mL), and the mixture was stirred at 50° C. for 1 hour. To the mixture was added tetrahydrofuran (1 mL), and the mixture was stirred at 50° C. for 1 hour. The reaction mixture was cooled to room temperature. To the mixture was added 1 mol/L hydrochloric acid (1.0 mL), and the mixture was stirred for 30 minutes. The precipitated crystals were collected by filtration. The collected crystals were washed with water and diethyl ether, and dried under reduced pressure to give 4-[2-chloro-5-(2,3-difluoro-6-methoxybenzyloxy)-4-methoxyphenylamino]-2-methoxypyrimidine-5-carboxylic acid (57 mg). To this material were added 1,4-dioxane (1 mL), triethylamine (0.049 mL) and diphenylphosphoryl azide (0.026 mL), and the mixture was stirred at room temperature for 1 hour, and then heated at reflux for 2 hours. The reaction mixture was concentrated under reduced pressure, and the residue was purified by column chromatography on silica gel (eluent: n-hexane/ethyl acetate=1/1–1/5). The product was suspended in a mixed solvent (n-hexane/ethyl acetate=1/1), and collected by filtration. The collected material was washed with the same solvent, and dried under reduced pressure to give the title compound (20 mg).

Example 16

9-[2-Chloro-5-(2,3-difluoro-6-methoxybenzyloxy)-4-methoxyphenyl]-2-cyano-7,9-dihydro-8H-purin-8-one A mixture of methyl 2,4-dichloropyrimidine-5-carboxylate (0.41 g), 2-chloro-5-(2,3-difluoro-6-methoxybenzyloxy)-4-methoxyaniline hydrochloride (0.81 g) and N,N-diisopropylethylamine (0.73 mL) in acetonitrile (9 mL) was stirred at 120° C. in a reaction vessel equipped with a reflux condenser for 2 hours. The reaction mixture was cooled to room temperature. To the mixture was added water (9 mL), and the mixture was stirred at room temperature for 1 hour. The precipitated crystals were collected by filtration. The collected crystals were washed with water, and dried under reduced pressure to give methyl 2-chloro-4-[2-chloro-5-(2,3-difluoro-6-methoxybenzyloxy)-4-methoxyphenylamino]-pyrimidine-5-carboxylate (0.88 g). To the suspension of the obtained methyl 2-chloro-4-[2-chloro-5-(2,3-difluoro-6-methoxybenzyloxy)-4-methoxyphenylamino]-pyrimidine-5-carboxylate (0.35 g) in dimethyl sulfoxide (6 mL) were added a solution of potassium cyanide (0.13 g) in water (1 mL) and 1,4-diazabicyclo[2,2,2]octane (25 mg), and the mixture was stirred at 30° C. for 10 hours. The reaction mixture was diluted with ethyl acetate, and the resulting mixture was washed with water twice and brine successively, and dried over anhydrous magnesium sulfate, and the solvent was removed under reduced pressure. The residual solids were suspended in a mixed solvent (n-hexane/ethyl acetate=1/1), and collected by filtration. The collected solids were washed with the same solvent, and dried under reduced pressure to give methyl 4-[2-chloro-5-(2,3-difluoro-6-methoxy-benzyloxy)-4-methoxyphenylamino]-2-cyanopyrimidine-5-carboxylate (0.22 g). To the obtained methyl 4-[2-chloro-5-(2,3-difluoro-6-methoxybenzyloxy)-4-methoxyphenylamino]-2-cyanopyrimidine-5-carboxylate (0.12 g) were added tetrahydrofuran (3 mL), water (1.5 mL) and lithium hydroxide monohydrate (30 mg), and the mixture was stirred at room temperature for 1 hour. The reaction mixture was acidified by adding 1 mol/L hydrochloric acid, and the resulting mixture was extracted with ethyl acetate. The extract was washed with water and brine, and dried over anhydrous sodium sulfate, and the solvent was removed under reduced pressure. The residual solids were suspended in a mixed solvent (n-hexane/ethyl acetate=1/1), and collected by filtration. The collected solids were washed with the same solvent, and dried under reduced pressure to give 4-[2-chloro-5-(2,3-difluoro-6-methoxybenzyloxy)-4-methoxyphenylamino]-2-cyanopyrimidine-5-carboxylic acid (75 mg). To this material were added 1,4-dioxane (2 mL), triethylamine (0.066 mL) and diphenylphosphoryl azide (0.034 mL), and the mixture was stirred at room temperature for 1 hour, and then heated at reflux for 2 hours. The reaction mixture was concentrated under reduced pressure, and the residue was purified by column chromatography on silica gel (eluent: n-hexane/ethyl acetate=1/1–1/3) to give the title compound (46 mg).

Example 17

2-Carbamoyl-9-[2-chloro-5-(2,3-difluoro-6-methoxybenzyloxy)-4-methoxyphenyl]-7,9-dihydro-8H-purin-8-one To a solution of 9-[2-chloro-5-(2,3-difluoro-6-methoxybenzyloxy)-4-methoxyphenyl]-2-cyano-7,9-dihydro-8H-purin-8-one (43 mg) in dimethyl sulfoxide (2 mL) were added 2 mol/L aqueous sodium hydroxide solution (0.14 mL) and 30% aqueous hydrogen peroxide solution (0.02 mL), and the mixture was stirred at room temperature for 1 hour. To the reaction mixture was added 10% aqueous sodium sulfite solution, and the resulting mixture was stirred at room temperature for 10 minutes, and extracted with ethyl acetate. The extract was washed with water and brine, and dried over anhydrous sodium sulfate, and the solvent was removed under reduced pressure. The residual solids were suspended in a mixed solvent (n-hexane/ethyl acetate=1/1), and collected by filtration. The collected solids were washed with the same solvent, and dried under reduced pressure to give the title compound (3 mg).

Example 18

2-Carboxy-9-[2-chloro-5-(2,3-difluoro-6-methoxybenzyloxy)-4-methoxyphenyl]-7,9-dihydro-8H-purin-8-one To 9-[2-chloro-5-(2,3-difluoro-6-methoxybenzyloxy)-4-methoxyphenyl]-2-cyano-7,9-dihydro-8H-purin-8-one (0.12 g) was added hydrochloric acid (20% ethanol solution, 3 mL), and the mixture was stirred at room temperature overnight. To the reaction mixture was added water, and the precipitated crystals were collected by filtration. The crystals were washed with water and diethyl ether, and dried under reduced pressure. The obtained crystals were purified by column chromatography on silica gel (eluent: ethyl acetate) to give 9-[2-chloro-5-(2,3-difluoro-6-methoxybenzyloxy)-4-methoxyphenyl]-2-ethoxycarbonyl-7,9-dihydro-8H-purin-8-one (93 mg). To the obtained 9-[2-chloro-5-(2,3-difluoro-6-methoxy-benzyloxy)-4-methoxyphenyl]-2-ethoxycarbonyl-7,9-dihydro-8H-purin-8-one (50 mg) were added tetrahydrofuran (4 mL), methanol (2 mL), water (2 mL) and lithium hydroxide monohydrate (40 mg), and the mixture was stirred at room temperature for 2 hours. The reaction mixture was acidified by adding 1 mol/L hydrochloric acid, and the resulting mixture was extracted with ethyl acetate. The extract was washed with water and brine, and the solvent was removed under reduced pressure. The residual solids were suspended in diethyl ether, and collected by filtration. The collected solids were washed with water and diethyl ether, and dried under reduced pressure to give the title compound (22 mg).

Example 19

2-Amino-9-[2-chloro-5-(2,3-difluoro-6-methoxybenzyloxy)-4-methoxyphenyl]-7,9-dihydro-8H-purin-8-one A mixture of methyl 2-chloro-4-[2-chloro-5-(2,3-difluoro-6-methoxybenzyl-oxy)-4-methoxyphenylamino]pyrimidine-5-carboxylate (0.58 g), sodium azide (0.37 g), water (1 mL) and N,N-dimethylformamide (5 mL) was stirred at 60° C. for 4 hours. The reaction mixture was cooled to room temperature. To the mixture was added water, and the resulting mixture was stirred for 10 minutes. The precipitated crystals were collected by filtration, and the collected crystals were washed with water, and dried under reduced pressure to give methyl 2-azido-4-[2-chloro-5-(2,3-difluoro-6-methoxybenzyloxy)-4-methoxyphenylamino]-pyrimidine-5-carboxylate (0.56 g). This material was dissolved in tetrahydrofuran (12 mL). To the solution were added triphenylphosphine (0.43 g) and water (1.5 mL), and the mixture was stirred at room temperature overnight, and then heated at reflux for 1 hour. The solvent was removed under reduced pressure. To the residue was added water, and the resulting mixture was extracted with ethyl acetate. The extract was washed with brine, and dried over anhydrous sodium sulfate, and the solvent was removed under reduced pressure. The residual solids were suspended in a mixed solvent (n-hexane/ethyl acetate=1/2), and collected by filtration. The collected solids were washed with the same solvent, and dried under reduced pressure. The obtained solids were dissolved in acetic acid (5 mL). To the solution was added water (5 mL), and the mixture was stirred at 100° C. for 11 hours. The reaction mixture was poured into a saturated aqueous sodium hydrogen carbonate solution, and the resulting mixture was extracted with ethyl acetate. The extract was washed with brine, and the solvent was removed under reduced pressure. To the residue were added tetrahydrofuran (4 mL), methanol (2 mL) and 2 mol/L aqueous sodium hydroxide solution (2 mL), and the mixture was stirred at 50° C. for 2 hours. The reaction mixture was cooled to room temperature. To the mixture were added 2 mol/L hydrochloric acid (2.5 mL) and water, and the mixture was stirred at room temperature for 10 minutes. The precipitated crystals were collected by filtration, and the collected crystals were washed with water and diethyl ether, and dried under reduced pressure to give 2-amino-4-[2-chloro-5-(2,3-difluoro-6-methoxybenzyloxy)-4-methoxyphenylamino]pyrimidine-5-carboxylic acid hydrochloride (58 mg). To this material was added 1,4-dioxane (1 mL), triethylamine (0.064 mL) and diphenylphosphoryl azide (0.027 mL), and the mixture was stirred at room temperature for 1 hour, and then heated at reflux overnight. The reaction mixture was purified by column chromatography on silica gel (eluent: ethyl acetate–ethyl acetate/methanol=10/1) to give the title compound (32 mg).

Example 20

3-[2-Chloro-5-(3,4-dihydroquinolin-1(2H)-ylsulfonyl)phenyl]-1,3-dihydro-2H-imidazo-[4,5-b]pyridin-2-one To a mixture of 2-chloronicotinic acid (0.13 g) and 2-chloro-5-(3,4-dihydroquinolin-1(2H)-ylsulfonyl)aniline (0.3 g) in N,N-dimethylformamide (2 mL) were added copper powder (6 mg) and potassium carbonate (0.13 g), and the mixture was heated at reflux for 8 hours. The reaction mixture was poured into 1 mol/L hydrochloric acid, and the resulting mixture was extracted with ethyl acetate. The extract was washed with water and brine, and dried over anhydrous magnesium sulfate. The solvent was removed under reduced pressure, and the residue was dissolved in 1,4-dioxane (10 mL) To the solution were added triethylamine (0.42 mL) and diphenylphosphoryl azide (0.26 mL), and the mixture was stirred at 100° C. for 3 hours. The reaction mixture was poured into 1 mol/L hydrochloric acid, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: n-hexane/ethyl acetate=1/1–1/2) to give the title compound (48 mg).

Example 21

The compound of Example 21 was prepared in a similar manner to that described in Example 20 using the corresponding starting materials.

Example 22

9-[2-Chloro-5-(3,4-dihydroquinolin-1(2H)-ylsulfonyl)phenyl]-7,9-dihydro-8H-purin-8-one A mixture of ethyl 4-chloropyrimidine-5-carboxylate (0.4 g), 2-chloro-5-(3,4-dihydroquinolin-1(2H)-ylsulfonyl)aniline (0.69 g) and sodium hydride (55%, 98 mg) in 1-methyl-2-pyrrolidone (8 mL) was stirred at 100° C. for 2 hours. The reaction mixture was poured into 0.5 mol/L hydrochloric acid, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: n-hexane/ethyl acetate=3/1–2/1) to give ethyl 4-[2-chloro-5-(3,4-dihydroquinolin-1(2H)-yl sulfonyl)phenylamino]pyrimidine-5-carboxylate (0.42 g). To this material were added ethanol (8 mL), tetrahydrofuran (2 mL) and 5 mol/L aqueous sodium hydroxide solution (1.77 mL), and the mixture was stirred at room temperature for 3 days. The reaction mixture was acidified by adding 1 mol/L hydrochloric acid, and the precipitated crystals were collected by filtration. The crystals were washed with water, and dried under reduced pressure to give 4-[2-chloro-5-(3,4-dihydroquinolin-1(2H)-ylsulfonyl)phenylamino]pyrimidine-5-carboxylic acid (0.37 g). The obtained 4-[2-chloro-5-(3,4-dihydroquinolin-1(2H)-ylsulfonyl)phenylamino]pyrimidine-5-carboxylic acid (0.1 g) was dissolved in 1,4-dioxane (2 mL). To the solution were added triethylamine (0.094 mL) and diphenylphosphoryl azide (0.058 mL), and the mixture was stirred at 100° C. for 3 hours. The reaction mixture was poured into water, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: n-hexane/ethyl acetate=1/2–ethyl acetate) to give the title compound (80 mg).

Example 23

The compound of Example 23 was prepared in a similar manner to that described in Example 22 using the corresponding starting materials.

Example 24

3-[2-Chloro-5-(1-methyl-1-phenylethyl sulfonyl)phenyl]-1,3-dihydro-2H-imidazo[4,5-b]-pyridin-2-one To a solution of 3-[2-chloro-5-(1-methyl-1-phenylethylthio)phenyl]-1,3-dihydro-2H-imidazo[4,5-b]pyridin-2-one (50 mg) in methylene chloride (2 mL) was added 3-chloroperoxybenzoic acid (78 mg), and the mixture was stirred at room temperature for 1 hour. To the reaction mixture was added 1 mol/L aqueous sodium thiosulfate solution, and the resulting mixture was extracted with ethyl acetate. The extract was washed with water and brine, and dried over anhydrous magnesium sulfate, and the solvent was removed under reduced pressure. The residual crystals were suspended in a mixed solvent (n-hexane/ethyl acetate=1/1), and collected by filtration. The collected crystals were washed with the same solvent, and dried under reduced pressure to give the title compound (42 mg).

Example 25

The compound of Example 25 was prepared in a similar manner to that described in Example 24 using the corresponding starting materials.

Example 26

3-[2-Chloro-5-(2,3-difluoro-6-methoxybenzyloxy)-4-methoxyphenyl]-1,3-dihydro-2H-imidazo[4,5-b]pyridine-2-thione A mixture of 2-chloro-3-nitropyridine (0.12 g), 2-chloro-5-(2,3-difluoro-6-methoxy-benzyloxy)-4-methoxyaniline (0.26 g) and N,N-diisopropylethylamine (0.14 mL) in acetonitrile (3 mL) was stirred at 130° C. in a reaction vessel equipped with a reflux condenser overnight. The reaction mixture was poured into water, and the resulting mixture was extracted with ethyl acetate. The extract was washed with water and brine, and dried over anhydrous sodium sulfate. The solvent was removed under reduced pressure, and the residue was dissolved in tetrahydrofuran (4 mL)-methanol (4 mL). To the solution were added nickel(II) bromide (9 mg) and sodium borohydride (89 mg) under ice-cooling, and the mixture was stirred under ice-cooling for 30 minutes, and then stirred at room temperature for 30 minutes. The reaction mixture was poured into a saturated aqueous sodium hydrogen carbonate solution, and the resulting mixture was extracted with ethyl acetate. The extract was washed with brine, and dried over anhydrous magnesium sulfate. The solvent was removed under reduced pressure, and the residue was purified by column chromatography on silica gel (eluent: n-hexane/ethyl acetate=67/33–35/65) to give 3-amino-2-[2-chloro-5-(2,3-difluoro-6-methoxybenzyloxy)-4-methoxyphenylamino]pyridine (62 mg). This material was dissolved in tetrahydrofuran (2 mL). To the solution were added sodium hydride (55%, 20 mg) and thiophosgene (0.012 mL), and the mixture was stirred at room temperature for 1 hour. To the reaction mixture was added N,N-dimethylformamide (1 mL), and the mixture was stirred at room temperature for 1 hour.

The reaction mixture was poured into 1 mol/L hydrochloric acid, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=1/1–1/2) to give the title compound (28 mg).

Example 27

1-[2-Chloro-5-(2,3-difluoro-6-methoxybenzyloxy)-4-methoxyphenyl]-1,3-dihydro-2H-imidazo[4,5-c]pyridin-2-one To a solution of 4-(tert-butoxycarbonylamino)-5-chloro-2-(2,3-difluoro-6-methoxy-benzyloxy)anisole (0.2 g) in N,N-dimethylformamide (2 mL) was added sodium hydride (55%, 21 mg), and the mixture was stirred at room temperature for 10 minutes. To the reaction mixture was added 4-chloro-3-nitropyridine (78 mg), and the mixture was stirred at room temperature overnight. The reaction mixture was poured into 0.5 mol/L hydrochloric acid, and the resulting mixture was extracted with ethyl acetate. The extract was washed with water and brine, and dried over anhydrous magnesium sulfate. The solvent was removed under reduced pressure, and the residue was dissolved in tetrahydrofuran (5 mL)—methanol (5 mL). To the solution were added nickel(II) bromide (5 mg) and sodium borohydride (53 mg) under ice-cooling, and the mixture was stirred under ice-cooling for 30 minutes, and then stirred at room temperature for 30 minutes. The reaction mixture was poured into a saturated aqueous sodium hydrogen carbonate solution, and the resulting mixture was extracted with ethyl acetate. The extract was washed with brine twice, and dried over anhydrous magnesium sulfate. The solvent was removed under reduced pressure, and the residue was purified by column chromatography on silica gel (eluent: ethyl acetate–ethyl acetate/methanol=9/1) to give 3-amino-4-{N-(tert-butoxycarbonyl)-N-[2-chloro-5-(2,3-difluoro-6-methoxybenzyloxy)-4-methoxyphenyl]amino}pyridine (53 mg). This material was dissolved in diglyme (1 mL), and the solution was stirred at 150° C. for 3 hours. The reaction mixture was poured into water, and the resulting mixture was extracted with ethyl acetate. The extract was washed with water and brine, and dried over anhydrous sodium sulfate. The solvent was removed under reduced pressure, and the residue was purified by column chromatography on silica gel (eluent: ethyl acetate/methanol=10/1). The obtained product was dissolved in ethyl acetate. To the solution were added diethyl ether and n-hexane, and the precipitated crystals were collected by filtration. The collected crystals were washed with diethyl ether, and dried under reduced pressure to give the title compound (6 mg).

Examples 28 to 30

The compounds of Examples 28 to 30 were prepared in a similar manner to that described in Example 1 using the corresponding starting materials.

Example 31

The compound of Example 31 was prepared in a similar manner to that described in Example 15 using the corresponding starting materials.

Example 32

The compound of Example 32 was prepared in a similar manner to that described in Example 1, Example 7 and Example 8 using the corresponding starting materials.

Examples 33 and 34

The compounds of Examples 33 and 34 were prepared in a similar manner to that described in Example 7 and Example 8 using the corresponding starting materials.

Examples 35 and 36

The compounds of Examples 35 and 36 were prepared in a similar manner to that described in Example 24 using the corresponding starting materials.

Example 37

3-[2-Chloro-5-(2,3-difluoro-6-methoxybenzyloxy)-4-methoxyphenyl]-5-methoxycarbonyl-1,3-dihydro-2H-imidazo[4,5-b]pyridin-2-one A mixture of methyl 5-(tert-butoxycarbonylamino)-6-iodopyridine-2-carboxylate (0.14 g), 2-chloro-5-(2,3-difluoro-6-methoxybenzyloxy)-4-methoxyaniline (0.18 g), tris-(dibenzylideneacetone)dipalladium(0) (10 mg), 4,5-bis(diphenylphosphino)-9,9-dimethylxanthene (13 mg) and sodium tert-butoxide (48 mg) in tetrahydrofuran (3 mL) was heated at reflux for 22 hours. The reaction mixture was cooled to room temperature. To the reaction mixture was added acetic acid (0.02 mL), and the mixture was directly purified by column chromatography on silica gel (eluent: n-hexane/ethyl acetate=1/2–1/3) to give the title compound (81 mg).

Example 38

9-[2-Chloro-5-(2,3-difluoro-6-methoxybenzyloxy)-4-methoxyphenyl]-6-ethoxy-7,9-dihydro-8H-purin-8-one To a suspension of 4,6-dichloro-5-nitropyrimidine (1.75 g) in acetonitrile (30 mL) were added 2-chloro-5-(2,3-difluoro-6-methoxybenzyloxy)-4-methoxyaniline (1.98 g) and N,N-diisopropylethylamine (1.15 mL) at −20° C., and the reaction mixture was allowed to warm slowly to room temperature, and stirred at room temperature for 2.5 days. To the reaction mixture were added water and ethyl acetate, and the resulting mixture was stirred for 10 minutes. The insoluble material was removed by filtration, and the organic layer of the filtrate was separated. The organic layer was washed with 10% aqueous sodium chloride solution and brine, and dried over anhydrous sodium sulfate. The solvent was removed under reduced pressure, and the residue was purified by column chromatography on silica gel (eluent: n-hexane/ethyl acetate=7/3–9/11). The product was suspended in a mixed solvent (n-hexane/diethyl ether=3/1), and collected by filtration. The collected crystals were washed with the same solvent, and dried under reduced pressure to give 6-chloro-4-[2-chloro-5-(2,3-difluoro-6-methoxybenzyloxy)-4-methoxyphenylamino]-5-nitropyrimidine (1.34 g). To the solution of the obtained 6-chloro-4-[2-chloro-5-(2,3-difluoro-6-methoxybenzyloxy)-4-methoxyphenylamino]-5-nitropyrimidine (0.15 in 1-methyl-2-pyrrolidone (1 mL) was added sodium ethoxide (20% ethanol solution, 0.21 g), and the mixture was stirred at 60° C. for 2 hours. The reaction mixture was poured into 0.5 mol/L hydrochloric acid, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=1/1) to give 4-[2-chloro-5-(2,3-difluoro-6-methoxy-benzyloxy)-4-methoxyphenylamino]-6-ethoxy-5-nitropyrimidine (0.12 g). This material was dissolved in tetrahydrofuran (3 mL)-methanol (3 mL). To the solution was added 10% platinum-carbon powder (20 mg), and the mixture was stirred at room temperature under a hydrogen atmosphere for 2 hours. The insoluble material was removed by filtration, and the filtrate was concentrated under reduced pressure. The residue was purified by column chromatography on silica gel (eluent: n-hexane/ethyl acetate=1/1–2/3) to give 5-amino-4-[2-chloro-5-(2,3-difluoro-6-methoxy-benzyloxy)-4-methoxyphenylamino]-6-ethoxypyrimidine (70 mg). This material was dissolved in tetrahydrofuran (3 mL). To the solution was added sodium hydride (55%, 23 mg), and the mixture was stirred at room temperature for 10 minutes. To the mixture was added triphosgene (18 mg), and the mixture was stirred at room temperature for 1 hour. To the reaction mixture was added 1 mol/L hydrochloric acid, and the resulting mixture was extracted with ethyl acetate. The extract was washed with water and brine, and dried over anhydrous sodium sulfate, and the solvent was removed under reduced pressure. The residual solids were suspended in a mixed solvent (n-hexane/ethyl acetate=1/1), and collected by filtration. The collected solids were washed with the same solvent, and dried under reduced pressure to give the title compound (42 mg).

Example 39

The compound of Example 39 was prepared in a similar manner to that described in Example 38 using the corresponding starting materials.

Example 40

3-[2-Chloro-4-methoxy-5-(1-methyl-1-phenylethylthio)phenyl]-5-ethoxycarbonyl-7-methyl-1,3-dihydro-2H-imidazo[4,5-b]pyridin-2-one A mixture of ethyl 5-(tert-butoxycarbonylamino)-6-iodo-4-methylpyridine-2-carboxylate (0.2 g), 2-chloro-4-methoxy-5-(1-methyl-1-phenylethylthio)aniline (0.15 g), tris(dibenzylideneacetone)dipalladium(0) (23 mg), 4,5-bis(diphenyl-phosphino)-9,9-dimethylxanthene (29 mg) and sodium tert-butoxide (66 mg) in tetrahydrofuran (4 mL) was heated at reflux under an argon atmosphere overnight. The reaction mixture was cooled to room temperature. To the reaction mixture was added ethyl acetate, and the insoluble material was removed by filtration. The filtrate was washed with 1 mol/L hydrochloric acid and brine, and dried over anhydrous magnesium sulfate. The solvent was removed under reduced pressure, and the residue was purified by column chromatography on silica gel (eluent: n-hexane/ethyl acetate=2/1–1/1) to give the title compound (90 mg).

Example 41

The compound of Example 41 was prepared in a similar manner to that described in Example 40 using the corresponding starting materials.

Example 42

3-[2-Chloro-4-methoxy-5-(1-methyl-1-phenylethylsulfonyl)phenyl]-5-ethoxycarbonyl-7-methyl-1,3-dihydro-2H-imidazo[4,5-b]pyridin-2-one To a solution of 3-[2-chloro-4-methoxy-5-(1-methyl-1-phenylethylthio)-phenyl]-5-ethoxycarbonyl-7-methyl-1,3-dihydro-2H-imidazo[4,5-b]pyridin-2-one (90 mg) in methylene chloride (4 mL) was added 3-chloroperoxybenzoic acid (76 mg), and the mixture was stirred at room temperature for 2 hours. To the reaction mixture was added 10% aqueous sodium sulfite solution, and the resulting mixture was stirred at room temperature for 10 minutes, and extracted with ethyl acetate. The extract was washed with brine, and dried over anhydrous magnesium sulfate. The solvent was removed under reduced pressure, and the residue was purified by column chromatography on silica gel (eluent: n-hexane/ethyl acetate=1/2) to give the title compound (71 mg).

Example 43

5-Carboxy-3-[2-chloro-4-methoxy-5-(1-methyl-1-phenylethylsulfonyl)phenyl]-7-methyl-1,3-dihydro-2H-imidazo[4,5-b]pyridin-2-one To a mixture of 3-[2-chloro-4-methoxy-5-(1-methyl-1-phenylethylsulfonyl)-phenyl]-5-ethoxycarbonyl-7-methyl-1,3-dihydro-2H-imidazo[4,5-b]pyridin-2-one (36 mg), tetrahydrofuran (2 mL), methanol (1 mL) and water (1 mL) was added lithium hydroxide monohydrate (56 mg), and the mixture was stirred at room temperature overnight. The reaction mixture was acidified by adding 1 mol/L hydrochloric acid, and the resulting mixture was extracted with ethyl acetate. The extract was washed with brine, and dried over anhydrous magnesium sulfate. The solvent was removed under reduced pressure to give the title compound (33 mg).

Examples 44 and 45

The compounds of Examples 44 and 45 were prepared in a similar manner to that described in Example 43 using the corresponding starting materials.

Examples 46 to 116

The compounds of Examples 46 to 116 were prepared in a similar manner to that described in Example 40 and Example 43 using the corresponding starting materials.

Examples 117 to 141

The compounds of Examples 117 to 141 were prepared in a similar manner to that described in Example 40, Example 42 and Example 43 using the corresponding starting materials.

Example 142

5-Carboxy-3-[2-fluoro-4-(2-hydroxyethoxy)-5-(2,3,4,5-tetrahydro-1H-1-benzoazepin-1-ylsulfonyl)phenyl]-7-methyl-1,3-dihydro-2H-imidazo[4,5-b]pyridin-2-one To a solution of 5-ethoxycarbonyl-3-{-4-[2-(tert-butyldimethylsilyloxy)-ethoxy]-2-fluoro-5-(2,3,4,5-tetrahydro-1H-1-benzoazepin-1-ylsulfonyl)phenyl}-7-methyl-1,3-dihydro-2H-imidazo[4,5-b]pyridin-2-one (15 mg), which was prepared in a similar manner to that described in Example 40 using 4-[2-(tert-butyldimethylsilyloxy)-ethoxy]-2-fluoro-5-(2,3,4,5-tetrahydro-1H-1-benzoazepin-1-ylsulfonyl) aniline instead of 2-chloro-4-methoxy-5-(1-methyl-1-phenylethylthio)aniline, in tetrahydrofuran (1.5 mL) was added tetra(n-butyl)ammonium fluoride (1 mol/L tetrahydrofuran solution, 0.031 mL), and the mixture was stirred at room temperature overnight. The reaction mixture was poured into 1 mol/L hydrochloric acid, and the resulting mixture was extracted with ethyl acetate. The extract was washed with water and brine, and dried over anhydrous magnesium sulfate, and the solvent was removed under reduced pressure to give 5-ethoxycarbonyl-3-[2-fluoro-4-(2-hydroxyethoxy)-5-(2,3,4,5-tetrahydro-1H-1-benzoazepin-1-ylsulfonyl)phenyl]-7-methyl-1,3-dihydro-2H-imidazo[4,5-b]pyridin-2-one (12 mg). The title compound was prepared in a similar manner to that described in Example 43 using this material instead of 3-[2-chloro-4-methoxy-5-(1-methyl-1-phenylethylsulfonyl)phenyl]-5-ethoxycarbonyl-7-methyl-1,3-dihydro-2H-imidazo[4,5-b]pyridin-2-one.

Examples 143 to 146

The compounds of Examples 143 to 146 were prepared in a similar manner to that described in Example 142 using the corresponding starting materials.

Example 147

3-[2-Chloro-4-methoxy-5-(1-methyl-1-phenylethylsulfonyl)phenyl]-5-[1-(ethoxycarbonyl-oxy)ethoxycarbonyl]-7-methyl-1,3-dihydro-2H-imidazo[4,5-b]pyridin-2-one To a mixture of 5-carboxy-3-[2-chloro-4-methoxy-5-(1-methyl-1-phenyl-ethylsulfonyl)phenyl]-7-methyl-1,3-dihydro-2H-imidazo[4,5-b]pyridin-2-one (49 mg), potassium carbonate (17 mg) and potassium iodide (8 mg) in N,N-dimethylformamide (1 mL) was added 1-ethoxycarbonyloxyethyl chloride (0.015 mL), and the mixture was stirred at 60° C. for 2.5 hours. The reaction mixture was diluted with ethyl acetate, and the resulting mixture was washed with 1 mol/L hydrochloric acid, water and brine successively, and dried over anhydrous magnesium sulfate. The solvent was removed under reduced pressure, and the residue was purified by column chromatography on silica gel (eluent: n-hexane/ethyl acetate=1/1–1/2) to give the title compound (29 mg).

Examples 148 to 150

The compounds of Examples 148 to 150 were prepared in a similar manner to that described in Example 147 using the corresponding starting materials.

Example 151

3-[2-Chloro-5-(2,3,4,5-tetrahydro-1H-1-benzoazepin-1-ylsulfonyl)phenyl]-5-(2-hydroxy-2-propyl)-7-methyl-1,3-dihydro-2H-imidazo[4,5-b]pyridin-2-one To a solution of 3-[2-chloro-5-(2,3,4,5-tetrahydro-1H-1-benzoazepin-1-ylsulfonyl)-phenyl]-5-ethoxycarbonyl-7-methyl-1,3-dihydro-2H-imidazo[4,5-b]pyridin-2-one (30 mg) in tetrahydrofuran (3 mL) was added methylmagnesium iodide (3 mol/L diethyl ether solution, 0.061 mL) under ice-cooling, and the mixture was stirred at room temperature overnight. To the reaction mixture was added a saturated aqueous ammonium chloride solution, and the resulting mixture was extracted with ethyl acetate. The extract was washed with brine, and dried over anhydrous magnesium sulfate. The solvent was removed under reduced pressure, and the residue was purified by column chromatography on silica gel (eluent: n-hexane–n-hexane/ethyl acetate=2/3) to give the title compound (4 mg).

Example 152

3-[2-Chloro-5-(2,3,4,5-tetrahydro-1H-1-benzoazepin-1-ylsulfonyl)phenyl]-5-hydroxymethyl-7-methyl-1,3-dihydro-2H-imidazo[4,5-b]pyridin-2-one To a solution of 3-[2-chloro-5-(2,3,4,5-tetrahydro-1H-1-benzoazepin-1-ylsulfonyl)-phenyl]-5-ethoxycarbonyl-7-methyl-1,3-dihydro-2H-imidazo[4,5-b]pyridin-2-one (87 mg) in tetrahydrofuran (1.6 mL) was added diisobutylaluminium hydride (0.99 mol/L toluene solution, 0.65 mL) under ice-cooling, and the mixture was stirred at room temperature overnight. To the reaction mixture was added 1 mol/L hydrochloric acid, and the resulting mixture was extracted with ethyl acetate. The extract was washed with brine, and dried over anhydrous magnesium sulfate. The solvent was removed under reduced pressure, and the residue was purified by column chromatography on silica gel (eluent: n-hexane–ethyl acetate) to give the title compound (63 mg).

Example 153

3-[2-Chloro-5-(2,3,4,5-tetrahydro-1H-1-benzoazepin-1-ylsulfonyl)phenyl]-5-formyl-7-methyl-1,3-dihydro-2H-imidazo[4,5-b]pyridin-2-one To a solution of 3-[2-chloro-5-(2,3,4,5-tetrahydro-1H-1-benzoazepin-1-ylsulfonyl)-phenyl]-5-hydroxymethyl-7-methyl-1,3-dihydro-2H-imidazo[4,5-b]pyridin-2-one (15 mg) in N,N-dimethylformamide (1 mL) was added manganese (IV) oxide (0.3 g), and the mixture was stirred at room temperature overnight. The reaction mixture was diluted with ethyl acetate, and the insoluble material was removed by filtration. The filtrate was concentrated under reduced pressure, and the residue was purified by column chromatography on silica gel (eluent: n-hexane–n-hexane/ethyl acetate=2/3) to give the title compound (12 mg).

Example 154

3-[2-Chloro-5-(2,3-difluoro-6-methoxybenzyloxy)-4-(2-hydroxyethoxy)phenyl]-5-hydroxymethyl-1,3-dihydro-2H-imidazo[4,5-b]pyridin-2-one To a solution of 5-carboxy-3-[2-chloro-5-(2,3-difluoro-6-methoxybenzyl-oxy)-4-(2-hydroxyethoxy)phenyl]-1,3-dihydro-2H-imidazo[4,5-b]pyridin-2-one (28 mg) in tetrahydrofuran (3 mL) was added borane-tetrahydrofuran complex (1.2 mol/L tetrahydrofuran solution, 0.21 mL), and the mixture was stirred at room temperature overnight. To the reaction mixture were added water and a saturated aqueous ammonium chloride solution, and the resulting mixture was stirred at room temperature for 5 minutes. The mixture was extracted with ethyl acetate twice, and the extracts were dried over anhydrous magnesium sulfate. The solvent was removed under reduced pressure, and the residue was purified by column chromatography on silica gel (eluent: n-hexane/ethyl acetate=1/1–ethyl acetate/methanol=10/1) to give the title compound (6 mg).

Example 155

The compound of Example 155 was prepared in a similar manner to that described in Example 154 using the corresponding starting materials.

Example 156

The compound of Example 156 was prepared in a similar manner to that described in Example 40 and Example 152 using the corresponding starting materials.

Example 157

3-{5-[6-(2-Acetylaminoethoxy)-2,3-difluorobenzyloxy]-2-chlorophenyl}-5-hydroxymethyl-1,3-dihydro-2H-imidazo[4,5-b]pyridin-2-one To 3-(5-{6-[2-(tert-butoxycarbonylamino)ethoxy]-2,3-difluorobenzyloxy}-2-chloro-phenyl)-5-hydroxymethyl-1,3-dihydro-2H-imidazo[4,5-b]pyridin-2-one (40 mg) was added hydrochloric acid (4 mol/L ethyl acetate solution, 2 mL), and the mixture was stirred at room temperature for 2 hours. To the reaction mixture was added diethyl ether, and the precipitated crystals were collected by filtration. The collected crystals were washed with diethyl ether, and dried under reduced pressure to give 3-{5-[6-(2-aminoethoxy)-2,3-difluorobenzyloxy]-2-chlorophenyl}-5-hydroxymethyl-1,3-dihydro-2H-imidazo[4,5-b]pyridin-2-one hydrochloride (12 mg). To this material were added methylene chloride (2 mL), tetrahydrofuran (1 mL), pyridine (0.1 mL) and acetic anhydride (0.003 mL), and the mixture was stirred at room temperature for 3 hours. The reaction mixture was poured into 1 mol/L hydrochloric acid, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: ethyl acetate–ethyl acetate/methanol=10/1) to give the title compound (10 mg).

Example 158

The compound of Example 158 was prepared in a similar manner to that described in Example 40 using the corresponding starting materials.

Example 159

3-[2-Chloro-5-(2,3,4,5-tetrahydro-1H-1-benzoazepin-1-ylsulfonyl)phenyl]-7-methyl-5-(tetrazol-5-yl)-1,3-dihydro-2H-imidazo[4,5-b]pyridin-2-one To a solution of 3-[2-chloro-5-(2,3,4,5-tetrahydro-1H-1-benzoazepin-1-ylsulfonyl)-phenyl]-5-cyano-7-methyl-1,3-dihydro-2H-imidazo[4,5-b]pyridin-2-one (47 mg) in N,N-dimethylformamide (1.5 mL) were added ammonium chloride (0.1 g) and sodium azide (0.12 g), and the mixture was stirred at 60° C. for 1 hour, and then stirred at 120° C. for 3 hours. The reaction mixture was cooled to room temperature, and diluted with ethyl acetate. To the mixture was added water, and the organic layer was separated. The organic layer was washed with water and brine, and dried over anhydrous magnesium sulfate, and the solvent was removed under reduced pressure. The residual solids were suspended in a mixed solvent (n-hexane/ethyl acetate=3/1), and collected by filtration. The collected solids were dried under reduced pressure to give the title compound (33 mg).

Example 160

3-[2-Chloro-5-(2,3,4,5-tetrahydro-1H-1-benzoazepin-1-ylsulfonyl)phenyl]-5-hydroxycarbamimidoyl-7-methyl-1,3-dihydro-2H-imidazo[4,5-b]pyridin-2-one To a solution of 3-[2-chloro-5-(2,3,4,5-tetrahydro-1H-1-benzoazepin-1-yl-sulfonyl)phenyl]-5-cyano-7-methyl-1,3-dihydro-2H-imidazo[4,5-b]pyridin-2-one (0.13 g) in ethanol (4 mL) were added hydroxylamine hydrochloride (91 mg) and potassium carbonate (0.2 g), and the mixture was stirred at room temperature for 1 hour. The reaction mixture was poured into 1 mol/L hydrochloric acid, and the resulting mixture was extracted with ethyl acetate. The extract was washed with water and brine, and dried over anhydrous magnesium sulfate, and the solvent was removed under reduced pressure. The residual solids were suspended in a mixed solvent (n-hexane/ethyl acetate=4/1), and collected by filtration. The collected solids were dried under reduced pressure to give the title compound (0.1 g).

Example 161

3-[2-Chloro-5-(2,3,4,5-tetrahydro-1H-1-benzoazepin-1-ylsulfonyl)phenyl]-7-methyl-5-(4H-[1,2,4]oxadiazol-5-one-3-yl)-1,3-dihydro-2H-imidazo[4,5-b]pyridin-2-one To a solution of 3-[2-chloro-5-(2,3,4,5-tetrahydro-1H-1-benzoazepin-1-ylsulfonyl)-phenyl]-5-hydroxycarbamimidoyl-7-methyl-1,3-dihydro-2H-imidazo[4,5-b]pyridin-2-one (0.1 g) in N,N-dimethylformamide (2 mL) was added 1,1'-carbonyldiimidazole (62 mg) at room temperature. To the mixture was added sodium hydride (55%, 38 mg) under ice-cooling, and the mixture was stirred at room temperature for 1 hour. To the reaction mixture was added water under ice-cooling, and the mixture was stirred for 30 minutes. The mixture was acidified by adding 1 mol/L hydrochloric acid, and the resulting mixture was extracted with ethyl acetate. The extract was washed with water and brine, and dried over anhydrous magnesium sulfate. The solvent was removed under reduced pressure to give the title compound (62 mg).

Example 162

The compound of Example 162 was prepared in a similar manner to that described in Example 17 using the corresponding starting materials.

Example 163

The compound of Example 163 was prepared in a similar manner to that described in Example 9 using the corresponding starting materials.

Example 164

5-Bromo-3-[2-chloro-5-(2,3-difluoro-6-methoxybenzyloxy)-4-methoxyphenyl]-1,3-dihydro-2H-imidazo[4,5-b]pyrazin-2-one A mixture of 3,5-dibromo-2-(tert-butoxycarbonylamino)pyrazine (0.26 g), 2-chloro-5-(2,3-difluoro-6-methoxybenzyloxy)-4-methoxyaniline (0.25 g), tris(dibenzylideneacetone)-dipalladium(0) (34 mg), 4,5-bis(diphenylphosphino)-9,9-dimethylxanthene (43 mg) and sodium tert-butoxide (0.1 g) in tetrahydrofuran (5 mL) was heated at reflux under an argon atmosphere for 1 hour. The reaction mixture was cooled to room temperature. To the reaction mixture was added ethyl acetate, and the insoluble material was removed by filtration. The filtrate was washed with 1 mol/L hydrochloric acid, water and brine successively, and dried over anhydrous magnesium sulfate, and the solvent was removed under reduced pressure. To the residue were added methylene chloride (5 mL) and trifluoroacetic acid (1 mL), and the mixture was stirred at room temperature for 3 hours. The reaction mixture was poured into a saturated aqueous sodium hydrogen carbonate solution, and the resulting mixture was extracted with ethyl acetate. The extract was washed with water and brine, and dried over anhydrous magnesium sulfate. The solvent was removed under reduced pressure, and the residue was dissolved in N,N-dimethylformamide (3 mL). To the solution were added 1,1'-carbonyldiimidazole (58 mg) and sodium hydride (55%, 32 mg) under ice-cooling, and the mixture was stirred at room temperature for 1 hour. The reaction mixture was poured into 1 mol/L hydrochloric acid, and the resulting mixture was extracted with ethyl acetate. The extract was washed with brine, and dried over anhydrous magnesium sulfate. The solvent was removed under reduced pressure, and the residue was purified by column chromatography on silica gel (eluent: n-hexane/ethyl acetate=1/1) to give the title compound (84 mg).

Example 165

The compound of Example 165 was prepared in a similar manner to that described in Example 7 and Example 8 using the corresponding starting materials.

Example 166

The compound of Example 166 was prepared in a similar manner to that described in Example 1, Example 7 and Example 8 using the corresponding starting materials.

Example 167

3-[2-Chloro-4-methoxy-5-(1-methyl-1-phenylethylthio)phenyl]-5-hydroxymethyl-7-methoxy-1,3-dihydro-2H-imidazo[4,5-b]pyridin-2-one To a solution of 5-(tert-butyldimethylsilyloxy)methyl-3-[2-chloro-4-methoxy-5-(1-methyl-1-phenylethylthio)phenyl]-7-methoxy-1,3-dihydro-2H-imidazo[4,5-b]pyridin-2-one (24 mg) in tetrahydrofuran (2 mL) was added tetra(n-butyl)ammonium fluoride hydrate (31 mg), and the mixture was stirred at room temperature for 5 hours. The reaction mixture was poured into 0.5 mol/L hydrochloric acid, and the resulting mixture was extracted with ethyl acetate. The extract was washed with brine, and dried over anhydrous magnesium sulfate. The solvent was removed under reduced pressure, and the residue was purified by column chromatography on silica gel (eluent: n-hexane/ethyl acetate=1/1–1/2) to give the title compound (10 mg).

Example 168

The compound of Example 168 was prepared in a similar manner to that described in Example 42 and Example 167 using the corresponding starting materials.

Example 169

5-Carboxy-3-[2-chloro-4-methoxy-5-(1-methyl-1-phenylethylsulfonyl)phenyl]-7-methoxy-1,3-dihydro-2H-imidazo[4,5-b]pyridin-2-one To a solution of 3-[2-chloro-4-methoxy-5-(1-methyl-1-phenylethylsulfonyl)-phenyl]-5-hydroxymethyl-7-methoxy-1,3-dihydro-2H-imidazo[4,5-b]pyridin-2-one (40 mg) in N,N-dimethylformamide (2 mL) was added manganese(IV) oxide (0.4 g), and the mixture was stirred at room temperature for 8 hours. The reaction mixture was diluted with ethyl acetate, and the insoluble material was removed by filtration. The filtrate was washed with water and brine, and dried over anhydrous magnesium sulfate, and the solvent was removed under reduced pressure. To the residue were added tert-butanol (1.5 mL), water (0.15 mL), sodium dihydrogen phosphate dihydrate (10 mg), 2-methyl-2-butene (18 mg) and a solution of sodium chlorite (20 mg) in water (0.3 mL) successively, and the mixture was stirred at room temperature for 3 hours. To the reaction mixture were added 1 mol/L hydrochloric acid and water, and the precipitated crystals were collected by filtration. The collected crystals were washed with water, and dried under reduced pressure to give the title compound (19 mg).

Example 170

9-[2-Chloro-4-ethoxycarbonylmethoxy-5-(2,3-difluoro-6-methoxybenzyloxy)phenyl]-6-methoxy-2-methyl-7,9-dihydro-8H-purin-8-one A mixture of 4-chloro-6-methoxy-2-methyl-5-nitropyrimidine (0.14 g), ethyl 2-[4-amino-5-chloro-2-(2,3-difluoro-6-methoxybenzyloxy)phenoxy]acetate (0.23 g) and N,N-diisopropylethylamine (0.11 mL) in acetonitrile (3 mL) was stirred at 105° C. in a reaction vessel equipped with a reflux condenser for 17 hours. The reaction mixture was cooled to room temperature. To the reaction mixture were added ethyl acetate and water, and the resulting mixture was stirred at room temperature for 30 minutes. The organic layer was separated, and washed with water and brine, and dried over anhydrous sodium sulfate. The solvent was removed under reduced pressure, and the residue was purified by column chromatography on silica gel (eluent: n-hexane/ethyl acetate=4/1–2/3) to give ethyl 2-[5-chloro-2-(2,3-difluoro-6-methoxybenzyloxy)-4-(6-methoxy-2-methyl-5-nitropyrimidin-4-ylamino)phenoxy]acetate (0.16 g). To this material were added tetrahydrofuran (4 mL), methanol (2 mL) and 10% platinum-carbon powder (30 mg), and the mixture was stirred at room temperature under a hydrogen atmosphere for 3 hours. The insoluble material was removed by filtration, and the filtrate was concentrated under reduced pressure. To the residue was added ethyl acetate, and the mixture was concentrated under reduced pressure. The residue was dissolved in N,N-dimethylformamide (5 mL). To the solution was added 1,1'-carbonyldiimidazole (88 mg) at room temperature. To the mixture was added sodium hydride (55%, 59 mg) under ice-cooling, and the mixture was stirred at room temperature for 1.5 hours. The reaction mixture was poured into 1 mol/L hydrochloric acid, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=3/2−3/7) to give the title compound (70 mg).

Example 171

9-[2-Chloro-4-ethoxycarbonylmethoxy-5-(2-fluoro-6-methoxybenzyloxy)phenyl]-6-methoxy-2-methoxymethyl-7,9-dihydro-8H-purin-8-one A mixture of 4-chloro-6-methoxy-2-methoxymethyl-5-nitropyrimidine (0.64 g), ethyl 2-[4-amino-5-chloro-2-(2-fluoro-6-methoxybenzyloxy)phenoxy]acetate (0.96 g) and N,N-diisopropylethylamine (0.46 mL) in acetonitrile (10 mL) was stirred at 100° C. in a reaction vessel equipped with a reflux condenser for 15 hours. The reaction mixture was cooled to room temperature. To the reaction mixture were added ethyl acetate and water, and the resulting mixture was stirred at room temperature for 30 minutes. The organic layer was separated, and washed with water and brine, and dried over anhydrous sodium sulfate. The solvent was removed under reduced pressure, and the residue was purified by column chromatography on silica gel (eluent: n-hexane/ethyl acetate=2/1–2/3) to give ethyl 2-[4-chloro-2-(2-fluoro-6-methoxybenzyloxy)-4-(6-methoxy-2-methoxymethyl-5-nitropyrimidin-4-ylamino)phenoxy]acetate (0.47 g). To this material were added tetrahydrofuran (8 mL), methanol (4 mL) and 10% platinum-carbon powder (0.1 g), and the mixture was stirred at room temperature under a hydrogen atmosphere for 1 hour. The insoluble material was removed by filtration, and the filtrate was concentrated under reduced pressure. To the residue was added ethyl acetate, and the mixture was concentrated under reduced pressure. The residue was dissolved in tetrahydrofuran (8 mL). To the solution was added triphosgene (95 mg) at room temperature. To the mixture was added sodium hydride (55%, 122 mg) under ice-cooling, and the mixture was stirred at room temperature for 1 hour. The reaction mixture was poured into 1 mol/L hydrochloric acid, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=1/1–1/3) to give the title compound (0.35 g).

Examples 172 to 218

The compounds of Examples 172 to 218 were prepared in a similar manner to that described in Example 170 or Example 171 using the corresponding starting materials.

Examples 219 to 225

The compounds of Examples 219 to 225 were prepared in a similar manner to that described in Example 170 or Example 171 and Example 167 using the corresponding starting materials.

Examples 226 to 232

The compounds of Examples 226 to 232 were prepared in a similar manner to that described in Example 42 using the corresponding starting materials.

Example 233

The compound of Example 233 was prepared in a similar manner to that described in Example 170, Example 42 and Example 167 using the corresponding starting materials.

Example 234

9-[2-Chloro-5-(2,3-difluoro-6-methoxybenzyloxy)-4-hydroxyphenyl]-6-methoxy-2-methyl-7,9-dihydro-8H-purin-8-one To a solution of 9-[2-chloro-5-(2,3-difluoro-6-methoxybenzyloxy)-4-methoxy-methyloxyphenyl]-6-methoxy-2-methyl-7,9-dihydro-8H-purin-8-one (80 mg) in tetrahydrofuran (2 mL)-methanol (1 mL) was added concentrated hydrochloric acid (0.1 mL), and the mixture was stirred at room temperature for 2 hours, and then stirred at 60° C. for 1 hour. The reaction mixture was diluted with water, and the resulting mixture was extracted with ethyl acetate. The extract was washed with brine, and dried over anhydrous sodium sulfate. The solvent was removed under reduced pressure, and the residue was purified by column chromatography on silica gel (eluent: n-hexane/ethyl acetate=1/1–1/3) to give the title compound (22 mg).

Example 235

The compound of Example 235 was prepared in a similar manner to that described in Example 234 using the corresponding starting materials.

Examples 236 to 241

The compounds of Examples 236 to 241 were prepared in a similar manner to that described in Example 170 or Example 171 and Example 234 using the corresponding starting materials.

Example 242

6-Chloro-9-[2-chloro-5-(2,3-difluoro-6-methoxybenzyloxy)-4-methoxycarbonylmethoxyphenyl]-2-methyl-7,9-dihydro-8H-purin-8-one To a solution of 4,6-dichloro-2-methyl-5-nitropyrimidine (2.7 g) and N,N-diisopropylethylamine (1.19 mL) in acetonitrile (30 mL) was added a solution of methyl 2-[4-amino-5-chloro-2-(2,3-difluoro-6-methoxybenzyloxy)phenoxy]acetate (2.52 g) in acetonitrile (20 mL) in a dropwise manner under ice-cooling. The reaction mixture was allowed to warm slowly to room temperature, and stirred at room temperature overnight. To the reaction mixture were added ethyl acetate and water, and the resulting mixture was stirred at room temperature for 30 minutes. The insoluble material was removed by filtration, and the organic layer of the filtrate was separated. The organic layer was washed with brine, and dried over anhydrous sodium sulfate. The solvent was removed under reduced pressure, and the residue was purified by column chromatography on silica gel (eluent: n-hexane/ethyl acetate=2/1–1/1) to give methyl 2-[4-chloro-2-(2,3-difluoromethoxy-benzyloxy)-4-(6-chloro-2-methyl-5-nitropyrimidin-4-ylamino)phenoxy]acetate (0.82 g). To this material were added tetrahydrofuran (20 mL), methanol (20 mL) and 10% platinum-carbon powder (0.1 g), and the mixture was stirred at room temperature under a hydrogen atmosphere overnight. The insoluble material was removed by filtration, and the filtrate was concentrated under reduced pressure. The residue was dissolved in N,N-dimethylformamide (15 mL). To the solution were added 1,1'-carbonyldiimidazole (0.48 g) and sodium hydride (55%, 0.19 g), and the mixture was stirred at room temperature for 1 hour. The reaction mixture was poured into 1 mol/L hydrochloric acid, and the precipitated crystals were collected by filtration. The crystals were washed with water, and dried under reduced pressure to give the title compound (0.77 g).

Examples 243 and 244

The compounds of Examples 243 and 244 were prepared in a similar manner to that described in Example 242 using the corresponding starting materials.

Example 245

9-[2-Chloro-5-(2,3-difluoro-6-methoxybenzyloxy)-4-(2-hydroxyethoxy)phenyl]-6-methoxy-2-methyl-7,9-dihydro-8H-purin-8-one To a mixture of 9-[2-chloro-5-(2,3-difluoro-6-methoxybenzyloxy)-4-methoxy-carbonylmethoxyphenyl]-6-methoxy-2-methyl-7,9-dihydro-8H-purin-8-one (0.58 g) in ethanol (15 mL)-tetrahydrofuran (7.5 mL) was added sodium borohydride (0.2 g), and the mixture was stirred at room temperature overnight. The reaction mixture was poured into 1 mol/L hydrochloric acid, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=1/2–ethyl acetate) to give the title compound (0.52 g).

Example 246

9-[2-Chloro-5-(2-fluoro-6-methoxybenzyloxy)-4-(2-hydroxyethoxy)phenyl]-2-hydroxymethyl-6-methoxy-7,9-dihydro-8H-purin-8-one To a solution of 2-acetyloxymethyl-9-[2-chloro-4-ethoxycarbonylmethoxy-5-(2-fluoro-6-methoxybenzyloxy)phenyl]-6-methoxy-7,9-dihydro-8H-purin-8-one (0.1 g) in tetrahydrofuran (3.3 mL) was added diisobutylaluminium hydride (0.99 mol/L toluene solution, 1 mL) under ice-cooling, and the mixture was stirred at the same temperature for 2 hours, and then stirred at room temperature for 1 hour. To the reaction mixture was added 1 mol/L hydrochloric acid, and the resulting mixture was extracted with ethyl acetate. The extract was washed with brine, and dried over anhydrous magnesium sulfate. The solvent was removed under reduced pressure, and the residue was purified by column chromatography on silica gel (eluent: ethyl acetate–ethyl acetate/methanol=6/1) to give the title compound (30 mg).

Examples 247 to 261

The compounds of Examples 247 to 261 were prepared in a similar manner to that described in Example 245 or Example 246 using the corresponding starting materials.

Example 262

The compound of Example 262 was prepared in a similar manner to that described in Example 157 using the corresponding starting materials.

Example 263

9-[4-(2-Aminoethoxy)-2-chloro-5-(2,3-difluoro-6-methoxybenzyloxy)phenyl]-6-methoxy-2-methyl-7,9-dihydro-8H-purin-8-one hydrochloride To a solution of 9-[2-chloro-5-(2,3-difluoro-6-methoxybenzyloxy)-4-(2-hydroxy-ethoxy)phenyl]-6-methoxy-2-methyl-7,9-dihydro-8H-purin-8-one (50 mg) and triethylamine (0.016 mL) in methylene chloride (2 mL) was added methanesulfonyl chloride (0.008 mL) under ice-cooling, and the mixture was stirred at the same temperature for 30 minutes. The reaction mixture was poured into 0.5 mol/L hydrochloric acid, and the resulting mixture was extracted with ethyl acetate. The extract was washed with water and brine, and dried over anhydrous sodium sulfate. The solvent was removed under reduced pressure, and the residue was dissolved in N,N-dimethylformamide (2 mL). To the solution was added sodium azide (12 mg), and the mixture was stirred at 110° C. for 1 hour. The reaction mixture was poured into 0.5 mol/L hydrochloric acid, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=1/1–3/7) to give 9-[4-(2-azidoethoxy)-2-chloro-5-(2,3-difluoro-6-methoxybenzyloxy)phenyl]-6-methoxy-2-methyl-7,9-dihydro-8H-purin-8-one (45 mg). This material was dissolved in tetrahydrofuran (2 mL)-methanol (1 mL). To the solution was added 10% platinum-carbon powder (20 mg), and the mixture was stirred at room temperature under a hydrogen atmosphere for 3 hours. The insoluble material was removed by filtration, and the filtrate was concentrated under reduced pressure. The residue was dissolved in methanol. To the solution was added hydrochloric acid (4 mol/L ethyl acetate solution, 0.05 mL), and the mixture was concentrated under reduced pressure to give the title compound (39 mg).

Example 264

The compound of Example 264 was prepared in a similar manner to that described in Example 157 using 9-[4-(2-aminoethoxy)-2-chloro-5-(2,3-difluoro-6-methoxybenzyloxy)phenyl]-6-methoxy-2-methyl-7,9-dihydro-8H-purin-8-one hydrochloride instead of 3-{5-[6-(2-aminoethoxy)-2,3-difluorobenzyloxy]-2-chlorophenyl}-5-hydroxymethyl-1,3-dihydro-2H-imidazo[4,5-b]pyridin-2-one hydrochloride.

Example 265

9-[2-Chloro-5-(2,3-difluoro-6-methoxybenzyloxy)-4-(2-hydroxy-2-methyl-1-propoxy)-phenyl]-6-methoxy-2-methyl-7,9-dihydro-8H-purin-8-one To a solution of 9-[2-chloro-5-(2,3-difluoro-6-methoxybenzyloxy)-4-methoxy-carbonylmethoxyphenyl]-6-methoxy-2-methyl-7,9-dihydro-8H-purin-8-one (34 mg) in tetrahydrofuran (3 mL) was added methylmagnesium bromide (1 mol/L tetrahydrofuran solution, 031 mL) under ice-cooling, and the mixture was stirred at room temperature for 2 hours. To the reaction mixture was added 1 mol/L hydrochloric acid, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=1/1−1/4) to give the title compound (4 mg).

Example 266

6-(n-Butoxycarbonyl)-9-[2-chloro-5-(2,3-difluoro-6-methoxybenzyloxy)-4-(2-hydroxy-ethoxy)phenyl]-2-methyl-7,9-dihydro-8H-purin-8-one A mixture of 6-chloro-9-[2-chloro-5-(2,3-difluoro-6-methoxybenzyl-oxy)-4-(2-hydroxyethoxy)phenyl]-2-methyl-7,9-dihydro-8H-purin-8-one (0.62 g), palladium(II) acetate (26 mg), 1,3-bis(diphenylphosphino)propane (48 mg) and N,N-diisopropylethylamine (1.0 mL) in n-butanol (8 mL)-dimethyl sulfoxide (12 mL) was stirred at 110° C. under a carbon monoxide atmosphere in a reaction vessel equipped with a reflux condenser for 6 hours. The insoluble material was removed by filtration. To the filtrate was added 0.5 mol/L hydrochloric acid, and the resulting mixture was extracted with ethyl acetate. The extract was washed with water, and dried over anhydrous magnesium sulfate, and the solvent was removed under reduced pressure. The residual crystals were suspended in diethyl ether, and collected by filtration. The collected crystals were washed with diethyl ether, and dried under reduced pressure to give the title compound (0.55 g).

Examples 267 and 268

The compounds of Examples 267 and 268 were prepared in a similar manner to that described in Example 266 using the corresponding starting materials.

Example 269

9-[2-Chloro-5-(2,3-difluoro-6-methoxybenzyloxy)-4-methoxyphenyl]-6-hydroxymethyl-7,9-dihydro-8H-purin-8-one To a solution of 6-(n-butoxycarbonyl)-9-[2-chloro-5-(2,3-difluoro-6-methoxy-benzyloxy)-4-methoxyphenyl]-7,9-dihydro-8H-purin-8-one (0.82 g) in tetrahydrofuran (25 mL) was added diisobutylaluminium hydride (0.93 mol/L n-hexane solution, 4.03 mL) under ice-cooling, and the mixture was stirred at the same temperature for 30 minutes, and then stirred at room temperature for 3 hours. To the reaction mixture was added 1 mol/L hydrochloric acid, and the resulting mixture was extracted with ethyl acetate. The extract was washed with water and brine, and dried over anhydrous sodium sulfate. The solvent was removed under reduced pressure, and the residue was purified by column chromatography on silica gel (eluent: ethyl acetate) to give the title compound (0.6 g).

Example 270

9-[2-Chloro-5-(2,3-difluoro-6-methoxybenzyloxy)-4-methoxyphenyl]-6-formyl-7,9-dihydro-8H-purin-8-one To a solution of 9-[2-chloro-5-(2,3-difluoro-6-methoxybenzyloxy)-4-methoxyphenyl]-6-hydroxymethyl-7,9-dihydro-8H-purin-8-one (0.1%) in methylene chloride (3 mL) was added manganese(IV) oxide (272 mg), and the mixture was stirred at room temperature for 2 hours. The insoluble material was removed by filtration, and the filtrate was concentrated under reduced pressure. The residue was purified by column chromatography on silica gel (eluent: n-hexane/ethyl acetate=3/1–1/3) to give the title compound (80 mg).

Example 271

The compound of Example 271 was prepared in a similar manner to that described in Example 265 using the corresponding starting materials.

Example 272

The compound of Example 272 was prepared in a similar manner to that described in Example 270 using the corresponding starting materials.

Example 273

9-[4-Carboxymethoxy-2-chloro-5-(2,3-difluoro-6-methoxybenzyloxy)phenyl]-2-hydroxymethyl-6-methoxy-7,9-dihydro-8H-purin-8-one A mixture of 2-acetyloxymethyl-9-[2-chloro-4-ethoxycarbonylmethoxy-5-(2,3-difluoro-6-methoxybenzyloxy)phenyl]-6-methoxy-7,9-dihydro-8H-purin-8-one (60 mg) and lithium hydroxide monohydrate (81 mg) in tetrahydrofuran (4 mL)-methanol (2 mL)-water (2 mL) was stirred at room temperature for 1 hour. The reaction mixture was poured into 1 mol/L hydrochloric acid, and the resulting mixture was extracted with ethyl acetate. The extract was washed with water and brine, and dried over anhydrous sodium sulfate. The solvent was removed under reduced pressure to give the title compound (42 mg).

Examples 274 to 290

The compounds of Examples 274 to 290 were prepared in a similar manner to that described in Example 273 using the corresponding starting materials.

Examples 291 to 298

The compounds of Examples 291 to 298 were prepared in a similar manner to that described in Example 170 or Example 171 and Example 273 using the corresponding starting materials.

Example 299

2-Carboxy-9-[2-chloro-5-(2,3-difluoro-6-methoxybenzyloxy)-4-methoxyphenyl]-6-methoxy-7,9-dihydro-8H-purin-8-one To a mixture of concentrated sulfuric acid (0.23 mL) and water (0.4 mL) was added chromium(VI) oxide (0.27 g), and the total volume was adjusted to 1 mL by adding water.

To a solution of 9-[2-chloro-5-(2,3-difluoro-6-methoxybenzyloxy)-4-methoxyphenyl]-2-hydroxymethyl-6-methoxy-7,9-dihydro-8H-purin-8-one (0.14 g) in acetone (5 mL) was added this solution in a dropwise manner under ice-cooling, and the mixture was stirred at the same temperature for 10 minutes, and then stirred at room temperature overnight. To the reaction mixture was added 2-propanol (2 mL), and the mixture was stirred at room temperature for 20 minutes. To the mixture were added water and ethyl acetate, and the insoluble material was removed by filtration. The insoluble material was washed with water, ethyl acetate and diethyl ether successively. The filtrate and washings were combined, and the organic layer was separated. The organic layer was washed with water and brine, and dried over anhydrous sodium sulfate. The solvent was removed under reduced pressure, and the residue was purified by column chromatography on silica gel (eluent: ethyl acetate–ethyl acetate/methanol=1/1) to give the title compound (4 mg).

Example 300

9-[4-Carboxy-2-chloro-5-(2,3-difluoro-6-methoxybenzyloxy)phenyl]-6-methoxy-2-methyl-7,9-dihydro-8H-purin-8-one To a solution of 9-[2-chloro-5-(2,3-difluoro-6-methoxybenzyloxy)-4-hydroxy-methylphenyl]-6-methoxy-2-methyl-7,9-dihydro-8H-purin-8-one (11 mg) in methylene chloride (2 mL) was added 1,1,1-tris(acetyloxy)-1,1-dihydro-1,2-benziodoxol-3(1H)-one (19 mg), and the mixture was stirred at room temperature for 1 hour. The reaction mixture was purified by column chromatography on silica gel (eluent: n-hexane/ethyl acetate=3/2–1/3) to give 9-[2-chloro-5-(2,3-difluoro-6-methoxybenzyloxy)-4-formylphenyl]-6-methoxy-2-methyl-7,9-dihydro-8H-purin-8-one (9 mg). To this material were added tert-butanol (1 mL), water (0.5 mL), tetrahydrofuran (1 mL), sodium dihydrogen phosphate (4 mg), 2-methyl-2-butene (0.006 mL) and sodium chlorite (6 mg) successively, and the mixture was stirred at 30° C. for 3 hours. The reaction mixture was poured into 1 mol/L hydrochloric acid, and the resulting mixture was extracted with ethyl acetate. The extract was washed with water and brine, and dried over anhydrous sodium sulfate, and the solvent was removed under reduced pressure. The residual crystals were suspended in a mixed solvent (n-hexane/ethyl acetate=3/1), and collected by filtration. The collected crystals were dried under reduced pressure to give the title compound (4 mg).

Example 301

The compound of Example 301 was prepared in a similar manner to that described in Example 300 using the corresponding starting materials.

Example 302

9-[2-Chloro-4-ethoxycarbonylmethoxy-5-(2,3-difluoro-6-methoxybenzyloxy)phenyl]-2-(1-hydroxyethyl)-6-methoxy-7,9-dihydro-8H-purin-8-one To a solution of 2-(1-acetyloxyethyl)-9-[2-chloro-4-ethoxycarbonylmethoxy-5-(2,3-difluoro-6-methoxybenzyloxy)phenyl]-6-methoxy-7,9-dihydro-8H-purin-8-one (0.33 g), which was prepared in a similar manner to that described in Example 171 using 2-(1-acetyloxyethyl)-4-chloro-6-methoxy-5-nitropyrimidine and ethyl 2-[4-amino-5-chloro-2-(2,3-difluoro-6-methoxybenzyloxy)phenoxy]acetate instead of 4-chloro-6-methoxy-2-methoxymethyl-5-nitropyrimidine and ethyl 2-[4-amino-5-chloro-2-(2-fluoro-6-methoxy-benzyloxy)phenoxy]acetate, respectively, in ethanol (2 mL)-tetrahydrofuran (3 mL) was added sodium ethoxide (20% ethanol solution, 0.5 mL), and the mixture was stirred at room temperature for 3 hours. The reaction mixture was poured into 1 mol/L hydrochloric acid, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=1/1–1/9) to give the title compound (0.17 g)

Example 303

The compound of Example 303 was prepared in a similar manner to that described in Example 302 using the corresponding starting materials.

Example 304

2-Acetyl-9-[2-chloro-4-ethoxycarbonylmethoxy-5-(2,3-difluoro-6-methoxybenzyloxy)-phenyl]-6-methoxy-7,9-dihydro-8H-purin-8-one To a solution of 9-[2-chloro-4-ethoxycarbonylmethoxy-5-(2,3-difluoro-6-methoxy-benzyloxy)phenyl]-2-(1-hydroxyethyl)-6-methoxy-7,9-dihydro-8H-purin-8-one (0.17 g) in methylene chloride (3 mL) was added 1,1,1-tris(acetyloxy)-1,1-dihydro-1,2-benziodoxol-3(1H)-one (0.37 g), and the mixture was stirred at room temperature for 3 hours. The reaction mixture was purified by column chromatography on silica gel (eluent: n-hexane/ethyl acetate=1/1–1/6) to give the title compound (0.1 g)

Examples 305 and 306

The compounds of Examples 305 and 306 were prepared in a similar manner to that described in Example 304 using the corresponding starting materials.

Example 307

2-Acetyl-9-[2-chloro-5-(2,3-difluoro-6-methoxybenzyloxy)-4-(2-hydroxyethoxy)phenyl]-6-methoxy-7,9-dihydro-8H-purin-8-one A mixture of 2-acetyl-9-[2-chloro-4-ethoxycarbonylmethoxy-5-(2,3-difluoro-6-methoxybenzyloxy)phenyl]-6-methoxy-7,9-dihydro-8H-purin-8-one (0.18 g), p-toluenesulfonic acid monohydrate (12 mg), trimethyl orthoformate (1 mL) and methanol (1 mL) was heated at reflux overnight. The reaction mixture was concentrated under reduced pressure, and the residue was purified by column chromatography on silica gel (eluent: n-hexane/ethyl acetate=1/1–ethyl acetate) to give 9-[2-chloro-4-ethoxycarbonylmethoxy-5-(2,3-difluoro-6-methoxybenzyloxy)phenyl]-6-methoxy-2-(1,1-dimethoxyethyl)-7,9-dihydro-8H-purin-8-one (74 mg). This material was dissolved in ethanol (1 mL)-tetrahydrofuran (1 mL). To the solution was added sodium borohydride (45 mg), and the mixture was stirred at room temperature overnight. To the reaction mixture was added 1 mol/L hydrochloric acid, and the resulting mixture was extracted with ethyl acetate. The extract was washed with water and brine, and dried over anhydrous sodium sulfate. The solvent was removed under reduced pressure, and the residue was dissolved in tetrahydrofuran (2 mL). To the solution were added concentrated hydrochloric acid (0.1 mL) and water (0.1 mL), and the mixture was stirred at room temperature for 2 hours. The reaction mixture was diluted with water, and the resulting mixture was extracted with ethyl acetate. The extract was washed with water and brine, and dried over anhydrous sodium sulfate. The solvent was removed under reduced pressure, and the residue was purified by column chromatography on silica gel (eluent: ethyl acetate) to give the title compound (25 mg).

Examples 308 and 309

The compounds of Examples 308 and 309 were prepared in a similar manner to that described in Example 273 using the corresponding starting materials.

Example 310

2-Carboxymethyl-9-[2-chloro-5-(2,3-difluoro-6-methoxybenzyloxy)-4-methoxyphenyl]-6-methoxy-7,9-dihydro-8H-purin-8-one A mixture of 2,4-dichloro-6-methoxy-5-nitropyrimidine (0.24 g), 2-chloro-5-(2,3-difluoro-6-methoxybenzyloxy)-4-methoxyaniline (0.26 g) and N,N-diisopropylethylamine (0.15 mL) in acetonitrile (4 mL) was stirred at room temperature overnight. To the reaction mixture were added ethyl acetate and water, and the resulting mixture was stirred at room temperature for 30 minutes. The insoluble material was removed by filtration, and the organic layer of the filtrate was separated. The organic layer was washed with water and brine, and dried over anhydrous sodium sulfate. The solvent was removed under reduced pressure, and the residue was purified by column chromatography on silica gel (eluent: n-hexane/ethyl acetate=2/1–1/2) to give 2-chloro-N-(2-chloro-6-methoxy-5-nitropyrimidin-4-yl)-5-(2,3-difluoro-6-methoxybenzyloxy)-4-methoxyaniline (0.4 g). A mixture of 2-chloro-N-(2-chloro-6-methoxy-5-nitropyrimidin-4-yl)-5-(2,3-difluoro-6-methoxy-benzyloxy)-4-methoxyaniline (0.29 g), diethyl malonate (0.1 mL) and cesium carbonate (1.83 g) in 1,2-dimethoxyethane (2 mL) was stirred at 100° C. in a reaction vessel equipped with a reflux condenser for 6 hours. The reaction mixture was poured into 1 mol/L hydrochloric acid, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=2/1–1/1) to give diethyl 2-{-4-[2-chloro-5-(2,3-difluoro-6-methoxybenzyloxy)-4-methoxyphenylamino]-6-methoxy-5-nitropyrimidin-2-yl}malonate (0.27 g). To this material were added tetrahydrofuran (6 mL); methanol (2 mL) and 10% platinum-carbon powder (50 mg), and the mixture was stirred at room temperature under a hydrogen atmosphere for 4 hours. The insoluble material was removed by filtration, and the filtrate was concentrated under reduced pressure. To the residue was added ethyl acetate, and the mixture was concentrated under reduced pressure. The residue was dissolved in tetrahydrofuran (5 mL). To the solution were added triphosgene (50 mg) and sodium hydride (55%, 64 mg) under ice-cooling, and the mixture was stirred at room temperature for 1 hour. The reaction mixture was poured into 1 mol/L hydrochloric acid, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=3/2–3/7) to give 9-[2-chloro-5-(2,3-difluoro-6-methoxybenzyloxy)-4-methoxyphenyl]-2-bis(ethoxycarbonyl)methyl-6-methoxy-7,9-dihydro-8H-purin-8-one (0.2 g). The mixture of the obtained 9-[2-chloro-5-(2,3-difluoro-6-methoxybenzyloxy)-4-methoxyphenyl]-2-bis(ethoxycarbonyl)methyl-6-methoxy-7,9-dihydro-8H-purin-8-one (80 mg), lithium hydroxide monohydrate (0.11 g), tetrahydrofuran (3 mL), methanol (1.5 mL) and water (1.5 mL) was stirred at room temperature overnight. The reaction mixture was poured into 1 mol/L hydrochloric acid, and the resulting mixture was extracted with ethyl acetate. The extract was washed with water and brine, and dried over anhydrous sodium sulfate. The solvent was removed under reduced pressure to give the title compound (67 mg).

Examples 311 and 312

The compounds of Examples 311 and 312 were prepared in a similar manner to that described in Example 310 using the corresponding starting materials.

Example 313

2-Carboxymethyl-9-[2-chloro-5-(2-fluoro-6-methoxybenzyloxy)-4-(2-hydroxyethoxy)-phenyl]-6-methoxy-7,9-dihydro-8H-purin-8-one To a solution of 9-{-4-[2-(tert-butyldimethylsilyloxy)ethoxy]-2-chloro-5-(2-fluoro-6-methoxybenzyloxy)phenyl}-2-bis(ethoxycarbonyl)methyl-6-methoxy-7,9-dihydro-8H-purin-8-one (0.32 g), which was prepared in a similar manner to that described in Example 310 using 4-[2-(tert-butyldimethylsilyloxy)ethoxy]-2-chloro-5-(2-fluoro-6-methoxy-benzyloxy)aniline instead of 2-chloro-5-(2,3-difluoro-6-methoxybenzyloxy)-4-methoxyaniline, in tetrahydrofuran (4.2 mL) was added tetra(n-butyl)ammonium fluoride (1 mol/L tetrahydrofuran solution, 8.4 mL), and the mixture was stirred at room temperature for 2.5 hours. The reaction mixture was concentrated under reduced pressure, and the residue was purified by column chromatography on silica gel (eluent: ethyl acetate-ethyl acetate/methanol=9/1) to give 9-[2-chloro-5-(2-fluoro-6-methoxybenzyloxy)-4-(2-hydroxyethoxy)-phenyl]-2-bis(ethoxycarbonyl)methyl-6-methoxy-7,9-dihydro-8H-purin-8-one (0.24 g). To this material were added tetrahydrofuran (7 mL), methanol (3.5 mL), water (3.5 mL) and lithium hydroxide monohydrate (0.31 g), and the mixture was stirred at room temperature overnight. The reaction mixture was poured into 1 mol/L hydrochloric acid, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: ethyl acetate–ethyl acetate/methanol=7/3) to give the title compound (0.14 g).

Example 314

9-[2-Chloro-5-(2-fluoro-6-methoxybenzyloxy)-4-methoxyphenyl]-2-(2-hydroxyethyl)-6-methoxy-7,9-dihydro-8H-purin-8-one To a solution of 2-carboxymethyl-9-[2-chloro-5-(2-fluoro-6-methoxy-benzyloxy)-4-methoxyphenyl]-6-methoxy-7,9-dihydro-8H-purin-8-one (20 mg) in tetrahydrofuran (2 mL) was added borane-tetrahydrofuran complex (1.03 mol/L tetrahydrofuran solution, 0.08 mL) under ice-cooling, and the mixture was stirred at the same temperature for 30 minutes, and then stirred at room temperature for 4 hours. To the reaction mixture was added 1 mol/L hydrochloric acid, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: n-hexane/ethyl acetate=1/1–ethyl acetate) to give the title compound (11 mg).

Example 315

The compound of Example 315 was prepared in a similar manner to that described in Example 314 using the corresponding starting materials.

Example 316

9-[2-Chloro-5-(2,3-difluoro-6-methoxybenzyloxy)-4-methoxyphenyl]-2-ethoxycarbonyl-methyl-6-methoxy-7,9-dihydro-8H-purin-8-one A mixture of 2-carboxymethyl-9-[2-chloro-5-(2,3-difluoro-6-methoxybenzyl-oxy)-4-methoxyphenyl]-6-methoxy-7,9-dihydro-8H-purin-8-one (67 mg) and p-toluenesulfonic acid monohydrate (5 mg) in ethanol (4 mL) was heated at reflux for 2 hours. The reaction mixture was concentrated under reduced pressure, and the residue was purified by column chromatography on silica gel (eluent: n-hexane/ethyl acetate=1/1–1/9) to give the title compound (65 mg).

Example 317

2-[5-Chloro-2-(2,3-difluoro-6-methoxybenzyloxy)-4-(6-methoxy-2-methyl-7,9-dihydro-8H-purin-8-one-9-yl)phenoxy]-N-methylacetamide To a solution of 9-[4-carboxymethoxy-2-chloro-5-(2,3-difluoro-6-methoxy-benzyloxy)phenyl]-6-methoxy-2-methyl-7,9-dihydro-8H-purin-8-one (80 mg) in tetrahydrofuran (2 mL) was added 1,1'-carbonyldiimidazole (48 mg), and the mixture was stirred at room temperature for 30 minutes. To the reaction mixture was added methylamine (40% methanol solution, 1 mL), and the mixture was stirred at room temperature overnight. The reaction mixture was poured into 2 mol/L hydrochloric acid, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: ethyl acetate–ethyl acetate/methanol=6/1) to give the title compound (63 mg).

Example 318

2-[5-Chloro-2-(2-fluoro-6-methoxybenzyloxy)-4-(2-hydroxymethyl-6-methoxy-7,9-dihydro-8H-purin-8-one-9-yl)phenoxy]-N-methylacetamide To a mixture of 9-[4-carboxymethoxy-2-chloro-5-(2-fluoro-6-methoxybenzyloxy)-phenyl]-2-hydroxymethyl-6-methoxy-7,9-dihydro-8H-purin-8-one (0.1 g), 40% aqueous methylamine solution (0.06 mL), 1-hydroxybenzo[r]azole monohydrate (34 mg) and triethylamine (0.1 mL) in N,N-dimethylformamide (2 mL) was added 1-ethyl-3-(3-dimethylaminopropyl)carbodiimide hydrochloride (72 mg), and the mixture was stirred at 60° C. overnight. The reaction mixture was poured into 1 mol/L hydrochloric acid, and the resulting mixture was extracted with ethyl acetate. The extract was washed with brine, and dried over anhydrous magnesium sulfate. The solvent was removed under reduced pressure, and the residue was purified by column chromatography on silica gel (eluent: ethyl acetate–ethyl acetate/methanol=9/1) to give the title compound (54 mg).

Examples 319 to 377

The compounds of Examples 319 to 377 were prepared in a similar manner to that described in Example 317 or Example 318 using the corresponding starting materials.

Examples 378 and 379

The compounds of Examples 378 and 379 were prepared in a similar manner to that described in Example 273 using the corresponding starting materials.

Example 380

9-[2-Chloro-5-(2,3-difluoro-6-methoxybenzyloxy)-4-methoxyphenyl]-6-methyl-7,9-dihydro-8H-purin-8-one A solution of ethyl 4-chloro-6-methylpyrimidine-5-carboxylate (0.3 g), 2-chloro-5-(2,3-difluoro-6-methoxybenzyloxy)-4-methoxyaniline (0.49 g) and N,N-diisopropylethylamine (0.26 mL) in acetonitrile (4.5 mL) was stirred at 130° C. in a reaction vessel equipped with a reflux condenser for 1 day. To the reaction mixture was added water (3 mL), and the resulting mixture was stirred at room temperature for 40 minutes. The insoluble material was collected by filtration. The collected material was washed with water and diethyl ether, and dried under reduced pressure to give ethyl 4-[2-chloro-5-(2,3-difluoro-6-methoxybenzyloxy)-4-methoxyphenylamino]-6-methylpyrimidine-5-carboxylate (0.71 g). The obtained ethyl 4-[2-chloro-5-(2,3-difluoro-6-methoxybenzyloxy)-4-methoxyphenylamino]-6-methylpyrimidine-5-carboxylate (0.2 g) was dissolved in tetrahydrofuran (1.6 mL)–methanol (1.2 mL). To the solution was added 2 mol/L aqueous sodium hydroxide solution (1.2 mL), and the mixture was stirred at 60° C. for 30 minutes. To the reaction mixture was added 1 mol/L hydrochloric acid (3 mL), and the precipitated crystals were collected by filtration. The collected crystals were washed with water, and dried under reduced pressure to give 4-[2-chloro-5-(2,3-difluoro-6-methoxybenzyloxy)-4-methoxyphenylamino]-6-methylpyrimidine-5-carboxylic acid (0.1 g). To this material were added 1,4-dioxane (4.5 mL), triethylamine (0.12 mL) and diphenylphosphoryl azide (0.071 mL), and the mixture was stirred at room temperature for 1 hour, and then heated at reflux for 1 hour. The reaction mixture was concentrated under reduced pressure, and the residue was purified by column chromatography on silica gel (eluent: ethyl acetate–ethyl acetate/methanol=9/1) to give the title compound (0.1 g).

Example 381

2-Amino-9-[2-chloro-5-(2,3-difluoro-6-methoxybenzyloxy)-4-methoxyphenyl]-6-methyl-7,9-dihydro-8H-purin-8-one To a suspension of methyl 2-chloro-4-[2-chloro-5-(2,3-difluoro-6-methoxy-benzyloxy)-4-methoxyphenylamino]-6-methylpyrimidine-5-carboxylate (0.42 g), which was prepared in a similar manner to that described in Example 380 using methyl 2,4-dichloro-6-methylpyrimidine-5-carboxylate instead of ethyl 4-chloro-6-methylpyrimidine-5-carboxylate, in N,N-dimethylformamide (12 mL) were added water (2 mL) and sodium azide (0.26 g), and the mixture was stirred at 60° C. for 2 hours. To the reaction mixture was added water, and the resulting mixture was extracted with ethyl acetate. The extract was washed with water and brine, and dried over anhydrous magnesium sulfate, and the solvent was removed under reduced pressure. To the residue were added tetrahydrofuran (12 mL), methanol (12 mL) and 10% platinum-carbon powder (0.1 g), and the mixture was stirred at room temperature under a hydrogen atmosphere for 3 hours. To the mixture were added tetrahydrofuran (12 mL) and 2 mol/L aqueous sodium hydroxide solution (12 mL), and the resulting mixture was stirred at 60° C. for 2 hours. The insoluble material was removed by filtration, and the filtrate was acidified by adding 1 mol/L hydrochloric acid. The precipitated crystals were collected by filtration. The crystals were washed with water, and dried under reduced pressure to give 2-amino-4-[2-chloro-5-(2,3-difluoro-6-methoxy-benzyloxy)-4-methoxyphenylamino]-6-methylpyrimidine-5-carboxylic acid (0.35 g). To this material were added 1,4-dioxane (30 mL), tetrahydrofuran (10 mL), triethylamine (3 mL) and diphenylphosphoryl azide (0.38 mL), and the reaction vessel was equipped with a reflux condenser, and the mixture was stirred at 100° C. overnight. The reaction mixture was concentrated under reduced pressure, and the residue was purified by column chromatography on silica gel (eluent: ethyl acetate–ethyl acetate/methanol=10/1) to give the title compound (0.2 g).

Example 382

9-[2-Chloro-5-(2,3-difluoro-6-methoxybenzyloxy)-4-methoxycarbonylmethoxyphenyl]-2,6-dimethyl-7,9-dihydro-8H-purin-8-one To a solution of methyl 2-[4-amino-5-chloro-2-(2,3-difluoro-6-methoxybenzyloxy)-phenoxy]acetate (0.3 g) and N,N-diisopropylethylamine (0.14 mL) in acetonitrile (6 mL) was added 4,6-dichloro-2-methyl-5-nitropyrimidine (0.48 g) at −20° C., and the reaction mixture was allowed to warm slowly to room temperature, and stirred at room temperature overnight. To the reaction mixture were added ethyl acetate and water, and the resulting mixture was stirred at room temperature for 30 minutes. The insoluble material was removed by filtration, and the organic layer of the filtrate was separated. The organic layer was washed with 10% aqueous sodium chloride solution and brine, and dried over anhydrous sodium sulfate. The solvent was removed under reduced pressure, and the residue was purified by column chromatography on silica gel (eluent: n-hexane/ethyl acetate=2/1–1/1) to give methyl 2-[5-chloro-4-(6-chloro-2-methyl-5-nitropyrimidin-4-ylamino)-2-(2,3-difluoro-6-methoxybenzyloxy)phenoxy]acetate (0.21 g). To this material were added 1,2-dimethoxyethane (10 mL), diethyl malonate (0.068 mL) and cesium carbonate (0.37 g), and the reaction vessel was equipped with a reflux condenser, and the mixture was stirred at 110° C. for 3 hours. The reaction mixture was cooled to room temperature. The reaction mixture was poured into 1 mol/L hydrochloric acid, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=2/1–1/1) to give diethyl 2-{6-[2-chloro-5-(2,3-difluoro-6-methoxybenzyloxy)-4-methoxycarbonyl-methoxyphenylamino]-2-methyl-5-nitropyrimidin-4-yl}malonate (0.13 g). This material was dissolved in dimethyl sulfoxide (3 mL). To the solution were added lithium chloride (63 mg) and water (13 mg), and the mixture was stirred at 100° C. overnight. The reaction mixture was poured into water, and the resulting mixture was extracted with ethyl acetate. The extract was washed with water and brine, and dried over anhydrous sodium sulfate, and the solvent was removed under reduced pressure. To the residue were added tetrahydrofuran (3 mL), methanol (3 mL) and 10% platinum-carbon powder (40 mg), and the mixture was stirred at room temperature under a hydrogen atmosphere for 2 hours. The insoluble material was removed by filtration, and the filtrate was concentrated under reduced pressure. The residue was purified by column chromatography on silica gel (eluent: n-hexane/ethyl acetate=3/2–1/4–ethyl acetate/methanol=9/1–3/2) to give methyl 2-[4-(5-amino-2,6-dimethylpyrimidin-4-ylamino)-5-chloro-2-(2,3-difluoro-6-methoxybenzyloxy)phenoxy]acetate (21 mg). This material was suspended in tetrahydrofuran (3 mL). To the suspension was added triphosgene (6 mg) at room temperature. To the mixture was added sodium hydride (55%, 6 mg) under ice-cooling, and the mixture was stirred at room temperature for 1 hour. The reaction mixture was poured into 1 mol/L hydrochloric acid, and the resulting mixture was extracted with ethyl acetate. The extract was washed with water and brine, and dried over anhydrous sodium sulfate. The solvent was removed under reduced pressure, and the residue was purified by column chromatography on silica gel (eluent: ethyl acetate–ethyl acetate/methanol=10/1) to give the title compound (14 mg).

Example 383

The compound of Example 383 was prepared in a similar manner to that described in Example 382 using the corresponding starting materials.

Example 384

The compound of Example 384 was prepared in a similar manner to that described in Example 273 using the corresponding starting materials.

Example 385

The compound of Example 385 was prepared in a similar manner to that described in Example 38 using the corresponding starting materials.

Examples 386 to 395

The compounds of Examples 386 to 395 were prepared in a similar manner to that described in Example 170 using the aniline derivatives prepared using the corresponding starting materials in a similar manner to that described in Reference Example 152, instead of ethyl 2-[4-amino-5-chloro-2-(2,3-difluoro-6-methoxybenzyloxy)phenoxy]acetate.

Example 396

2-Carboxymethoxy-9-[2-chloro-5-(2,3-difluoro-6-methoxybenzyloxy)-4-methoxyphenyl]-6-methoxy-7,9-dihydro-8H-purin-8-one To a solution of 2-chloro-N-(2-chloro-6-methoxy-5-nitropyrimidin-4-yl)-5-(2,3-difluoro-6-methoxybenzyloxy)-4-methoxyaniline (0.13 g) and ethyl glycolate (38 mg) in 1-methyl-2-pyrrolidone (2 mL) was added sodium hydride (55%, 21 mg) under ice-cooling, and the mixture was stirred at 80° C. overnight. The reaction mixture was poured into 1 mol/L hydrochloric acid, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=7/3–2/3) to give ethyl 2-{4-[2-chloro-5-(2,3-difluoro-6-methoxybenzyloxy)-4-methoxyphenylamino]-6-methoxy-5-nitropyrimidin-2-yloxy}acetate (22 mg). The title compound was prepared in a similar manner to that described in Example 310 using this material instead of diethyl 2-{4-[2-chloro-5-(2,3-difluoro-6-methoxybenzyloxy)-4-methoxyphenylamino]-6-methoxy-5-nitropyrimidin-2-yl}malonate.

Example 397

2-Amino-9-[2-chloro-5-(2,3-difluoro-6-methoxybenzyloxy)-4-methoxyphenyl]-6-methoxy-7,9-dihydro-8H-purin-8-one To a solution of 2-chloro-N-(2-chloro-6-methoxy-5-nitropyrimidin-4-yl)-5-(2,3-difluoro-6-methoxybenzyloxy)-4-methoxyaniline (0.33 g) in 1-methyl-2-pyrrolidone (5 mL) was added potassium phthalimide (0.26 g), and the mixture was stirred at 65° C. for 2 hours. The reaction mixture was poured into 0.5 mol/L hydrochloric acid, and the resulting mixture was extracted with ethyl acetate. The extract was washed with water and brine, and dried over anhydrous sodium sulfate, and the solvent was removed under reduced pressure. The residual solids were suspended in a mixed solvent (n-hexane/ethyl acetate=2/1), and collected by filtration. The collected solids were dried under reduced pressure to give 2-chloro-N-[6-methoxy-5-nitropyrimidin-2-(1,3-dioxo-1,3-dihydroisoindol-2-yl)-4-yl]-difluoro-6-methoxybenzyloxy)-4-methoxyaniline (0.26 g). To this material were added tetrahydrofuran (8 mL), methanol (3 mL) and 10% platinum-carbon powder (50 mg), and the mixture was stirred at room temperature under a hydrogen atmosphere for 5 hours. The insoluble material was removed by filtration, and the filtrate was concentrated under reduced pressure. To the suspension of the residue in tetrahydrofuran (6 mL) was added triphosgene (50 mg) at room temperature. To the mixture was added sodium hydride (55%, 64 mg) under ice-cooling, and the mixture was stirred at room temperature for 1 hour. The reaction mixture was poured into 1 mol/L hydrochloric acid, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ ethyl acetate=1/1–1/9) to give 9-[2-chloro-5-(2,3-difluoro-6-methoxybenzyloxy)-4-methoxyphenyl]-6-methoxy-2-(1,3-dioxo-1,3-dihydroisoindol-2-yl)-7,9-dihydro-8H-purin-8-one (0.1 g). This material was dissolved in tetrahydrofuran (3 mL). To the solution was added hydrazine monohydrate (0.039 mL), and the reaction vessel was equipped with a reflux condenser, and the mixture was stirred at 90° C. for 2 hours. The reaction mixture was diluted with ethyl acetate, and the insoluble material was removed by filtration. The filtrate was concentrated under reduced pressure, and the residue was purified by column chromatography on silica gel (eluent: n-hexane/ethyl acetate=1/1–ethyl acetate) to give the title compound (71 mg).

Example 398

2-Amino-9-[2-chloro-5-(2-fluoro-6-methoxybenzyloxy)-4-methoxyphenyl]-6-methoxy-7,9-dihydro-8H-purin-8-one To a solution of 2,4-dichloro-6-methoxy-5-nitropyrimidine (1.79 g) in acetonitrile (21 mL) were added 2-chloro-5-(2-fluoro-6-methoxybenzyloxy)-4-methoxyaniline (2.18 g) and N,N-diisopropylethylamine (1.28 mL), and the mixture was stirred at 40° C. for 3 days. To the reaction mixture was added water, and the resulting mixture was extracted with ethyl acetate. The extract was washed with water and brine, and dried over anhydrous sodium sulfate, and the solvent was removed under reduced pressure. The residual solids were suspended in a mixed solvent (n-hexane/ethyl acetate=3/1), and collected by filtration. The collected solids were dried under reduced pressure to give 2-chloro-N-(2-chloro-6-methoxy-5-nitropyrimidin-4-yl)-5-(2-fluoro-6-methoxybenzyloxy)-4-methoxyaniline (3.15 g). The title compound was prepared in a similar manner to that described in Example 397 using this material instead of 2-chloro-N-(2-chloro-6-methoxy-5-nitropyrimidin-4-yl)-5-(2,3-difluoro-6-methoxybenzyloxy)-4-methoxyaniline.

Example 399

2-Chloro-9-[2-chloro-5-(2-fluoro-6-methoxybenzyloxy)-4-methoxyphenyl]-6-methoxy-7,9-dihydro-8H-purin-8-one The title compound was prepared in a similar manner to that described in Example 171 using 2-chloro-N-(2-chloro-6-methoxy-5-nitropyrimidin-4-yl)-5-(2-fluoro-6-methoxybenzyloxy)-4-methoxyaniline instead of ethyl 2-[4-chloro-2-(2-fluoro-6-methoxy-benzyloxy)-4-(6-methoxy-2-methoxymethyl-5-nitropyrimidin-4-ylamino)phenoxy]acetate.

Example 400

2-Acetylamino-9-[2-chloro-5-(2,3-difluoro-6-methoxybenzyloxy)-4-methoxyphenyl]-6-methoxy-7,9-dihydro-8H-purin-8-one A mixture of 2-amino-9-[2-chloro-5-(2,3-difluoro-6-methoxybenzyloxy)-4-methoxyphenyl]-6-methoxy-7,9-dihydro-8H-purin-8-one (29 mg) and acetic anhydride (3 mL) was stirred at 110° C. in a reaction vessel equipped with a reflux condenser for 3 hours. The reaction mixture was concentrated under reduced pressure, and the residue was dissolved in methanol (2 mL). To the solution were added sodium methoxide (28% methanol solution, 2 mL) and water (1 mL), and the mixture was stirred at room temperature for 15 minutes. The reaction mixture was poured into 1 mol/L hydrochloric acid, and the resulting mixture was extracted with ethyl acetate. The extract was washed with water and brine, and dried over anhydrous sodium sulfate, and the solvent was removed under reduced pressure. To the residue was added a mixed solvent (n-hexane/ethyl acetate=1/1), and the precipitated crystals were collected by filtration. The collected crystals were washed with diethyl ether, and dried under reduced pressure to give the title compound (20 mg).

Example 401

9-[2-Chloro-5-(2,3-difluoro-6-methoxybenzyloxy)-4-methoxyphenyl]-6-methoxy-2-dimethylamino-7,9-dihydro-8H-purin-8-one A mixture of 2-chloro-N-(2-chloro-6-methoxy-5-nitropyrimidin-4-yl)-5-(2,3-difluoro-6-methoxybenzyloxy)-4-methoxyaniline (0.1 g), dimethylamine hydrochloride (41 mg) and N,N-diisopropylethylamine (0.13 mL) in acetonitrile (2 mL) was stirred at 60° C. for 2 hours. The reaction mixture was diluted with water, and the precipitated crystals were collected by filtration. The crystals were washed with water and diethyl ether, and dried under reduced pressure to give 2-chloro-5-(2,3-difluoro-6-methoxybenzyloxy)-N-(6-methoxy-2-dimethylamino-5-nitropyrimidin-4-yl)-4-methoxyaniline (86 mg). The title compound was prepared in a similar manner to that described in Example 171 using this material instead of ethyl 2-[4-chloro-2-(2-fluoro-6-methoxybenzyloxy)-4-(6-methoxy-2-methoxymethyl-5-nitropyrimidin-4-ylamino)phenoxy]acetate.

Example 402

9-[2-Chloro-5-(2,3-difluoro-6-methoxybenzyloxy)-4-methoxyphenyl]-2-(2-hydroxyacetyl-amino)-6-methoxy-7,9-dihydro-8H-purin-8-one To a mixture of 2-amino-9-[2-chloro-5-(2,3-difluoro-6-methoxybenzyloxy)-4-methoxyphenyl]-6-methoxy-7,9-dihydro-8H-purin-8-one (40 mg) and N,N-diisopropyl-ethylamine (0.15 mL) in ethyl acetate (4 mL) was added acetoxyacetyl chloride (0.078 mL), and the mixture was stirred at room temperature overnight. To the reaction mixture was added 1 mol/L hydrochloric acid, and the resulting mixture was extracted with ethyl acetate. The extract was washed with water and brine, and dried over anhydrous sodium sulfate. The solvent was removed under reduced pressure, and the residue was dissolved in methanol (1 mL)-tetrahydrofuran (2 mL). To the solution was added sodium methoxide (28% methanol solution, 0.05 mL), and the mixture was stirred at room temperature for 1 hour. To the reaction mixture was added 1 mol/L hydrochloric acid, and the mixture was poured into a saturated aqueous ammonium chloride solution, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=1/1–ethyl acetate) to give the title compound (4 mg).

Example 403

2-Carboxymethylamino-9-[2-chloro-5-(2,3-difluoro-6-methoxybenzyloxy)-4-methoxyphenyl]-6-methoxy-7,9-dihydro-8H-purin-8-one To a mixture of 9-[2-chloro-5-(2,3-difluoro-6-methoxybenzyloxy)-4-methoxyphenyl]-6-methoxy-2-(1,3-dioxo-1,3-dihydroisoindol-2-yl)-7,9-dihydro-8H-purin-8-one (0.27 g), potassium carbonate (0.12 g) and sodium iodide (13 mg) in N,N-dimethylformamide (5 mL) was added 1-bromo-3,3-dimethoxypropane (0.087 mL), and the mixture was stirred at room temperature overnight. The reaction mixture was poured into water, and the resulting mixture was extracted with ethyl acetate. The extract was washed with water and brine, and dried over anhydrous sodium sulfate. The solvent was removed under reduced pressure, and the residue was dissolved in tetrahydrofuran (5 mL). To the solution was added hydrazine monohydrate (0.1 mL), and the reaction vessel was equipped with a reflux condenser, and the mixture was stirred at 80° C. for 1 hour. The reaction mixture was diluted with ethyl acetate, and the insoluble material was removed by filtration. The filtrate was concentrated under reduced pressure, and the residue was purified by column chromatography on silica gel (eluent: n-hexane/ethyl acetate=1/1–ethyl acetate) to give 2-amino-9-[2-chloro-5-(2,3-difluoro-6-methoxybenzyloxy)-4-methoxyphenyl]-6-methoxy-7-(3,3-dimethoxypropyl)-7,9-dihydro-8H-purin-8-one (0.23 g). To the solution of the obtained 2-amino-9-[2-chloro-5-(2,3-difluoro-6-methoxybenzyloxy)-4-methoxyphenyl]-6-methoxy-7-(3-dimethoxy-propyl)-7,9-dihydro-8H-purin-8-one (0.15 g) in tetrahydrofuran (4 mL) were added 4-dimethylaminopyridine (9 mg) and di(tert-butyl)dicarbonate (0.1 g), and the mixture was heated at reflux for 1.5 hours. The reaction mixture was poured into 0.5 mol/L hydrochloric acid, and the resulting mixture was extracted with ethyl acetate. The extract was washed with water and brine, and dried over anhydrous sodium sulfate, and the solvent was removed under reduced pressure. To the residue were added methanol (4 mL) and potassium carbonate (0.1 g), and the mixture was heated at reflux for 1.5 hours. To the reaction mixture was added water, and the resulting mixture was extracted with ethyl acetate. The extract was dried over anhydrous sodium sulfate, and the solvent was removed under reduced pressure. The residue was purified by column chromatography on silica gel (eluent: n-hexane/ethyl acetate=1/1–1/9) to give 2-(tert-butoxycarbonylamino)-9-[2-chloro-5-(2,3-difluoro-6-methoxybenzyloxy)-4-methoxyphenyl]-6-methoxy-7-(3,3-dimethoxy propyl)-7,9-dihydro-8H-purin-8-one (0.14 g). This material was dissolved in N,N-dimethylformamide (2 mL). To the solution were added sodium hydride (55%, 17 mg) and methyl bromoacetate (0.037 mL), and the mixture was stirred at room temperature for 3 hours. To the reaction mixture was added 1 mol/L hydrochloric acid, and the mixture was poured into water, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=1/1–1/4) to give 2-[N-(tert-butoxycarbonyl)-N-methoxycarbonylmethylamino]-9-[2-chloro-5-(2,3-difluoro-6-methoxybenzyloxy)-4-methoxyphenyl]-6-methoxy-7-(3,3-dimethoxypropyl)-7,9-dihydro-8H-purin-8-one (0.14 g). This material was dissolved in tetrahydrofuran (4 mL). To the solution were added concentrated hydrochloric acid (0.15 mL) and water (0.15 mL), and the mixture was stirred at room temperature for 2 hours. To the reaction mixture were added lithium hydroxide monohydrate (0.19 g), methanol (2 mL) and water (2 mL), and the mixture was stirred at room temperature for 2 hours. The reaction mixture was poured into 0.5 mol/L hydrochloric acid, and the resulting mixture was extracted with ethyl acetate. The extract was washed with water and brine, and dried over anhydrous sodium sulfate. The solvent was removed under reduced pressure, and the residue was purified by column chromatography on silica gel (eluent: ethyl acetate–ethyl acetate/methanol=4/1) to give 2-[N-(tert-butoxycarbonyl)-N-carboxymethylamino]-9-[2-chloro-5-(2,3-difluoro-6-methoxy-benzyloxy)-4-methoxyphenyl]-6-methoxy-7,9-dihydro-8H-purin-8-one (0.11 g). To this material was added hydrochloric acid (4 mol/L ethyl acetate solution, 3 mL), and the mixture was stirred at room temperature for 3 hours. The reaction mixture was neutralized by adding 1 mol/L aqueous sodium hydroxide solution. The mixture was poured into a saturated aqueous ammonium chloride solution, and the resulting mixture was extracted with ethyl acetate. The extract was washed with water and brine, and dried over anhydrous sodium sulfate. The solvent was removed under reduced pressure, and the residue was purified by column chromatography on silica gel (eluent: ethyl acetate–ethyl acetate/methanol=4/1). The obtained product was suspended in a mixed solvent (n-hexane/ethyl acetate=1/3), and collected by filtration. The collected material was dried under reduced pressure to give the title compound (30 mg).

Examples 404 and 405

The compounds of Examples 404 and 405 were prepared in a similar manner to that described in Example 403 using the corresponding starting materials.

Example 406

The compound of Example 406 was prepared in a similar manner to that described in Example 314 using the corresponding starting materials.

Example 407

9-[2-Chloro-5-(2-fluoro-6-methoxybenzyloxy)-4-methoxyphenyl]-2-(2-hydroxyethylamino)-6-methoxy-7,9-dihydro-8H-purin-8-one A mixture of 2-chloro-9-[2-chloro-5-(2-fluoro-6-methoxybenzyloxy)-4-methoxyphenyl]-6-methoxy-7,9-dihydro-8H-purin-8-one (50 mg), 2-aminoethanol (19 mg), ethanol (1 mL) and 1-methyl-2-pyrrolidone (0.5 mL) was stirred at 150° C. in a sealed tube under microwave irradiation for 30 minutes. The reaction mixture was poured into a saturated aqueous ammonium chloride solution, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=2/3–ethyl acetate). The obtained product was suspended in a mixed solvent (n-hexane/ethyl acetate=2/1), and collected by filtration. The collected material was dried under reduced pressure to give the title compound (5 mg).

Examples 408 and 409

The compounds of Examples 408 and 409 were prepared in a similar manner to that described in Example 407 using the corresponding starting materials.

Example 410

9-[2-Chloro-5-(2,3-difluoro-6-methoxybenzyloxy)-4-methoxyphenyl]-6-methoxy-2-dimethylaminomethyl-7,9-dihydro-8H-purin-8-one To a solution of 9-[2-chloro-5-(2,3-difluoro-6-methoxybenzyloxy)-4-methoxyphenyl]-2-hydroxymethyl-6-methoxy-7,9-dihydro-8H-purin-8-one (0.34 g) and triphenylphosphine (0.43 g) in N,N-dimethylformamide (4 mL) was added carbon tetrachloride (1 mL), and the mixture was stirred at room temperature for 2 hours. The reaction mixture was poured into 10% aqueous sodium chloride solution, and the resulting mixture was extracted with ethyl acetate. The extract was washed with brine, and dried over anhydrous sodium sulfate. The solvent was removed under reduced pressure, and the residue was purified by column chromatography on silica gel (eluent: n-hexane/ethyl acetate=1/1–1/20) to give 9-[2-chloro-5-(2,3-difluoro-6-methoxybenzyloxy)-4-methoxyphenyl]-2-chloromethyl-6-methoxy-7,9-dihydro-8H-purin-8-one (0.34 g). The mixture of the obtained 9-[2-chloro-5-(2,3-difluoro-6-methoxybenzyloxy)-4-methoxyphenyl]-2-chloromethyl-6-methoxy-7,9-dihydro-8H-purin-8-one (50 mg), dimethylamine (50% aqueous solution, 0.1 mL) and sodium iodide (14 mg) in 2-propanol (1 mL)-acetonitrile (1 mL) was stirred at 60° C. for 4 hours. The reaction mixture was poured into a saturated aqueous ammonium chloride solution, and the resulting mixture was extracted with ethyl acetate. The extract was washed with brine, and dried over anhydrous sodium sulfate. The solvent was removed under reduced pressure, and the residue was purified by column chromatography on silica gel (eluent: ethyl acetate–ethyl acetate/methanol=7/3). The obtained product was suspended in diethyl ether, and collected by filtration. The collected material was dried under reduced pressure to give the title compound (12 mg).

Examples 411 and 412

The compounds of Examples 411 and 412 were prepared in a similar manner to that described in Example 410 using the corresponding starting materials.

Example 413

2-(tert-Butoxycarbonylaminomethyl)-9-[2-chloro-5-(2,3-difluoro-6-methoxybenzyloxy)-4-methoxyphenyl]-6-methoxy-7,9-dihydro-8H-purin-8-one A mixture of 9-[2-chloro-5-(2,3-difluoro-6-methoxybenzyloxy)-4-methoxyphenyl]-2-chloromethyl-6-methoxy-7,9-dihydro-8H-purin-8-one (0.1 g) and sodium azide (15 mg) in N,N-dimethylformamide (2 mL) was stirred at 100° C. for 1.5 hours. The reaction mixture was cooled to room temperature, and poured into 0.5 mol/L hydrochloric acid, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=1/1–1/4). The obtained product was suspended in a mixed solvent (n-hexane/ethyl acetate=1/1), and collected by filtration. The collected material was dried under reduced pressure to give 2-azidomethyl-9-[2-chloro-5-(2,3-difluoro-6-methoxybenzyloxy)-4-methoxyphenyl]-6-methoxy-7,9-dihydro-8H-purin-8-one (74 mg). To this material were added tetrahydrofuran (5 mL), ethanol (1 mL) and 10% platinum-carbon powder (20 mg), and the mixture was stirred at room temperature under a hydrogen atmosphere overnight. The insoluble material was removed by filtration, and the filtrate was concentrated under reduced pressure. The residue was purified by column chromatography on silica gel (eluent: ethyl acetate/methanol=9/1–methanol) to give 2-aminomethyl-9-[2-chloro-5-(2,3-difluoro-6-methoxybenzyloxy)-4-methoxyphenyl]-6-methoxy-7,9-dihydro-8H-purin-8-one (44 mg). To this material were added tetrahydrofuran (3 mL), triethylamine (0.1 mL) and di(tert-butyl)dicarbonate (28 mg), and the mixture was stirred at room temperature for 3 hours. The reaction mixture was poured into a saturated aqueous ammonium chloride solution, and the resulting mixture was extracted with ethyl acetate. The extract was washed with brine, and dried over anhydrous sodium sulfate. The solvent was removed under reduced pressure, and the residue was purified by column chromatography on silica gel (eluent: n-hexane/ethyl acetate=1/1–1/4) to give the title compound (36 mg).

Example 414

2-Aminomethyl-9-[2-chloro-5-(2,3-difluoro-6-methoxybenzyloxy)-4-methoxyphenyl]-6-methoxy-7,9-dihydro-8H-purin-8-one hydrochloride To a solution of 2-(tert-butoxycarbonylaminomethyl)-9-[2-chloro-5-(2,3-difluoro-6-methoxybenzyloxy)-4-methoxyphenyl]-6-methoxy-7,9-dihydro-8H-purin-8-one (36 mg) in tetrahydrofuran (1 mL) was added hydrochloric acid (4 mol/L ethyl acetate solution, 2 mL) under ice-cooling, and the mixture was stirred at the same temperature for 1 hour, and then stirred at room temperature for 3 hours. To the reaction mixture was added diethyl ether, and the insoluble material was collected by filtration. The collected material was washed with diethyl ether, and dried under reduced pressure to give the title compound (14 mg).

Example 415

The compound of Example 415 was prepared in a similar manner to that described in Example 302 using the corresponding starting materials.

Example 416

2-Aminomethyl-9-[2-chloro-5-(2-fluoro-6-methoxybenzyloxy)-4-methoxyphenyl]-6-methoxy-7,9-dihydro-8H-purin-8-one 9-[2-Chloro-5-(2-fluoro-6-methoxybenzyloxy)-4-methoxyphenyl]-2-chloromethyl-6-methoxy-7,9-dihydro-8H-purin-8-one was prepared in a similar manner to that described in Example 410 using the corresponding starting materials. 2-Azidomethyl-9-[2-chloro-5-(2-fluoro-6-methoxybenzyloxy)-4-methoxyphenyl]-6-methoxy-7,9-dihydro-8H-purin-8-one was prepared in a similar manner to that described in Example 413 using 9-[2-chloro-5-(2-fluoro-6-methoxybenzyloxy)-4-methoxyphenyl]-2-chloromethyl-6-methoxy-7,9-dihydro-8H-purin-8-one instead of 9-[2-chloro-5-(2,3-difluoro-6-methoxybenzyloxy)-4-methoxyphenyl]-2-chloromethyl-6-methoxy-7,9-dihydro-8H-purin-8-one. To 2-azidomethyl-9-[2-chloro-5-(2-fluoro-6-methoxybenzyloxy)-4-methoxyphenyl]-6-methoxy-7,9-dihydro-8H-purin-8-one (0.1 g) were added tetrahydrofuran (10 mL) and 10% platinum-carbon powder (50 mg), and the mixture was stirred at room temperature under a hydrogen atmosphere for 4 hours. The insoluble material was removed by filtration, and the filtrate was concentrated under reduced pressure to give the title compound (94 mg).

Example 417

2-Acetylaminomethyl-9-[2-chloro-5-(2-fluoro-6-methoxybenzyloxy)-4-methoxyphenyl]-6-methoxy-7,9-dihydro-8H-purin-8-one To a mixture of 2-aminomethyl-9-[2-chloro-5-(2-fluoro-6-methoxybenzyloxy)-4-methoxyphenyl]-6-methoxy-7,9-dihydro-8H-purin-8-one (94 mg) and pyridine (0.1 mL) in methylene chloride (3 mL) was added acetic anhydride (0.055 mL), and the mixture was stirred at room temperature for 5 days. The reaction mixture was poured into 1 mol/L hydrochloric acid, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=1/1–ethyl acetate). The obtained product was suspended in diethyl ether, and collected by filtration. The collected material was dried under reduced pressure to give the title compound (44 mg).

Example 418

2-[5-Chloro-2-(2-fluoro-6-methoxybenzyloxy)-4-(5-hydroxymethyl-7-methyl-1,3-dihydro-2H-imidazo[4,5-b]pyridin-2-one-3-yl)phenoxy]-N,N-dimethylacetamide To a solution of 2-{4-[5-(tert-butyldimethylsilyloxy)methyl-7-methyl-1,3-dihydro-2H-imidazo[4,5-b]pyridin-2-one-3-yl]-5-chloro-2-(2-fluoro-6-methoxybenzyloxy)phenoxy}-N,N-dimethylacetamide (40 mg) in tetrahydrofuran (0.6 mL) was added tetra(n-butyl)ammonium fluoride (1 mol/L tetrahydrofuran solution, 1.2 mL), and the mixture was stirred at room temperature for 3 hours. The reaction mixture was diluted with ethyl acetate, and the mixture was washed with 1 mol/L hydrochloric acid, water and brine successively, and dried over anhydrous magnesium sulfate, and the solvent was removed under reduced pressure. The residual solids were suspended in a mixed solvent (n-hexane/ethyl acetate=2/1), and collected by filtration. The collected solids were dried under reduced pressure to give the title compound (16 mg).

Example 419

The compound of Example 419 was prepared in a similar manner to that described in Example 43 using 2-[5-chloro-2-(2-fluoro-6-methoxybenzyloxy)-4-(5-hydroxymethyl-7-methyl-1,3-dihydro-2H-imidazo[4,5-b]pyridin-2-one-3-yl)phenoxy]-N,N-dimethylacetamide instead of 3-[2-chloro-4-methoxy-5-(1-methyl-1-phenylethylsulfonyl)phenyl]-5-ethoxycarbonyl-7-methyl-1,3-dihydro-2H-imidazo[4,5-b]pyridin-2-one.

Examples 420 to 424

The compounds of Examples 420 to 424 were prepared in a similar manner to that described in Example 170 or Example 171 using the corresponding starting materials.

Examples 425 to 432

The compounds of Examples 425 to 432 were prepared in a similar manner to that described in Example 170 or Example 171 and Example 418 using the corresponding starting materials.

Examples 433 and 434

The compounds of Examples 433 and 434 were prepared in a similar manner to that described in Example 245 using the corresponding starting materials.

Examples 435 to 441

The compounds of Examples 435 to 441 were prepared in a similar manner to that described in Example 273 using the corresponding starting materials.

Example 442

The compound of Example 442 was prepared in a similar manner to that described in Example 170 and Example 273 using the corresponding starting materials.

Examples 443 to 460

The compounds of Examples 443 to 460 were prepared in a similar manner to that described in Example 317 or Example 318 using the corresponding starting materials.

Examples 461 and 462

The compounds of Examples 461 and 462 were prepared in a similar manner to that described in Example 170, Example 273 and Example 318 using the corresponding starting materials.

Example 463

The compound of Example 463 was prepared in a similar manner to that described in Example 154 using the corresponding starting materials.

The compounds described in Table 105 can be prepared easily in a similar manner to that described in the above Examples and Reference Examples.

Tables 1 to 29 and Tables 30 to 104 show the chemical structure and $^1$H-NMR data of the above compounds of Reference Examples 1 to 211 and Examples 1 to 463, respectively.

The abbreviations in these Tables: "Ref No.", "Ex No.", "Strc" and "Solv", represent Reference Example number, Example number, chemical structure and measurement solvent of $^1$H-NMR, respectively.

TABLE 1

| Ref No. | Strc | (Solv) $^1$H-NMR δ ppm: |
|---|---|---|
| 1 | | (CDCl3) 3.88 (3H, s), 4.6-4.75 (2H, m), 6.55-6.65 (1H, m), 7.05-7.15 (1H, m) |
| 2 | | (CDCl3) 3.817 (3H, s), 3.822 (3H, s), 5.05-5.2 (2H, m), 6.55-6.65 (1H, m), 6.8-6.9 (2H, m), 6.9-6.95 (1H, m), 7.05-7.15 (1H, m) |
| 3 | | (CDCl3) 3.81 (3H, s), 3.82 (3H, s), 5.05-5.2 (2H, m), 6.5-6.65 (3H, m), 6.9-6.95 (1H, m), 7.05-7.15 (1H, m) |
| 4 | | (CDCl3) 3.88 (3H, s), 3.92 (3H, s), 5.2-5.3 (2H, m), 6.6-6.65 (1H, m), 6.92 (1H, s), 7.1-7.2 (1H, m), 7.86 (1H, s) |
| 5 | | (CDCl3) 3.89 (3H, s), 3.92 (3H, s), 5.2-5.3 (2H, m), 6.6-6.65 (1H, m), 6.7 (1H, d, J = 12.4 Hz), 7.1-7.2 (1H, m), 7.86 (1H, d, J = 7.1 Hz) |

TABLE 1-continued

| Ref No. | Strc | (Solv) ¹H-NMR δ ppm: |
|---|---|---|
| 6 | [Structure: H₂N-, Cl-substituted phenyl-O-CH₂- connected to F, F, OMe-substituted phenyl with OMe] | (CDCl3) 3.4-40 (8H, m), 5.05-5.15 (2H, m), 6.53 (1H, s), 6.55-6.65 (1H, m), 6.8 (1H, s), 7.05-7.15 (1H, m) |
| 7 | [Structure: H₂N-, F-substituted phenyl-O-CH₂- connected to F, F, OMe-substituted phenyl with OMe] | (CDCl3) 3.2-3.6 (2H, br), 3.75 (3H, s), 3.82 (3H, s), 5.05-5.15 (2H, m), 6.53 (1H, d, J = 9, 0 Hz), 6.55-6.7 (2H, m), 7.05-7.15 (1H, m) |
| 8 | [Structure: Cl⁻ H₂N⁺-, Cl-substituted phenyl-O-CH₂- connected to F, F, OMe-substituted phenyl with OMe] | (DMSO-d6) 3.65 (3H, s), 3.82 (3H, s), 4.97 (2H, s), 6.81 (1H, s), 6.9-6.95 (2H, m), 7.4-7.55 (1H, m) |
| 9 | [Structure: Cl⁻ H₂N⁺-, F-substituted phenyl-O-CH₂- connected to F, F, OMe-substituted phenyl with OMe] | (DMSO-d6) 3.72 (3H, s), 3.81 (3H, s), 4.95-5.05 (2H, m), 6.85-7.1 (3H, m), 7.4-7.55 (1H, m) |

TABLE 2

| Ref No. | Strc | (Solv) ¹H-NMR δ ppm: |
|---|---|---|
| 10 | [Structure: H₂N-, Cl-substituted phenyl-SH] | (DMSO-d6) 5.28 (1H, s), 5.38 (2H, s), 6.44 (1H, dd, J = 8.4 Hz, 2.3 Hz), 6.68 (1H, d, J = 2.3 Hz), 7.03 (1H, d, J = 8.4 Hz) |
| 11 | [Structure: H₂N-, Cl-substituted phenyl-S-C(CH₃)₂-phenyl] | (DMSO-d6) 1.62 (6H, s), 5.39 (2H, s), 6.23 (1H, dd, J = 8.1 Hz, 2.1 Hz), 6.77 (1H, d, J = 2.1 Hz), 7.03 (1H, d, J = 8.1 Hz), 7.2-7.25 (1H, m), 7.25-7.35 (2H, m), 7.4-7.5 (2H, m) |
| 12 | [Structure: H₂N-, Cl-substituted phenyl-SO₂-N(tetrahydroquinoline)] | (CDCl3) 1.6-1.75 (2H, m), 2.49 (2H, t, J = 6.5 Hz), 3.75-3.85 (2H, m), 4.2 (2H, brs), 6.8-6.9 (1H, m), 6.96 (1H, d, J = 1.8 Hz), 7.0-7.3 (4H, m), 7.7-7.8 (1H, m) |

TABLE 2-continued
| Ref No. | Strc | (Solv) ¹H-NMR δ ppm: |
|---|---|---|
| 13 | 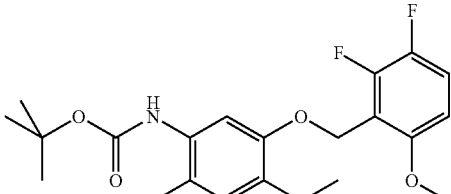 | (CDCl3) 3.77 (3H, s), 3.82 (3H, s), 5.15-5.2 (2H, m), 6.55-6.65 (1H, m), 6.78 (1H, brs), 6.84 (1H, s), 7.05-7.15 (1H, m), 7.97 (1H, brs) |
| 14 | 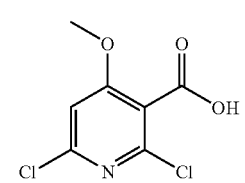 | (DMSO-d6) 3.96 (3H, s), 7.42 (1H, s) |
| 15 | 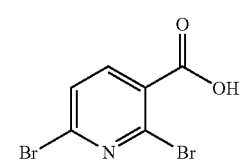 | (DMSO-d6) 7.83 (1H, d, J = 7.9 Hz), 8.08 (1H, d, J = 7.9 Hz), 13.94 (1H, brs) |
| 16 | 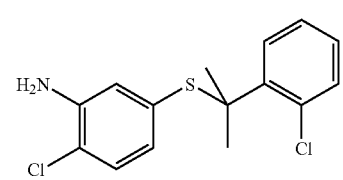 | (CDCl3) 1.81 (6H, s), 3.84 (2H, brs), 6.35-6.45 (2H, m), 6.99 (1H, d, J = 8.0 Hz), 7.05-7.2 (3H, m), 7.44 (1H, dd, J = 7.9 Hz, 1.2 Hz) |
| 17 | 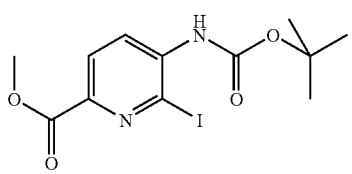 | (DMSO-d6) 1.49 (9H, s), 3.87 (3H, s), 7.95-8.05 (2H, m), 8.68 (1H, s) |
| 18 | 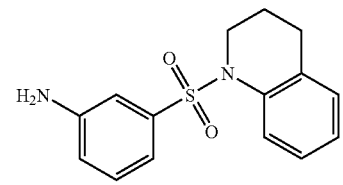 | (CDCl3) 1.6-1.75 (2H, m), 2.48 (2H, t, J = 6.5 Hz), 3.7-3.85 (4H, m), 6.75-6.8 (1H, m), 6.85-7.25 (6H, m), 7.7-7.8 (1H, m) |
TABLE 3
| Ref No. | Strc | (Solv) ¹H-NMR δ ppm: |
|---|---|---|
| 19 | 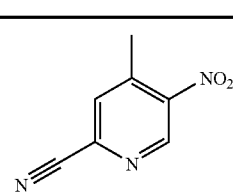 | (CDCl3) 2.72 (3H, s), 7.7-7.75 (1H, m), 9.21 (1H, s) |

TABLE 3-continued

| Ref No. | Strc | (Solv) $^1$H-NMR δ ppm: |
|---|---|---|
| 20 | | (CDCl3) 1.47 (3H, t, J = 7.2 Hz), 2.72 (3H, s), 4.52 (2H, q, J = 7.2 Hz), 8.13 (1H, s), 9.22 (1H, s) |
| 21 | | (CDCl3) 2.18 (3H, s), 4.11 (2H, brs), 7.36 (1H, s), 8.04 (1H, s) |
| 22 | | (CDCl3) 1.42 (3H, t, J = 7.1 Hz), 2.21 (3H, s), 4.02 (2H, brs), 4.42 (2H, q, J = 7.1 Hz), 7.86 (1H, s), 8.09 (1H, s) |
| 23 | | (CDCl3) 1.42 (3H, t, J = 7.2 Hz), 1.51 (9H, s), 2.41 (3H, s), 4.44 (2H, q, J = 7.2 Hz), 6.16 (1H, brs), 7.9 (1H, s) |
| 24 | | (CDCl3) 1.52 (9H, s), 2.4 (3H, s), 6.22 (1H, brs), 7.49 (1H, s) |
| 25 | | (CDCl3) 1.55 (9H, s), 7.35 (1H, brs), 8.42 (1H, s) |
| 26 | | (DMSO-d6) 0.12 (6H, s), 0.93 (9H, s), 3.91 (3H, s), 4.7 (2H, s), 7.13 (1H, s), 13.65 (1H, brs) |
| 27 | | (CDCl3) 4.12 (3H, s), 7.02 (1H, d, J = 10.6 Hz), 7.8-7.9 (2H, m), 7.95-8.05 (3H, m) |

TABLE 4

| Ref No. | Strc | (Solv) ¹H-NMR δ ppm: |
|---|---|---|
| 28 | 4-chloro-5-methoxy-2-(phthalimido)benzenesulfonyl chloride | (CDCl3) 4.13 (3H, s), 7.32 (1H, s), 7.8-7.9 (2H, m), 7.95-8.05 (3H, m) |
| 29 | 4-chloro-5-fluoro-2-(phthalimido)benzenesulfonyl chloride | (CDCl3) 7.61 (1H, d, J = 8.7 Hz), 7.85-7.9 (2H, m), 7.95-8.05 (3H, m) |
| 30 | 4,5-difluoro-2-(phthalimido)benzenesulfonyl chloride | (CDCl3) 7.25-7.35 (1H, m), 7.8-7.9 (2H, m), 7.95-8.1 (3H, m) |
| 31 | 4-fluoro-3-nitrobenzenesulfonyl chloride | (CDCl3) 7.55-7.65 (1H, m), 8.3-8.4 (1H, m), 8.75-8.8 (1H, m) |
| 32 | 4-chloro-5-methoxy-2-(phthalimido)thiophenol | (CDCl3) 3.87 (1H, s), 3.95 (3H, s), 7.02 (1H, s), 7.23 (1H, s), 7.75-7.85 (2H, m), 7.9-8.0 (2H, m) |
| 33 | 4-fluoro-5-methoxy-2-(phthalimido)thiophenol | (CDCl3) 3.76 (1H, s), 3.94 (3H, s), 6.79 (1H, d, J = 11.3 Hz), 7.25 (1H, d, J = 7.9 Hz), 7.75-7.85 (2H, m), 7.9-8.0 (2H, m) |
| 34 | 2-amino-4-chloro-5-methoxythiophenol | (DMSO-d6) 3.71 (3H, s), 4.71 (1H, s), 4.88 (2H, s), 6.76 (1H, s), 6.86 (1H, s) |
| 35 | 2-amino-4-fluoro-5-methoxythiophenol | (CDCl3) 3.41 (2H, brs), 3.68 (1H, s), 3.8 (3H, s), 6.61 (1H, d, J = 12.4 Hz), 6.73 (1H, d, J = 9.5 Hz) |

TABLE 4-continued

| Ref No. | Strc | (Solv) ¹H-NMR δ ppm: |
|---|---|---|
| 36 | 2-amino-5-methoxythiophenol | (CDCl3) 3.42 (1H, s), 3.64 (2H, brs), 3.84 (3H, s), 6.2-6.3 (2H, m), 7.07 (1H, d, J = 7.9 Hz) |

TABLE 5

| Ref No. | Strc | (Solv) ¹H-NMR δ ppm: |
|---|---|---|
| 37 | 2-amino-4-chloro-5-fluorothiophenol | (CDCl3) 3.53 (1H, d, J = 2.0 Hz), 3.88 (2H, brs), 6.68 (1H, d, J = 7.2 Hz), 7.01 (1H, d, J = 8.2 Hz) |
| 38 | 2-amino-4,5-difluorothiophenol | (CDCl3) 3.44 (1H, s), 3.56 (2H, brs), 6.65-6.75 (1H, m), 6.75-6.85 (1H, m) |
| 39 | 2-amino-4-fluorothiophenol | (CDCl3) 3.34 (1H, s), 3.71 (2H, brs), 6.55-6.65 (1H, m), 6.7-6.75 (1H, m), 6.84 (1H, dd, J = 10.8 Hz, 8.3 Hz) |
| 40 | 4-chloro-5-methoxy-2-nitroaniline | (CDCl3) 3.94 (3H, s), 4.05 (2H, brs), 6.82 (1H, s), 7.36 (1H, s) |
| 41 | 2-(bromomethyl)-3-fluoro-1-methoxybenzene | (CDCl3) 3.91 (3H, s), 4.55-4.65 (2H, m), 6.65-6.75 (2H, m), 7.2-7.3 (1H, m) |
| 42 | 2-(bromomethyl)-3,4-difluoro-1-methoxybenzene | (CDCl3) 3.89 (3H, s), 4.55-4.6 (2H, m), 6.55-6.6 (1H, m), 7.0-7.15 (1H, m) |
| 43 | 2-(bromomethyl)-3,4-difluoro-1-(2-methoxyethoxy)benzene | (CDCl3) 3.47 (3H, s), 3.75-3.85 (2H, m), 4.15-4.2 (2H, m), 4.55-4.6 (2H, m), 6.55-6.65 (1H, m), 7.0-7.1 (1H, m) |

TABLE 5-continued
| Ref No. | Strc | (Solv) ¹H-NMR δ ppm: |
|---|---|---|
| 44 | 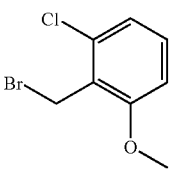 | (CDCl3) 3.91 (3H, s), 4.72 (2H, s), 6.8 (1H, d, J = 8.3 Hz), 6.95-7.05 (1H, m), 7.15-7.25 (1H, m) |
| 45 | 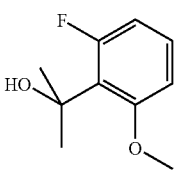 | (CDCl3) 1.66 (3H, s), 1.67 (3H, s), 3.93 (3H, s), 5.08 (1H, s), 6.65-6.75 (2H, m), 7.1-7.2 (1H, m) |
TABLE 6
| Ref No. | Strc | (Solv) ¹H-NMR δ ppm: |
|---|---|---|
| 46 | 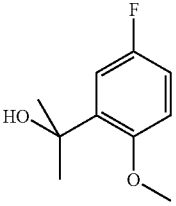 | (CDCl3) 1.59 (6H, s), 3.89 (3H, s), 4.05 (1H, s), 6.8-6.95 (2H, m), 7.0-7.1 (1H, m) |
| 47 | 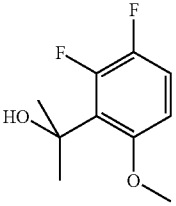 | (CDCl3) 1.67 (3H, s), 1.68 (3H, s), 3.91 (3H, s), 5.04 (1H, s), 6.6-6.7 (1H, m), 6.95-7.05 (1H, m) |
| 48 | 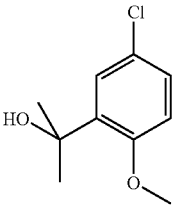 | (CDCl3) 1.59 (6H, s), 3.86 (1H, s), 3.9 (3H, s), 6.84 (1H, d, J = 8.7 Hz), 7.19 (1H, dd, J = 8.7 Hz, 2.6 Hz), 7.31 (1H, d, J = 2.6 Hz) |
| 49 | 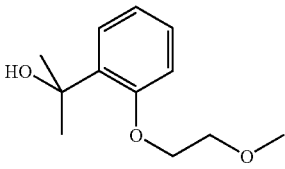 | (CDCl3) 1.63 (6H, s), 3.44 (3H, s), 3.75-3.85 (2H, m), 4.15-4.25 (2H, m), 4.63 (1H, s), 6.85-7.0 (2H, m), 7.15-7.25 (1H, m), 7.25-7.35 (1H, m) |
| 50 | 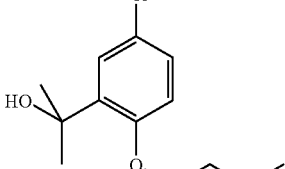 | (CDCl3) 1.61 (6H, s), 3.44 (3H, s), 3.7-3.8 (2H, m), 4.15-4.2 (2H, m), 4.41 (1H, s), 6.82 (1H, d, J = 8.6 Hz), 7.17 (1H, dd, J = 8.6 Hz, 2.5 Hz), 7.29 (1H, d, J = 2.5 Hz) |
| 51 | 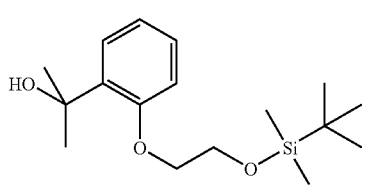 | (CDCl3) 0.11 (6H, s), 0.92 (9H, s), 1.63 (6H, s), 3.95-4.05 (2H, m), 4.1-4.2 (2H, m), 4.35 (1H, s), 6.85-7.0 (2H, m), 7.15-7.25 (1H, m), 7.25-7.35 (1H, m) |

TABLE 6-continued

| Ref No. | Strc | (Solv) ¹H-NMR δ ppm: |
|---|---|---|
| 52 | | (CDCl3) 1.73 (6H, s), 3.5 (2H, brs), 3.6 (3H, s), 3.93 (3H, s), 6.35 (1H, s), 6.7 (1H, s), 6.75-6.85 (1H, m), 6.9-7.0 (1H, m), 7.06 (1H, dd, J = 7.8 Hz, 1.7 Hz), 7.15-7.3 (1H, m) |
| 53 | | (CDCl3) 1.72 (6H, s), 3.83 (2H, brs), 3.92 (3H, s), 6.35-6.45 (2H, m), 6.8-6.85 (1H, m), 6.9-7.05 (2H, m), 7.05-7.1 (1H, m), 7.2-7.3 (1H, m) |

TABLE 7

| Ref No. | Strc | (Solv) ¹H-NMR δ ppm: |
|---|---|---|
| 54 | | (CDCl3) 1.8-1.85 (6H, m), 3.89 (2H, brs), 6.46 (1H, dd, J = 8.2 Hz, 2.1 Hz), 6.55 (1H, d, J = 2.1 Hz), 6.75-6.85 (2H, m), 7.04 (1H, d, J = 8.2 Hz), 7.1-7.2 (1H, m) |
| 55 | | (CDCl3) 1.83 (3H, s), 1.84 (3H, s), 3.79 (3H, s), 3.91 (2H, brs), 6.44 (1H, dd, J = 8.2 Hz, 1.9 Hz), 6.55-6.65 (2H, m), 6.95-7.1 (2H, m) |
| 56 | | (CDCl3) 1.74 (6H, s), 3.64 (2H, brs), 3.93 (3H, s), 6.21 (1H, d, J = 6.3 Hz), 6.75-6.85 (1H, m), 6.9-7.0 (2H, m), 7.05 (1H, dd, J = 7.8 Hz, 1.8 Hz), 7.2-7.3 (1H, m) |
| 57 | | (CDCl3) 1.73 (6H, s), 3.34 (2H, brs), 3.93 (3H, s), 6.2-6.3 (1H, m), 6.65-6.75 (1H, m), 6.75-6.85 (1H, m), 6.9-7.0 (1H, m), 7.0-7.05 (1H, m), 7.2-7.3 (1H, m) |
| 58 | | (CDCl3) 1.65 (6H, s), 3.6 (3H, s), 3.76 (2H, brs), 6.05-6.15 (2H, m), 6.87 (1H, d, J = 8.3 Hz), 7.1-7.2 (1H, m), 7.2-7.3 (2H, m), 7.35-7.45 (2H, m) |
| 59 | | (CDCl3) 1.71 (6H, s), 3.21 (2H, brs), 3.57 (3H, s), 3.93 (3H, s), 6.39 (1H, d, J = 10.0 Hz), 6.51 (1H, d, J = 12.3 Hz), 6.75-6.85 (1H, m), 6.9-7.0 (1H, m), 7.01 (1H, dd, J = 7.7 Hz, 1.7 Hz), 7.15-7.25 (1H, m) |
| 60 | | (CDCl3) 1.82 (3H, s), 1.83 (3H, s), 3.55 (2H, brs), 3.81 (3H, s), 6.45-6.55 (3H, m), 6.65-6.8 (2H, m), 7.1-7.2 (1H, m) |
| 61 | | (CDCl3) 1.81 (3H, s), 1.82 (3H, s), 2.7-4.0 (8H, m), 6.52 (1H, d, J = 12.6 Hz), 6.55-6.7 (2H, m), 6.9-7.05 (1H, m) |

TABLE 8

| Ref No. | Strc | (Solv) ¹H-NMR δ ppm: |
|---|---|---|
| 62 | | (CDCl3) 1.68 (6H, s), 3.27 (2H, brs), 3.56 (3H, s), 3.91 (3H, s), 6.45-6.55 (2H, m), 6.76 (1H, dd, J = 10.7 Hz, 2.9 Hz), 6.8-6.95 (2H, m) |

TABLE 8-continued

| Ref No. | Strc | (Solv) ¹H-NMR δ ppm: |
|---|---|---|
| 63 | (structure) | (CDCl3) 1.81 (3H, s), 1.82 (3H, s), 3.25 (2H, brs), 3.54 (3H, s), 3.84 (3H, s), 6.45-6.65 (3H, m), 6.65-6.75 (1H, m), 7.05-7.2 (1H, m) |
| 64 | (structure) | (CDCl3) 1.68 (6H, s), 3.57 (2H, brs), 3.9 (3H, s), 6.4-6.55 (2H, m), 6.7-6.8 (2H, m), 6.8-6.95 (2H, m) |
| 65 | (structure) | (CDCl3) 1.73 (6H, s), 3.48 (3H, s), 3.75-3.9 (4H, m), 4.2-4.25 (2H, m), 6.35-6.45 (2H, m), 6.8-6.85 (1H, m), 6.9-7.05 (2H, m), 7.08 (1H, dd, J = 7.8 Hz, 1.9 Hz), 7.2-7.25 (1H, m) |
| 66 | (structure) | (DMSO-d6) 1.72 (3H, s), 1.73 (3H, s), 3.42 (3H, s), 3.79 (3H, s), 4.78 (2H, s), 6.6-6.7 (1H, m), 6.72 (1H, s), 6.79 (1H, s), 6.83 (1H, d, J = 8.7 Hz), 7.15-7.25 (1H, m) |
| 67 | (structure) | (CDCl3) 1.81 (6H, s), 3.51 (2H, brs), 3.55 (3H, s), 6.41 (1H, s), 6.69 (1H, s), 7.05-7.2 (3H, m), 7.4-7.45 (1H, m) |
| 68 | (structure) | (CDCl3) 1.8-1.85 (6H, m), 3.52 (3H, s), 3.59 (2H, brs), 6.6 (1H, s), 6.71 (1H, s), 6.75-6.85 (2H, m), 7.05-7.2 (1H, m) |

TABLE 9

| Ref No. | Strc | (Solv) ¹H-NMR δ ppm: |
|---|---|---|
| 69 | (structure) | (CDCl3) 1.83 (3H, s), 1.84 (3H, s), 3.81 (3H, s), 3.86 (2H, brs), 6.46 (1H, dd, J = 8.1 Hz, 2.1 Hz), 6.5 (1H, d, J = 2.1 Hz), 6.55-6.65 (1H, m), 6.65-6.75 (1H, m), 7.03 (1H, d, J = 8.1 Hz), 7.1-7.2 (1H, m) |
| 70 | (structure) | (CDCl3) 1.726 (3H, s), 1.728 (3H, s), 3.86 (2H, brs), 6.4-6.5 (2H, m), 6.95-7.15 (4H, m), 7.2-7.3 (1H, m) |
| 71 | (structure) | (CDCl3) 1.69 (6H, s), 3.8-3.95 (5H, m), 6.41 (1H, dd, J = 8.2 Hz, 2.1 Hz), 6.49 (1H, d, J = 2.1 Hz), 6.75-6.95 (3H, m), 7.02 (1H, d, J = 8.2 Hz) |

TABLE 9-continued

| Ref No. | Strc | (Solv) ¹H-NMR δ ppm: |
|---|---|---|
| 72 | | (CDCl3) 1.68 (6H, s), 3.8-3.95 (5H, m), 6.42 (1H, dd, J = 8.2 Hz, 2.1 Hz), 6.47 (1H, d, J = 2.1 Hz), 6.86 (1H, d, J = 8.6 Hz), 7.0-7.05 (2H, m), 7.2 (1H, dd, J = 8.6 Hz, 2.7 Hz) |
| 73 | | (CDCl3) 1.7 (6H, s), 3.47 (3H, s), 3.8-3.95 (4H, m), 4.15-4.25 (2H, m), 6.41 (1H, dd, J = 8.2 Hz, 2.1 Hz), 6.47 (1H, d, J = 2.1 Hz), 6.88 (1H, d, J = 8.5 Hz), 7.04 (1H, d, J = 8.2 Hz), 7.05 (1H, d, J = 2.6 Hz), 7.18 (1H, dd, J = 8.5 Hz, 2.6 Hz) |
| 74 | | (CDCl3) 1.69 (6H, s), 3.52 (2H, brs), 3.63 (3H, s), 6.37 (1H, s), 6.74 (1H, s), 7.15-7.25 (1H, m), 7.25-7.3 (2H, m), 7.4-7.45 (2H, m) |
| 75 | | (CDCl3) 1.68 (6H, s), 3.24 (2H, brs), 3.6 (3H, s), 6.43 (1H, d, J = 10.1 Hz), 6.55 (1H, d, J = 12.8 Hz), 7.15-7.3 (3H, m), 7.35-7.45 (2H, m) |

TABLE 10

| Ref No. | Strc | (Solv) ¹H-NMR δ ppm: |
|---|---|---|
| 76 | | (CDCl3) 1.72 (3H, s), 1.73 (3H, s), 3.24 (2H, brs), 3.54 (3H, s), 6.45-6.55 (2H, m), 6.9-7.0 (1H, m), 7.0-7.1 (2H, m), 7,15-7.25 (1H, m) |
| 77 | | (CDCl3) 1.8 (6H, s), 3.22 (2H, brs), 3.53 (3H, s), 6.4-6.55 (2H, m), 7.05-7.2 (3H, m), 7.4-7.45 (1H, m) |

TABLE 10-continued

| Ref No. | Strc | (Solv) $^1$H-NMR δ ppm: |
|---|---|---|
| 78 | | (CDCl3) 1.72 (6H, s), 2.84 (3H, s), 3.19 (2H, brs), 3.61. (3H, s), 6.32 (1H, d, J = 10.2 Hz), 6.53 (1H, d, J = 12.6 Hz), 6.95-7.25 (4H, m) |
| 79 | | (CDCl3) 1.8-1.85 (6H, m), 3.28 (2H, brs), 3.51 (3H, s), 6.51 (1H, d, J = 12.6 Hz), 6.62 (1H, d, J = 9.8 Hz), 6.7-6.85 (2H, m), 7.05-7.2 (1H, m) |
| 80 | | (CDCl3) 1.66 (6H, s), 3.29 (2H, brs), 3.6 (3H, s), 6.45-6.6 (2H, m), 6.85-6.95 (1H, m), 7.05-7.3 (3H, m) |
| 81 | | (CDCl3) 1.67 (6H, s), 3.5-3.7 (5H, m), 6.47 (1H, s), 6.75 (1H, s), 6.85-6.95 (1H, m), 7.1-7.3 (3H, m) |
| 82 | | (CDCl3) 1.67 (6H, s), 3.5-3.65 (5H, m), 6.49 (1H, s), 6.74 (1H, s), 7.15-7.3 (3H, m), 7.35-7.45 (1H, m) |
| 83 | | (CDCl3) 1.74 (6H, s), 3.45-3.6 (5H, m), 6.45 (1H, s), 6.7 (1H, s), 6.9-7.0 (1H, m), 7.0-7.1 (2H, m), 7.15-7.25 (1H, m) |

TABLE 11

| Ref No. | Strc | (Solv) ¹H-NMR δ ppm: |
|---|---|---|
| 84 | | (CDCl3) 1.738 (3H, s), 1.741 (3H, s), 3.5-3.65 (5H, m), 6.55 (1H, s), 6.69 (1H, s), 6.75-6.95 (2H, m), 7.0-7.1 (1H, m) |
| 85 | | (CDCl3) 1.4-2.25 (6H, m), 2.7-2.85 (1H, m), 3.3-3.85 (6H, m), 4.5-4.6 (1H, m), 6.63 (1H, s), 6.76 (1H, s), 6.9-7.05 (2H, m), 7.05-7.1 (2H, m) |
| 86 | | (CDCl3) 1.45-1.65 (2H, m), 175-1.9 (2H, m), 2.4-2.5 (2H, m), 3.2-4.2 (4H, m), 6.95-7.3 (7H, m) |
| 87 | | (CDCl3) 1.5-1.65 (2H, m), 1.7-1.9 (2H, m), 2.4-2.5 (2H, m), 3.55-3.85 (2H, m), 4.22 (2H, brs), 7.0-7.05 (1H, m), 7.09 (1H, d, J = 2.0 Hz), 7.1-7.3 (4H, m), 7.31 (1H, d, J = 8.4 Hz) |
| 88 | | (CDCl3) 3.2 (3H, s), 3.48 (3H, s), 4.2 (2H, brs), 6.75-6.85 (1H, m), 6.9-6.95 (1H, m), 6.99 (1H, dd, J = 8.2 Hz, 2.1 Hz,) 7.04 (1H, d, J = 2.1 Hz), 7.25-7.35 (3H, m) |
| 89 | | (CDCl3) 3.75-3.9 (4H, m), 4.24 (2H, brs), 6.83 (1H, dd, J = 8.1 Hz, 1.5 Hz), 6.85-7.0 (3H, m), 7.05-7.15 (1H, m), 7.29 (1H, d, J = 8.3 Hz), 7.81 (1H, dd, J = 8.3 Hz, 1.5 Hz) |
| 90 | | (CDCl3) 1.8-1.95 (2H, m), 3.6-4.05 (4H, m), 4.19 (2H, brs), 6.9-7.1 (4H, m), 7.2-7.3 (2H, m), 7.46 (1H, dd, J = 7.9 Hz, 1.6 Hz) |

TABLE 12

| Ref No. | Strc | (Solv) ¹H-NMR δ ppm: |
|---|---|---|
| 91 | | (CDCl3) 3.21 (3H, s), 4.26 (2H, brs), 7.05-7.1 (1H, m), 7.14 (1H, d, J = 1.9 Hz), 7.2-7.3 (3H, m), 7.36 (1H, d, J = 8.0 Hz), 7.4-7.45 (1H, m) |
| 92 | | (CDCl3) 1.45-1.55 (2H, m), 1.7-1.8 (2H, m), 2.25-2.4 (2H, m), 3.5-3.9 (2H, m), 4.22 (2H, brs), 6.9-7.05 (4H, m), 7.3 (1H, d, J = 8.2 Hz) |
| 93 | | (CDCl3) 1.4-1.5 (2H, m), 1.65-1.75 (2H, m), 2.15-2.3 (2H, m), 2.37 (3H, d, J = 0.8 Hz), 3.5-3.8 (2H, m), 4.23 (2H, brs), 6.7-6.75 (1H, m), 6.98 (1H, dd, J = 8.4 Hz, 1.9 Hz), 7.04 (1H, d, J = 1.9 Hz), 7.3 (1H, d, J = 8.4 Hz) |
| 94 | | (CDCl3) 1.4-1.65 (2H, m), 1.75-1.9 (2H, m), 2.4-2.5 (2H, m), 3.3-4.0 (4H, m), 6.75-6.85 (1H, m), 6.95-7.05 (1H, m), 7.05-7.35 (6H, m) |
| 96 | | (CDCl3) 3.2-3.25 (3H, m), 4.25 (2H, brs), 6.97 (1H, dd, J = 8.3 Hz, 2.1 Hz), 7.0-7.1 (2H, m), 7.1-7.15 (1H, m), 7.25-7.35 (3H, m) |
| 97 | | (CDCl3) 1.4-1.6 (2H, m), 1.75-1.85 (2H, m), 2.3-2.4 (2H, m), 3.5-3.95 (5H, m), 4.23 (2H, brs), 6.74 (1H, dd, J = 8.4 Hz, 2.7 Hz), 6.84 (1H, d, J = 2.7 Hz), 7.0-7.05 (2H, m), 7.1 (1H, d, J = 2.4 Hz), 7.32 (1H, d, J = 8.0 Hz) |
| 98 | | (CDCl3) 3.14 (3H, s), 3.63 (3H, s), 4.24 (2H, brs), 6.6-6.7 (1H, m), 6.7-6.8 (1H, m), 7.11 (1H, dd, J = 8.3 Hz, 2.1 Hz), 7.19 (1H, d, J = 2.1 Hz), 7.2-7.3 (1H, m), 7.34 (1H, d, J = 8.3 Hz) |

TABLE 13

| Ref No. | Strc | (Solv) ¹H-NMR δ ppm: |
|---|---|---|
| 99 | | (DMSO-d6) 3.14 (3H, s), 5.87 (2H, s), 6.94 (1H, dd, J = 8.2 Hz, 2.4 Hz), 7.27 (1H, d, J = 2.4 Hz), 7.4-7.45 (2H, m), 7.55-7.6 (2H, m) |
| 100 | | (CDCl3) 1.05 (3H, t, J = 7.2 Hz), 3.47 (3H, s), 3.5-3.75 (2H, m), 4.19 (2H, brs), 6.75-6.85 (1H, m), 6.9-7.1 (3H, m), 7.2-7.35 (3H, m) |
| 101 | | (CDCl3) 1.02 (3H, d, J = 6.6 Hz), 1.08 (3H, d, J = 6.3 Hz), 3.68 (3H, s), 4.2 (2H, brs), 4.3-4.45 (1H, m), 6.85-6.95 (2H, m), 7.05-7.25 (3H, m), 7.3-7.4 (2H, m) |

TABLE 13-continued

| Ref No. | Strc | (Solv) ¹H-NMR δ ppm: |
|---|---|---|
| 102 | | (CDCl3) 0.89 (3H, t, J = 7.4 Hz), 1.35-1.5 (2H, m), 3.4-3.65 (5H, m), 4.18 (2H, brs), 6.75-6.85 (1H, m), 6.9-7.05 (3H, m), 7.2-7.35 (3H, m) |
| 103 | | (CDCl3) 2.72 (1H, t, J = 6.5 Hz), 3.4-3.9 (7H, m), 4.25 (2H, brs), 6.85-7.05 (3H, m), 7.05-7.15 (2H, m), 7.3-7.4 (2H, m) |
| 104 | | (CDCl3) 3.32 (3H, s), 3.36 (3H, s), 3.73 (2H, brs), 3.9 (3H, s), 6.69 (1H, s), 6.76 (1H, s), 6.85-6.95 (1H, m), 6.95-7.05 (1H, m), 7.4-7.5 (1H, m), 7.65-7.75 (1H, m) |
| 105 | | (CDCl3) 3.02 (3H, s), 3.6-3.75 (8H, m), 4.89 (2H, s), 6.4-6.5 (1H, m), 6.55 (1H, s), 6.77 (1H, s), 6.9-7.05 (1H, m) |

TABLE 14

| Ref No. | Strc | (Solv) ¹H-NMR δ ppm: |
|---|---|---|
| 106 | | (CDCl3) 2.99 (3H, s), 3.7 (3H, s), 4.03 (2H, brs), 4.85-4.95 (2H, m), 6.4-6.55 (2H, m), 6.64 (1H, d, J = 2.3 Hz), 6.95-7.15 (2H, m) |
| 107 | | (CDCl3) 1.55-1.75 (2H, m), 1.85-2.0 (2H, m), 2.8-2.9 (2H, m), 3.4-4.0 (7H, m), 6.7-6.8 (2H, m), 6.95-7.05 (1H, m), 7.1-7.25 (2H, m), 7.33 (1H, d, J = 9.9 Hz) |

TABLE 14-continued

| Ref No. | Strc | (Solv) $^1$H-NMR δ ppm: |
|---|---|---|
| 108 | | (CDCl3) 3.33 (3H, s), 3.57 (3H, s), 3.6-3.9 (5H, m), 6.8-6.85 (1H, m), 6.85-7.0 (2H, m), 7.15-7.3 (3H, m) |
| 109 | | (CDCl3) 3.35 (3H, s), 3.71 (3H, s), 3.84 (2H, brs), 6.9 (1H, s), 7.15-7.25 (4H, m), 7.25-7.3 (2H, m) |
| 110 | | (CDCl3) 3.3-3.35 (3H, m), 3.7-3.9 (5H, m), 6.94 (1H, s), 6.95-7.15 (2H, m), 7.2-7.3 (2H, m), 7.3-7.4 (1H, m) |
| 111 | | (CDCl3) 3.33 (3H, s), 3.7 (3H, s), 3.87 (2H, brs), 6.85-7.05 (4H, m), 7.2-7.3 (2H, m) |
| 112 | | (CDCl3) 1.8-1.9 (2H, m), 2.7 (2H, t, J = 6.6 Hz), 3.52 (3H, s), 3.8-4.0 (4H, m), 6.83 (1H, s), 6.95-7.15 (3H, m), 7.45-7.55 (2H, m) |

TABLE 15

| Ref No. | Strc | (Solv) $^1$H-NMR δ ppm: |
|---|---|---|
| 113 | | (CDCl3) 1.55-1.75 (2H, m), 1.85-2.0 (2H, m), 2.8-2.9 (2H, m), 3.5-4.0 (7H, m), 6.7-6.8 (1H, m), 6.95-7.1 (2H, m), 7.1-7.25 (2H, m), 7.3 (1H, s). |

TABLE 15-continued

| Ref No. | Strc | (Solv) $^1$H-NMR δ ppm: |
|---|---|---|
| 114 | | (CDCl3) 1.5-1.8 (2H, m), 1.85-2.0 (2H, m), 2.7-2.95 (2H, m), 3.3-4.2 (10H, m), 6.52(1H, dd, J = 8.8 Hz, 2.8 Hz), 6.64 (1H, d, J = 8.8 Hz), 6.72 (1H, d, J = 2.8 Hz), 6.98 (1H, s), 7.28 (1H, s) |
| 115 | | (CDCl3) 1.0-4.5 (15H, m), 6.55-6.65 (1H, m), 6.95-7.1 (2H, m), 7.15-7.3 (3H,m) |
| 116 | | (CDCl3) 1.55-1.7 (2H, m), 1.85-1.95 (2H, m), 2.7-2.85 (2H, m), 3.5-4.0 (10H, m), 6.34 (1H, d, J = 2.6 Hz), 6.68 (1H, dd, J = 8.4 Hz, 2.6 Hz), 6.98 (1H, s), 7.07 (1H, d, J = 8.4 Hz), 7.32 (1H, s) |
| 117 | | (CDCl3) 1.55-1.7 (2H, m), 1.8-1.95 (2H, m), 2.7-2.8 (2H, m), 3.65-3.8 (5H, m), 3.89 (2H, brs), 6.64 (1H, d, J = 5.4 Hz), 6.82 (1H, d, J = 5.4 Hz), 6.94 (1H, s), 7.35 (1H, s) |
| 118 | | (CDCl3) 1.45-1.75 (2H, m), 1.85-2.0 (2H, m), 2.8-3.1 (2H, m), 3.2-4.2 (10H, m), 6.3-6.4 (1H, m), 6.7-6.8 (1H, m), 6.9-7.0 (2H, m), 7.3 (1H, s) |
| 119 | | (CDCl3) 1.5-1.7 (2H, m), 1.85-1.95 (2H, m), 2.75-2.85 (2H, m), 3.5-4.0 (7H, m), 6.55-6.65 (1H, m), 6.8-6.9 (1H, m), 6.98 (1H, s), 7.1-7.2 (1H, m), 7.31 (1H, s) |

TABLE 16

| Ref No. | Strc | (Solv) ¹H-NMR δ ppm: |
|---|---|---|
| 120 | | (CDCl3) 3.3-3.35 (3H, m), 3.52 (3H, s), 3.98 (2H, brs), 6.75-6.85 (1H, m), 6.85-6.95 (1H, m), 7.0-7.05 (1H, m), 7.1-7.2 (1H, m), 7.25-7.35 (2H, m) |
| 121 | | (CDCl3) 2.7 (3H, s), 3.8-4.0 (5H, m), 4.32 (2H, s), 6.97 (1H, s), 7.25-7.4 (5H, m), 7.42 (1H, s) |
| 122 | | (CDCl3) 1.62 (6H, s), 2.79 (3H, s), 3.8-4.05 (5H, m), 6.98 (1H, s), 7.15-7.4 (6H, m) |
| 123 | | (CDCl3) 1.43 (3H, d, J = 7.0 Hz), 2.68 (3H, s), 3.77 (3H, s), 3.92 (2H, brs), 5.15 (1H, q, J = 7.0 Hz), 6.93 (1H, s), 7.2-7.35 (5H, m), 7.45 (1H, s) |
| 124 | | (CDCl3) 1.43 (3H, d, J = 7.0 Hz), 2.68 (3H, s), 3.77 (3H, s), 3.92 (2H, brs), 5.15 (1H, q, J = 7.0 Hz), 6.93 (1H, s), 7.2-7.35 (5H, m), 7.45 (1H, s) |
| 125 | | (CDCl3) 1.06 (3H, t, J = 7.3 Hz), 3.51 (3H, s), 3.65-3.95 (7H, m), 6.75-6.85 (1H, m), 6.85-6.95 (2H, m), 7.13 (1H, s), 7.15-7.3 (2H, m) |
| 126 | | (CDCl3) 0.87 (3H, t, J = 7.4 Hz), 1.75-2.05 (2H, m), 2.79 (3H, s), 3.56 (3H, s), 3.8-3.95 (2H, m), 4.76 (1H, t, J = 7.7 Hz), 6.8 (1H, s), 7.0-7.1 (2H, m), 7.2-7.3 (3H, m), 7.42 (1H, s) |

TABLE 17

| Ref No. | Strc | (Solv) ¹H-NMR δ ppm: |
|---|---|---|
| 127 | | (CDCl3) 1.41 (3H, d, J = 7.1 Hz), 2.23 (3H, s), 2.67 (3H, s), 3.4-3.55 (2H, m), 3.77 (3H, s), 5.1-5.2 (1H, m), 6.73 (1H, s), 7.2-7.35 (6H, m) |
| 128 | | (DMSO-d6) 4.15 (2H, s), 5.37 (2H, s), 6.5 (1H, dd, J = 8.2 Hz, 2.2 Hz), 6.77 (1H, d, J = 2.2 Hz), 7.08 (1H, d, J = 8.2 Hz), 7.2-7.4 (5H, m) |
| 129 | | (CDCl3) 3.83 (3H, s), 3.99 (2H, brs), 4.1 (2H, s), 6.6-6.75 (2H, m), 6.8-6.9 (2H, m), 7.11 (1H, d, J = 8.2 Hz), 7.15-7.3 (2H, m) |
| 130 | | (DMSO-d6) 3.79 (3H, s), 4.05-4.1 (2H, m), 5.4 (2H, brs), 6.51 (1H, dd, J = 8.3 Hz, 2.3 Hz), 6.75-6.9 (3H, m), 7.11 (1H, d, J = 8.3 Hz), 7.25-7.35 (1H, m) |
| 131 | | (CDCl3) 3.74 (3H, s), 4.0 (2H, brs), 4.26 (2H, s), 6.7-6.85 (3H, m), 6.95-7.0 (1H, m), 7.1-7.2 (2H, m) |
| 132 | | (CDCl3) 1.81 (3H, s), 3.55-3.75 (8H, m), 4.7-4.8 (1H, m), 5.1-5.25 (1H, m), 6.31 (1H, m), 6.35-6.45 (1H, m), 6.76 (1H, s), 6.9-7.0 (1H, m) |
| 133 | | (CDCl3) 1.87 (3H, s), 3.66 (3H, s), 4.03 (2H, brs), 5.0 (2H, s), 6.29 (1H, dd, J = 8.3 Hz, 2.2 Hz), 6.4-6.5 (2H, m), 6.9-7.05 (1H, m), 7.1 (1H, d, J = 8.3 Hz) |

TABLE 18

| Ref No. | Strc | (Solv) ¹H-NMR δ ppm: |
|---|---|---|
| 134 | | (CDCl3) 1.2-2.0 (4H, m), 2.5-2.65 (2H, m), 2.7-4.9 (2H, br), 6.86 (1H, d, J = 10.7 Hz), 7.15-7.35 (4H, m), 7.62 (1H, d, J = 7.8 Hz), 7.75-7.85 (2H, m), 7.9-8.0 (2H, m), 8.88 (1H, d, J = 1.5 Hz) |
| 135 | | (CDCl3) 1.2-2.2 (4H, m), 2.4-5.0 (4H, m), 7.15-7.35 (5H, m), 7.54 (1H, s), 7.75-7.85 (2H, m), 7.9-8.0 (2H, m), 8.81 (1H, s) |
| 136 | | (CDCl3) 1.4-1.75 (2H, m), 1.75-1.9 (2H, m), 2.45-2.6 (2H, m), 3.0-4.4 (4H, m), 6.89 (1H, s), 6.97 (1H, s), 7.1-7.3 (4H, m), 7.99 (1H, s) |
| 137 | | (CDCl3) 0.04 (6H, s), 0.87 (9H, s), 1.55-1.75 (2H, m), 1.85-2.0 (2H, m), 2.8-2.95 (2H, m), 3.45-3.95 (6H, m), 4.09 (2H, t, J = 5.6 Hz), 6.7-6.85 (1H, m), 6.88 (1H, d, J = 12.0 Hz), 6.95-7.05 7.05 (1H, m), 7.1-7.25 (2H, m), 7.3 (1H, d, J = 9.5 Hz) |
| 138 | | (CDCl3) 0.11 (6H, s), 0.91 (9H, s), 1.67 (6H, s), 3.23 (2H, brs), 3.85-3.95 (4H, m), 6.38 (1H, d, J = 10.0 Hz), 6.66 (1H, d, J = 12.8 Hz), 7.15-7.3 (3H, m), 7.35-7.45 (2H, m) |
| 139 | | (CDCl3) 1.4-1.7 (4H, m), 2.55-2.65 (5H, m), 3.4-3.95 (2H, m), 4.0 (2H, s), 4.34 (2H, s), 6.88 (1H, s), 6.95-7.05 (1H, m), 7.1-7.3 (4H, m), 7.38 (1H, s) |

TABLE 19
| Ref No. | Strc | (Solv) $^1$H-NMR δ ppm: |
|---|---|---|
| 140 | | (CDCl3) 0.12 (6H, s), 0.92 (9H, s), 1.73 (6H, s), 3.82 (2H, brs), 4.05-4.2 (4H, m), 6.35-6.45 (2H, m), 6.75-6.85 (1H, m), 6.9-7.05 (2H, m), 7.05-7.1 (1H, m), 7.15-7.25 (1H, m) |
| 141 | | (CDCl3) 3.47 (3H, s), 3.98 (2H, brs), 6.4-6.5 (1H, m), 6.85 (1H, d, J = 1.8 Hz), 6.96 (1H, d, J = 8.3 Hz), 7.0-7.1 (2H, m), 7.1-7.2 (1H, m), 7.2-7.3 (2H, m) |
| 142 | | (CDCl3) 0.087 (3H, s), 0.091 (3H, s), 0.95 (9H, s), 1.74 (3H, s), 1.75 (3H, s), 3.67 (3H, s), 3.97 (3H, s), 4.6-4.75 (2H, m), 6.9-7.45 (8H, m), 8.67 (1H, s) |
| 143 | | (DMSO-d6) 6.96 (1H, s), 7.52 (1H, s), 10.27 (1H, brs), 10.86 (1H, brs) |
| 144 | | (CDCl3) 3.91 (3H, s), 5.25-5.3 (2H, m), 6.41 (1H, s), 6.6-6.7 (1H, m), 7.04 (1H, s), 7.1-7.25 (1H, m), 7.9 (1H, s) |
| 145 | | (CDCl3) 3.93 (3H, s), 5.2-5.3 (2H, m), 6.45 (1H, s), 6.7-6.8 (2H, m), 7.03 (1H, s), 7.3-7.4 (1H, m), 7.91 (1H, s) |
TABLE 20
| Ref No. | Strc | (Solv) $^1$H-NMR δ ppm: |
|---|---|---|
| 146 | 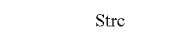 | (CDCl3) 4.0 (3H, s), 5.71 (1H, s), 6.94 (1H, s), 7.61 (1H, s) |

TABLE 20-continued

| Ref No. | Strc | (Solv) $^1$H-NMR δ ppm: |
|---|---|---|
| 147 | | (CDCl3) 5.91 (1H, s), 7.57 (1H, s), 7.7 (1H, s) |
| 148 | | (CDCl3) 3.26 (1H, t, J = 7.0 Hz), 3.38 (3H, s), 3.85-3.95 (2H, m), 4.15-4.25 (2H, m), 4.65-4.8 (4H, m), 6.55-6.65 (1H, m), 7.0-7.1 (1H, m) |
| 149 | | (CDCl3) 1.45 (9H, s), 2.9-3.0 (1H, m), 3.5-3.6 (2H, m), 4.04 (2H, t, J = 5.0 Hz), 4.7-4.8 (2H, m), 5.02 (1H, brs), 6.5-6.6 (1H, m), 7.0-7.1 (1H, m) |
| 150 | | (CDCl3) 3.87 (3H, s), 4.5 (2H, s), 6.75-6.85 (1H, m), 6.95-7.0 (1H, m), 7.0-7.1 (1H, m) |
| 151 | | (CDCl3) 3.41 (3H, s), 3.9-4.0 (2H, m), 4.15-4.25 (2H, m), 4.55-4.6 (2H, m), 4.73 (2H, s), 6.55-6.65 (1H, m), 7.0-7.15 (1H, m) |
| 152 | | (CDCl3) 3.5-3.9 (8H, m), 5.05-5.15 (2H, m), 6.55 (1H, s), 6.65-6.75 (2H, m), 6.79 (1H, s), 7.2-7.35 (1H, m) |

TABLE 21

| Ref No. | Strc | (Solv) $^1$H-NMR δ ppm: |
|---|---|---|
| 153 | | (CDCl3) 3.7 (2H, brs), 3.82 (3H, s), 3.84 (3H, s), 5.09 (2H, s), 6.36 (1H, s), 6.75-6.85 (2H, m), 6.9-7.0 (1H, m), 7.15-7.25 (1H, m) |
| 154 | | (CDCl3) 3.83 (3H, s), 4.0 (2H, brs), 5.0-5.1 (2H, m), 6.38 (1H, dd, J = 8.8 Hz, 2.8 Hz), 6.42 (1H, d, J = 2.8 Hz), 6.55-6.65 (1H, m), 7.05-7.2 (2H, m) |
| 155 | | (CDCl3) 3.42 (3H, s), 3.7-3.8 (2H, m), 4.0-4.3 (4H, m), 5.1-5.15 (2H, m), 6.36 (1H, dd, J = 8.7 Hz, 2.9 Hz), 6.53 (1H, d, J = 2.9 Hz), 6.55-6.65 (1H, m), 7.05-7.15 (2H, m) |
| 156 | | (CDCl3) 3.33 (3H, s), 3.85-3.9 (2H, m), 4.0-4.2 (4H, m), 4.66 (2H, s), 5.05-5.15 (2H, m), 6.36 (1H, dd, J = 8.7 Hz, 2.7 Hz), 6.5 (1H, d, J = 2.7 Hz), 6.6-6.65 (1H, m), 7.05-7.15 (2H, m) |
| 157 | | (CDCl3) 1.43 (9H, s), 3.4-3.55 (2H, m), 3.95-4.15 (4H, m), 4.9-5.1 (3H, m), 6.35-6.5 (2H, m), 6.55-6.65 (1H, m), 7.05-7.15 (2H, m) |

TABLE 21-continued

| Ref No. | Strc | (Solv) $^1$H-NMR δ ppm: |
|---|---|---|
| 158 | | (CDCl3) 1.26 (3H, t, J = 7.2 Hz), 3.75-3.95 (5H, m), 4.18 (2H, q, J = 7.2 Hz), 4.53 (2H, s), 5.05-5.15 (2H, m), 6.54 (1H, s), 6.65-6.75 (2H, m), 6.99 (1H, s), 7.25-7.35 (1H, m) |

TABLE 22

| Ref No. | Strc | (Solv) $^1$H-NMR δ ppm: |
|---|---|---|
| 159 | | (CDCl3) 1.27 (3H, t, J = 7.1 Hz), 3.6-4.0 (5H, m), 4.2 (2H, q, J = 7.1 Hz), 4.52 (2H, s), 5.05-5.15 (2H, m), 6.51 (1H, s), 6.55-6.65 (1H, m), 6.98 (1H, s), 7.05-7.2 (1H, m) |
| 160 | | (CDCl3) 3.73 (3H, s), 3.75-3.9 (5H, m), 4.54 (2H, s), 5.05-5.15 (2H, m), 6.52 (1H, s), 6.55-6.65 (1H, m), 6.98 (1H, s), 7.05-7.2 (1H, m) |
| 161 | | (CDCl3) 2.93 (3H, s), 2.99 (3H, s), 3.7-3.9 (5H, m), 4.57 (2H, s), 5.05-5.15 (2H, m), 6.52 (1H, s), 6.55-6.65 (1H, m), 6.98 (1H, s), 7.05-7.2 (1H, m) |

TABLE 22-continued

| Ref No. | Strc | (Solv) ¹H-NMR δ ppm: |
|---|---|---|
| 162 | | (CDCl3) 3.39 (3H, s), 3.6-3.7 (2H, m), 3.7-3.9 (5H, m), 4.0-4.1 (2H, m), 5.05-5.15 (2H, m), 6.51 (1H, s), 6.55-6.65 (1H, m), 6.91 (1H, s), 7.05-7.2 (1H, m) |
| 163 | | (CDCl3) 0.02 (6H, s), 0.87 (9H, s), 1.85-2.0 (2H, m), 3.65-3.9 (7H, m), 3.98 (2H, t, J = 6.2 Hz), 5.05-5.15 (2H, m), 6.51 (1H, s), 6.55-6.65 (1H, m), 6.84 (1H, s), 7.05-7.15 (1H, m) |

TABLE 23

| Ref No. | Strc | (Solv) ¹H-NMR δ ppm: |
|---|---|---|
| 164 | | (CDCl3) 1.24 (3H, t, J = 7.1 Hz), 1.95-2.1 (2H, m), 2.46 (2H, t, J = 7.5 Hz), 3.65-3.9 (5H, m), 3.92 (2H, t, 3.65-3.9 95H, m), 3.92 (2H, t, J = 6.2 Hz), 4.12 (2H, q, J = 7.1 Hz), 5.05-5.15 (2H, m), 6.51 (1H, s), 6.55-6.65 (1H, m), 6.84 (1H, s), 7.05-7.15 (1H, m) |
| 165 | | (CDCl3) 0.02 (6H, s), 0.87 (9H, s), 1.85-1.95 (2H, m), 3.65-3.8 (4H, m), 3.84 (3H, s), 3.97 (2H, t, J = 6.3 Hz), 5.05-5.1 (2H, m), 6.52 (1H, s), 6.65-6.75 (2H, m), 6.83 (1H, s), 7.2-7.3 (1H, m) |

TABLE 23-continued

| Ref No. | Strc | (Solv) ¹H-NMR δ ppm: |
|---------|------|----------------------|
| 166 | | (CDCl3) 2.63 (3H, d, J = 4.9 Hz), 3.6-4.2 (5H, m), 4.36 (2H, s), 5.05-5.15 (2H, m), 6.57 (1H, s), 6.7-6.8 (2H, m), 6.89 (1H, s), 7.04 (1H, brs), 7.25-7.4 (1H, m) |
| 167 | | (CDCl3) 3.47 (3H, s), 3.65-4.0 (5H, m), 5.01 (2H, s), 5.05-5.15 (2H, m), 6.52 (1H, s), 6.55-6.65 (1H, m), 7.03 (1H, s), 7.05-7.2 (1H, m) |
| 168 | | (CDCl3) 3.75-3.9 (5H, m), 4.05-4.2 (2H, m), 4.55-4.75 (2H, m), 5.05-5.15 (2H, m), 6.52 (1H, s), 6.55-6.65 (1H, m), 6.92 (1H, s), 7.05-7.2 (1H, m) |
| 169 | | (CDCl3) 1.35 (3H, s), 1.38 (3H, s), 3.7-3.9 (7H, m), 3.95-4.1 (2H, m), 4.3-4.4 (1H, m), 5.0-5.15 (2H, m), 6.51 (1H, s), 6.55-6.65 (1H, m), 6.89 (1H, s), 7.05-7.2 (1H, m) |

TABLE 24

| Ref No. | Strc | (Solv) ¹H-NMR δ ppm: |
|---|---|---|
| 170 | | (CDCl3) 1.4 (3H, s), 1.45 (3H, s), 3.8-4.05 (10H, m), 5.05-5.1 (2H, m), 6.51 (1H, s), 6.55-6.65 (1H, m), 6.96 (1H, s), 7.05-7.2 (1H, m) |
| 171 | | (CDCl3) 3.89 (3H, s), 5.25-5.35 (2H, m), 6.6-6.7 (1H, m), 7.1-7.25 (1H, m), 7.72 (1H, s), 7.77 (1H, s) |
| 172 | | (CDCl3) 1.31 (3H, s), 1.36 (3H, s), 2.55-2.7 (1H, m), 2.75-2.85 (1H, m), 3.5-3.6 (1H, m), 3.8-3.9 (4H, m), 3.97 (2H, brs), 4.2-4.3 (1H, m), 4.95-5.1 (2H, m), 6.48 (1H, s), 6.55-6.65 (1H, m), 7.03 (1H, s), 7.05-7.2 (1H, m) |
| 173 | | (CDCl3) 1.2 (3H, t, J = 7.1 Hz), 2.45-2.55 (2H, m), 2.7-2.8 (2H, m), 3.83 (3H, s), 3.95 (2H, brs), 4.07 (2H, q, J = 7.1 Hz), 5.0-5.1 (2H, m), 6.48 (1H, s), 6.55-6.65 (1H, m), 7.0 (1H, s), 7.05-7.2 (1H, m) |
| 174 | | (CDCl3) 1.6-1.7 (1H, m), 2.71 (2H, t, J = 6.2 Hz), 3.65-3.75 (2H, m), 3.8-3.9 (3H, m), 3.99 (2H, brs), 5.0-5.1 (2H, m), 6.51 (1H, s), 6.55-6.65 (1H, m), 7.02 (1H, s), 7.05-7.2 (1H, m) |

TABLE 24-continued

| Ref No. | Strc | (Solv) $^1$H-NMR δ ppm: |
|---|---|---|
| 175 | [structure] | (CDCl3) 1.22 (3H, t, J = 7.2 Hz), 1.75-1.85 (2H, m), 2.15-2.25 (2H, m), 2.4-2.5 (2H, m), 3.83 (3H, s), 3.96 (2H, brs), 4.07 (2H, q, J = 7.2 Hz), 5.0-5.05 (2H, m), 6.49 (1H, s), 6.55-6.65 (1H, m), 6.96 (1H, s), 7.05-7.2 (1H, m) |

TABLE 25

| Ref No. | Strc | (Solv) $^1$H-NMR δ ppm: |
|---|---|---|
| 176 | [structure] | (CDCl3) 0.02 (6H, s), 0.89 (9H, s), 3.82 (3H, s), 3.97 (2H, brs), 4.56 (2H, s), 5.0-5.05 (2H, m), 6.48 (1H, s), 6.55-6.65 (1H, m), 7.05-7.2 (1H, m), 7.25 (1H, s) |
| 177 | [structure] | (DMSO-d6) 2.31 (3H, s), 12.98 (2H, brs) |
| 178 | [structure] | (CDCl3) 2.79 (3H, s) |
| 179 | [structure] | (CDCl3) 2.67 (3H, s), 4.11 (3H, s) |
| 180 | [structure] | (CDCl3) 4.15 (3H, s), 8.65 (1H, s) |

TABLE 25-continued

| Ref No. | Strc | (Solv) $^1$H-NMR δ ppm: |
|---|---|---|
| 181 | [structure: 1-acetyl-6-chloro-2-methyl-5-nitropyrimidine] | (CDCl3) 2.72 (3H, s), 2.87 (3H, s) |
| 182 | [structure: 2-(fluoromethyl)-5-nitropyrimidine-4,6-diol] | (DMSO-d6) 5.32 (2H, d, J = 45.4 Hz) |
| 183 | [structure: 2-(methoxymethyl)-5-nitropyrimidine-4,6-diol] | (DMSO-d6) 3.35 (3H, s), 4.36 (2H, s) |

TABLE 26

| Ref No. | Strc | (Solv) $^1$H-NMR δ ppm: |
|---|---|---|
| 184 | [structure: 2-methoxy-5-nitropyrimidine-4,6-diol] | (DMSO-d6) 3.94 (3H, s) |
| 185 | [structure: 2-(difluoromethyl)-5-nitropyrimidine-4,6-diol] | (DMSO-d6) 6.67 (1H, t, J = 52.9 Hz) |
| 186 | [structure: (4,6-dihydroxy-5-nitropyrimidin-2-yl)methyl acetate] | (DMSO-d6) 2.14 (3H, s), 4.97 (2H, s) |
| 187 | [structure: 1-(4,6-dihydroxy-5-nitropyrimidin-2-yl)ethyl acetate] | (DMSO-d6) 1.51 (3H, d, J = 6.8 Hz), 2.11 (3H, s), 5.33 (1H, q, J = 6.8 Hz) |

TABLE 26-continued

| Ref No. | Strc | (Solv) $^1$H-NMR δ ppm: |
|---|---|---|
| 188 | | (DMSO-d6) 1.62 (6H, s), 2.06 (3H, s) |
| 189 | | (CDCl3) 4.17 (3H, s), 5.43 (2H, d, J = 46.5 Hz) |
| 190 | | (CDCl3) 3.55 (3H, s), 4.16 (3H, s), 4.6 (2H, s) |
| 191 | | (CDCl3) 4.08 (3H, s), 4.11 (3H, s) |

TABLE 27

| Ref No. | Strc | (Solv) $^1$H-NMR δ ppm: |
|---|---|---|
| 192 | | (CDCl3) 4.23 (3H, s), 6.51 (1H, t, J = 53.9 Hz) |
| 193 | | (CDCl3) 2.23 (3H, s), 4.12 (3H, s), 5.2 (2H, s) |
| 194 | | (CDCl3) 1.62 (3H, d, J = 6.9 Hz), 2.18 (3H, s), 4.12 (3H, s), 5.67 (1H, q, J = 6.9 Hz) |

TABLE 27-continued

| Ref No. | Strc | (Solv) ¹H-NMR δ ppm: |
|---|---|---|
| 195 | | (CDCl3) 1.73 (6H, s), 2.09 (3H, s), 4.1 (3H, s) |
| 196 | | (CDCl3) 1.39 (3H, t, J = 7.1 Hz), 2.43 (3H, s), 4.41 (2H, q, J = 7.1 Hz), 8.13 (1H, s) |
| 197 | | (DMSO-d6) 2.17 (3H, s), 3.7 (3H, s), 11.25 (2H, brs) |
| 198 | | (DMSO-d6) 4.03 (3H, s) |
| 199 | | (CDCl3) 1.43 (3H, t, J = 7.2 Hz), 2.57 (3H, s), 4.48 (2H, q, J = 7.2 Hz), 8.88 (1H, s) |

TABLE 28

| Ref No. | Strc | (Solv) ¹H-NMR δ ppm: |
|---|---|---|
| 200 | | (CDCl3) 2.57 (3H, s), 4.0 (3H, s) |
| 201 | | (CDCl3) 4.18 (3H, s) |
| 202 | | (CDCl3) 2.76 (3H, s), 5.62 (2H, d, J = 46.2 Hz) |

TABLE 28-continued

| Ref No. | Strc | (Solv) ¹H-NMR δ ppm: |
|---|---|---|
| 203 | | (CDCl3) 2.25 (3H, s), 2.71 (3H, s), 5.38 (2H, s) |
| 204 | | (CDCl3) 0.01 (6H, s), 0.86 (9H, s), 3.75 (2H, brs), 3.81 (3H, s), 3.85-4.0 (4H, m), 5.05-5.15 (2H, m), 6.5 (1H, s), 6.55-6.65 (1H, m), 6.87 (1H, s), 7.05-7.2 (1H, m) |
| 205 | | (CDCl3) 0.01 (6H, s), 0.86 (9H, s), 3.65-3.9 (7H, m), 3.9-4.0 (2H, m), 5.05-5.1 (2H, m), 6.51 (1H, s), 6.65-6.75 (2H, m), 6.86 (1H, s), 7.2-7.35 (1H, m) |
| 206 | | (CDCl3) 3.71 (3H, s), 3.75-3.95 (5H, m), 4.54 (2H, s), 5.05-5.15 (2H, m), 6.53 (1H, s), 6.65-6.75 (2H, m), 6.99 (1H, s), 7.2-7.35 (1H, m) |

TABLE 29

| Ref No. | Strc | (Solv) ¹H-NMR δ ppm: |
|---|---|---|
| 207 | | (DMSO-d6) 1.22 (3H, t, J = 7.7 Hz), 2.56 (2H, q, J = 7.7 Hz), 12.3-14.0 (2H, br) |

TABLE 29-continued

| Ref No. | Strc | (Solv) $^1$H-NMR δ ppm: |
|---|---|---|
| 208 | | (CDCl3) 1.35 (3H, t, J = 7.6 Hz), 2.92 (2H, q, J = 7.6 Hz), 4.12 (3H, s) |
| 209 | | (CDCl3) 2.91 (3H, s), 2.96 (3H, s), 3.75-3.9 (5H, m), 4.56 (2H, s), 5.05-5.15 (2H, m), 6.54 (1H, s), 6.65-6.75 (2H, m), 6.98 (1H, s), 7.25-7.35 (1H, m) |
| 210 | | (CDCl3) 0.11 (6H, s), 0.95 (9H, s), 2.36 (3H, s), 4.76 (2H, s), 5.8-6.2 (1H, br), 7.29 (1H, s) |
| 211 | | (DMSO-d6) 0.05 (6H, s), 0.88 (9H, s), 2.36 (3H, s), 2.83 (3H, s), 2.95 (3H, s), 3.81 (3H, s), 4.59 (2H, s), 4.85-5.05 (4H, m), 6.8-7.0 (3H, m), 7.12 (1H, s), 7.36 (1H, s), 7.4-7.5 (1H, m), 11.39 (1H, s) |

TABLE 30

| Ex No. | Strc | (Solv) $^1$H-NMR δ ppm: |
|---|---|---|
| 1 | | (DMSO-d6) 3.79 (3H, s), 3.82 (3H, s), 4.95-5.05 (2H, m), 6.85-6.95 (1H, m), 7.05-7.1 (1H, m), 7.26 (1H, s), 7.35-7.45 (2H, m), 7.45-7.55 (1H, m), 7.85-7.9 (1H, m), 11.35 (1H, s) |
| 2 | | (DMSO-d6) 1.65-1.7 (6H, m), 7.05-7.1 (1H, m), 7.15-7.25 (2H, m), 7.25-7.5 (6H, m), 7.58 (1H, d, J = 8.4 Hz), 7.85-7.9 (1H, m), 11.38 (1H, brs) |

TABLE 30-continued

| Ex No. | Strc | (Solv) ¹H-NMR δ ppm: |
|---|---|---|
| 3 | | (DMSO-d6) 3.65-3.75 (2H, m), 3.78 (3H, s), 3.83 (3H, s), 3.95-4.05 (2H, m), 4.9-5.05 (3H, m), 6.85-6.95 (1H, m), 7.1-7.2 (1H, m), 7.27 (1H, s), 7.39 (1H, s), 7.45-7.55 (1H, m), 7.6-7.7 (1H, m), 7.9-7.95 (1H, m) |
| 4 | | (DMSO-d6) 3.79 (3H, s), 3.82 (3H, s), 5.01 (2H, s), 6.85-6.95 (1H, m), 7.1-7.2 (2H, m), 7.32 (1H, d, J = 7.3 Hz), 7.4-7.55 (2H, m), 11.58 (1H, s) |
| 5 | | (DMSO-d6) 1.6-1.75 (2H, m), 2.45-2.55 (2H, m), 3.7-3.85 (2H, m), 7.05-7.2 (3H, m), 7.56 (1H, d, J = 8.6 Hz), 7.6-7.7 (2H, m), 7.89 (1H, d, J = 8.8 Hz), 8.0 (1H, d, J = 2.0 Hz), 8.06 (1H, d, J = 2.4 Hz), 11.7 (1H, s) |
| 6 | | (DMSO-d6) 3.79 (3H, s), 3.81 (3H, s), 4.95-5.05 (2H, m), 6.85-6.95 (1H, m), 7.05-7.1 (1H, m). 7.15 (1H, d, J = 11.7 Hz), 7.29 (1H, d, J = 7.5 Hz), 7.35-7.55 (2H, m), 7.85-7.95 (1H, m), 11.36 (1H, s) |
| 7 | | (DMSO-d6) 0.89 (3H, t, J = 7.4 Hz), 1.3-1.45 (2H, m), 1.6-1.7 (2H, m), 3.79 (3H, s), 3.82 (3H, s), 4.24 (2H, t, J = 6.6 Hz), 5.0 (2H, s), 6.85-6.95 (1H, m), 7.19 (1H, d, J = 11.6 Hz), 7.35 (1H, d, J = 7.3 Hz), 7.4-7.55 (2H, m), 7.87 (1H, d, J = 8.2 Hz), 11.82 (1H, s) |
| 8 | | (DMSO-d6) 3.79 (3H, s), 3.83 (3H, s), 5.01 (2H, s), 6.85-6.95 (1H, m), 7.19 (1H, d, J = 11.4 Hz), 7.34 (1H, d, J = 7.3 Hz), 7.4-7.55 (2H, m), 7.86 (1H, d, J = 8.1 Hz), 11.77 (1H, s), 12.82 (1H, s) |

TABLE 30-continued

| Ex No. | Strc | (Solv) ¹H-NMR δ ppm: |
|---|---|---|
| 9 | | (DMSO-d6) 3.8 (3H, s), 3.83 (3H, s), 4.95-5.05 (2H, m), 6.85-6.95 (1H, m), 7.16 (1H, d, J = 8.3 Hz), 7.28 (1H, s), 7.4-7.55 (3H, m), 11.58 (1H, s) |

TABLE 31

| Ex No. | Strc | (Solv) ¹H-NMR δ ppm: |
|---|---|---|
| 10 | | (DMSO-d6) 3.67 (3H, s), 3.78 (3H, s), 3.83 (3H, s), 4.95-5.1 (2H, m), 6.49 (1H, d, J = 8.1 Hz), 6.85-6.95 (1H, m), 7.26 (1H, s), 7.35-7.45 (2H, m), 7.45-7.55 (1H, m), 11.09 (1H, s) |
| 11 | | (CDCl3) 2.41 (3H, s), 3.77 (3H, s), 3.87 (3H, s), 5.1-5.2 (2H, m), 6.55-6.6 (1H, m), 6.8-6.9 (2H, m), 7.05-7.2 (2H, m), 7.96 (1H, d, J = 5.3 Hz), 9.5 (1H, s) |
| 12 | | (DMSO-d6) 3.79 (3H, s), 3.84 (3H, s), 5.01 (2H, s), 6.85-6.95 (1H, m), 7.3 (1H, s), 7.4-7.55 (3H, m), 7.86 (1H, d, J = 7.8 Hz), 11.77 (1H, s), 12.87 (1H, s) |
| 13 | | (DMSO-d6) 1.65-1.75 (2H, m), 2.45-2.6 (2H, m), 3.75-3.85 (2H, m), 7.05-7.2 (3H, m), 7.57 (1H, d, J = 8.2 Hz), 7.69 (1H, dd, J = 8.7 Hz, 2.2 Hz), 7.75 (1H, d, J = 1.3 Hz), 7.9 (1H, d, J = 8.7 Hz), 8.11 (1H, d, J = 2.2 Hz), 8.49 (1H, d, J = 1.3 Hz), 11.72 (1H, s), 13.19 (1H, s) |
| 14 | | (DMSO-d6) 3.79 (3H, s), 3.84 (3H, s), 5.01 (2H, s), 6.85-6.95 (1H, m), 7.29 (1H, s), 7.4-7.55 (3H, m), 11.96 (1H, s), 13.15 (1H, brs) |

TABLE 31-continued
| Ex No. | Strc | (Solv) $^1$H-NMR δ ppm: |
|---|---|---|
| 15 | 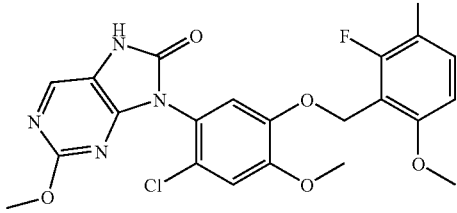 | (DMSO-d6) 3.8 (3H, s), 3.81 (3H, s), 3.83 (3H, s), 5.0 (2H, s), 6.85-6.95 (1H, m), 7.28 (1H, s), 7.4-7.55 (2H, m), 8.11 (1H, s), 11.43 (1H, s) |
| 16 | 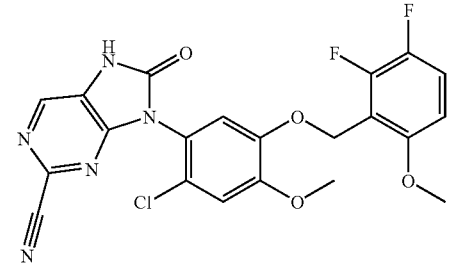 | (DMSO-d6) 3.8 (3H, s), 3.85 (3H, s), 5.01 (2H, s), 6.9-6.95 (1H, m), 7.33 (1H, s), 7.45-7.55 (2H, m), 8.55 (1H, s), 12.4 (1H, brs) |
| 17 | 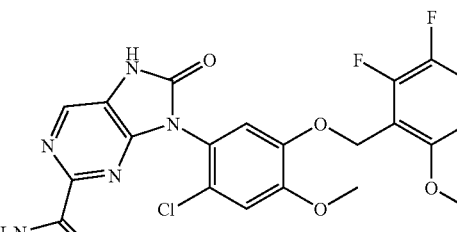 | (DMSO-d6) 3.8 (3H, s), 3.84 (3H, s), 5.02 (2H, s), 6.85-6.95 (1H, m), 7.31 (1H, s), 7.45-7.55 (2H, m), 7.6 (1H, s), 7.92 (1H, s), 8.42 (1H, s), 11.96 (1H, brs) |
TABLE 32
| Ex No. | Strc | (Solv) $^1$H-NMR δ ppm: |
|---|---|---|
| 18 | 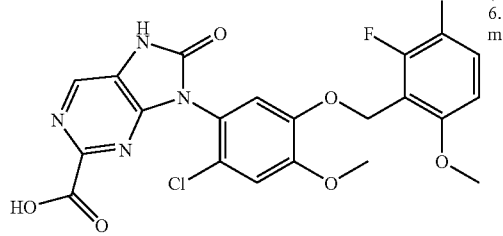 | (DMSO-d6) 3.8 (3H, s), 3.85 (3H, s), 5.01 (2H, s), 6.85-6.95 (1H, m), 7.32 (1H, s), 7.45-7.55 (2H, m), 8.48 (1H, s), 12.06 (1H, s), 13.24 (1H, brs) |
| 19 | 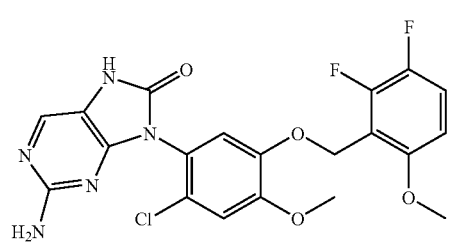 | (DMSO-d6) 3.8 (3H, s), 3.81 (3H, s), 5.0 (2H, s), 6.26 (2H, s), 6.85-6.95 (1H, m), 7.24 (1H, s), 7.43 (1H, s), 7.45-7.55 (1H, m), 7.83 (1H, s), 10.94 (1H, s) |

TABLE 32-continued

| Ex No. | Strc | (Solv) ¹H-NMR δ ppm: |
|---|---|---|
| 20 | | (DMSO-d6) 1.65-1.75 (2H, m), 2.4-2.6 (2H, m), 3.7-3.85 (2H, m), 7.05-7.2 (4H, m), 7.35-7.45 (1H, m), 7.55-7.6 (1H, m), 7.65-7.7 (1H, m), 7.85-7.9 (2H, m), 7.97 (1H, d, J = 2.3 Hz), 11.43 (1H, s) |
| 21 | | (DMSO-d6) 1.65-1.75 (2H, m), 2.45-2.55 (2H, m), 3.75-3.85 (2H, m), 7.05-7.25 (4H, m), 7.4-7.45 (1H, m), 7.5-7.55 (1H, m), 7.62 (1H, d, J = 8.3 Hz), 7.65-7.75 (1H, m), 7.9-8.0 (1H, m), 8.05-8.1 (1H, m), 8.15-8.2 (1H, m), 11.51 (1H, s) |
| 22 | | (DMSO-d6) 1.65-1.75 (2H, m), 2.45-2.6 (2H, m), 3.7-3.85 (2H, m), 7.05-7.2 (3H, m), 7.56 (1H, d, J = 8.4 Hz), 7.65-7.75 (1H, m), 7.91 (1H, d, J = 8.4 Hz), 8.12 (1H, d, J = 2.1 Hz), 8.38 (1H, s), 8.55 (1H, s), 11.76 (1H, s) |
| 23 | | (DMSO-d6) 1.65-1.75 (2H, m), 2.41 (3H, s), 2.4-2.6 (2H, m), 3.7-3.9 (2H, m), 7.05-7.15 (2H, m), 7.15-7.25 (1H, m), 7.57 (1H, d, J = 8.2 Hz), 7.64 (1H, dd, J = 8.5 Hz, 2.2 Hz), 7.89 (1H, d, J = 8.5 Hz), 8.16 (1H, d, J = 2.2 Hz), 8.26 (1H, s), 11.64 (1H, s) |
| 24 | | (DMSO-d6) 1.735 (3H, s), 1.744 (3H, s), 7.05-7.15 (1H, m), 7.25-7.45 (7H, m), 7.7 (1H, d, J = 2.2 Hz), 7.8-7.95 (2H, m), 11.48 (1H, s) |
| 25 | | (DMSO-d6) 1.65-1.75 (2H, m), 2.4-2.6 (2H, m), 3.28 (3H, s), 3.7-3.9 (2H, m), 7.05-7.15 (2H, m), 7.15-7.25 (1H, m), 7.57 (1H, d, J = 8.2 Hz), 7.66 (1H, dd, J = 8.6 Hz, 2.2 Hz), 8.59 (1H, d, J = 8.6 Hz), 8.25 (1H, d, J = 2.2 Hz), 8.55 (1H, s), 12.31 (1H, brs) |

TABLE 33

| Ex No. | Strc | (Solv) ¹H-NMR δ ppm: |
|---|---|---|
| 26 | | (DMSO-d6) 3.79 (3H, s), 3.85 (3H, s), 4.95-5.05 (2H, m), 6.85-6.95 (1H, m), 7.2-7.3 (2H, m), 7.36 (1H, s), 7.45-7.55 (1H, m), 7.6-7.65 (1H, m), 8.05-8.15 (1H, m), 13.24 (1H, s) |

TABLE 33-continued

| Ex No. | Strc | (Solv) ¹H-NMR δ ppm: |
|---|---|---|
| 27 | | (DMSO-d6) 3.78 (3H, s), 3.83 (3H, s), 5.0-5.1 (2H, m), 6.72 (1H, dd, J = 5.4 Hz, 0.6 Hz), 6.85-6.95 (1H, m), 7.3 (1H, s), 7.42 (1H, s), 7.45-7.55 (1H, m), 8.17 (1H, d, J = 5.4 Hz), 8.29 (1H, d, J = 0.6 Hz), 11.39 (1H, brs) |
| 28 | | (DMSO-d6) 3.79 (3H, s), 3.82 (3H, s), 3.96 (3H, s), 4.95-5.05 (2H, m), 6.85-6.95 (2H, m), 7.24 (1H, s), 7.35 (1H, s), 7.4-7.55 (1H, m), 7.83 (1H, d, J = 6.0 Hz), 11.44 (1H, s) |
| 29 | | (DMSO-d6) 1.68 (3H, s), 1.69 (3H, s), 7.15-7.25 (2H, m), 7.25-7.35 (3H, m), 7.35-7.5 (4H, m), 7.59 (1H, d, J = 8.6 Hz), 11.6 (1H, s) |
| 30 | | (DMSO-d6) 1.81 (3H, s), 1.83 (3H, s), 7.1-7.6 (9H, m), 11.61 (1H, s) |
| 31 | | (DMSO-d6) 3.79 (3H, s), 3.83 (3H, s), 4.95-5.05 (2H, m), 6.85-6.95 (1H, m), 7.29 (1H, s), 7.45-7.55 (2H, m), 8.37 (1H, s), 8.55 (1H, s), 11.68 (1H, s) |
| 32 | | (DMSO-d6) 3.79 (3H, s), 3.83 (3H, s), 4.03 (3H, s), 5.02 (2H, s), 6.85-6.95 (1H, m), 7.27 (1H, s), 7.4-7.55 (2H, m), 7.6 (1H, s), 11.86 (1H, s), 12.94 (1H, brs) |
| 33 | | (DMSO-d6) 1.68 (3H, s), 1.69 (3H, s), 7.15-7.35 (4H, m), 7.4-7.55 (4H, m), 7.6 (1H, d, J = 8.0 Hz), 7.87 (1H, d, J = 8.2 Hz), 11.79 (1H, brs), 12.8 (1H, brs) |

TABLE 33-continued

| Ex No. | Strc | (Solv) $^1$H-NMR δ ppm: |
|---|---|---|
| 34 | | (DMSO-d6) 1.81 (3H, s), 1.83 (3H, s), 7.05-7.25 (3H, m), 7.3-7.4 (2H, m), 7.4-7.6 (3H, m), 7.87 (1H, d, J = 8.3 Hz), 11.78 (1H, s), 12.82 (1H, brs) |

TABLE 34

| Ex No. | Strc | (Solv) $^1$H-NMR δ ppm: |
|---|---|---|
| 35 | | (DMSO-d6) 1.74 (3H, s), 1.76 (3H, s), 7.25-7.45 (7H, m), 7.65-7.75 (1H, m), 7.8-7.9 (2H, m) |
| 36 | | (DMSO-d6) 1.97 (3H, s), 1.98 (3H, s), 7.25-7.6 (4H, m), 7.65-7.75 (1H, m), 7.85-7.95 (3H, m), 7.98 (1H, d, J = 2.2 Hz), 11.84 (1H, s), 12.5-13.5 (1H, br) |
| 37 | | (DMSO-d6) 3.792 (3H, s), 3.796 (3H, s), 3.84 (3H, s), 5.01 (2H, s), 6.85-6.95 (1H, m), 7.3 (1H, s), 7.4-7.55 (3H, m), 7.89 (1H, d, J = 8.0 Hz), 11.83 (1H, s) |
| 38 | | (DMSO-d6) 1.4 (3H, t, J = 7.1 Hz), 3.79 (3H, s), 3.83 (3H, s), 4.55 (2H, q, J = 7.1 Hz), 4.95-5.05 (2H, m), 6.85-6.95 (1H, m), 7.27 (1H, s), 7.41 (1H, s), 7.45-7.55 (1H, m), 8.24 (1H, s), 11.7 (1H, s) |
| 39 | | (DMSO-d6) 3.8 (3H, s), 3.83 (3H, s), 4.05 (3H, s), 4.95-5.05 (2H, m), 6.85-6.95 (1H, m), 7.27 (1H, s), 7.43 (1H, s), 7.45-7.55 (1H, m), 8.27 (1H, s), 11.77 (1H, s) |

TABLE 35
| Ex No. | Strc | (Solv) ¹H-NMR δ ppm: |
|---|---|---|
| 40 | 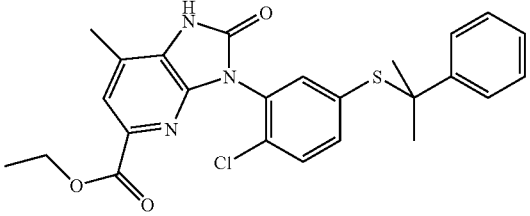 | (DMSO-d6) 1.24 (3H, t, J = 7.1 Hz), 1.65 (3H, s), 1.66 (3H, s), 2.42 (3H, s), 3.75 (3H, s), 4.2-4.3 (2H, m), 7.1-7.15 (1H, m), 7.2-7.25 (3H, m), 7.31 (1H, s), 7.4-7.5 (2H, m), 7.74 (1H, s), 11.86 (1H, s) |
| 41 | 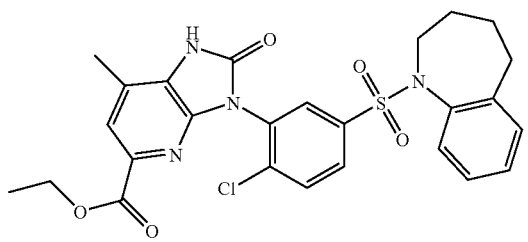 | (DMSO-d6) 1.23 (3H, t, J = 7.2 Hz), 1.4-1.7 (2H, m), 1.7-1.85 (2H, m), 2.4-2.65 (5H, m), 3.4-3.85 (2H, m), 4.2-4.3 (2H, m), 7.1-7.3 (4H, m), 7.77 (1H, s), 7.85-8.05 (2H, m), 8.1-8.2 (1H, m), 12.0 (1H, s) |
| 42 | 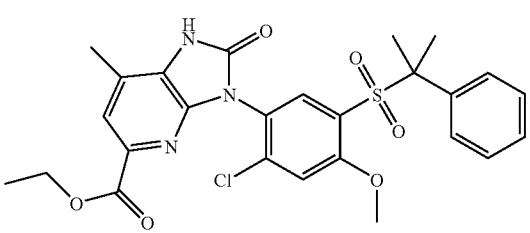 | (DMSO-d6) 1.24 (3H, t, J = 7.1 Hz), 1.74 (6H, s), 2.42 (3H, s), 3.63 (3H, s), 4.2-4.3 (2 H, m), 7.25-7.4 (3H, m), 7.4-7.45 (2H, m), 7.49 (1H, s), 7.74 (1H, s), 7.76 (1H, s), 11.92 (1H, s) |
| 43 | 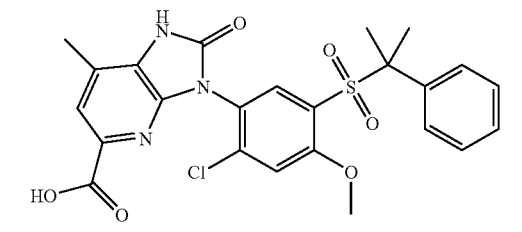 | (DMSO-d6) 1.73 (3H, s), 1.74 (3H, s), 2.41 (3H, s), 3.66 (3H, s), 7.25-7.45 (5H, m), 7.5 (1H, s), 7.7 (1H, s), 7.74 (1H, s), 11.87 (1H, s), 12.7 (1H, brs) |
| 44 | 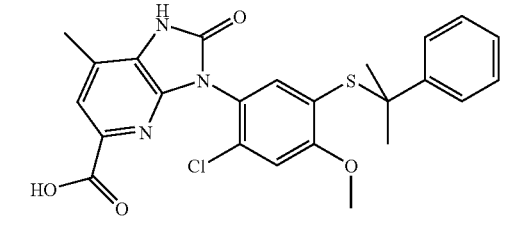 | (DMSO-d6) 1.65 (6H, s), 2.41 (3H, s), 3.76 (3H, s), 7.05-7.3 (4H, m), 7.32 (1H, s), 7.4-7.5 (2H, m), 7.7-7.75 (1H, m), 11.81 (1H, s), 12.73 (1H, brs) |
| 45 | 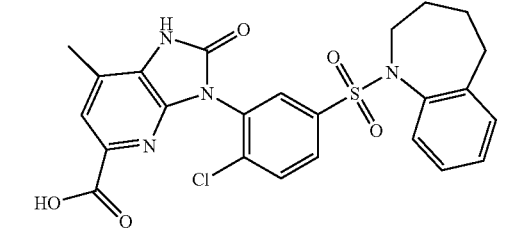 | (DMSO-d6) 1.4-1.9 (4H, m), 2.4-2.6 (5H, m), 3.4-3.8 (2H, m), 7.1-7.3 (4H, m), 7.74 (1H, s), 7.85-8.05 (2H, m), 8.13 (1H, s), 11.84 (1H, s), 12.81 (1H, brs) |

TABLE 35-continued

| Ex No. | Strc | (Solv) ¹H-NMR δ ppm: |
|---|---|---|
| 46 | | (DMSO-d6) 2.42 (3H, s), 3.79 (3H, s), 3.84 (3H, s), 5.02 (2H, s), 6.85-6.95 (1H, m), 7.28 (1H, s), 7.4-7.55 (2H, m), 7.73 (1H, s), 11.84 (1H, s), 12.73 (1H, brs) |

TABLE 36

| Ex No. | Strc | (Solv) ¹H-NMR δ ppm: |
|---|---|---|
| 47 | | (DMSO-d6) 1.68 (3H, s), 1.69 (3H, s), 2.42 (3H, s), 7.15-7.35 (4H, m), 7.4 (1H, d, J = 2.5 Hz), 7.45-7.5 (2H, m), 7.59 (1H, d, J = 8.6 Hz), 7.74 (1H, d, J = 0.5 Hz), 11.89 (1H, s), 12.76 (1H, s) |
| 48 | | (DMSO-d6) 1.72 (3H, s), 1.73 (3H, s), 3.84 (3H, s), 6.7-6.8 (1H, m), 7.01 (1H, d, J = 7.4 Hz), 7.1-7.25 (3H, m), 7.27 (1H, d, J = 2.4 Hz), 7.45 (1H, d, J = 7.8 Hz), 7.53 (1H, d, J = 8.2 Hz), 7.85 (1H, d, J = 7.8 Hz), 11.0-14.0 (2H, br) |
| 49 | | (DMSO-d6) 1.83 (6H, s), 6.95-7.05 (2H, m), 7.15-7.45 (4H, m), 7.62 (1H, d, J = 8.4 Hz), 7.8 (1H, d, J = 7.7 Hz), 11.0-14.0 (2H, br) |
| 50 | | (DMSO-d6) 3.2 (3H, s), 3.59 (2H, t, J = 4.6 Hz), 4.05-4.2 (2H, m), 5.15 (2H, s), 6.9-6.95 (1H, m), 7.25-7.3 (1H, m), 7.35-7.55 (3H, m), 7.62 (1H, d, J = 9.0 Hz), 7.86 (1H, d, J = 8.0 Hz), 11.77 (1H, s), 12.82 (1H, s) |

TABLE 36-continued

| Ex No. | Strc | (Solv) ¹H-NMR δ ppm: |
|---|---|---|
| 51 | | (DMSO-d6) 3.82 (3H, s), 5.1 (2H, s), 6.85-6.95 (1H, m), 7.25-7.3 (1H, m), 7.39 (1H, d, J = 3.0 Hz), 7.45-7.55 (2H, m), 7.64 (1H, d, J = 8.9 Hz), 7.86 (1H, d, J = 8.1 Hz), 11.78 (1H, s), 12.84 (1H, brs) |
| 52 | | (DMSO-d6) 1.84 (6H, s), 3.72 (3H, s), 6.75-6.85 (1H, m), 7.1-7.3 (2H, m), 7.3-7.45 (2H, m), 7.6 (1H, d, J = 8.3 Hz), 7.79 (1H, d, J = 8.1 Hz), 11.0-14.0 (2H, br) |
| 53 | | (DMSO-d6) 4.25-4.4 (2H, m), 7.2-7.55 (7H, m), 7.55-7.7 (2H, m), 7.83 (1H, d, J = 7.6 Hz), 11.0-14.0 (2H, br) |

TABLE 37

| Ex No. | Strc | (Solv) ¹H-NMR δ ppm: |
|---|---|---|
| 54 | | (DMSO-d6) 3.29 (3H, s), 3.55 (3H, s), 4.03 (3H, s), 6.85-7.05 (2H, m), 7.15-7.3 (2H, m), 7.44 (1H, d, J = 8.1 Hz), 7.69 (2H, s), 7.83 (1H, d, J = 8.1 Hz), 11.7 (1H, s), 12.78 (1H, brs) |
| 55 | | (DMSO-d6) 2.38 (3H, s), 3.29 (3H, s), 3.55 (3H, s), 4.03 (3H, s), 6.85-7.0 (2H, m), 7.1-7.3 (2H, m), 7.65 (1H, s), 7.68 (1H, s), 7.7 (1H, s), 11.8 (1H, s), 12.73 (1H, brs) |

TABLE 37-continued

| Ex No. | Strc | (Solv) $^1$H-NMR δ ppm: |
|---|---|---|
| 56 | | (DMSO-d6) 2.4 (3H, s), 3.32 (3H, s), 3.9 (3H, s), 7.2-7.3 (3H, m), 7.3-7.4 (2H, m), 7.64 (1H, s), 7.72 (1H, s), 7.88 (1H, s), 11.84 (1H, s), 12.73 (1H, brs) |
| 57 | | (DMSO-d6) 2.4 (3H, s), 3.27 (3H, s), 3.96 (3H, s), 71-7.45 (4H, m), 7.69 (1H, s), 7.72 (1H, d, J = 0.8 Hz), 7.87 (1H, s), 11.84 (1H, s), 12.73 (1H, brs) |
| 58 | | (DMSO-d6) 2.4 (3H, s), 3.31 (3H, s), 3.86 (3H, s), 7.0-7.25 (3H, m), 7.35-7.45 (1H, m), 7.64 (1H, s), 7.72 (1H, d, J = 0.7 Hz), 7.97 (1H, s), 11.85 (1H, s), 12.7 (1H, brs) |
| 59 | | (DMSO-d6) 2.42 (3H, s), 3.19 (3H, s), 3.49 (3H, s), 6.85-7.0 (2H, m), 7.2-7.35 (2H, m), 7.7-7.8 (2H, m), 7.9-8.0 (2H, m), 11.94 (1H, s), 12.77 (1H, brs) |
| 60 | | (DMSO-d6) 2.4-2.45 (3H, m), 3.15-3.2 (3H, m), 3.45-3.55 (3H, m), 6.8-6.95 (2H, m), 7.25-7.4 (1H, m), 7.7-8.1 (4H, m), 11.9-12.0 (1H, m), 12.8 (1H, brs) |

TABLE 38

| Ex No. | Strc | (Solv) $^1$H-NMR δ ppm: |
|---|---|---|
| 61 | | (DMSO-d6) 2.43 (3H, s), 3.19 (3H, s), 7.4-7.45 (1H, m), 7.5-7.6 (2H, m), 7.75 (1H, s), 7.95-8.05 (2H, m), 8.22 (1H, s), 11.95 (1H, s), 12.76 (1H, brs) |

TABLE 38-continued

| Ex No. | Strc | (Solv) ¹H-NMR δ ppm: |
|---|---|---|
| 62 | | (DMSO-d6) 2.42 (3H, s), 2.71 (3H, s), 4.04 (3H, s), 4.35 (2H, s), 7.25-7.45 (5H, m), 7.67 (1H, s), 7.74 (1H, s), 8.04 (1H, s), 11.9 (1H, s), 12.76 (1H, brs) |
| 63 | | (DMSO-d6) 2.42 (3H, s), 3.75-4.05 (4H, m), 6.8-7.0 (2H, m), 7.05-7.15 (1H, m), 7.65-7.8 (3H, m), 7.94 (1H, d, J = 8.5 Hz), 8.26 (1H, d, J = 2.3 Hz), 11.97 (1H, s), 12.84 (1H, brs) |
| 64 | | (DMSO-d6) 0.97 (3H, t, J = 7.2 Hz), 2.42 (3H, s), 3.45-3.8 (5H, m), 6.9-7.0 (2H, m), 7.2 (1H, dd, J = 7.7 Hz, 1.7 Hz), 7.25-7.35 (1H, m), 7.7-7.8 (2H, m), 7.9-8.0 (2H, m), 11.94 (1H, s), 12.76 (1H, brs) |
| 65 | | (DMSO-d6) 0.85-1.1 (6H, m), 2.43 (3H, s), 3.5-3.65 (3H, m), 4.3-4.45 (1H, m), 6.85-7.0 (1H, m), 7.0-7.2 (2H, m), 7.3-7.4 (1H, m), 7.7-7.8 (1H, m), 7.9-8.05 (3H, m), 11.9-12.0 (1H, m), 12.71 (1H, brs) |
| 66 | | (DMSO-d6) 1.8-2.05 (2H, m), 2.43 (3H, s), 3.6-4.1 (4H, m), 7.0-7.15 (2H, m), 7.25-7.35 (2H, m), 7.64 (1H, dd, J = 8.5 Hz, 2.3 Hz), 7.76 (1H, d, J = 0.5 Hz), 7.92 (1H, d, J = 8.5 Hz), 8.17 (1H, d, J = 2.3 Hz), 11.95 (1H, s), 12.78 (1H, brs) |

TABLE 39

| Ex No. | Strc | (Solv) ¹H-NMR δ ppm: |
|---|---|---|
| 67 | | (DMSO-d6) 1.8-1.9 (2H, m), 2.42 (3H, s), 2.74 (2H, t, J = 6.6 Hz), 3.7-3.9 (5H, m), 6.95-7.15 (3H, m), 7.32 (1H, d, J = 7.6 Hz), 7.59 (1H, s), 7.74 (1H, s), 8.16 (1H, s), 11.88 (1H, s), 12.79 (1H, brs) |

TABLE 39-continued

| Ex No. | Strc | (Solv) ¹H-NMR δ ppm: |
|---|---|---|
| 68 | | (DMSO-d6) 0.84 (3H, t, J = 7.3 Hz), 1.25-1.4 (2H, m), 2.42 (3H, s), 3.1-3.8 (5H, m), 6.9-7.0 (2H, m), 7.22 (1H, dd, J = 7.6 Hz, 1.8 Hz), 7.25-7.35 (1H, m), 7.65-7.8 (2H, m), 7.9-7.95 (2H, m), 11.94 (1H, s), 12.77 (1H, brs) |
| 69 | | (DMSO-d6) 2.42 (3H, s), 3.1-3.5 (7H, m), 4.67 (1H, t, J = 5.7 Hz), 6.9-7.0 (2H, m), 7.25-7.35 (2H, m), 7.65-7.8 (2H, m), 7.85-7.95 (2H, m), 11.94 (1H, s), 12.8 (1H, brs) |
| 70 | | (DMSO-d6) 1.5-1.7 (2H, m), 1.75-1.9 (2H, m), 2.4 (3H, s), 2.7-2.85 (2H, m), 3.5-3.85 (2H, m), 4.03 (3H, s), 6.7-6.8 (1H, m), 7.05-7.2 (2H, m), 7.25-7.3 (1H, m), 7.7-7.75 (2H, m), 7.91 (1H, s), 11.84 (1H, s), 12.76 (1H, brs) |
| 71 | | (DMSO-d6) 2.42 (3H, s), 3.18 (3H, s), 7.1-7.45 (3H, m), 7.58 (1H, dd, J = 8.1 Hz, 1.6 Hz), 7.76 (1H, s), 7.8-8.2 (3H, m), 11.95 (1H, s), 12.79 (1H, brs) |
| 72 | | (DMSO-d6) 2.4 (3H, s), 3.21 (3H, s), 3.64 (3H, s), 3.85 (3H, s), 6.95-7.05 (1H, m), 7.22 (1H, d, J = 8.2 Hz), 7.37.4 (2H, m), 7.55-7.7 (2H, m), 7.72 (1H, s), 11.85 (1H, s), 12.79 (1H, brs) |

TABLE 40

| Ex No. | Strc | (Solv) ¹H-NMR δ ppm: |
|---|---|---|
| 73 | | (DMSO-d6) 2.4 (3H, s), 3.08 (3H, s), 3.6 (3H, s), 3.88 (3H, s), 4.6-4.9 (2H, m), 6.65-6.75 (1H, m), 7.15-7.35 (2H, m), 7.41 (1H, s), 7.71 (1H, s), 11.78 (1H, s), 12.74 (1H, brs) |
| 74 | | (DMSO-d6) 1.65-1.8 (3H, m), 2.35-2.45 (3H, m), 3.5-3.6 (3H, m), 3.75-3.85 (3H, m), 4.55-4.75 (1H, m), 4.9-5.05 (1H, m), 6.6-6.7 (1H, m), 7.05-7.3 (2H, m), 7.35-7.45 (1H, m), 7.65-7.75 (1H, m), 11.7-11.9 (1H, m), 12.72 (1H, brs) |
| 75 | | (DMSO-d6) 1.5-1.75 (2H, m), 1.75-1.9 (2H, m), 2.4 (3H, s), 2.65-2.85 (2H, m), 3.4-4.0 (5H, m), 4.05 (3H, s), 6.6-6.7 (2H, m), 6.83 (1H, d, J = 2.5 Hz), 7.72 (2H, s), 7.87 (1H, s), 11.84 (1H, s), 12.77 (1H, brs) |
| 76 | | (DMSO-d6) 1.2-4.2 (16H, m), 6.7-6.8 (1H, m), 7.1-7.35 (3H, m), 7.65-7.8 (3H, m), 11.82 (1H, s), 12.75 (1H, brs) |
| 77 | | (DMSO-d6) 2.42 (3H, s), 3.11 (3H, s), 3.59 (3H, s), 4.8-4.95 (2H, m), 6.65-6.75 (1H, m), 7.2-7.45 (2H, m), 7.65-7.8 (3H, m), 11.92 (1H, s), 12.77 (1H, brs) |
| 78 | | (DMSO-d6) 1.4-2.0 (4H, m), 2.4 (3H, s), 2.65-2.8 (2H, m), 3.45-4.1 (8H, m), 6.22 (1H, d, J = 2.6 Hz), 6.73 (1H, dd, J = 8.3 Hz, 2.6 Hz), 7.17 (1H, d, J = 8.3 Hz), 7.7-7.8 (2H, m), 7.96 (1H, s), 11.85 (1H, s), 12.72 (1H, brs) |

TABLE 41
| Ex No. | Strc | (Solv) ¹H-NMR δ ppm: |
|---|---|---|
| 79 | 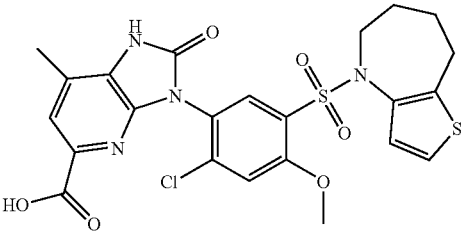 | (DMSO-d6) 1.5-1.65 (2H, m), 1.7-1.9 (2H, m), 2.41 (3H, s), 2.6-2.75 (2H, m), 3.55-3.7 (2H, m), 3.95 (3H, s), 6.63 (1H, d, J = 5.3 Hz), 7.08 (1H, d, J = 5.3 Hz), 7.68 (1H, s), 7.72 (1H, s), 7.97 (1H, s), 11.85 (1H, s), 12.70 (1H, brs) |
| 80 | 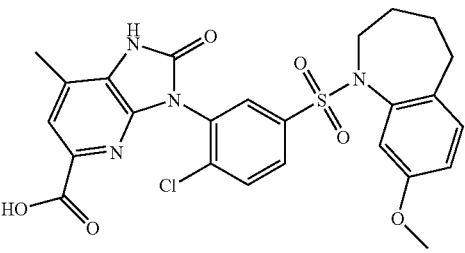 | (DMSO-d6) 1.4-1.6 (2H, m), 1.7-1.85 (2H, m), 2.35-2.55 (5H, m), 3.45-3.8 (5H, m), 6.62 (1H, d, J = 2.7 Hz), 6.79 (1H, dd, J = 8.3 Hz, 2.7 Hz), 7.13 (1H, d, J = 8.3 Hz), 7.74 (1H, s), 7.87 (1H, dd, J = 8.5 Hz, 2.2 Hz), 7.97 (1H, d, J = 8.5 Hz), 8.16 (1H, d, J = 2.2 Hz), 11.94 (1H, s), 12.76 (1H, brs) |
| 81 | 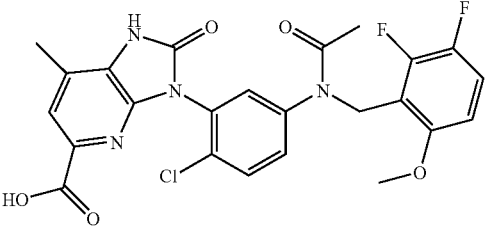 | (DMSO-d6) 1.83 (3H, s), 2.41 (3H, s), 3.56 (3H, s), 4.85-5.0 (2H, m), 6.65-6.75 (1H, m), 7.15-7.4 (2H, m), 7.51 (1H, s), 7.6-7.75 (2H, m), 11.89 (1H, s), 12.72 (1H, brs) |
| 82 | 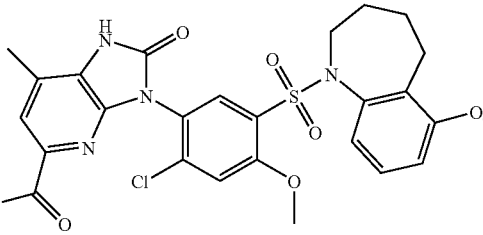 | (DMSO-d6) 1.4-1.65 (2H, m), 1.8-1.9 (2H, m), 2.39 (3H, s), 2.75-3.0 (2H, m), 3.4-3.9 (5H, m), 4.06 (3H, s), 6.33 (1H, d, J = 7.9 Hz), 6.89 (1H, d, J = 7.9 Hz), 7.0-7.1 (1H, m), 7.7 (1H, s), 7.73 (1H, s), 7.88 (1H, s), 11.82 (1H, s), 12.76 (1H, brs) |
| 83 | 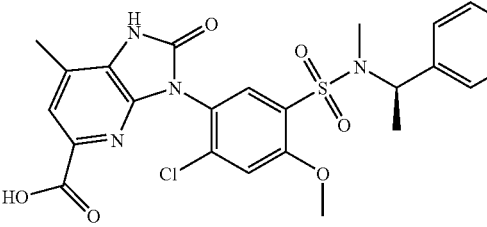 | (DMSO-d6) 1.35-1.5 (3H, m), 2.42 (3H, s), 2.65-2.75 (3H, m), 3.93 (3H, s), 5.0-5.15 (1H, m), 7.2-7.4 (5H, m), 7.55-7.65 (1H, m), 7.7-7.75 (1H, m), 8.0-8.1 (1H, m), 11.9 (1H, s), 12.73 (1H, brs) |
| 84 | 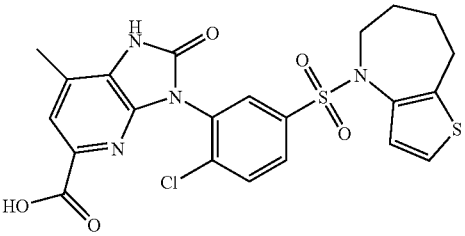 | (DMSO-d6) 1.35-1.55 (2H, m), 1.65-1.8 (2H, m), 2.25-2.6 (5H, m), 3.55-3.75 (2H, m), 6.94 (1H, d, J = 5.4 Hz), 7.17 (1H, d, J = 5.4 Hz), 7.7-7.8 (2H, m), 7.9-8.0 (2H, m), 11.93 (1H, s), 12.78 (1H, brs) |

TABLE 42

| Ex No. | Strc | (Solv) ¹H-NMR δ ppm: |
|---|---|---|
| 85 | | (DMSO-d6) 1.35-1.5 (3H, m), 2.42 (3H, s), 2.65-2.75 (3H, m), 3.93 (3H, s), 5.0-5.15 (1H, m), 7.2-7.4 (5H, m), 7.55-7.65 (1H, m), 7.7-7.75 (1H, m), 8.0-8.1 (1H, m), 11.9 (1H, s), 12.73 (1H, brs) |
| 86 | | (DMSO-d6) 1.4-1.9 (4H, m), 2.4 (3H, s), 2.65-2.8 (2H, m), 3.4-3.9 (2H, m), 3.97 (3H, s), 6.6-6.7 (1H, m), 7.0-7.1 (1H, m), 7.25-7.4 (1H, m), 7.7-7.75 (2H, m), 7.98 (1H, s), 11.85 (1H, s), 12.72 (1H, brs) |
| 87 | | (DMSO-d6) 0.99 (3H, t, J = 7.2Hz), 2.38 (3H, s), 3.51 (3H, s), 3.65-3.95 (2H, m), 4.04 (3H, s), 6.85-6.95 (1H, m), 6.98 (1H, dd, J = 8.5 Hz, 1.1 Hz), 7.15 (1H, dd, J = 7.9 Hz, 1.9 Hz), 7.2-7.3 (1H, m), 7.6 (1H, s), 7.65-7.75 (2H, m), 11.8 (1H, s), 12.77 (1H, brs) |
| 88 | | (DMSO-d6) 1.56 (3H, s), 1.57 (3H, s), 2.41 (3H, s), 2.73 (3H, s), 4.09 (3H, s), 7.15-7.4 (5H, m), 7.65-7.75 (2H, m), 7.95 (1H, s), 11.87 (1H, s), 12.68 (1H, brs) |
| 89 | | (DMSO-d6) 2.33 (3H, s), 3.38 (3H, s), 7.1-7.7 (9H, m), 11.57 (1H, brs) |
| 90 | | (DMSO-d6) 1.55-1.7 (2H, m), 1.8-1.95 (2H, m), 2.39 (3H, s), 2.75-2.9 (2H, m), 3.5-3.9 (2H, m), 6.75-6.85 (1H, m), 7.05-7.2 (2H, m), 7.25-7.3 (1H, m), 7.34 (1H, s), 7.7-7.75 (1H, m), 7.81 (1H, s), 11.83 (1H, s), 11.92 (1H, s), 12.78 (1H, brs) |

TABLE 43

| Ex No. | Strc | (Solv) ¹H-NMR δ ppm: |
|---|---|---|
| 91 | | (DMSO-d6) 1.35-1.55 (2H, m), 1.65-1.8 (2H, m), 2.2-2.6 (8H, m), 3.5-3.7 (2H, m), 6.6-6.7 (1H, m), 7.7-7.8 (2H, m), 7.9-8.05 (2H, m), 11.94 (1H, s), 12.77 (1H, s) |
| 92 | | (DMSO-d6) 1.5-1.7 (2H, m), 1.75-1.9 (2H, m), 2.4 (3H, s), 2.65-2.85 (2H, m), 3.55-3.8 (2H, m), 4.0 (3H, s), 6.75-6.85 (1H, m), 7.05-7.3 (3H, m), 7.57 (1H, d, J = 11.8 Hz), 7.73 (1H, s), 7.94 (1H, d, J = 8.3 Hz), 11.89 (1H, s), 12.76 (1H, brs) |
| 93 | | (DMSO-d6) 1.4-1.9 (4H, m), 2.35-2.65 (5H, m), 3.3-3.9 (2H, m), 7.1-7.3 (4H, m), 7.65-7.8 (2H, m), 7.85-7.95 (1H, m), 8.17 (1H, dd, J = 6.7 Hz, 2.4 Hz), 11.99 (1H, s), 12.8 (1H, brs) |
| 94 | | (DMSO-d6) 0.7-0.85 (3H, m), 1.8-2.0 (2H, m), 2.43 (3H, s), 2.75-2.9 (3H, m), 3.65-3.75 (3H, m), 4.62 (1H, t, J = 7.7 Hz), 7.05-7.45 (6H, m), 7.7-7.8 (1H, m), 7.95-8.05 (1H, m), 11.85-11.95 (1H, m), 12.72 (1H, brs) |
| 95 | | (DMSO-d6) 1.4-1.65 (2H, m), 1.75-1.9 (2H, m), 2.3-2.65 (5H, m), 3.4-3.9 (2H, m), 7.15-7.3 (4H, m), 7.65-7.85 (3H, m), 8.1-8.15 (1H, m), 8.25-8.35 (1H, m), 11.99 (1H, s), 12.81 (1H, brs) |
| 96 | | (DMSO-d6) 2.42 (3H, s), 3.18 (3H, s), 3.49 (3H, s), 6.85-7.0 (2H, m), 7.2-7.35 (2H, m), 7.65-7.8 (3H, m), 7.97 (1H, dd, J = 6.8 Hz, 2.4 Hz), 11.99 (1H, s), 12.81 (1H, brs) |

TABLE 44
| Ex No. | Strc | (Solv) $^1$H-NMR δ ppm: |
|---|---|---|
| 97 | 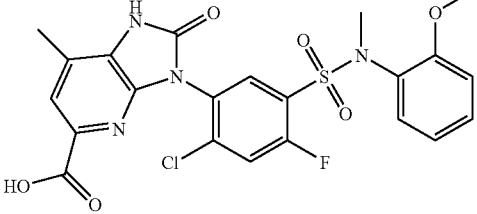 | (DMSO-d6) 2.39 (3H, s), 3.25-3.35 (3H, m), 3.52 (3H, s), 6.9-7.05 (2H, m), 7.25-7.35 (2H, m), 7.7-7.75 (1H, m), 7.86 (1H, d, J = 6.8 Hz), 8.15 (1H, d, J = 9.8 Hz), 11.9 (1H, s), 12.83 (1H, brs) |
| 98 | 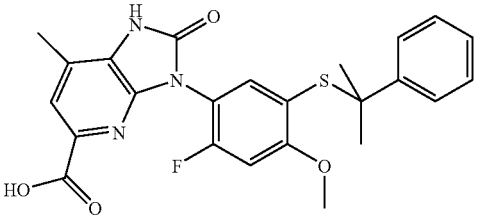 | (DMSO-d6) 1.64 (6H, s), 2.41 (3H, s), 3.72 (3H, s), 7.1-7.35 (5H, m), 7.4-7.5 (2H, m), 7.7-7.75 (1H, m), 11.85 (1H, s), 12.76 (1H, brs) |
| 99 | 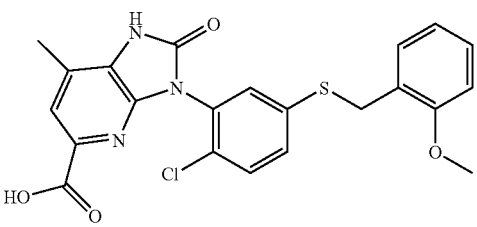 | (DMSO-d6) 2.42 (3H, s), 3.78 (3H, s), 4.23 (2H, s), 6.8-7.05 (2H, m), 7.2-7.35 (2H, m), 7.45-7.55 (1H, m), 7.6-7.7 (2H, m), 7.7-7.75 (1H, m), 11.89 (1H, s), 12.78 (1H, brs) |
| 100 | 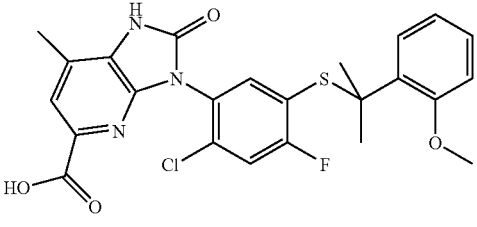 | (DMSO-d6) 1.73 (3H, s), 1.74 (3H, s), 2.41 (3H, s), 3.82 (3H, s), 6.65-6.75 (1H, m), 6.95-7.0 (1H, m), 7.1-7.2 (2H, m), 7.28 (1H, d, J = 7.3 Hz), 7.7-7.8 (2H, m), 11.88 (1H, s), 12.79 (1H, brs) |
| 101 | 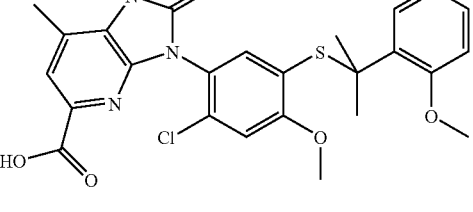 | (DMSO-d6) 1.7 (6H, s), 2.4 (3H, s), 3.72 (3H, s), 3.81 (3H, s), 6.6-6.7 (1H, m), 6.95 (1H, dd, J = 8.1 Hz, 1.2 Hz), 7.05-7.2 (3H, m), 7.25 (1H, s), 7.7-7.75 (1H, m), 11.81 (1H, s), 12.77 (1H, brs) |
| 102 | 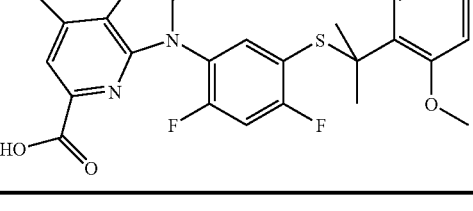 | (DMSO-d6) 1.73 (6H, s), 2.41 (3H, s), 3.83 (3H, s), 6.65-6.8 (1H, m), 6.95-7.0 (1H, m), 7.1-7.2 (2H, m), 7.3-7.45 (1H, m), 7.5-7.6 (1H, m), 7.75 (1H, s), 11.92 (1H, s), 12.79 (1H, brs) |

TABLE 45

| Ex No. | Strc | (Solv) $^1$H-NMR δ ppm: |
|---|---|---|
| 103 | | (DMSO-d6) 1.66 (6H, s), 2.4 (3H, s), 3.72 (3H, s), 7.15 (1H, d, J = 8.3 Hz), 7.2-7.3 (2H, m), 7.3-7.4 (2H, m), 7.45-7.6 (3H, m), 7.7-7.8 (1H, m), 11.91 (1H, s), 12.74 (1H, s), |
| 104 | | (DMSO-d6) 1.69 (6H, s), 2.4 (3H, s), 3.67 (3H, s), 3.82 (3H, s), 6.65-6.75 (1H, m), 6.9-7.0 (1H, m), 7.05-7.2 (4H, m), 7.7-7.75 (1H, m), 11.85 (1H, s), 12.77 (1H, brs) |
| 105 | | (DMSO-d6) 1.82 (3H, s), 1.83 (3H, s), 2.41 (3H, s), 3.73 (3H, s), 6.6-6.7 (1H, m), 6.8 (1H, d, J = 8.5 Hz), 7.1-7.25 (2H, m), 7.3-7.45 (2H, m), 7.7-7.8 (1H, m), 11.93 (1H, s), 12.76 (1H, brs) |
| 106 | | (DMSO-d6) 1.35-1.45 (3H, m), 2.18 (3H, s), 2.42 (3H, s), 2.6-2.7 (3H, m), 3.85-3.95 (3H, m), 5.0-5.15 (1H, m), 7.2-7.4 (6H, m), 7.72 (1H, s), 7.15-7.8 (1H, m), 11.85 (1H, s), 12.68 (1H, brs) |
| 107 | | (DMSO-d6) 2.42 (3H, s), 3.8 (3H, s), 4.81 (2H, s), 5.04 (2H, s), 6.85-6.95 (1H, m), 7.18 (1H, s), 7.4-7.55 (2H, m), 7.7-7.75 (1H, m), 11.86 (1H, s), 12.79 (1H, brs), 13.12 (1H, brs) |
| 108 | | (DMSO-d6) 1.7 (6H, s), 2.41 (3H, s), 3.59 (3H, s), 6.9-7.0 (1H, m), 7.05-7.25 (4H, m), 7.29 (1H, d, J = 8.6 Hz), 7.7-7.75 (1H, m), 11.86 (1H, s), 12.77 (1H, brs) |

TABLE 46

| Ex No. | Strc | (Solv) ¹H-NMR δ ppm: |
|---|---|---|
| 109 | | (DMSO-d6) 1.78 (6H, s), 2.4 (3H, s), 3.6 (3H, s), 7.05-7.2 (3H, m), 7.24 (1H, d, J = 8.9 Hz), 7.29 (1H, dd, J = 7.8 Hz, 1.7 Hz), 7.41 (1H, dd, J = 7.8 Hz, 1.5 Hz), 7.7-7.75 (1H, m), 11.86 (1H, s), 12.77 (1H, brs) |
| 110 | | (DMSO-d6) 1.69 (6H, s), 2.41 (3H, s), 2.78 (3H, s), 3.68 (3H, s), 6.9-7.0 (1H, m), 7.0-7.1 (1H, m), 7.1-7.25 (3H, m), 7.34 (1H, d, J = 8.7 Hz), 7.7-7.75 (1H, m), 11.86 (1H, s), 12.76 (1H, brs) |
| 111 | | (DMSO-d6) 1.75-1.85 (6H, m), 2.4 (3H, s), 3.55 (3H, s), 6.9-7.0 (2H, m), 7.1-7.3 (2H, m), 7.37 (1H, d, J = 8.5 Hz), 7.7-7.75 (1H, m), 11.86 (1H, s), 12.74 (1H, brs) |
| 112 | | (DMSO-d6) 1.8 (3H, s), 1.81 (3H, s), 2.4 (3H, s), 3.6 (3H, s), 3.7-3.75 (3H, m), 6.7-6.8 (1H, m), 7.1-7.25 (2H, m), 7.3-7.4 (1H, m), 7.72 (1H, s), 11.88 (1H, s), 12.76 (1H, s) |
| 113 | | (DMSO-d6) 1.68 (6H, s), 2.4 (3H, s), 3.66 (3H, s), 3.81 (3H, s), 6.9-7.0 (3H, m), 7.12 (1H, d, J = 12.0 Hz), 7.28 (1H, d, J = 8.5 Hz), 7.7-7.75 (1H, m), 11.86 (1H, s), 12.76 (1H, brs) |
| 114 | | (DMSO-d6) 1.79 (3H, s), 1.8 (3H, s), 2.4 (3H, s), 3.62 (3H, s), 3.74 (3H, s), 6.55-6.7 (1H, m), 6.7-6.8 (1H, m), 7.05-7.2 (2H, m), 7.24 (1H, d, J = 8.6 Hz), 7.71 (1H, s), 11.83 (1H, brs), 12.79 (1H, brs) |

TABLE 47

| Ex No. | Strc | (Solv) $^1$H-NMR δ ppm: |
|---|---|---|
| 115 | | (DMSO-d6) 1.65 (6H, s), 2.41 (3H, s), 3.69 (3H, s), 6.9-7.05 (1H, m), 7.17 (1H, d, J = 12.0 Hz), 7.2-7.35 (3H, m), 7.39 (1H, d, J = 8.6 Hz), 7.7-7.75 (1H, m), 11.88 (1H, s), 12.75 (1H, s) |
| 116 | | (DMSO-d6) 1.7 (6H, s), 2.41 (3H, s), 3.84 (3H, s), 6.9-7.05 (3H, m), 7.1-7.2 (1H, m), 7.3-7.45 (2H, m), 7.75 (1H, s), 11.93 (1H, s), 12.79 (1H, brs) |
| 117 | | (DMSO-d6) 1.74 (3H, s), 1.76 (3H, s), 2.4 (3H, s), 7.25-7.9 (9H, m), 11.0-14.0 (2H, br) |
| 118 | | (DMSO-d6) 1.878 (3H, s), 1.882 (3H, s), 3.4 (3H, s), 6.8-6.95 (2H, m), 7.15-7.25 (1H, m), 7.35-7.5 (3H, m), 7.65 (1H, s), 7.8-7.9 (2H, m), 11.0-14.0 (2H, br) |
| 119 | | (DMSO-d6) 1.9 (3H, s), 1.93 (3H, s), 7.05-7.15 (2H, m), 7.3-7.45 (2H, m), 7.7-7.85 (3H, m), 7.96 (1H, d, J = 8.8 Hz), 11.0-14.0 (2H, br) |
| 120 | | (DMSO-d6) 4.8 (2H, s), 7.2-7.45 (6H, m), 7.75-7.9 (2H, m), 7.95 (1H, d, J = 8.4H), 8.13 (1H, s), 11.0-14.0 (2H, br) |

TABLE 48

| Ex No. | Strc | (Solv) $^1$H-NMR δ ppm: |
|---|---|---|
| 121 | | (DMSO-d6) 1.88 (3H, s), 1.89 (3H, s), 3.2 (3H, s), 3.3-3.45 (2H, m), 3.8-3.95 (2H, m), 6.8-6.95 (2H, m), 7.1-7.2 (1H, m), 7.39 (1H, d, J = 2.1 Hz), 7.4-7.5 (1H, m), 7.52 (1H, d, J = 8.1 Hz), 7.55-7.6 (1H, m), 7.85-7.95 (2H, m), 11.87 (1H, s), 12.89 (1H, brs) |
| 122 | | (DMSO-d6) 1.72 (3H, s), 1.74 (3H, s), 3.68 (3H, s), 7.25-7.85 (9H, m), 11.0-14.0 (2H, br) |
| 123 | | (DMSO-d6) 1.85 (3H, s), 1.88 (3H, s), 2.41 (3H, s), 3.47 (3H, s), 3.68 (3H, s), 6.85-6.9 (2H, m), 7.1-7.2 (1H, m), 7.35-7.45 (1H, m), 7.46 (1H, s), 7.5 (1H, s), 7.73 (1H, s), 11.86 (1H, s), 12.78 (1H, brs) |
| 124 | | (DMSO-d6) 1.9-2.0 (6H, m), 2.41 (3H, s), 3.49 (3H, s), 3.63 (3H, s), 6.65-6.75 (1H, m), 7.15-7.25 (1H, m), 7.35-7.45 (1H, m), 7.46 (1H, s), 7.64 (1H, s), 7.74 (1H, s), 11.87 (1H, s), 12.76 (1H, brs) |
| 125 | | (DMSO-d6) 1.95 (6H, s), 2.41 (3H. s), 3.6 (3H, s), 7.25-7.35 (2H, m), 7.35-7.45 (1H, m), 7.48 (1H, s), 7.5-7.6 (1H, m), 7.73 (1H, s), 7.79 (1H, s), 11.86 (1H, s), 12.7 (1H, brs) |
| 126 | | (DMSO-d6) 1.85-1.95 (6H, m), 2.41 (3H, s), 3.68 (3H, s), 7.0-7.1 (2H, m), 7.35-7.45 (1H, m), 7.56 (1H, s), 7.73 (1H, s), 7.79 (1H, s), 11.87 (1H, s), 12.72 (1H, brs) |

TABLE 49
| Ex No. | Strc | (Solv) $^1$H-NMR δ ppm: |
|---|---|---|
| 127 | 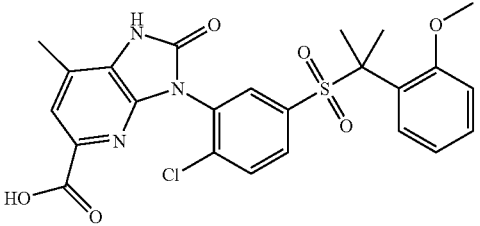 | (DMSO-d6) 1.88 (3H, s), 1.89 (3H, s), 2.43 (3H, s), 3.39 (3H, s), 6.8-6.95 (2H, m), 7.2-7.25 (1H, m), 7.37 (1H, dd, J = 8.6 Hz, 2.2 Hz), 7.4-7.5 (1H, m), 7.67 (1H, d, J = 2.2 Hz), 7.76 (1H, s), 7.86 (1H, d, J = 8.6 Hz), 11.95 (1H, s), 12.75 (1H, brs) |
| 128 | 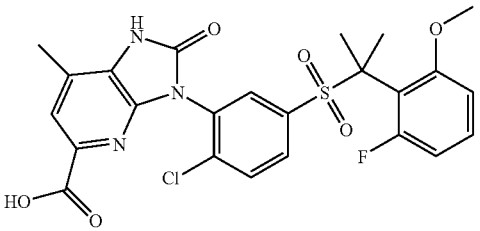 | (DMSO-d6) 1.96 (3H, s), 1.97 (3H, s), 2.42 (3H, s), 3.4 (3H, s), 6.65-6.8 (2H, m), 7.2-7.3 (1H, m), 7.48 (1H, dd, J = 8.5 Hz, 2.2 Hz), 7.7-7.8 (2H, m), 7.88 (1H, d, J = 8.5 Hz), 11.95 (1H, s), 12.76 (1H, brs) |
| 129 | 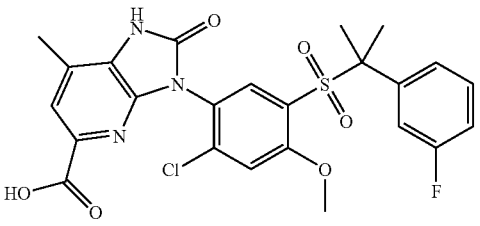 | (DMSO-d6) 1.72 (3H, s), 1.73 (3H, s), 2.41 (3H, s), 3.69 (3H, s), 7.1-7.35 (3H, m), 7.35-7.45 (1H, m), 7.53 (1H, s), 7.74 (1H, s), 7.78 (1H, s), 11.88 (1H, s), 12.68 (1H, brs) |
| 130 | 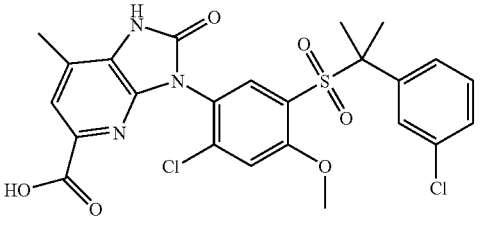 | (DMSO-d6) 1.72 (3H, s), 1.73 (3H, s), 2.42 (3H, s), 3.67 (3H, s), 7.35-7.45 (3H, m), 7.51 (1H, s), 7.52 (1H, s), 7.74 (1H, s), 7.83 (1H, s), 11.88 (1H, s), 12.72 (1H, brs) |
| 131 | 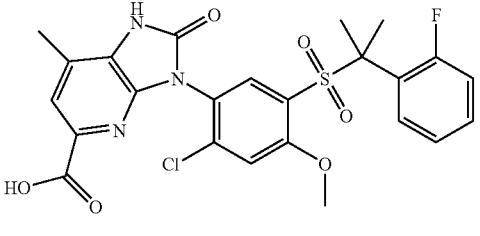 | (DMSO-d6) 1.82 (6H, s), 2.41 (3H, s), 3.66 (3H, s), 7.1-7.2 (2H, m), 7.3-7.4 (2H, m), 7.52 (1H, s), 7.71 (1H, s), 7.73 (1H, s), 11.87 (1H, s), 12.74 (1H, brs) |
| 132 | 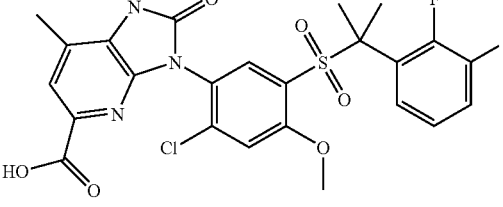 | (DMSO-d6) 1.81 (3H, s), 1.82 (3H, s), 2.41 (3H, s), 3.67 (3H, s), 7.1-7.25 (2H, m), 7.35-7.5 (1H, m), 7.55 (1H, s), 7.73 (1H, d, J = 0.7 Hz), 7.84 (1H, s), 11.87 (1H, s), 12.67 (1H, brs) |

TABLE 50

| Ex No. | Strc | (Solv) $^1$H-NMR δ ppm: |
|---|---|---|
| 133 | | (DMSO-d6) 1.84 (6H, s), 2.42 (3H, s), 7.1-7.2 (2H, m), 7.3-7.45 (2H, m), 7.56 (1H, dd, J = 8.6 Hz, 2.3 Hz), 7.76 (1H, s), 7.81 (1H, d, J = 2.3 Hz), 7.91 (1H, d, J = 8.6 Hz), 11.95 (1H, s), 12.75 (1H, brs) |
| 134 | | (DMSO-d6) 1.968 (3H, s), 1.974 (3H, s), 2.43 (3H, s), 7.25-7.4 (3H, m), 7.43 (1H, dd, J = 8.4 Hz, 2.2 Hz), 7.55-7.6 (1H, m), 7.75 (1H, d, J = 0.6 Hz), 7.87 (1H, d, J = 8.4 Hz), 7.91 (1H, d, J = 2.2 Hz), 11.94 (1H, s), 12.74 (1H, brs) |
| 135 | | (DMSO-d6) 1.97 (3H, s), 1.98 (3H, s), 2.42 (3H, s), 3.38 (3H, s), 6.65-6.75 (1H, m), 7.3-7.4 (1H, m), 7.53 (1H, dd, J = 8.4 Hz, 2.1 Hz), 7.76 (1H, d, J = 0.4 Hz), 7.86 (1H, d, J = 2.1 Hz), 7.89 (1H, d, J = 8.4 Hz), 11.95 (1H, s), 12.79 (1H, brs) |
| 136 | | (DMSO-d6) 2.42 (3H, s), 3.49 (3H, s), 4.64 (2H, s), 6.7-6.9 (2H, m), 7.25-7.35 (1H, m), 7.7-7.8 (2H, m), 7.9-8.0 (2H, m), 11.97 (1H, s), 12.78 (1H, brs) |
| 137 | | (DMSO-d6) 2.42 (3H, s), 3.48 (3H, s), 4.7-4.85 (2H, m), 6.91 (1H, d, J = 7.8 Hz), 7.05-7.1 (1H, m), 7.25-7.35 (1H, m), 7.7-7.8 (2H, m), 7.95-8.05 (2H, m), 11.97 (1H, s), 12.83 (1H, brs) |
| 138 | | (DMSO-d6) 1.73 (6H, s), 2.41 (3H, s), 3.6 (3H, s), 7.2-7.4 (4H, m), 7.4-7.5 (2H, m), 7.7-7.85 (2H, m), 11.92 (1H, s), 12.73 (1H, brs) |

TABLE 51

| Ex No. | Strc | (Solv) ¹H-NMR δ ppm: |
|---|---|---|
| 139 | | (DMSO-d6) 1.3-2.8 (11H, m), 4.05-4.15 (3H, m), 4.95-5.1 (1H, m), 7.05-7.3 (4H, m), 7.7-7.75 (2H, m), 7.85-7.95 (1H, m), 11.8-11.95 (1H, m), 12.75 (1H, s) |
| 140 | | (DMSO-d6) 1.96 (3H, s), 1.97 (3H, s), 2.42 (3H, s), 3.4 (3H, s), 6.6-6.8 (2H, m), 7.2-7.3 (1H, m), 7.45-7.55 (1H, m), 7.6-7.7 (1H, m), 7.75-7.85 (2H, m), 11.99 (1H, s), 12.8 (1H, s) |
| 141 | | (DMSO-d6) 1.74 (6H, s), 2.41 (3H, s), 3.64 (3H, s), 7.3-7.5 (5H, m), 7.6 (1H, d, J = 8.7 Hz), 7.66 (1H, dd, J = 8.7 Hz, 1.8 Hz), 7.75-7.8 (1H, m), 7.95 (1H, d, J = 1.8 Hz), 12.06 (1H, s), 12.81 (1H, brs) |
| 142 | | (DMSO-d6) 1.5-1.75 (2H, m), 1.8-1.95 (2H, m), 2.39 (3H, s), 2.75-2.9 (2H, m), 3.6-3.9 (4H, m), 4.33 (2H, t, J = 5.0 Hz), 4.88 (1H, t, J = 5.1 Hz), 6.71 (1H, dd, J = 7.8 Hz, 1.4 Hz), 7.05-7.2 (2H, m), 7.27 (1H, dd, J = 7.4 Hz, 1.3 Hz), 7.62 (1H, d, J = 11.7 Hz), 7.7-7.75 (1H, m), 7.9 (1H, d, J = 8.6 Hz), 11.89 (1H, s), 12.78 (1H, brs) |
| 143 | | (DMSO-d6) 1.5-1.7 (2H, m), 1.8-1.95 (2H, m), 2.39 (3H, s), 2.75-2.9 (2H, m), 3.6-3.9 (4H, m), 4.37 (2H, t, J = 5.1 Hz), 4.8-4.95 (1H, m), 6.69 (1H, dd, J = 7.8 Hz, 1.4 Hz), 7.05-7.2 (2H, m), 7.27 (1H, dd, J = 7.6 Hz, 1.5 Hz), 7.7-7.75 (1H, m), 7.78 (1H, s), 7.88 (1H, s), 11.84 (1H, s), 12.77 (1H, brs) |
| 144 | | (DMSO-d6) 1.65 (6H, s), 2.41 (3H, s), 3.7-3.8 (2H, m), 4.1 (2H, t, J = 5.2 Hz), 4.89 (1H, t, J = 5.3 Hz), 7.1-7.35 (5H, m), 7.4-7.5 (2H, m), 7.7-7.75 (1H, m), 11.85 (1H, s), 12.76 (1H, brs) |

TABLE 52
| Ex No. | Strc | (Solv) ¹H-NMR δ ppm: |
|---|---|---|
| 145 | 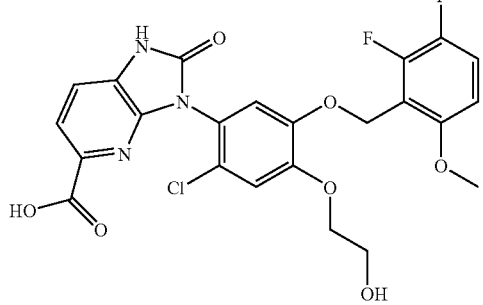 | (DMSO-d6) 3.65-3.75 (2H, m), 3.79 (3H, s), 4.05-4.15 (2H, m), 4.88 (1H, t, J = 5.4 Hz), 5.04 (2H, s), 6.85-6.95 (1H, m), 7.35 (1H, s), 7.4-7.55 (3H, m), 7.86 (1H, d, J = 7.8 Hz), 11.76 (1H, s), 12.85 (1H, brs) |
| 146 | 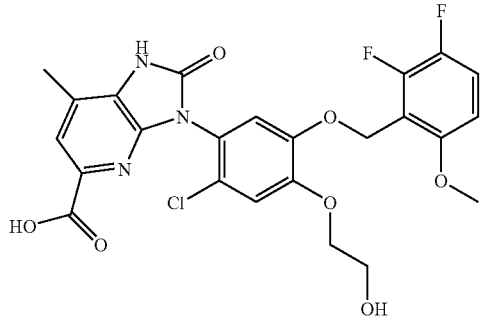 | (DMSO-d6) 2.42 (3H, s), 3.65-3.75 (2H, m), 3.79 (3H, s), 4.05-4.15 (2H, m), 4.88 (1H, t, J = 5.4 Hz), 5.04 (2H, s), 6.85-6.95 (1H, m), 7.34 (1H, s), 7.4-7.55 (2H, m), 7.7-7.75 (1H, m), 11.86 (1H, s), 12.78 (1H, brs) |
| 147 | 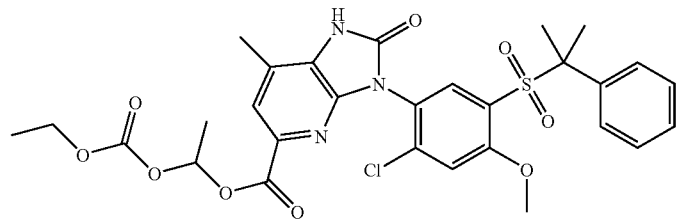 | (CDCl3) 1.2-1.35 (3H, m), 1.55-1.65 (3H, m), 1.85-1.95 (6H, m), 2.45 (3H, s), 3.4-3.5 (3H, m), 4.1-4.25 (2H, m), 6.9-7.05 (2H, m), 7.2-7.4 (3H, m), 7.45-7.55 (2H, m), 7.8-7.95 (2H, m), 9.27 (1H, s) |
| 148 | 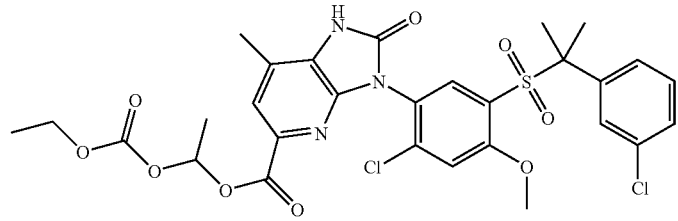 | (CDCl3) 1.2-1.3 (3H, m), 1.61 (3H, d, J = 5.5 Hz), 1.8-1.9 (6H, m), 2.44 (3H, s), 3.45-3.55 (3H, m), 4.1-4.25 (2H, m), 6.95-7.05 (2H, m), 7.25-7.45 (3H, m), 7.5-7.6 (1H, m), 7.8-7.9 (1H, m), 7.95-8.0 (1H, m), 10.75 (1H, s) |
| 149 | 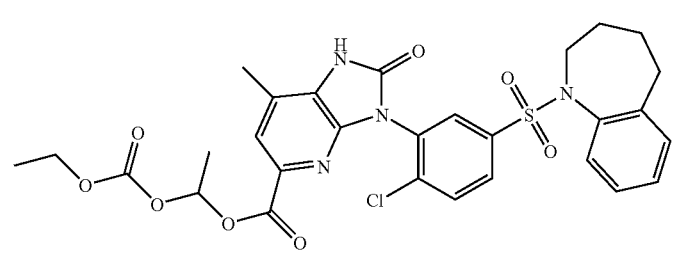 | (DMSO-d6) 1.1-1.25 (3H, m), 1.4-1.65 (5H, m), 1.7-1.85 (2H, m), 2.35-2.7 (5H, m), 3.3-3.9 (2H, m), 4.05-4.2 (2H, m), 6.75-6.85 (1H, m), 7.1-7.3 (4H, m), 7.79 (1H, s), 7.85-8.0 (2H, m), 8.1-8.15 (1H, m), 12.07 (1H, brs) |

TABLE 52-continued

| Ex No. | Strc | (Solv) $^1$H-NMR δ ppm: |
|---|---|---|
| 150 | | (CDCl3) 1.15-1.95 (13H, m), 2.05-2.15 (6H, m), 2.43 (3H, s), 3.49 (3H, s), 4.5-4.7 (1H, m), 6.5-6.75 (2H, m), 6.95-7.2 (2H, m), 7.45-7.65 (2H, m), 7.8-7.9 (2H, m), 9.87 (1H, s) |

TABLE 53

| Ex No. | Strc | (Solv) $^1$H-NMR δ ppm: |
|---|---|---|
| 151 | | (DMSO-d6) 1.29 (3H, s), 1.31 (3H, s), 1.4-1.85 (4H, m), 2.3-2.6 (5H, m), 3.4-3.9 (2H, m), 5.01 (1H, s), 7.1-7.3 (5H, m) 7.74 (1H, dd, J = 8.5 Hz, 2.3 Hz), 7.92 (1H, d, J = 8.5 Hz), 8.06 (1H, d, J = 2.3 Hz), 11.46 (1H, s) |
| 152 | | (DMSO-d6) 1.4-1.7 (2H, m), 1.7-1.9 (2H, m), 2.37 (3H, s), 2.4-2.6 (2H, m), 3.3-3.9 (2H, m), 4.38 (2H, d, J = 5.7 Hz), 5.26 (1H, t, J = 5.7 Hz), 7.03 (1H, s), 7.15-7.3 (4H, m), 7.8 (1H, dd, J = 8.5 Hz, 2.3 Hz), 7.93 (1H, d, J = 8.5 Hz), 8.04 (1H, d, J = 2.3 Hz), 11.5 (1H, s) |
| 153 | | (DMSO-d6) 1.4-1.9 (4H, m), 2.4-2.65 (5H, m), 3.4-3.9 (2H, m), 7.15-7.3 (4H, m), 7.65-7.7 (1H, m), 7.86 (1H, dd, J = 8.5 Hz, 2.2 Hz), 7.97 (1H, d, J = 8.5 Hz), 8.2 (1H, d, J = 2.2 Hz), 9.73 (1H, s), 12.15 (1H, brs) |
| 154 | | (DMSO-d6) 3.65-3.75 (2H, m), 3.77 (3H, s), 4.05-4.15 (2H, m), 4.41 (2H, d, J = 5.8 Hz), 4.8-4.95 (1H, m), 5.04 (2H, s), 5.29 (1H, t, J = 5.8 Hz), 6.85-6.95 (1H, m), 7.15 (1H, d, J = 7.6 Hz), 7.25-7.55 (4H, m), 11.27 (1H, s) |

TABLE 53-continued

| Ex No. | Strc | (Solv) $^1$H-NMR δ ppm: |
|---|---|---|
| 155 | | (DMSO-d6) 2.36 (3H, s), 3.65-3.75 (2H, m), 3.78 (3H, s), 4.05-4.15 (2H, m), 4.37 (2H, d, J = 5.9 Hz), 4.86 (1H, t, J = 5.4 Hz), 5.04 (2H, s), 5.23 (1H, t, J = 5.9 Hz), 6.85-6.95 (1H, m), 7.0 (1H, s), 7.3 (1H, s), 7.33 (1H, s), 7.4-7.55 (1H, m), 11.36 (1H, s) |
| 156 | | (DMSO-d6) 1.33 (9H, s), 3.15-3.3 (2H, m), 3.9-4.05 (2H, m), 4.38 (2H, d, J = 5.7 Hz), 5.19 (2H, s), 5.27 (1H, t, J = 5.7 Hz), 6.85-6.95 (1H, m), 6.95-7.05 (1H, m), 7.14 (1H, d, J = 8.0 Hz), 7.2-7.35 (2H, m), 7.35-7.5 (2H, m), 7.59 (1H, d, J = 9.1 Hz), 11.31 (1H, brs) |

TABLE 54

| Ex No. | Strc | (Solv) $^1$H-NMR δ ppm: |
|---|---|---|
| 157 | | (DMSO-d6) 1.75 (3H, s), 3.25-3.4 (2H, m), 3.9-4.1 (2H, m), 4.39 (2H, d, J = 5.6 Hz), 5.18 (2H, s), 5.28 (1H, t, J = 5.6 Hz), 6.85-6.95 (1H, m), 7.15 (1H, d, J = 7.8 Hz), 7.24 (1H, dd, J = 8.7 Hz, 3.1 Hz), 7.32 (1H, d, J = 3.1 Hz), 7.35-7.5 (2H, m), 7.6 (1H, d, J = 8.7 Hz), 7.95-8.05 (1H, m), 11.33 (1H, brs) |
| 158 | | (DMSO-d6) 1.35-1.9 (4H, m), 2.3-2.7 (5H, m), 3.3-4.0 (2H, m), 7.15-7.35 (4H, m), 7.68 (1H, s), 7.8-7.85 (1H, m), 7.96 (1H, d, J = 8.6 Hz), 8.16 (1H, s), 12.2 (1H, brs) |
| 159 | | (DMSO-d6) 1.4-1.9 (4H, m), 2.4-2.7 (5H, m), 3.3-3.9 (2H, m), 7.0-7.3 (4H, m), 7.82 (1H, s), 7.9-8.05 (2H, m), 8.15-8.2 (1H, m), 11.91 (1H, s) |

TABLE 54-continued

| Ex No. | Strc | (Solv) ¹H-NMR δ ppm: |
|---|---|---|
| 160 | | (CD3OD) 1.4-2.0 (4H, m), 2.45-2.6 (5H, m), 3.4-4.0 (2H, m), 7.1-7.3 (4H, m), 7.5-7.6 (1H, m), 7.8-7.9 (2H, m), 7.9-8.0 (1H, m) |
| 161 | | (DMSO-d6) 1.45-1.65 (2H, m), 1.7-1.9 (2H, m), 2.35-2.7 (5H, m), 3.4-3.9 (2H, m), 7.1-7.3 (4H, m), 7.55-7.65 (1H, m), 7.89 (1H, dd, J = 8.5 Hz, 2.3 Hz), 7.97 (1H, d, J = 8.5 Hz), 8.15 (1H, d, J = 2.3 Hz), 12.01 (1H, s), 12.7 (1H, brs) |
| 162 | | (DMSO-d6) 1.4-1.9 (4H, m), 2.3-2.65 (5H, m), 3.4-3.9 (2H, m), 7.1-7.35 (5H, m), 7.42 (1H, s), 7.7 (1H, s), 7.85 (1H, dd, J = 8.5 Hz, 2.3 Hz), 7.96 (1H, d, J = 8.5 Hz), 8.14 (1H, d, J = 2.3 Hz), 11.88 (1H, s) |

TABLE 55

| Ex No. | Strc | (Solv) ¹H-NMR δ ppm: |
|---|---|---|
| 163 | | (DMSO-d6) 2.3 (3H, s), 3.79 (3H, s), 3.82 (3H, s), 4.95-5.05 (2H, m), 6.85-6.95 (1H, m), 7.2-7.3 (2H, m), 7.37 (1H, s), 7.45-7.55 (1H, m), 7.7-7.75 (1H, m), 11.26 (1H, s) |
| 164 | | (DMSO-d6) 3.8 (3H, s), 3.84 (3H, s), 5.01 (2H, s), 6.85-6.95 (1H, m), 7.31 (1H, s), 7.45-7.55 (2H, m), 8.16 (1H, s), 12.56 (1H, s) |

TABLE 55-continued

| Ex No. | Strc | (Solv) $^1$H-NMR δ ppm: |
|---|---|---|
| 165 | | (DMSO-d6) 3.8 (3H, s), 3.85 (3H, s), 5.0 (2H, s), 6.85-6.95 (1H, m), 7.32 (1H, s), 7.4-7.55 (2H, m), 8.67 (1H, s), 12.77 (1H, brs), 13.21 (1H, brs) |
| 166 | | (DMSO-d6) 3.8 (3H, s), 3.85 (3H, s), 5.0 (2H, s), 6.85-6.95 (1H, m), 7.32 (1H, s), 7.45-7.55 (2H, m), 7.97 (1H, s), 12.67 (1H, s), 13.13 (1H, s) |
| 167 | | (CDCl3) 1.74 (3H, s), 1.75 (3H, s), 3.0-3.15 (1H, m), 3.69 (3H, s), 3.96 (3H, s), 4.65 (2H, d, J = 4.0 Hz), 6.65 (1H, s), 6.97 (1H, s), 7.05-7.15 (1H, m), 7.15-7.3 (3H, m), 7.4-7.45 (2H, m), 8.83 (1H, s) |
| 168 | | (DMSO-d6) 1.73 (6H, s), 3.67 (3H, s), 3.97 (3H, s), 4.39 (2H, d, J = 5.8 Hz), 5.34 (1H, t, J = 5.8 Hz), 6.97 (1H, s), 7.25-7.4 (3H, m), 7.4-7.45 (2H, m), 7.48 (1H, s), 7.58 (1H, s), 11.43 (1H, s) |

Table 56

| Ex No. | Strc | (Solv) $^1$H-NMR δ ppm: |
|---|---|---|
| 169 | | (DMSO-d6) 1.72 (3 H, s), 1.73 (3 H, s), 3.66 (3 H, s), 4.03 (3 H, s), 7.25-7.4 (3 H, m), 7.4-7.55 (3 H, m), 7.61 (1 H, s), 7.65-7.7 (1 H, m), 11.91 (1 H, s), 12.89 (1 H, brs) |

| Ex No. | Strc | (Solv) $^1$H-NMR δ ppm: |
|---|---|---|
| 170 | | (DMSO-d6) 1.21 (3 H, t, J = 7.1 Hz), 2.43 (3 H, s), 3.8 (3 H, s), 4.02 (3 H, s), 4.16 (2 H, q, J = 7.1 Hz), 4.92 (2 H, s), 5.05 (2 H, s), 6.85-6.95 (1 H, m), 7.22 (1 H, s), 7.4-7.55 (2 H, m), 11.61 (1 H, s) |
| 171 | | (DMSO-d6) 1.21 (3 H, t, J = 7.1 Hz), 3.33 (3 H, s), 3.82 (3 H, s), 4.05 (3 H, s), 4.16 (2 H, q, J = 7.1 Hz), 4.37 (2 H, s), 4.92 (2 H, s), 4.95-5.05 (2 H, m), 6.85-7.0 (2 H, m), 7.21 (1 H, s), 7.4-7.5 (2 H, m), 11.77 (1 H, s) |
| 172 | | (DMSO-d6) 2.43 (3 H, s), 3.8 (3 H, s), 3.83 (3 H, s), 4.02 (3 H, s), 5.01 (2 H, s), 6.85-6.95 (1 H, m), 7.26 (1 H, s), 7.4 (1 H, s), 7.45-7.55 (1 H, m), 11.59 (1 H, s) |
| 173 | | (DMSO-d6) 2.55 (3 H, s), 2.65 (3 H, s), 3.79 (3 H, s), 3.84 (3 H, s), 5.01 (2 H, s), 6.85-6.95 (1 H, m), 7.29 (1 H, s), 7.4-7.55 (2 H, m), 12.0 (1 H, s) |
| 174 | | (DMSO-d6) 2.43 (3 H, s), 3.79 (3 H, s), 4.02 (3 H, s), 4.25-4.45 (2 H, m), 4.6-4.85 (2 H, m), 5.05 (2 H, s), 6.85-6.95 (1 H, m), 7.34 (1 H, s), 7.4-7.55 (2 H, m), 11.59 (1 H, s) |

Table 57
| Ex No. | Strc | (Solv) $^1$H-NMR δ ppm: |
|---|---|---|
| 175 | 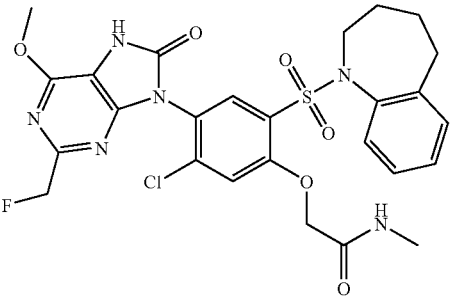 | (DMSO-d6) 1.45-1.65 (2 H, m), 1.7-1.85 (2 H, m), 2.57 (3 H, d, J = 4.6 Hz), 2.65-2.8 (2 H, m), 3.4-3.9 (2 H, m), 4.05 (3 H, s), 4.82 (2 H, s), 5.3 (2 H, d, J = 46.9 Hz), 6.9-7.0 (1 H, m), 7.05-7.3 (3 H, m), 7.5-7.6 (1 H, m), 7.64 (1 H, s), 8.03 (1 H, s), 11.87 (1 H, s) |
| 176 | 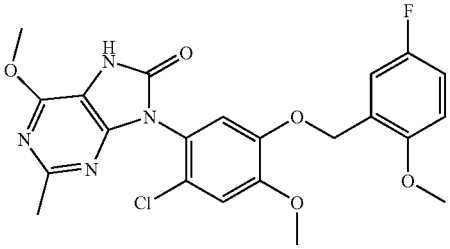 | (DMSO-d6) 2.41 (3 H, s), 3.77 (3 H, s), 3.87 (3 H, s), 4.01 (3 H, s), 4.99 (2 H, s), 7.0-7.1 (1 H, m), 7.1-7.25 (1 H, m), 7.25-7.4 (3 H, m), 11.54 (1 H, s) |
| 177 | 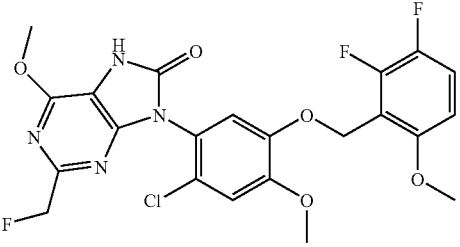 | (DMSO-d6) 3.79 (3 H, s), 3.83 (3 H, s), 4.06 (3 H, s), 5.01 (2 H, s), 5.31 (2 H, d, J = 46.9 Hz), 6.85-6.95 (1 H, m), 7.28 (1 H, s), 7.43 (1 H, s), 7.45-7.55 (1 H, m), 11.86 (1 H, s) |
| 178 | 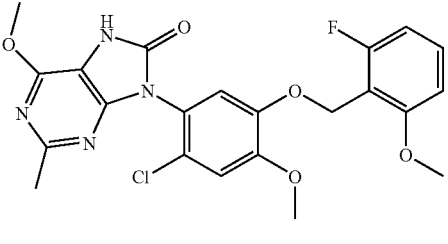 | (DMSO-d6) 2.43 (3 H, s), 3.81 (3 H, s), 3.82 (3 H, s), 4.02 (3 H, s), 4.97 (2 H, s), 6.85-7.0 (2 H, m), 7.24 (1 H, s), 7.35-7.5 (2 H, m), 11.58 (1 H, s) |
| 179 | 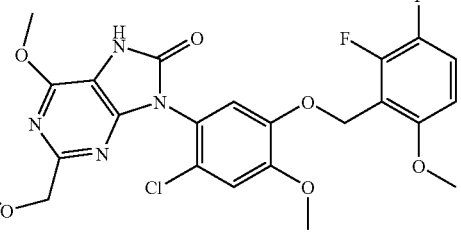 | (DMSO-d6) 3.32 (3 H, s), 3.79 (3 H, s), 3.83 (3 H, s), 4.05 (3 H, s), 4.36 (2 H, s), 5.01 (2 H, s), 6.85-6.95 (1 H, m), 7.27 (1 H, s), 7.4-7.55 (2 H, m), 11.72 (1 H, s) |

Table 57-continued

| Ex No. | Strc | (Solv) ¹H-NMR δ ppm: |
|---|---|---|
| 180 | | (DMSO-d6) 3.8 (6 H, s), 3.82 (3 H, s), 4.03 (3 H, s), 4.95-5.05 (2 H, m), 6.85-6.95 (1 H, m), 7.26 (1 H, s), 7.39 (1 H, s), 7.45-7.55 (1 H, m), 11.45 (1 H, s) |

Table 58

| Ex No. | Strc | (Solv) ¹H-NMR δ ppm: |
|---|---|---|
| 181 | | (DMSO-d6) 2.43 (3 H, s), 3.27 (3 H, s), 3.6-3.7 (2 H, m), 3.78 (3 H, s), 4.02 (3 H, s), 4.15-4.25 (2 H, m), 5.04 (2 H, s), 6.85-6.95 (1 H, m), 7.31 (1 H, s), 7.38 (1 H, s), 7.4-7.55 (1 H, m), 11.58 (1 H, s) |
| 182 | | (DMSO-d6) 3.79 (3 H, s), 3.84 (3 H, s), 4.1 (3 H, s), 4.95-5.1 (2 H, m), 6.6-6.95 (2 H, m), 7.29 (1 H, s), 7.4-7.55 (2 H, m), 12.09 (1 H, s) |
| 183 | | (DMSO-d6) 2.43 (3 H, s), 3.79 (3 H, s), 3.81 (3 H, s), 4.01 (3 H, s), 5.0 (2 H, s), 6.85-6.95 (1 H, m), 7.16 (1 H, d, J = 11.7 Hz), 7.28 (1 H, d, J = 7.4 Hz), 7.4-7.55 (1 H, m), 11.62 (1 H, brs) |
| 184 | | (DMSO-d6) 2.56 (3 H, s), 2.65 (3 H, s), 3.38 (3 H, s), 3.79 (3 H, s), 5.05 (2 H, s), 5.27 (2 H, s), 6.85-6.95 (1 H, m), 7.42 (1 H, s), 7.45-7.55 (2 H, m), 12.02 (1 H, brs) |

Table 58-continued

| Ex No. | Strc | (Solv) ¹H-NMR δ ppm: |
|---|---|---|
| 185 | | (DMSO-d6) 2.43 (3 H, s), 3.37 (3 H, s), 3.79 (3 H, s), 4.02 (3 H, s), 5.05 (2 H, s), 5.25 (2 H, s), 6.85-6.95 (1 H, m), 7.39 (1 H, s), 7.4-7.55 (2 H, m), 11.62 (1 H, brs) |
| 186 | | (DMSO-d6) 1.32 (9 H, s), 3.2-3.3 (2 H, m), 3.9-4.1 (5 H, m), 5.19 (2 H, s), 6.85-6.95 (1 H, m), 7.0-7.1 (1 H, m), 7.27 (1 H, dd, J = 9.0 Hz, 3.0 Hz), 7.34 (1 H, d, J = 3.0 Hz), 7.4-7.5 (1 H, m), 7.61 (1 H, d, J = 9.0 Hz), 8.25 (1 H, s), 11.81 (1 H, s) |

TABLE 77

| Ex No. | Strc | (Solv) ¹H-NMR δ ppm: |
|---|---|---|
| 295 | | (DMSO-d6) 2.45-2.8(10H, m), 3.8(3H, s), 5.08(2H, s), 6.9-7.0(1H, m), 7.4-7.55 (3H, m), 12.04(1H, s), 12.15(1H, s) |
| 296 | | (DMSO-d6) 3.79(3H, s), 3.83(3H, s), 4.06(3H, s), 4.4(2H, d, J = 6.2 Hz), 4.9-5.1(2H, m), 5.13(1H, t, J = 6.2 Hz), 6.85-6.95(1H, m), 7.27(1H, s), 7.35-7.55 (2H, m), 11.66(1H, s) |
| 297 | | (DMSO-d6) 1.41(3H, s), 1.42(3H, s), 3.79(3H, s), 3.83(3H, s), 4.08(3H, s), 4.77(1H, s), 4.95-5.1(2H, m), 6.85-6.95 (1H, m), 7.27(1H, s), 7.4-7.55(2H, m), 11.67(1H, s) |

TABLE 77-continued

| Ex No. | Strc | (Solv) ¹H-NMR δ ppm: |
|---|---|---|
| 298 | | (DMSO-d6) 1.34(3H, d, J = 6.5 Hz), 3.79 (3H, s), 3.83(3H, s), 4.0-4.1(3H, m), 4.5-4.65(1H, m), 4.95-5.1(3H, m), 6.85-6.95(1H, m), 7.25-7.3(1H, m), 7.4-7.55 (2H, m), 11.67(1H, s) |
| 299 | | (DMSO-d6) 3.8(3H, s), 3.82(3H, s), 3.99(3H, s), 5.01(2H, s), 6.85-6.95(1H, m), 7.25(1H, s), 7.37(1H, s), 7.4-7.55 (1H, m), 11.48(1H, brs) |
| 300 | | (DMSO-d6) 2.44(3H, s), 3.77(3H, s), 4.03(3H, s), 5.12(2H, s), 6.85-6.95(1H, m), 7.4-7.55(1H, m), 7.67(1H, s), 7.84 (1H, s), 11.72(1H, s), 13.13(1H, brs) |

TABLE 78

| Ex No. | Strc | (Solv) ¹H-NMR δ ppm: |
|---|---|---|
| 301 | | (DMSO-d6) 2.44(3H, s), 3.5(2H, s), 3.78(3H, s), 4.02(3H, s), 5.06(2H, s), 6.85-6.95(1H, m), 7.4-7.6(3H, m), 11.63 (1H, s), 12.3(1H, brs) |
| 302 | | (DMSO-d6) 1.21(3H, t, J = 7.1 Hz), 1.34 (3H, d, J = 6.6 Hz), 3.8(3H, s), 4.05-4.1 (3H, m), 4.16(2H, q, J = 7.1 Hz), 4.5-4.65 (1H, m), 4.93(2H, s), 4.95-5.1(2H, m), 6.85-7.0(1H, m), 7.2-7.25(1H, m), 7.45-7.55(2H, m), 11.69(1H, s) |

TABLE 78-continued

| Ex No. | Strc | (Solv) ¹H-NMR δ ppm: |
|---|---|---|
| 303 | | (DMSO-d6) 1.21(3H, t, J = 7.1 Hz), 1.34 (3H, d, J = 6.5 Hz), 3.82(3H, s), 4.0-4.1 (3H, m), 4.16(2H, q, J = 7.1 Hz), 4.5-4.65 (1H, m), 4.85-5.15(4H, m), 6.8-7.0(2H, m), 7.15-7.25(1H, m), 7.4-7.5(2H, m), 11.69(1H, s) |
| 304 | | (DMSO-d6) 1.21(3H, t, J = 7.1 Hz), 2.57 (3H, s), 3.8(3H, s), 4.1-4.2(5H, m), 4.92 (2H, s), 5.0-5.1(2H, m), 6.85-6.95(1H, m), 7.26(1H, s), 7.4-7.55(2H, m), 12.18 (1H, s) |
| 305 | | (DMSO-d6) 1.2(3H, t, J = 7.3 Hz), 2.58 (3H, s), 3.82(3H, s), 4.05-4.2(5H, m), 4.91(2H, s), 4.95-5.05(2H, m), 6.8-7.0 (2H, m), 7.24(1H, s), 7.35-7.55(2H, m), 12.18(1H, s) |
| 306 | | (DMSO-d6) 2.58(3H, s), 3.79(3H, s), 3.84(3H, s), 4.13(3H, s), 4.95-5.05(2H, m), 6.85-6.95(1H, m), 7.3(1H, s), 7.4-7.55(2H, m), 12.19(1H, s) |

Table 59

| Ex No. | Strc | (Solv) ¹H-NMR δ ppm: |
|---|---|---|
| 187 | | (DMSO-d6) 3.21 (3 H, s), 3.59 (2 H, t, J = 4.5 Hz), 4.0-4.2 (5 H, m), 5.13 (2 H, s), 6.9-7.0 (1 H, m), 7.26 (1 H, dd, J = 8.9 Hz, 2.9 Hz), 7.36 (1 H, d, J = 2.9 Hz), 7.4-7.5 (1 H, m), 7.6 (1 H, d, J = 8.9 Hz), 8.25 (1 H, s), 11.78 (1 H, s) |

Table 59-continued

| Ex No. | Strc | (Solv) $^1$H-NMR δ ppm: |
|---|---|---|
| 188 | 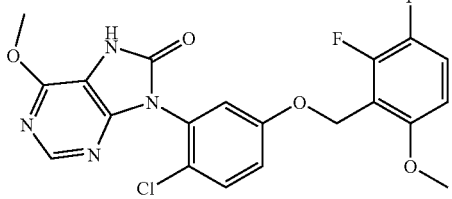 | (CDCl3) 3.82 (3 H, s), 4.12 (3 H, s), 5.05-5.15 (2 H, m), 6.55-6.65 (1 H, m), 7.05-7.2 (3 H, m), 7.45-7.55 (1 H, m), 7.92 (1 H, brs), 8.36 (1 H, s) |
| 189 | 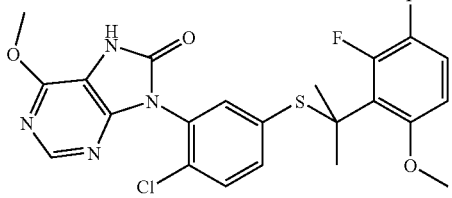 | (DMSO-d6) 1.8-1.85 (6 H, m), 3.74 (3 H, s), 4.05 (3 H, s), 6.75-6.85 (1 H, m), 7.15-7.3 (2 H, m), 7.35 (1 H, d, J = 2.4 Hz), 7.61 (1 H, d, J = 8.7 Hz), 8.25 (1 H, s), 11.78 (1 H, s) |
| 190 | 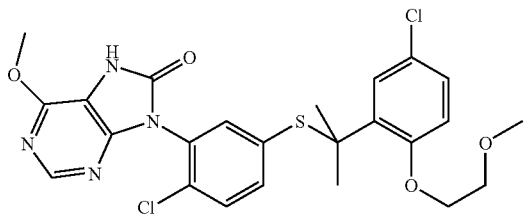 | (DMSO-d6) 1.69 (3 H, s), 1.72 (3 H, s), 3.32 (3 H, s), 3.7-3.75 (2 H, m), 4.05 (3 H, s), 4.1-4.2 (2 H, m), 7.05 (1 H, d, J = 8.7 Hz), 7.09 (1 H, d, J = 2.7 Hz), 7.2 (1 H, dd, J = 8.4 Hz, 2.2 Hz), 7.25 (1 H, dd, J = 8.7 Hz, 2.7 Hz), 7.35 (1 H, d, J = 2.2 Hz), 7.58 (1 H, d, J = 8.4 Hz), 8.26 (1 H, s), 11.79 (1 H, s) |
| 191 | 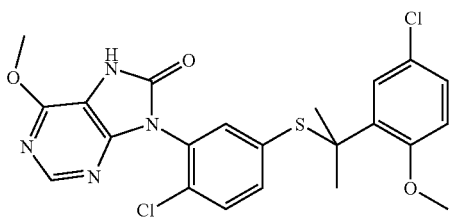 | (CDCl3) 1.72 (3 H, s), 1.75 (3 H, s), 3.86 (3 H, s), 4.12 (3 H, s), 6.82 (1 H, d, J = 8.4 Hz), 7.1-7.2 (3 H, m), 7.23 (1 H, d, J = 1.9 Hz), 7.39 (1 H, d, J = 8.1 Hz), 7.74 (1 H, brs), 8.35 (1 H, s) |
| 192 | 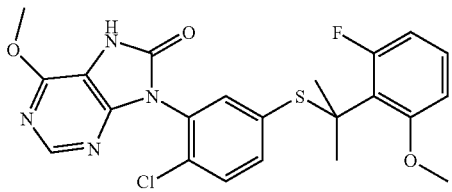 | (CDCl3) 1.85-1.95 (6 H, m), 3.77 (3 H, s), 4.12 (3 H, s), 6.5-6.65 (2 H, m), 7.0-7.15 (1 H, m), 7.17 (1 H, dd, J = 8.2 Hz, 2.0 Hz), 7.24 (1 H, d, J = 2.0 Hz), 7.38 (1 H, d, J = 8.2 Hz), 7.76 (1 H, brs), 8.32 (1 H, s) |

Table 60

| Ex No. | Strc | (Solv) $^1$H-NMR δ ppm: |
|---|---|---|
| 193 | | (CDCl3) 1.72 (3 H, s), 1.76 (3 H, s), 3.86 (3 H, s), 4.12 (3 H, s), 6.8-6.9 (3 H, m), 7.14 (1 H, dd, J = 8.5 Hz, 2.0 Hz), 7.19 (1 H, d, J = 2.0 Hz), 7.38 (1 H, d, J = 8.5 Hz), 7.88 (1 H, brs), 8.34 (1 H, s) |

Table 60-continued

| Ex No. | Strc | (Solv) ¹H-NMR δ ppm: |
|---|---|---|
| 194 | | (DMSO-d6) 1.72 (3 H, s), 1.73 (3 H, s), 3.33 (3 H, s), 3.7-3.8 (2 H, m), 4.05 (3 H, s), 4.15-4.2 (2 H, m), 6.75-6.85 (1 H, m), 7.0-7.05 (1 H, m), 7.1-7.25 (3 H, m), 7.31 (1 H, d, J = 2.0 Hz), 7.54 (1 H, d, J = 8.5 Hz), 8.26 (1 H, s), 11.79 (1 H, s) |
| 195 | | (DMSO-d6) 1.67 (6 H, s), 4.05 (3 H, s), 7.15-7.25 (2 H, m), 7.25-7.35 (2 H, m), 7.4-7.5 (3 H, m), 7.59 (1 H, d, J = 8.4 Hz), 8.27 (1 H, s), 11.82 (1 H, s) |
| 196 | | (DMSO-d6) 1.55-1.7 (2 H, m), 1.75-1.9 (2 H, m), 2.54 (3 H, s), 2.63 (3 H, s), 2.7-2.85 (2 H, m), 3.55-3.8 (2 H, m), 4.03 (3 H, s), 6.65-6.75 (1 H, m), 7.05-7.15 (1 H, m), 7.15-7.25 (1 H, m), 7.25-7.35 (1 H, m), 7.72 (1 H, s), 8.01 (1 H, s), 11.97 (1 H, s) |
| 197 | | (DMSO-d6) 3.28 (3 H, s), 3.52 (3 H, s), 4.015 (3 H, s), 4.023 (3 H, s), 6.85-6.95 (1 H, m), 6.99 (1 H, dd, J = 8.4 Hz, 1.1 Hz), 7.16 (1 H, dd, J = 7.8 Hz, 1.6 Hz), 7.25-7.35 (1 H, m), 7.66 (1 H, s), 7.68 (1 H, s), 8.23 (1 H, s), 11.71 (1 H, s) |
| 198 | | (DMSO-d6) 3.19 (3 H, s), 4.05 (3 H, s), 7.15-7.35 (3 H, m), 7.35-7.45 (1 H, m), 7.83 (1 H, dd, J = 8.5 Hz, 2.2 Hz), 7.99 (1 H, d, J = 8.5 Hz), 8.01 (1 H, d, J = 2.2 Hz), 8.3 (1 H, s), 11.84 (1 H, s) |

Table 61

| Ex No. | Strc | (Solv) ¹H-NMR δ ppm: |
|---|---|---|
| 199 | | (DMSO-d6) 3.18 (3 H, s), 3.46 (3 H, s), 4.05 (3 H, s), 6.9-7.0 (2 H, m), 7.2-7.35 (2 H, m), 7.7-7.8 (1 H, m), 7.9-8.0 (2 H, m), 8.29 (1 H, s), 11.84 (1 H, s) |

| Ex No. | Strc | (Solv) $^1$H-NMR δ ppm: |
|---|---|---|
| 200 | | (DMSO-d6) 1.6-1.75 (2 H, m), 2.45-2.6 (2 H, m), 3.75-3.85 (2 H, m), 4.05 (3 H, s), 7.05-7.2 (3 H, m), 7.56 (1 H, d, J = 7.9 Hz), 7.69 (1 H, dd, J = 8.5 Hz, 2.4 Hz), 7.89 (1 H, d, J = 8.5 Hz), 8.04 (1 H, d, J = 2.4 Hz), 8.26 (1 H, s), 11.84 (1 H, s) |
| 201 | | (DMSO-d6) 1.21 (3 H, t, J = 6.9 Hz), 2.44 (3 H, s), 3.82 (3 H, s), 4.02 (3 H, s), 4.16 (2 H, q, J = 6.9 Hz), 4.91 (2 H, s), 4.95-5.1 (2 H, m), 6.85-7.0 (2 H, m), 7.2 (1 H, s), 7.4-7.5 (2 H, m), 11.6 (1 H, s) |
| 202 | | (DMSO-d6) 2.43 (3 H, s), 3.7 (3 H, s), 3.8 (3 H, s), 4.02 (3 H, s), 4.94 (2 H, s), 5.05 (2 H, s), 6.85-6.95 (1 H, m), 7.24 (1 H, s), 7.4-7.55 (2 H, m), 11.59 (1 H, s) |
| 203 | | (DMSO-d6) 1.2 (3 H, t, J = 7.1 Hz), 2.07 (3 H, s), 3.82 (3 H, s), 4.02 (3 H, s), 4.16 (2 H, q, J = 7.1 Hz), 4.85-5.1 (6 H, m), 6.8-7.0 (2 H, m), 7.21 (1 H, s), 7.35-7.5 (2 H, m), 11.78 (1 H, s) |
| 204 | | (DMSO-d6) 1.21 (3 H, t, J = 7.1 Hz), 2.07 (3 H, s), 3.8 (3 H, s), 4.03 (3 H, s), 4.16 (2 H, q, J = 7.1 Hz), 4.92 (2 H, s), 4.95-5.1 (4 H, m), 6.85-6.95 (1 H, m), 7.23 (1 H, s), 7.4-7.55 (2 H, m), 11.76 (1 H, s) |

Table 62

| Ex No. | Str | (Solv) ¹H-NMR δ ppm: |
|---|---|---|
| 205 | | (DMSO-d6) 1.21 (3 H, t, J = 7.1 Hz), 3.32 (3 H, s), 3.8 (3 H, s), 4.05 (3 H, s), 4.16 (2 H, q, J = 7.1 Hz), 4.36 (2 H, s), 4.92 (2 H, s), 5.04 (2 H, s), 6.85-6.95 (1 H, m), 7.23 (1 H, s), 7.4-7.55 (2 H, m), 11.76 (1 H, s) |
| 206 | | (CDCl3) 1.28 (3 H, t, J = 7.2 Hz), 1.69 (3 H, s), 1.7 (3 H, s), 2.0 (3 H, s), 3.81 (3 H, s), 4.07 (3 H, s), 4.22 (2 H, q, J = 7.2 Hz), 4.6-4.75 (2 H, m), 5.1-5.2 (2 H, m), 6.65-6.75 (2 H, m), 7.1 (1 H, s), 7.17 (1 H, s), 7.25-7.35 (1 H, m), 7.98 (1 H, s) |
| 207 | | (DMSO-d6) 1.2 (3 H, t, J = 7.1 Hz), 1.6 (3 H, s), 1.63 (3 H, s), 1.92 (3 H, s), 3.8 (3 H, s), 4.02 (3 H, s), 4.16 (2 H, q, J = 7.1 Hz), 4.92 (2 H, s), 5.0-5.1 (2 H, m), 6.85-6.95 (1 H, m), 7.22 (1 H, s), 7.4-7.55 (2 H, m), 11.72 (1 H, s) |
| 208 | | (DMSO-d6) 1.21 (3 H, t, J = 7.0 Hz), 3.8 (3 H, s), 4.1 (3 H, s), 4.17 (2 H, q, J = 7.0 Hz), 4.93 (2 H, s), 5.05 (2 H, s), 6.65-6.95 (2 H, m), 7.25 (1 H, s), 7.4-7.55 (2 H, m), 12.09 (1 H, s) |
| 209 | | (DMSO-d6) 1.21 (3 H, t, J = 7.1 Hz), 3.82 (3 H, s), 4.07 (3 H, s), 4.16 (2 H, q, J = 7.1 Hz), 4.92 (2 H, s), 4.95-5.05 (2 H, m), 5.32 (2 H, d, J = 46.8 Hz), 6.85-7.0 (2 H, m), 7.22 (1 H, s), 7.4-7.55 (2 H, m), 11.88 (1 H, s) |

Table 62-continued

| Ex No. | Strc | (Solv) ¹H-NMR δ ppm: |
|---|---|---|
| 210 | | (DMSO-d6) 1.21 (3 H, t, J = 7.1 Hz), 3.8 (3 H, s), 4.06 (3 H, s), 4.16 (2 H, q, J = 7.1 Hz), 4.92 (2 H, s), 5.0-5.1 (2 H, m), 5.31 (2 H, d, J = 47.0 Hz), 6.85-6.95 (1 H, m), 7.24 (1 H, s), 7.45-7.55 (2 H, m), 11.88 (1 H, s) |

Table 63

| Ex No. | Strc | (Solv) ¹H-NMR δ ppm: |
|---|---|---|
| 211 | | (DMSO-d6) 3.69 (3 H, s), 3.8 (3 H, s), 4.05 (3 H, s), 4.93 (2 H, s), 5.0-5.1 (2 H, m), 6.85-6.95 (1 H, m), 7.25 (1 H, s), 7.45-7.55 (2 H, m), 8.26 (1 H, s), 11.76 (1 H, s) |
| 212 | | (DMSO-d6) 2.07 (3 H, s), 2.62 (3 H, d, J = 4.4 Hz), 3.81 (3 H, s), 4.03 (3 H, s), 4.58 (2 H, s), 4.95-5.1 (4 H, m), 6.85-7.0 (2 H, m), 7.2 (1 H, s), 7.4-7.5 (2 H, m), 7.85-7.95 (1 H, m), 11.77 (1 H, s) |
| 213 | | (DMSO-d6) 1.14 (3 H, t, J = 7.1 Hz), 2.42 (3 H, s), 2.45-2.65 (2 H, m), 2.75-2.85 (2 H, m), 3.8 (3 H, s), 3.95-4.1 (5 H, m), 5.09 (2 H, s), 6.85-7.0 (1 H, m), 7.4-7.55 (3 H, m), 11.63 (1 H, s) |

Table 63-continued
| Ex No. | Strc | (Solv) ¹H-NMR δ ppm: |
|---|---|---|
| 214 | 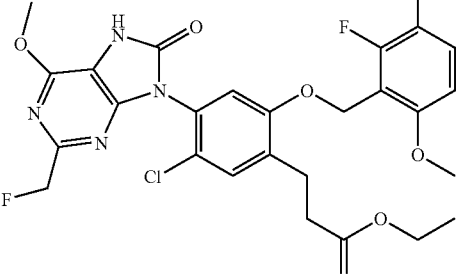 | (DMSO-d6) 1.14 (3 H, t, J = 7.1 Hz), 2.5-2.65 (2 H, m), 2.75-2.85 (2 H, m), 3.8 (3 H, s), 3.95-4.1 (5 H, m), 5.08 (2 H, s), 5.31 (2 H, d, J = 46.8 Hz), 6.85-7.0 (1 H, m), 7.4-7.55 (3 H, m), 11.92 (1 H, s) |
| 215 | 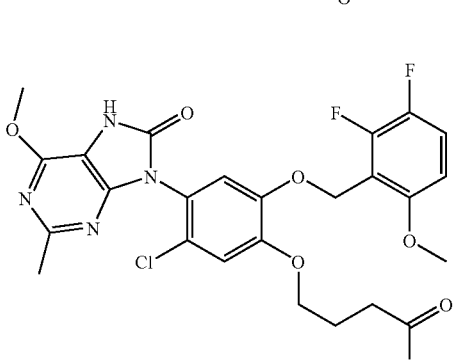 | (DMSO-d6) 1.17 (3 H, t, J = 7.0 Hz), 1.85-2.0 (2 H, m), 2.35-2.45 (5 H, m), 3.78 (3 H, s), 3.95-4.15 (7 H, m), 5.04 (2 H, s), 6.85-6.95 (1 H, m), 7.29 (1 H, s), 7.38 (1 H, s), 7.4-7.55 (1 H, m), 11.58 (1 H, s) |
| 216 | 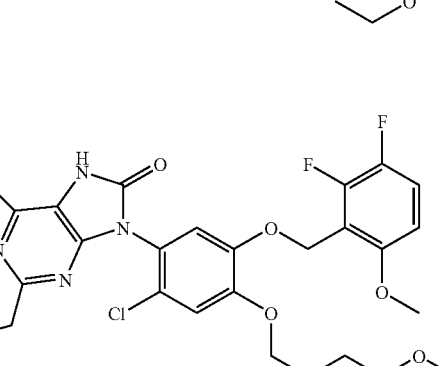 | (DMSO-d6) 1.16 (3 H, t, J = 7.1 Hz), 1.85-2.0 (2 H, m), 2.41 (2 H, t, J = 7.4 Hz), 3.78 (3 H, s), 4.0-4.15 (7 H, m), 5.0-5.1 (2 H, m), 5.3 (2 H, d, J = 47.0 Hz), 6.85-6.95 (1 H, m), 7.31 (1 H, s), 7.4-7.55 (2 H, m), 11.86 (1 H, s) |
Table 64
| Ex No. | Strc | (Solv) ¹H-NMR δ ppm: |
|---|---|---|
| 217 |  | (DMSO-d6) 2.43 (3 H, s), 2.65-2.75 (2 H, m), 3.5-3.6 (2 H, m), 3.79 (3 H, s), 4.02 (3 H, s), 4.65 (1 H, t, J = 5.4 Hz), 5.06 (2 H, s), 6.85-6.95 (1 H, m), 7.4-7.55 (3 H, m), 11.62 (1 H, s) |

Table 64-continued

| Ex No. | Strc | (Solv) $^1$H-NMR δ ppm: |
|---|---|---|
| 218 | | (DMSO-d6) 2.54 (3 H, s), 2.6-2.75 (5 H, m), 3.5-3.65 (2 H, m), 3.8 (3 H, s), 4.66 (1 H, t, J = 5.3 Hz), 5.05 (2 H, s), 6.85-7.0 (1 H, m), 7.4-7.55 (3 H, m), 12.03 (1 H, s) |
| 219 | | (DMSO-d6) 1.75-1.9 (2 H, m), 2.42 (3 H, s), 3.45-3.55 (2 H, m), 3.78 (3 H, s), 4.02 (3 H, s), 4.13 (2 H, t, J = 6.3 Hz), 4.53 (1 H, t, J = 5.2 Hz), 5.04 (2 H, s), 6.85-6.95 (1 H, m), 7.28 (1 H, s), 7.36 (1 H, s), 7.4-7.55 (1 H, m), 11.58 (1 H, s) |
| 220 | | (DMSO-d6) 1.8-1.9 (2 H, m), 3.45-3.55 (2 H, m), 3.78 (3 H, s), 4.06 (3 H, s), 4.13 (2 H, t, J = 6.2 Hz), 4.51 (1 H, t, J = 5.2 Hz), 5.0-5.1 (2 H, m), 5.3 (2 H, d, J = 46.8 Hz), 6.85-6.95 (1 H, m), 7.29 (1 H, s), 7.35-7.55 (2 H, m), 11.84 (1 H, s) |
| 221 | | (DMSO-d6) 1.75-1.9 (2 H, m), 3.45-3.55 (2 H, m), 3.8 (3 H, s), 4.06 (3 H, s), 4.13 (2 H, t, J = 6.4 Hz), 4.51 (1 H, t, J = 5.2 Hz), 4.95-5.05 (2 H, m), 5.3 (2 H, d, J = 46.9 Hz), 6.8-6.95 (2 H, m), 7.28 (1 H, s), 7.35-7.5 (2 H, m), 11.84 (1 H, s) |
| 222 | | (DMSO-d6) 2.42 (3 H, s), 3.79 (3 H, s), 4.02 (3 H, s), 4.44 (2 H, d, J = 5.8 Hz), 5.08 (2 H, s), 5.3 (1 H, t, J = 5.8 Hz), 6.85-6.95 (1 H, m), 7.4-7.55 (2 H, m), 7.57 (1 H, s), 11.63 (1 H, s) |

Table 65

| Ex No. | Strc | (Solv) $^1$H-NMR δ ppm: |
|---|---|---|
| 223 | | (DMSO-d6) 1.8-1.9 (2 H, m), 2.55 (3 H, s), 2.65 (3 H, s), 3.45-3.6 (2 H, m), 3.78 (3 H, s), 4.14 (2 H, t, J = 6.3 Hz), 4.53 (1 H, t, J = 5.3 Hz), 5.04 (2 H, s), 6.85-6.95 (1 H, m), 7.31 (1 H, s), 7.4-7.55 (2 H, m), 11.99 (1 H, s) |
| 224 | | (DMSO-d6) 1.72 (3 H, s), 1.74 (3 H, s), 3.8-3.85 (2 H, m), 4.0-4.15 (5 H, m), 4.75 (1 H, t, J = 5.3 Hz), 6.75-6.8 (1 H, m), 7.03 (1 H, d, J = 8.2 Hz), 7.1-7.25 (3 H, m), 7.31 (1 H, d, J = 2.1 Hz), 7.53 (1 H, d, J = 8.0 Hz), 8.26 (1 H, s), 11.78 (1 H, s) |
| 225 | | (CDCl3) 2.39 (1 H, t, J = 6.7 Hz), 2.69 (3 H, s), 2.76 (3 H, s), 3.8 (3 H, s), 3.85-3.95 (2 H, m), 4.15 (2 H, t, J = 4.4 Hz), 5.1-5.2 (2 H, m), 6.55-6.65 (1 H, m), 7.1-7.2 (3 H, m), 8.98 (1 H, s) |
| 226 | | (DMSO-d6) 1.736 (3 H, s), 1.741 (3 H, s), 4.06 (3 H, s), 7.3-7.45 (6 H, m), 7.78 (1 H, d, J = 2.2 Hz), 7.85 (1 H, d, J = 8.5 Hz), 8.29 (1 H, s), 11.86 (1 H, s) |
| 227 | | (DMSO-d6) 1.87 (6 H, s), 3.21 (3 H, s), 3.35-3.4 (2 H, m), 3.75-3.85 (2 H, m), 4.05 (3 H, s), 6.8-6.95 (2 H, m), 7.2-7.3 (1 H, m), 7.4-7.5 (2 H, m), 7.54 (1 H, d, J = 1.9 Hz), 7.87 (1 H, d, J = 8.5 Hz), 8.29 (1 H, s), 11.85 (1 H, s) |
| 228 | | (DMSO-d6) 1.86 (6 H, s), 3.29 (3 H, s), 4.06 (3 H, s), 6.8-6.9 (1 H, m), 7.1-7.2 (1 H, m), 7.27 (1 H, dd, J = 11.0 Hz, 3.2 Hz), 7.42 (1 H, dd, J = 8.3 Hz, 2.1 Hz), 7.84 (1 H, d, J = 2.1 Hz), 7.87 (1 H, d, J = 8.3 Hz), 8.29 (1 H, s), 11.85 (1 H, s) |

Table 66

| Ex No. | Strc | (Solv) ¹H-NMR δ ppm: |
|---|---|---|
| 229 | | (DMSO-d6) 1.95 (3 H, s), 1.96 (3 H, s), 3.36 (3 H, s), 4.06 (3 H, s), 6.65-6.8 (2 H, m), 7.25-7.4 (1 H, m), 7.45 (1 H, dd, J = 8.5 Hz, 2.1 Hz), 7.8-7.9 (2 H, m), 8.29 (1 H, s), 11.85 (1 H, s) |
| 230 | | (DMSO-d6) 1.87 (6 H, s), 3.32 (3 H, s), 4.06 (3 H, s), 6.86 (1 H, d, J = 8.7 Hz), 7.35-7.45 (3 H, m), 7.85-7.9 (2 H, m), 8.29 (1 H, s), 11.85 (1 H, s) |
| 231 | | (DMSO-d6) 1.86 (6 H, s), 3.2 (3 H, s), 3.3-3.4 (2 H, m), 3.75-3.85 (2 H, m), 4.05 (3 H, s), 6.92 (1 H, d, J = 9.0 Hz), 7.34 (1 H, dd, J = 9.0 Hz, 2.6 Hz), 7.41 (1 H, d, J = 2.6 Hz), 7.56 (1 H, dd, J = 8.5 Hz, 2.2 Hz), 7.67 (1 H, d, J = 2.2 Hz), 7.92 (1 H, d, J = 8.5 Hz), 8.29 (1 H, s), 11.84 (1 H, s) |
| 232 | | (DMSO-d6) 1.97 (6 H, s), 3.34 (3 H, s), 4.06 (3 H, s), 6.6-6.75 (1 H, m), 7.35-7.5 (1 H, m), 7.5-7.6 (1 H, m), 7.85-7.95 (2 H, m), 8.3 (1 H, s), 11.84 (1 H, s) |
| 233 | | (DMSO-d6) 1.88 (6 H, s), 3.49 (2 H, t, J = 5.2 Hz), 3.75 (2 H, t, J = 5.2 Hz), 4.05 (3 H, s), 4.45-4.65 (1 H, br), 6.85-6.95 (2 H, m), 7.2-7.3 (1 H, m), 7.35-7.45 (1 H, m), 7.5 (1 H, dd, J = 8.5 Hz, 2.3 Hz), 7.56 (1 H, d, J = 2.3 Hz), 7.86 (1 H, d, J = 8.5 Hz), 8.29 (1 H, s), 11.86 (1 H, s) |
| 234 | | (DMSO-d6) 2.42 (3 H, s), 3.8 (3 H, s), 4.01 (3 H, s), 5.01 (2 H, s), 6.85-6.95 (1 H, m), 7.02 (1 H, s), 7.3 (1 H, s), 7.4-7.55 (1 H, m), 10.07 (1 H, brs), 11.54 (1 H, brs) |

TABLE 67

| Ex No. | Strc | (Solv) $^1$H-NMR δ ppm: |
|---|---|---|
| 235 | | (DMSO-d6) 2.55 (3H, s), 2.65 (3H, s), 3.8 (3H, s), 5.01 (2H, s), 6.85-6.95 (1H, m), 7.05 (1H, s), 7.38 (1H, s), 7.4-7.55 (1H, m), 10.1 (1H, brs), 11.97 (1H, brs) |
| 236 | | (DMSO-d6) 2.42 (3H, s), 3.35-3.45 (2H, m), 3.7-3.85 (4H, m), 3.95-4.15 (5H, m), 4.65 (1H, t, J = 5.6 Hz), 4.96 (1H, d, J = 5.1 Hz), 5.05 (2H, s), 6.85-6.95 (1H, m), 7.31 (1H, s), 7.35 (1H, s), 7.4-7.55 (1H, m), 11.58 (1H, brs) |
| 237 | | (DMSO-d6) 2.55 (3H, s), 2.65 (3H, s), 3.35-3.5 (2H, m), 3.7-3.85 (4H, m), 3.95-4.05 (1H, m), 4.05-4.15 (1H, m), 4.66 (1H, t, J = 5.8 Hz), 4.96 (1H, d, J = 5.0 Hz), 5.05 (2H, s), 6.85-6.95 (1H, m), 7.34 (1H, s), 7.4-7.55 (2H, m), 11.99 (1H, s) |
| 238 | | (DMSO-d6) 2.43 (3H, s), 3.45-3.65 (4H, m), 3.78 (3H, s), 4.01 (3H, s), 4.2-4.35 (1H, m), 4.7-4.85 (2H, m), 5.06 (2H, s), 6.85-6.95 (1H, m), 7.3-7.55 (3H, m), 11.59 (1H, brs) |
| 239 | | (DMSO-d6) 2.56 (3H, s), 2.65 (3H, s), 3.45-3.7 (4H, m), 3.78 (3H, s), 4.25-4.35 (1H, m), 4.79 (2H, brs), 5.0-5.1 (2H, m), 6.85-6.95 (1H, m), 7.4-7.55 (3H, m), 11.99 (1H, s) |

TABLE 67-continued

| Ex No. | Strc | (Solv) $^1$H-NMR δ ppm: |
|---|---|---|
| 240 | | (DMSO-d6) 2.4-2.55 (4H, m), 2.7-2.8 (1H, m), 3.2-3.35 (2H, m), 3.6-3.75 (1H, m), 3.75-3.85 (3H, m), 4.02 (3H, s), 4.45-4.6 (2H, m), 5.0-5.15 (2H, m), 6.85-6.95 (1H, m), 7.35-7.55 (3H, m), 11.02 (1H, s) |

Table 68

| Ex No. | Strc | (Solv) $^1$H-NMR δ ppm: |
|---|---|---|
| 241 | | (DMSO-d6) 3.6-3.7 (2 H, m), 3.95-4.1 (5 H, m), 4.85-4.95 (1 H, m), 5.18 (2 H, s), 6.9-6.95 (1 H, m), 7.25-7.3 (1 H, m), 7.35-7.5 (2 H, m), 7.55-7.65 (1 H, m), 8.25 (1 H, s), 11.81 (1 H, s) |
| 242 | | (DMSO-d6) 2.48 (3 H, s), 3.7 (3 H, s), 3.8 (3 H, s), 4.96 (2 H, s), 5.04 (2 H, s), 6.85-6.95 (1 H, m), 7.27 (1 H, s), 7.45-7.55 (2 H, m), 12.24 (1 H, s) |
| 243 | | (DMSO-d6) 3.69 (3 H, s), 3.8 (3 H, s), 4.9-5.1 (4 H, m), 6.85-6.95 (1 H, m), 7.28 (1 H, s), 7.4-7.55 (2 H, m), 8.42 (1 H, s), 12.42 (1 H, brs) |
| 244 | | (DMSO-d6) 3.8 (3 H, s), 3.84 (3 H, s), 4.95-5.05 (2 H, m), 6.85-6.95 (1 H, m), 7.3 (1 H, s), 7.45-7.55 (2 H, m), 8.42 (1 H, s), 12.39 (1 H, s) |

TABLE 68-continued

| Ex No. | Strc | (Solv) ¹H-NMR δ ppm: |
|---|---|---|
| 245 | | (DMSO-d6) 2.43 (3 H, s), 3.65-3.75 (2 H, m), 3.79 (3 H, s), 4.02 (3 H, s), 4.09 (2 H, t, J = 4.9 Hz), 4.87 (1 H, t, J = 5.3 Hz), 5.04 (2 H, s), 6.85-6.95 (1 H, m), 7.31 (1 H, s), 7.38 (1 H, s), 7.4-7.55 (1 H, m), 11.58 (1 H, s) |
| 246 | | (DMSO-d6) 3.65-3.75 (2 H, m), 3.81 (3 H, s), 4.0-4.15 (5 H, m), 4.4 (2 H, d, J = 6.3 Hz), 4.87 (1 H, t, J = 5.4 Hz), 4.99 (2 H, s), 5.1-5.2 (1 H, m), 6.8-7.0 (2 H, m), 7.3 (1 H, s), 7.35-7.5 (2 H, m), 11.67 (1 H, s) |

TABLE 69

| Ex No. | Strc | (Solv) ¹H-NMR δ ppm: |
|---|---|---|
| 247 | | (DMSO-d6) 2.43 (3 H, s), 3.65-3.75 (2 H, m), 3.81 (3 H, s), 4.02 (3 H, s), 4.08 (2 H, t, J = 5.0 Hz), 4.87 (1 H, t, J = 5.3 Hz), 5.0 (2 H, s), 6.8-7.0 (2 H, m), 7.3 (1 H, s), 7.35-7.5 (2 H, m), 11.58 (1 H, s) |
| 248 | | (DMSO-d6) 3.65-3.75 (2 H, m), 3.79 (3 H, s), 4.05 (3 H, s), 4.09 (2 H, t, J = 4.9 Hz), 4.85 (1 H, t, J = 5.4 Hz), 5.0-5.1 (2 H, m), 6.85-6.95 (1 H, m), 7.32 (1 H, s), 7.39 (1 H, s), 7.4-7.55 (1 H, m), 8.26 (1 H, s), 11.74 (1 H, s) |

Table 69-continued

| Ex No. | Strc | (Solv) $^1$H-NMR δ ppm: |
|---|---|---|
| 249 | | (DMSO-d6) 3.65-3.75 (2 H, m), 3.79 (3 H, s), 4.05-4.15 (5 H, m), 4.88 (1 H, t, J = 5.3 Hz), 5.04 (2 H, s), 6.6-6.95 (2 H, m), 7.34 (1 H, s), 7.4-7.55 (2 H, m), 12.08 (1 H, s) |
| 250 | | (DMSO-d6) 3.65-3.75 (2 H, m), 3.79 (3 H, s), 4.0-4.15 (5 H, m), 4.88 (1 H, t, J = 5.3 Hz), 5.0-5.1 (2 H, m), 5.31 (2 H, d, J = 46.8 Hz), 6.85-6.95 (1 H, m), 7.33 (1 H, s), 7.35-7.55 (2 H, m), 11.86 (1 H, s) |
| 251 | | (DMSO-d6) 3.65-3.75 (2 H, m), 3.81 (3 H, s), 4.0-4.15 (5 H, m), 4.87 (1 H, t, J = 5.5 Hz), 4.95-5.05 (2 H, m), 5.31 (2 H, d, J = 7.0 Hz), 6.8-7.0 (2 H, m), 7.32 (1 H, s), 7.4-7.5 (2 H, m), 11.87 (1 H, s) |
| 252 | | (DMSO-d6) 3.32 (3 H, s), 3.65-3.75 (2 H, m), 3.81 (3 H, s), 4.04 (3 H, s), 4.08 (2 H, t, J = 5.0 Hz), 4.36 (2 H, s), 4.89 (1 H, t, J = 5.3 Hz), 4.9-5.05 (2 H, m), 6.8-7.0 (2 H, m), 7.31 (1 H, s), 7.4-7.5 (2 H, m), 11.75 (1 H, s) |

TABLE 70

| Ex No. | Strc | (Solv) $^1$H-NMR δ ppm: |
|---|---|---|
| 253 | | (DMSO-d6) 3.32(3H, s), 3.65-3.75(2H, m), 3.79(3H, s), 4.04(3H, s), 4.09(2H, t, J = 4.8 Hz), 4.36(2H, s), 4.89(1H, t, J = 5.2 Hz), 4.95-5.1(2H, m), 6.85-6.95 (1H, m), 7.33(1H, s), 7.4-7.55(2H, m), 11.75(1H, s) |

TABLE 70-continued

| Ex No. | Strc | (Solv) $^1$H-NMR δ ppm: |
|---|---|---|
| 254 | | (DMSO-d6) 3.65-3.75(2H, m), 3.79(3H, s), 4.1(2H, t, J = 4.9 Hz), 4.86(1H, t, J = 5.4 Hz), 4.95-5.1(2H, m), 6.85-6.95 (1H, m), 7.35(1H, s), 7.40-7.55(2H, m), 8.42(1H, s), 12.39(1H, s) |
| 255 | | (DMSO-d6) 2.47(3H, s), 3.7(2H, t, J = 5.0 Hz), 3.79(3H, s), 4.1(2H, t, J = 5.0 Hz), 4.7-5.1(3H, m), 6.85-6.95 (1H, m), 7.34(1H, s), 7.4-7.55(2H, m), 12.22(1H, s) |
| 256 | | (DMSO-d6) 3.65-3.75(2H, m), 3.79(3H, s), 4.0-4.15(5H, m), 4.39(2H, d, J = 6.3 Hz), 4.86(1H, t, J = 5.2 Hz), 5.04 (2H, s), 5.13(1H, t, J = 6.3 Hz), 6.85-6.95 (1H, m), 7.32(1H, s), 7.35-7.55(2H, m), 11.66(1H, s) |
| 257 | | (DMSO-d6) 1.409(3H, s), 1.417(3H, s), 3.65-3.75(2H, m), 3.79(3H, s), 4.0-4.15 (5H, m), 4.78(1H, s), 4.89(1H, t, J = 5.4 Hz), 4.95-5.1(2H, m), 6.85-6.95 (1H, m), 7.32(1H, s), 7.35-7.55(2H, m), 11.68(1H, s) |
| 258 | | (DMSO-d6) 1.41(3H, s), 1.42(3H, s), 3.65-3.75(2H, m), 3.81(3H, s), 4.0-4.15 (5H, m), 4.78(1H, s), 4.88(1H, t, J = 5.4 Hz), 4.9-5.05(2H, m), 6.8-7.0(2H, m), 7.3(1H, s), 7.35-7.5(2H, m), 11.68 (1H, s) |

TABLE 71

| Ex No. | Strc | (Solv) ¹H-NMR δ ppm: |
|---|---|---|
| 259 | | (DMSO-d6) 1.55-1.75(2H, m), 2.35-2.6 (5H, m), 3.2-3.5(2H, m), 3.79(3H, s), 4.02(3H, s), 4.4-4.5(1H, m), 5.07(2H, s), 6.85-7.0(1H, m), 7.35-7.6(3H, m), 11.63(1H, s) |
| 260 | | (DMSO-d6) 1.45-1.6(2H, m), 1.65-1.8 (2H, m), 2.42(3H, s), 3.35-3.5(2H, m), 3.78(3H, s), 4.02(3H, s), 4.06(2H, t, J = 6.6 Hz), 4.42(1H, t, J = 5.0 Hz), 5.04 (2H, s), 6.85-6.95(1H, m), 7.27(1H, s), 7.36(1H, s), 7.4-7.55(1H, m), 11.67 (1H, s) |
| 261 | | (DMSO-d6) 1.3-1.6(4H, m), 2.43(3H, s), 2.45-2.6(2H, m), 3.25-3.45(2H, m), 3.79(3H, s), 4.02(3H, s), 4.33(1H, t, J = 5.3 Hz), 5.07(2H, s), 6.85-6.95(1H, m), 7.4-7.55(3H, m), 11.62(1H, s) |
| 262 | | (DMSO-d6) 1.75(3H, s), 3.25-3.45(2H, m), 3.95-4.1(5H, m), 5.18(2H, s), 6.9-7.0(1H, m), 7.27(1H, dd, J = 9.0 Hz, 2.9 Hz), 7.36(1H, d, J = 2.9 Hz), 7.4-7.5 (1H, m), 7.62(1H, d, J = 9.0 Hz), 8.0-8.1 (1H, m), 8.25(1H, s), 11.82(1H, s) |
| 263 | | (DMSO-d6) 2.42(3H, s), 3.1-3.25(2H, m), 3.79(3H, s), 4.02(3H, s), 4.2-4.3 (2H, m), 5.08(2H, s), 6.8-7.0(1H, m), 7.35-7.55(3H, m), 7.8-8.2(3H, br), 11.61(1H, s) |

TABLE 71-continued
| Ex No. | Strc | (Solv) $^1$H-NMR δ ppm: |
|---|---|---|
| 264 | 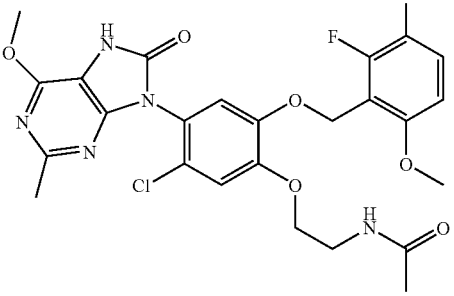 | (DMSO-d6) 1.79(3H, s), 2.42(3H, s), 3.25-3.45(2H, m), 3.78(3H, s), 3.95-4.1 (5H, m), 5.05(2H, s), 6.8-6.95(1H, m), 7.3-7.55(3H, m), 8.03(1H, t, J = 5.6 Hz), 11.6(1H, brs) |
TABLE 72
| Ex No. | Strc | (Solv) $^1$H-NMR δ ppm: |
|---|---|---|
| 265 | 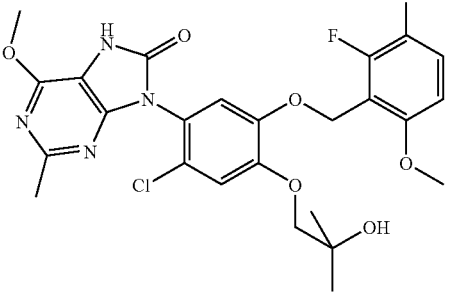 | (DMSO-d6) 1.16(6H, s), 2.42(3H, s), 3.77(3H, s), 3.8(2H, s), 4.02(3H, s), 4.6 (1H, s), 5.08(2H, s), 6.8-6.95(1H, m), 7.25-7.55(3H, m), 11.57(1H, s) |
| 266 | 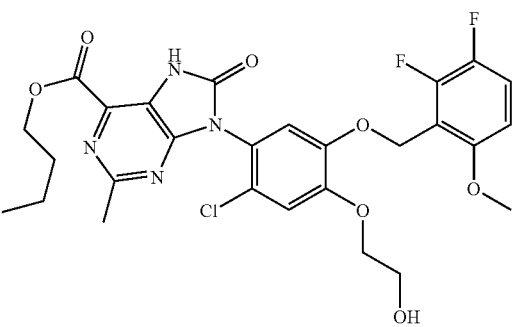 | (DMSO-d6) 0.94(3H, t, J = 7.4 Hz), 1.3-1.45(2H, m), 1.7-1.8(2H, m), 2.52(3H, s), 3.65-3.75(2H, m), 3.79(3H, s), 4.11 (2H, t, J = 5.0 Hz), 4.35-4.45(2H, m), 4.85-4.95(1H, m), 5.04(2H, s), 6.85-6.95(1H, m), 7.35(1H, s), 7.4-7.55(2H, m), 11.84(1H, s) |
| 267 | 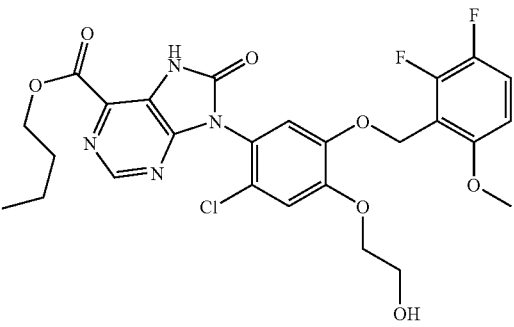 | (DMSO-d6) 0.94(3H, t, J = 7.4 Hz), 1.35-1.5(2H, m), 1.7-1.8(2H, m), 3.65-3.75 (2H, m), 3.79(3H, s), 4.1(2H, t, J = 4.9 Hz), 4.35-4.45(2H, m), 4.86(1H, t, J = 5.4 Hz), 4.95-5.1(2H, m), 6.85-6.95 (1H, m), 7.36(1H, s), 7.4-7.55(2H, m), 8.62(1H, s), 12.0(1H, s) |

TABLE 72-continued

| Ex No. | Strc | (Solv) ¹H-NMR δ ppm: |
|---|---|---|
| 268 | | (DMSO-d6) 0.94(3H, t, J = 7.4 Hz), 1.35-1.45(2H, m), 1.7-1.8(2H, m), 3.8(3H, s), 3.84(3H, s), 4.35-4.45(2H, m), 4.95-5.05(2H, m), 6.85-6.95(1H, m), 7.31 (1H, s), 7.45-7.55(2H, m), 8.62(1H, s), 12.0(1H, s) |
| 269 | | (DMSO-d6) 3.8(3H, s), 3.83(3H, s), 4.68(2H, d, J = 5.7 Hz), 4.95-5.05(2H, m), 5.57(1H, t, J = 5.7 Hz), 6.85-6.95(1H, m), 7.28(1H, s), 7.4-7.55(2H, m), 8.47 (1H, s), 11.49(1H, s) |
| 270 | | (DMSO-d6) 3.8(3H, s), 3.84(3H, s), 4.95-5.05(2H, m), 6.85-6.95(1H, m), 7.31(1H, s), 7.45-7.55(2H, m), 8.72 (1H, s), 10.08(1H, s), 12.48(1H, s) |

TABLE 73

| Ex No. | Strc | (Solv) ¹H-NMR δ ppm: |
|---|---|---|
| 271 | | (DMSO-d6) 1.4-1.5(3H, m), 3.8(3H, s), 3.83(3H, s), 4.85-5.05(3H, m), 5.5-1.7 (1H, m), 6.85-6.95(1H, m), 7.25-7.3 (1H, m), 7.4-7.55(2H, m), 8.45-8.5(1H, m), 11.25-11.4(1H, m) |
| 272 | | (DMSO-d6) 2.68(3H, s), 3.8(3H, s), 3.84(3H, s), 4.95-5.05(2H, m), 6.85-6.95(1H, m), 7.3(1H, s), 7.45-7.55(2H, m), 8.66(1H, s), 12.15(1H, s) |

TABLE 73-continued
| Ex No. | Strc | (Solv) ¹H-NMR δ ppm: |
|---|---|---|
| 273 | 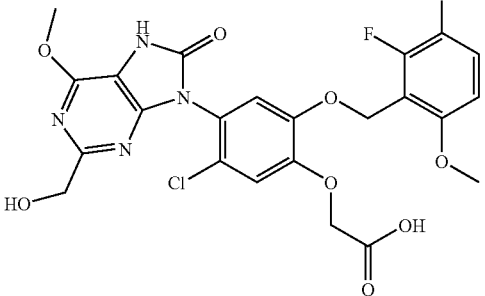 | (DMSO-d6) 3.8(3H, s), 4.06(3H, s), 4.4 (2H, d, J = 6.3 Hz), 4.82(2H, s), 5.04(2H, s), 5.19(1H, t, J = 6.3 Hz), 6.85-6.95(1H, m), 7.16(1H, s), 7.4-7.55(2H, m), 11.67 (1H, s), 13.13(1H, brs) |
| 274 | 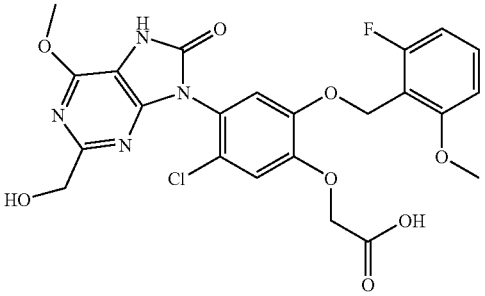 | (DMSO-d6) 3.82(3H, s), 4.06(3H, s), 4.4(2H, d, J = 6.4 Hz), 4.82(2H, s), 4.95-5.05(2H, m), 5.21(1H, t, J = 6.4 Hz), 6.8-7.0(2H, m), 7.14(1H, s), 7.35-7.5(2H, m), 11.68(1H, s), 13.14(1H, brs) |
| 275 | 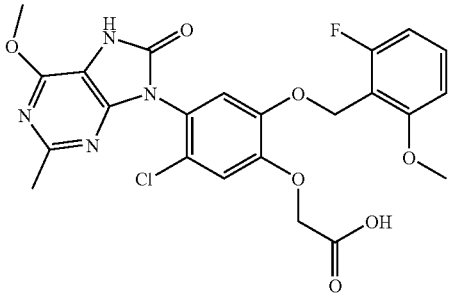 | (DMSO-d6) 2.44(3H, s), 3.82(3H, s), 4.02(3H, s), 4.82(2H, s), 5.0(2H, s), 6.85-7.0(2H, m), 7.14(1H, s), 7.4-7.5 (2H, m), 11.59(1H, s), 13.13(1H, brs) |
| 276 | 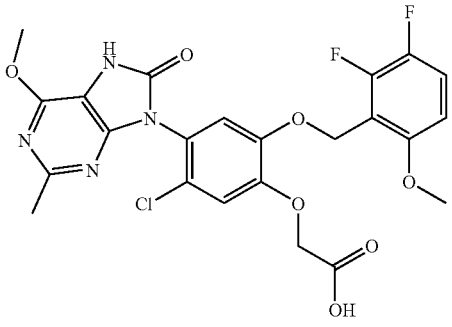 | (DMSO-d6) 2.43(3H, s), 3.8(3H, s), 4.02(3H, s), 4.83(2H, s), 5.04(2H, s), 6.85-6.95(1H, m), 7.16(1H, s), 7.44 (1H, s), 7.45-7.55(1H, m), 11.59(1H, s), 12.5-14.0(1H, br) |
TABLE 74
| Ex No. | Strc | (Solv) ¹H-NMR δ ppm: |
|---|---|---|
| 277 | 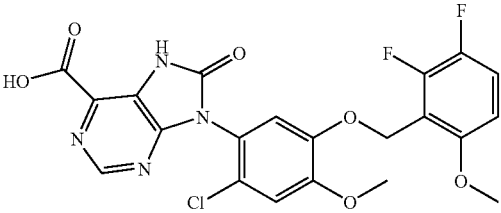 | (DMSO-d6) 3.8(3H, s), 3.84(3H, s), 4.95-5.05(2H, m), 6.85-6.95(1H, m), 7.3 (1H, s), 7.45-7.55(2H, m), 8.61(1H, s), 11.89(1H, brs), 13.93(1H, brs) |

| Ex No. | Strc | (Solv) ¹H-NMR δ ppm: |
|---|---|---|
| 278 | | (DMSO-d6) 3.65-3.75(2H, m), 3.79(3H, s), 4.1(2H, t, J = 5.0 Hz), 4.8-4.9(1H, m), 4.95-5.1(2H, m), 6.85-6.95(1H, m), 7.35 (1H, s), 7.4-7.55(2H, m), 8.6(1H, s), 11.89(1H, s), 13.0-15.0(1H, br) |
| 279 | | (DMSO-d6) 3.8(3H, s), 4.05(3H, s), 4.81(2H, s), 5.0-5.1(2H, m), 6.85-6.95 (1H, m), 7.17(1H, s), 7.4-7.55(2H, m), 8.26(1H, s), 11.75(1H, s), 13.1(1H, brs) |
| 280 | | (DMSO-d6) 2.4-2.6(5H, m), 2.7-2.8(2H, m), 3.8(3H, s), 4.02(3H, s), 5.08(2H, s), 6.9-7.0(1H, m), 7.4-7.55(3H, m), 11.63(1H, s), 12.16(1H, brs) |
| 281 | | (DMSO-d6) 1.85-1.95(2H, m), 2.33(2H, t, J = 7.3 Hz), 2.42(3H, s), 3.78(3H, s), 4.01(3H, s), 4.07(2H, t, J = 6.6 Hz), 5.05 (2H, s), 6.85-6.95(1H, m), 7.3(1H, s), 7.37(1H, s), 7.4-7.55(1H, m), 11.58 (1H, brs), 12.17(1H, brs) |

TABLE 74-continued
| Ex No. | Strc | (Solv) $^1$H-NMR δ ppm: |
|---|---|---|
| 282 | 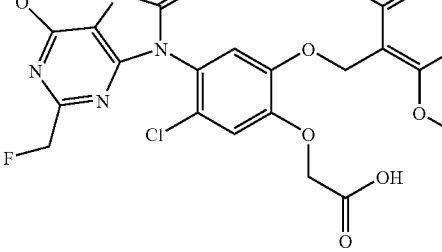 | (DMSO-d6) 3.8(3H, s), 4.1(3H, s), 4.84 (2H, s), 5.04(2H, s), 6.65-6.95(2H, m), 7.19(1H, s), 7.4-7.55(2H, m), 12.1(1H, s) |
TABLE 75
| Ex No. | Strc | (Solv) $^1$H-NMR δ ppm: |
|---|---|---|
| 283 | 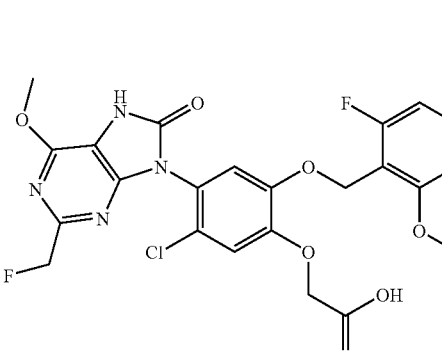 | (DMSO-d6) 3.8(3H, s), 4.06(3H, s), 4.83(2H, s), 5.0-5.1(2H, m), 5.32(2H, d, J = 47.0 Hz), 6.85-6.95(1H, m), 7.18 (1H, s), 7.45-7.55(2H, m), 11.88(1H, s), 13.14(1H, brs) |
| 284 | 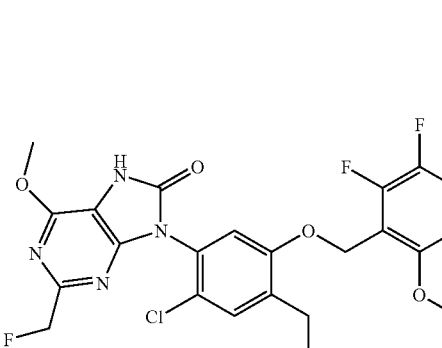 | (DMSO-d6) 3.82(3H, s), 4.07(3H, s), 4.82(2H, s), 4.95-5.05(2H, m), 5.32 (2H, d, J = 46.9 Hz), 6.85-7.0(2H, m), 7.15(1H, s), 7.4-7.5(2H, m), 11.87(1H, s), 13.14(1H, brs) |
| 285 | | (DMSO-d6) 2.45-2.55(2H, m), 2.7-2.8 (2H, m), 3.8(3H, s), 4.07(3H, s), 5.08 (2H, s), 5.31(2H, d, J = 46.8 Hz), 6.85-6.95(1H, m), 7.4-7.55(3H, m), 11.92 (1H, brs), 12.15(1H, brs) |

TABLE 75-continued

| Ex No. | Strc | (Solv) $^1$H-NMR δ ppm: |
|---|---|---|
| 286 | | (DMSO-d6) 1.85-2.0(2H, m), 2.3-2.4 (2H, m), 3.78(3H, s), 4.0-4.15(5H, m), 5.0-5.1(2H, m), 5.3(2H, d, J = 46.6 Hz), 6.85-6.95(1H, m), 7.32(1H, s), 7.35-7.55(2H, m), 11.86(1H, brs), 12.15(1H, brs) |
| 287 | | (DMSO-d6) 3.32(3H, s), 3.8(3H, s), 4.05(3H, s), 4.37(2H, s), 4.81(2H, s), 5.0-5.1(2H, m), 6.85-6.95(1H, m), 7.16 (1H, s), 7.4-7.55(2H, m), 11.75(1H, s), 13.14(21H, brs) |
| 288 | | (DMSO-d6) 3.33(3H, s), 3.82(3H, s), 4.05(3H, s), 4.37(2H, s), 4.83(2H, s), 4.9-5.05(2H, m), 6.85-7.0(2H, m), 7.15 (1H, s), 7.4-7.5(2H, m), 11.76(1H, s), 13.15(1H, brs) |

TABLE 76

| Ex No. | Strc | (Solv) $^1$H-NMR δ ppm: |
|---|---|---|
| 289 | | (DMSO-d6) 1.42(3H, s), 1.43(3H, s), 3.82(3H, s), 4.07(3H, s), 4.83(2H, s), 4.95-5.05(2H, m), 6.85-7.0(2H, m), 7.14 (1H, s), 7.35-7.5(2H, m), 11.69(1H, s), 13.15(1H, brs) |

TABLE 76-continued

| Ex No. | Strc | (Solv) $^1$H-NMR δ ppm: |
|---|---|---|
| 290 | | (DMSO-d6) 1.42(3H, s), 1.43(3H, s), 3.8(3H, s), 4.08(3H, s), 4.82(1H, s), 4.84(2H, s), 4.95-5.1(2H, m), 6.85-6.95 (1H, m), 7.17(1H, s), 7.4-7.55(2H, m), 11.7(1H, s), 13.14(1H, brs) |
| 291 | | (DMSO-d6) 1.85-2.0(2H, m), 2.35(2H, t, J = 7.3 Hz), 2.56(3H, s), 2.65(3H, s), 3.78(3H, s), 4.09(2H, t, J = 6.5 Hz), 5.05 (2H, s), 6.85-6.95(1H, m), 7.34(1H, s), 7.4-7.55(2H, m), 11.99(1H, brs), 12.15 (1H, brs) |
| 292 | | (DMSO-d6) 1.65-1.8(2H, m), 2.1-2.2 (2H, m), 2.43(3H, s), 2.45-2.6(2H, m), 3.78(3H, s), 4.02(3H, s), 5.07(2H, s), 6.85-6.95(1H, m), 7.4-7.55(3H, m), 11.63(1H, s), 12.02(1H, s) |
| 293 | | (DMSO-d6) 1.7-1.8(2H, m), 2.1-2.25 (2H, m), 2.45-2.65(5H, m), 2.66(3H, s), 3.79(3H, s), 5.06(2H, s), 6.85-6.95(1H, m), 7.4-7.55(3H, m), 11.95-12.1(2H, m) |
| 294 | | (DMSO-d6) 2.55(3H, s), 2.65(3H, s), 3.81(3H, s), 4.29(2H, s), 5.0(2H, s), 6.85-7.0(2H, m), 7.38(1H, s), 7.4-7.55 (1H, m), 11.5-12.5(1H, br) |

TABLE 79

| Ex No. | Strc | (Solv) ¹H-NMR δ ppm: |
|---|---|---|
| 307 | | (DMSO-d6) 2.57 (3H, s), 3.65-3.75 (2H, m), 3.78 (3H, s), 4.05-4.15 (5H, m), 4.86 (1H, t, J = 5.4 Hz), 5.0-5.1 (2H, m), 6.85-6.95 (1H, m), 7.35 (1H, s), 7.4-7.55 (2H, m), 12.16 (1H, s) |
| 308 | | (DMSO-d6) 2.58 (3H, s), 3.8 (3H, s), 4.13 (3H, s), 4.84 (2H, s), 4.95-5.1 (2H, m), 6.85-6.95 (1H, m), 7.2 (1H, s), 7.45-7.55 (2H, m), 12.21 (1H, s), 13.16 (1H, brs) |
| 309 | | (DMSO-d6) 2.58 (3H, s), 3.82 (3H, s), 4.13 (3H, s), 4.84 (2H, s), 4.95-5.05 (2H, m), 6.85-7.0 (2H, m), 7.18 (1H, s), 7.4-7.55 (2H, m), 12.21 (1H, s), 13.14 (1H, brs) |
| 310 | | (DMSO-d6) 3.61 (2H, s), 3.79 (3H, s), 3.83 (3H, s), 4.01 (3H, s), 5.01 (2H, s), 6.85-6.95 (1H, m), 7.26 (1H, s), 7.35-7.55 (2H, m), 11.67 (1H, s), 12.62 (1H, brs) |
| 311 | | (DMSO-d6) 3.67 (2H, s), 3.81 (3H, s), 3.82 (3H, s), 4.02 (3H, s), 4.9-5.05 (2H, m), 6.8-7.0 (2H, m), 7.24 (1H, s), 7.35-7.5 (2H, m), 11.69 (1H, s), 12.39 (1H, brs) |

281 282
TABLE 79-continued
| Ex No. | Strc | (Solv) ¹H-NMR δ ppm: |
|---|---|---|
| 312 | 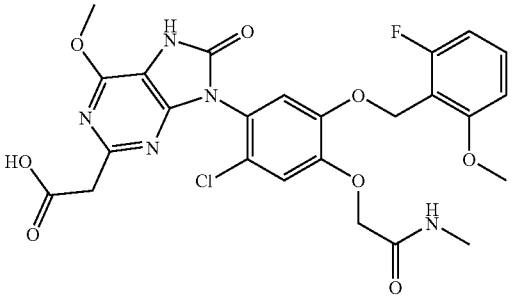 | (DMSO-d6) 2.62 (3H, d, J = 4.7 Hz), 3.54 (2H, s), 3.81 (3H, s), 4.0 (3H, s), 4.58 (2H, s), 4.95-5.1 (2H, m), 6.8-7.0 (2H, m), 7.18 (1H, s), 7.4-7.5 (2H, m), 7.85-7.95 (1H, m), 11.61 (1H, s) |
TABLE 80
| Ex No. | Strc | (Solv) ¹H-NMR δ ppm: |
|---|---|---|
| 313 | 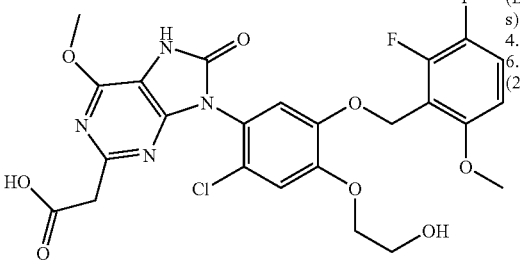 | (DMSO-d6) 3.65-3.75(4H, m), 3.8(3H, s), 4.02(3H, s), 4.08(2H, t, J = 5.1 Hz), 4.86(1H, t, J = 5.3 Hz), 4.95-5.05(2H, m), 6.8-6.95(2H, m), 7.3(1H, s), 7.35-7.5 (2H, m), 11.7(1H, s), 12.43(1H, brs) |
| 314 | 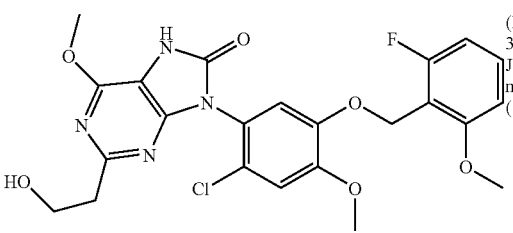 | (DMSO-d6) 2.83(2H, t, J = 6.9 Hz), 3.7-3.85(8H, m), 4.03(3H, s), 4.53(1H, t, J = 5.4 Hz), 4.9-5.05(2H, m), 6.8-7.0(2H, m), 7.25(1H, s), 7.35-7.5(2H, m), 11.58 (1H, s) |
| 315 | 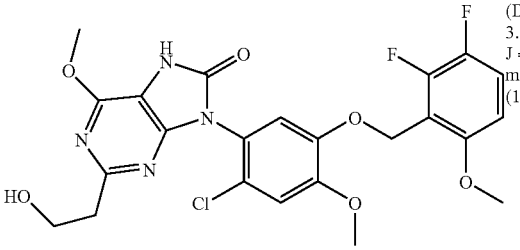 | (DMSO-d6) 2.82(2H, t, J = 6.9 Hz), 3.7-3.85(8H, m), 4.03(3H, s), 4.54(1H, t, J = 5.4 Hz), 5.01(2H, s), 6.85-6.95(1H, m), 7.26(1H, s), 7.39(1H, s), 7.45-7.55 (1H, m), 11.6(1H, s) |
| 316 | 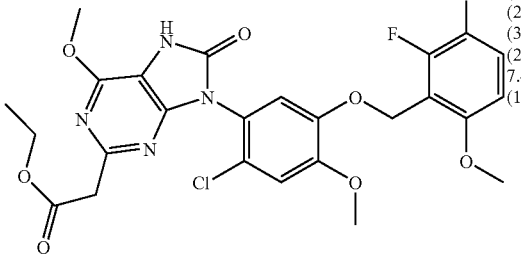 | (DMSO-d6) 1.14(3H, t, J = 7.1 Hz), 3.76 (2H, s), 3.79(3H, s), 3.82(3H, s), 4.01 (3H, s), 4.08(2H, q, J = 7.1 Hz), 4.95-5.05 (2H, m), 6.85-6.95(1H, m), 7.26(1H, s), 7.41(1H, s), 7.45-7.55(1H, m), 11.72 (1H, s) |

TABLE 80-continued
| Ex No. | Strc | (Solv) $^1$H-NMR δ ppm: |
|---|---|---|
| 317 | 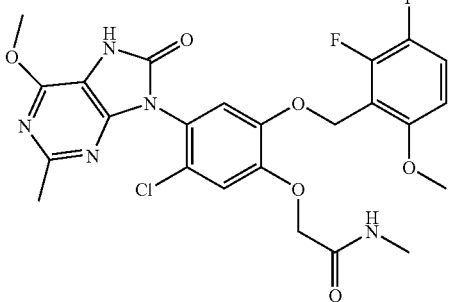 | (DMSO-d6) 2.43(3H, s), 2.63(3H, d, J = 4.4 Hz), 3.8(3H, s), 4.02(3H, s), 4.59 (2H, s), 5.07(2H, s), 6.85-7.0(1H, m), 7.2(1H, s), 7.4-7.55(2H, m), 7.8-7.95 (1H, m), 11.59(1H, s) |
| 318 | 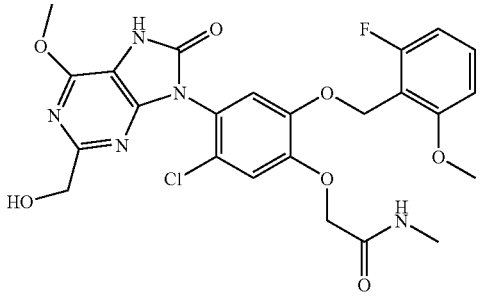 | (DMSO-d6) 2.62(3H, d, J = 4.6 Hz), 3.82 (3H, s), 4.06(3H, s), 4.44(2H, d, J = 6.3 Hz), 4.59(2H, s), 4.95-5.1(2H, m), 5.2(1H, t, J = 6.3 Hz), 6.85-7.0(2H, m), 7.18(1H, s), 7.4-7.55(2H, m), 7.91(1H, q, J = 4.6 Hz), 11.69(1H, s) |
TABLE 81
| Ex No. | Strc | (Solv) $^1$H-NMR δ ppm: |
|---|---|---|
| 319 | 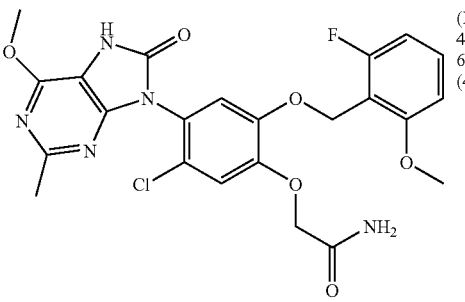 | (DMSO-d6) 2.43(3H, s), 3.82(3H, s), 4.02(3H, s), 4.57(2H, s), 5.02(2H, s), 6.85-7.0(2H, m), 7.15(1H, s), 7.3-7.5 (4H, m), 11.6(1H, s) |
| 320 | 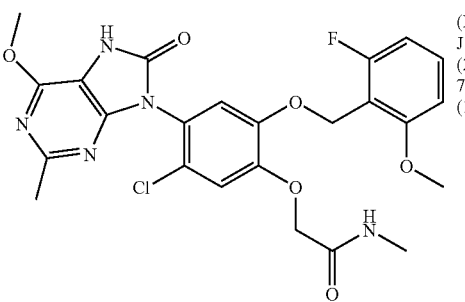 | (DMSO-d6) 2.43(3H, s), 2.62(3H, d, J = 4.6 Hz), 3.82(3H, s), 4.02(3H, s), 4.58 (2H, s), 5.02(2H, s), 6.85-7.0(2H, m), 7.18(1H, s), 7.4-7.5(2H, m), 7.85-7.95 (1H, m), 11.6(1H, s) |

TABLE 81-continued
| Ex No. | Strc | (Solv) $^1$H-NMR δ ppm: |
|---|---|---|
| 321 | 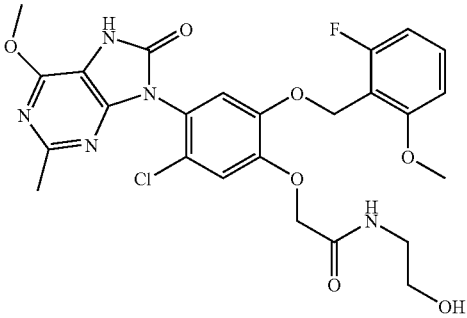 | (DMSO-d6) 2.43(3H, s), 3.1-3.2(2H, m), 3.35-3.45(2H, m) ,3.82(3H, s), 4.02 (3H, s), 4.6(2H, s), 4.7(1H, t, J = 5.6 Hz), 5.02(2H, s), 6.85-7.0(2H, m), 7.18(1H, s), 7.4-7.5(2H, m), 7.95(1H, t, J = 5.7 Hz), 11.6(1H, s) |
| 322 | 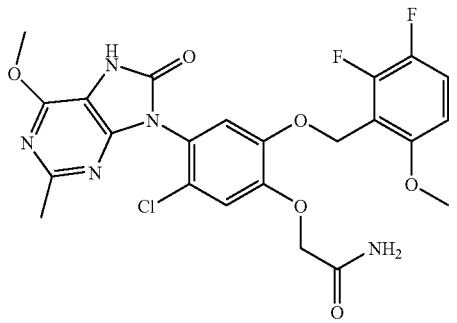 | (DMSO-d6) 2.43(3H, s), 3.8(3H, s), 4.02(3H, s), 4.58(2H, s), 5.06(2H, s), 6.85-6.95(1H, m), 7.17(1H, s), 7.3-7.55 (4H, m), 11.6(1H, s) |
| 323 | 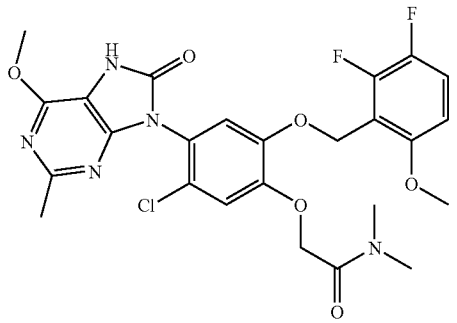 | (DMSO-d6) 2.44(3H, s), 2.84(3H, s), 2.96(3H, s), 3.8(3H, s), 4.02(3H, s), 4.96(2H, s), 5.05(2H, s), 6.85-6.95(1H, m), 7.15(1H, s), 7.35-7.55(2H, m), 11.57(1H, s) |
| 324 | 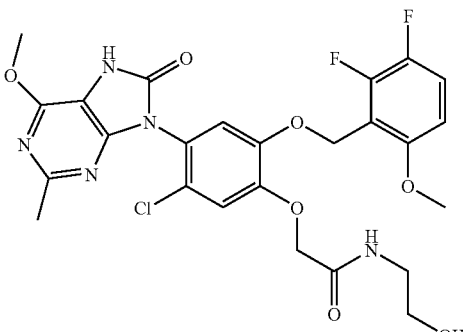 | (DMSO-d6) 2.43(3H, s), 3.1-3.25(2H, m), 3.35-3.45(2H, m), 3.8(3H, s), 4.02 (3H, s), 4.61(2H, s), 4.7(1H, t, J = 5.6 Hz), 5.06(2H, s), 6.85-6.95(1H, m), 7.19(1H, s), 7.4-7.55(2H, m), 7.96 (1H, t, J = 5.7 Hz), 11.6(1H, s) |

TABLE 82
| Ex No. | Strc | (Solv) ¹H-NMR δ ppm: |
|---|---|---|
| 325 | 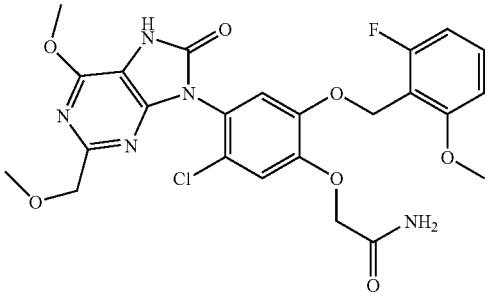 | (DMSO-d6) 3.33(3H, s), 3.82(3H, s), 4.05(3H, s), 4.37(2H, s), 4.58(2H, s), 4.95-5.05(2H, m), 6.85-7.0(2H, m), 7.16 (1H, s), 7.35-7.55(4H, m), 11.77(1H, s) |
| 326 | 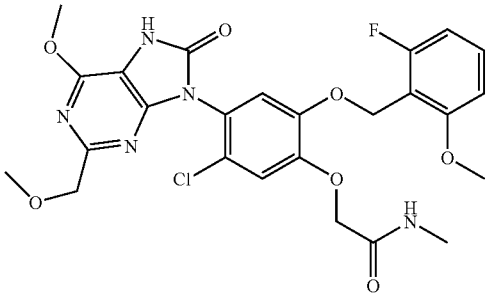 | (DMSO-d6) 2.62(3H, d, J = 4.9 Hz), 3.32 (3H, s), 3.82(3H, s), 4.05(3H, s), 4.36 (2H, s), 4.59(2H, s), 4.95-5.05(2H, m), 6.85-7.0(2H, m), 7.19(1H, s), 7.4-7.55 (2H, m), 7.85-8.0(1H, m), 11.77(1H, s), |
| 327 | 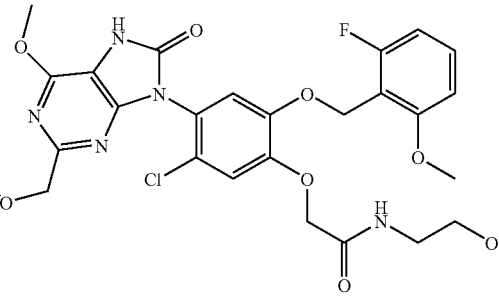 | (DMSO-d6) 3.1-3.2(2H, m), 3.3-3.45 (5H, m), 3.82(3H, s), 4.05(3H, s), 4.37 (2H, s), 4.61(2H, s), 4.71(1H, t, J = 5.5 Hz), 4.95-5.05(2H, m), 6.85-7.0 (2H, m), 7.18(1H, s), 7.4-7.55(2H, m), 7.98(1H, t, J = 5.5 Hz), 11.77(1H, s) |
| 328 | 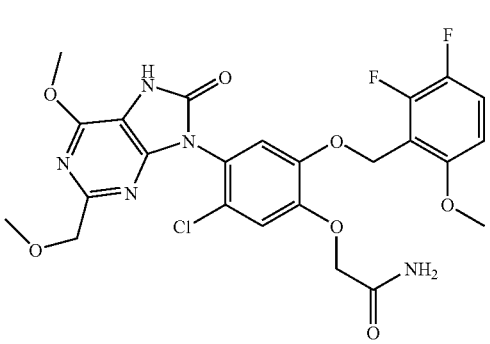 | (DMSO-d6) 3.32(3H, s), 3.8(3H, s), 4.05(3H, s), 4.36(2H, s), 4.58(2H, s), 5.05(2H, s), 6.85-6.95(1H, m), 7.18 (1H, s), 7.3-7.55(4H, m), 11.75(1H, s) |
| 329 | 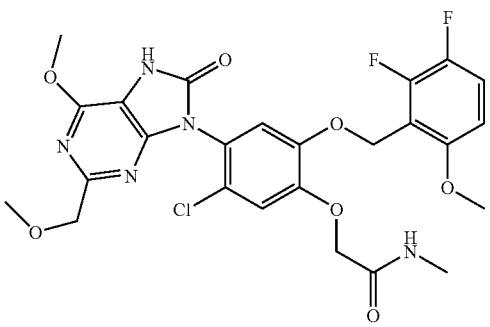 | (DMSO-d6) 2.62(3H, d, J = 4.6 Hz), 3.32 (3H, s), 3.8(3H, s), 4.05(3H, s), 4.36 (2H, s), 4.59(2H, s), 5.0-5.1(2H, m), 6.85-6.95(1H, m), 7.21(1H, s), 7.45-7.55(2H, m), 7.85-7.95(1H, m), 11.75 (1H, s) |

TABLE 82-continued

| Ex No. | Strc | (Solv) ¹H-NMR δ ppm: |
|---|---|---|
| 330 | | (DMSO-d6) 3.1-3.25(2H, m), 3.3-3.45 (5H, m), 3.8(3H, s), 4.05(3H, s), 4.36 (2H, s), 4.61(2H, s), 4.7(1H, t, J = 5.6 Hz), 5.0-5.1(2H, m), 6.85-6.95 (1H, m), 7.2(1H, s), 7.4-7.55(2H, m), 7.95(1H, t, J = 5.5 Hz), 11.75(1H, s) |

TABLE 83

| Ex No. | Strc | (Solv) ¹H-NMR δ ppm: |
|---|---|---|
| 331 | | (DMSO-d6) 3.82(3H, s), 4.06(3H, s), 4.58(2H, s), 4.95-5.1(2H, m), 5.31(2H, d, J = 46.9 Hz), 6.8-7.0(2H, m), 7.16(1H, s), 7.3-7.55(4H, m), 11.87(1H, s) |
| 332 | | (DMSO-d6) 2.62(3H, d, J = 4.6 Hz), 3.81 (3H, s), 4.06(3H, s), 4.58(2H, s), 4.95-5.1(2H, m), 5.31(2H, d, J = 47.0 Hz), 6.85-7.0(2H, m), 7.19(1H, s), 7.4-7.55 (2H, m), 7.85-7.95(1H, m), 11.89(1H, brs) |
| 333 | | (DMSO-d6) 3.1-3.2(2H, m), 3.35-3.45 (2H, m), 3.81(3H, s), 4.06(3H, s), 4.61 (2H, s), 4.7(1H, t, J = 5.5 Hz), 4.95-5.05 (2H, m), 5.32(2H, d, J = 46.6 Hz), 6.8-7.0 (2H, m), 7.19(1H, s), 7.4-7.55(2H, m), 7.9-8.0(1H, m), 11.88(1H, s) |

TABLE 83-continued
| Ex No. | Strc | (Solv) $^1$H-NMR δ ppm: |
|---|---|---|
| 334 | 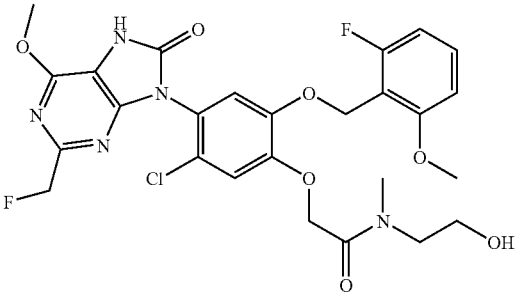 | (DMSO-d6) 2.8-3.05(3H, m), 3.25-3.65 (4H, m), 3.82(3H, s), 4.06(3H, s), 4.55-5.1(5H, m), 5.32(2H, d, J = 47.0 Hz), 6.8-7.0(2H, m), 7.1-7.15(1H, m), 7.4-7.5 (2H, m), 11.86(1H, s) |
| 335 | 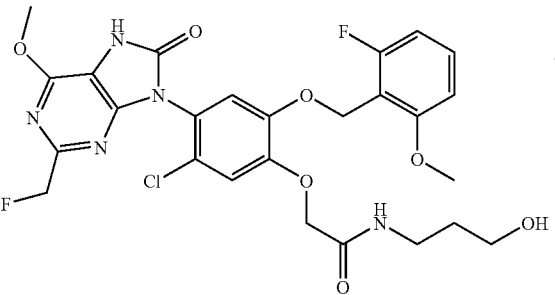 | (DMSO-d6) 1.45-1.6(2H, m), 3.1-3.2 (2H, m), 3.35-3.45(2H, m), 3.82(3H, s), 4.06(3H, s), 4.43(1H, t, J = 5.3 Hz), 4.59 (2H, s), 4.95-5.05(2H, m), 5.32(2H, d, J = 46.7 Hz), 6.85-7.0(2H, m), 7.18(1H, s), 7.4-7.55(2H, m), 7.95(1H, t, J = 5.7 Hz), 11.88(1H, s) |
| 336 | 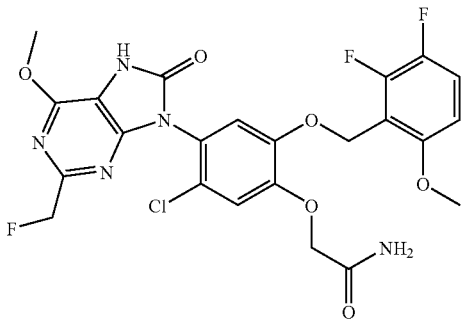 | (DMSO-d6) 3.8(3H, s), 4.06(3H, s), 4.59(2H, s), 5.0-5.1(2H, m), 5.31(2H, d, J = 46.9 Hz), 6.85-6.95(1H, m), 7.18 (1H, s), 7.35-7.55(4H, m), 11.88(1H, s) |
TABLE 84
| Ex No. | Strc | (Solv) $^1$H-NMR δ ppm: |
|---|---|---|
| 337 | 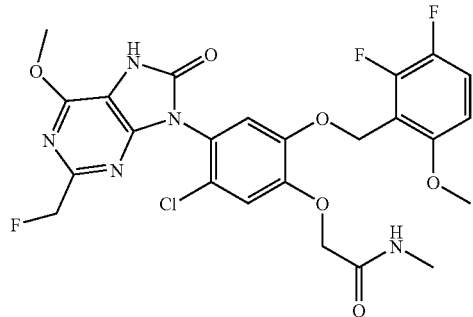 | (DMSO-d6) 2.62 (3H, d, J = 4.6 Hz), 3.8 (3H, s), 4.06 (3H, s), 4.6 (2H, s), 5.0-5.1 (2H, m), 5.31 (2H, d, J = 47.1 Hz), 6.85-6.95 (1H, m), 7.21 (1H, s), 7.45-7.55 (2H, m), 7.85-7.95 (1H, m), 11.88 (1H, s) |

TABLE 84-continued

| Ex No. | Strc | (Solv) ¹H-NMR δ ppm: |
|---|---|---|
| 338 | | (DMSO-d6) 2.84 (3H, s), 2.96 (3H, s), 3.8 (3H, s), 4.06 (3H, s), 4.97 (2H, s), 5.0-5.1 (2H, m), 5.32 (2H, d, J = 47.0 Hz), 6.85-6.95 (1H, m), 7.16 (1H, s), 7.4-7.55 (2H, m), 11.86 (1H, s) |
| 339 | | (DMSO-d6) 1.0 (3H, t, J = 7.3 Hz), 3.05-3.2 (2H, m), 3.8 (3H, s), 4.06 (3H, s), 4.59 (2H, s), 5.0-5.1 (2H, m), 5.31 (2H, d, J = 46.7 Hz), 6.85-6.95 (1H, m), 7.2 (1H, s), 7.45-7.55 (2H, m), 7.93 (1H, t, J = 5.3Hz), 11.88 (1H, s) |
| 340 | | (DMSO-d6) 3.63 (3H, s), 3.8 (3H, s), 3.9 (2H, d, J = 5.9 Hz), 4.06 (3H, s), 4.7 (2H, s), 5.0-5.1 (2H, m), 5.31 (2H, d, J = 46.6 Hz), 6.85-6.95 (1H, m), 7.2 (1H, s), 7.45-7.55 (2H, m), 8.47 (1H, t, J = 5.9 Hz), 11.87 (1H, s) |
| 341 | | (DMSO-d6) 3.1-3.25 (2H, m), 3.35-3.45 (2H, m), 3.8 (3H, s), 4.06 (3H, s), 4.62 (2H, s), 4.7 (1H, t, J = 5.4 Hz), 5.0-5.1 (2H, m), 5.31 (2H, d, J = 46.8 Hz), 6.85-6.95 (1H, m), 7.2 (1H, s), 7.4-7.55 (2H, m), 7.96 (1H, t, J = 5.6 Hz), 11.88 (1H, s) |

TABLE 84-continued
| Ex No. | Strc | (Solv) $^1$H-NMR δ ppm: |
|---|---|---|
| 342 | 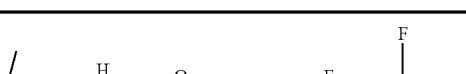 | (DMSO-d6) 2.1 (6H, s), 2.26 (2H, t, J = 6.6 Hz), 3.15-3.25 (2H, m), 3.8 (3H, s), 4.06 (3H, s), 4.61 (2H, s), 5.0-5.1 (2H, m), 5.31 (2H, d, J = 46.8 Hz), 6.85-6.95 (1H, m), 7.21 (1H, s), 7.45-7.55 (2H, m), 7.81 (1H, t, J = 5.5 Hz), 11.89 (1H, brs) |
TABLE 85
| Ex No. | Strc | (Solv) $^1$H-NMR δ ppm: |
|---|---|---|
| 343 | | (DMSO-d6) 3.8 (3H, s), 4.1 (3H, s), 4.6 (2H, s), 5.05 (2H, s), 6.65-6.95 (2H, m), 7.19 (1H, s), 7.35-7.55 (4H, m), 12.11 (1H, s) |
| 344 | | (DMSO-d6) 2.63 (3H, d, J = 4.7 Hz), 3.8 (3H, s), 4.09 (3H, s), 4.6 (2H, s), 5.06 (2H, s), 6.6-6.95 (2H, m), 7.21 (1H, s), 7.4-7.55 (2H, m), 7.85-7.95 (1H, m), 11.5-12.5 (1H, br) |
| 345 | 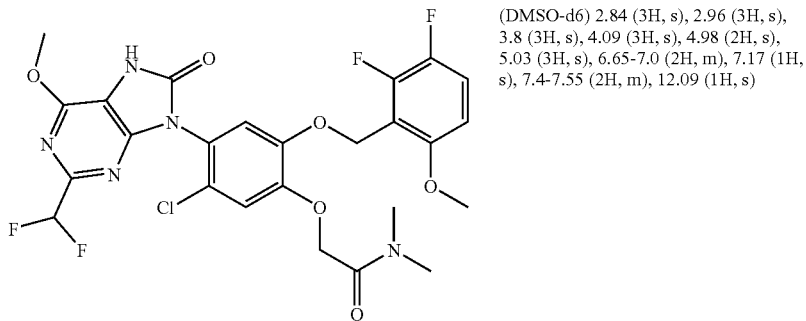 | (DMSO-d6) 2.84 (3H, s), 2.96 (3H, s), 3.8 (3H, s), 4.09 (3H, s), 4.98 (2H, s), 5.03 (3H, s), 6.65-7.0 (2H, m), 7.17 (1H, s), 7.4-7.55 (2H, m), 12.09 (1H, s) |

TABLE 85-continued
| Ex No. | Strc | (Solv) $^1$H-NMR δ ppm: |
|---|---|---|
| 346 | 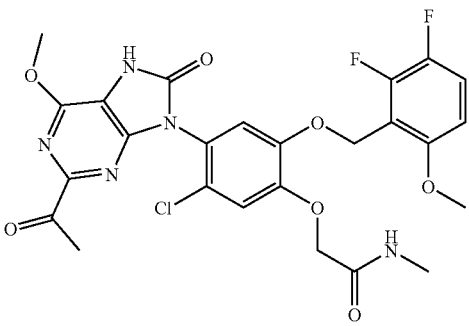 | (DMSO-d6) 2.58 (3H, s), 2.63 (3H, d, J = 4.5 Hz), 3.8 (3H, s), 4.13 (3H, s), 4.6 (2H, s), 5.0-5.1 (2H, m), 6.85-6.95 (1H, m), 7.23 (1H, s), 7.45-7.55 (2H, m), 7.85-8.0 (1H, m), 12.22 (1H, s) |
| 347 | 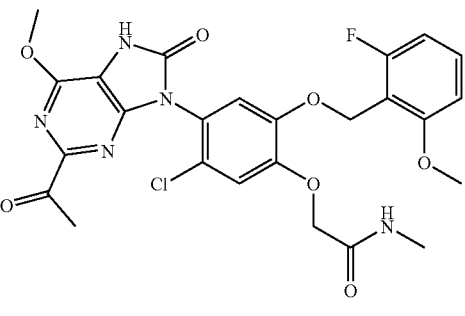 | (DMSO-d6) 2.58 (3H, s), 2.62 (3H, d, J = 4.7 Hz), 3.82 (3H, s), 4.13 (3H, s), 4.59 (2H, s), 4.95-5.05 (2H, m), 6.85-7.0 (2H, m), 7.21 (1H, s), 7.4-7.5 (1H, m), 7.52 (1H, s), 7.85-8.0 (1H, m), 12.22 (1H, s) |
| 348 | 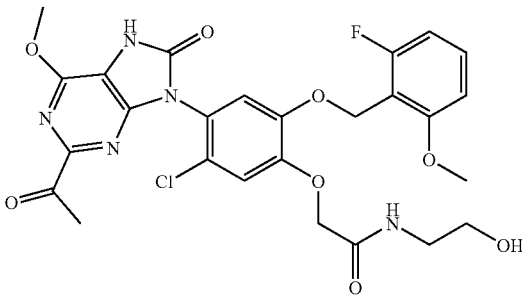 | (DMSO-d6) 2.58 (3H, s), 3.1-3.25 (2H, m), 3.3-3.45 (2H, m), 3.82 (3H, s), 4.13 (3H, s), 4.61 (2H, s), 4.95-5.05 (2H, m), 6.85-7.0 (2H, m), 7.21 (1H, s), 7.4-7.5 (1H, m), 7.52 (1H, s), 7.97 (1H, t, J = 5.5 Hz), 12.22 (1H, s) |
TABLE 86
| Ex No. | Strc | (Solv) $^1$H-NMR δ ppm: |
|---|---|---|
| 349 | 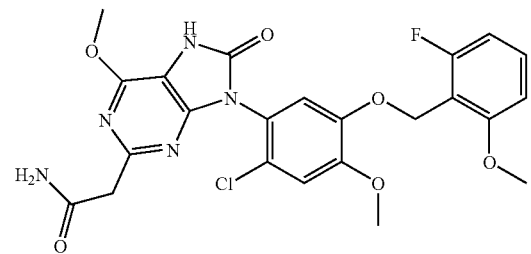 | (DMSO-d6) 3.53 (2H, s), 3.81 (3H, s), 3.82 (3H, s), 4.03 (3H, s), 4.9-5.05 (2H, m), 6.8-7.05 (3H, m), 7.24 (1H, s), 7.33 (1H, s), 7.35-7.5 (2H, m), 11.66 (1H, s) |

TABLE 86-continued
| Ex No. | Strc | (Solv) $^1$H-NMR δ ppm: |
|---|---|---|
| 350 | 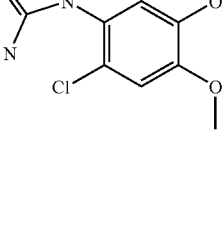 | (DMSO-d6) 2.57 (3H, d, J = 4.6 Hz), 3.54 (2H, s), 3.81 (3H, s), 3.82 (3H, s), 4.02 (3H, s), 4.9-5.05 (2H, m), 6.8-7.0 (2H, m), 7.25 (1H, s), 7.35-7.5 (2H, m), 7.75-7.85 (1H, m), 11.67 (1H, s) |
| 351 | 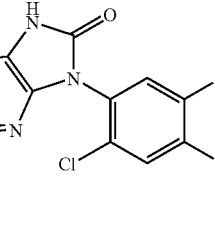 | (DMSO-d6) 2.81 (3H, s), 3.0 (3H, s), 3.79 (2H, s), 3.808 (3H, s), 3.813 (3H, s), 4.0 (3H, s), 4.9-5.05 (2H, m), 6.8-7.0 (2H, m), 7.24 (1H, s), 7.35-7.5 (2H, m), 11.66 (1H, s) |
| 352 | 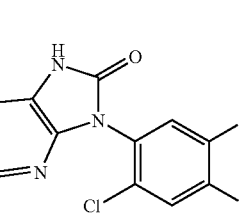 | (DMSO-d6) 3.05-3.2 (2H, m), 3.35-3.45 (2H, m), 3.56 (2H, s), 3.81 (3H, s), 3.82 (3H, s), 4.02 (3H, s), 4.63 (1H, t, J = 5.5 Hz), 4.9-5.05 (2H, m), 6.8-7.0 (2H, m), 7.24 (1H, s), 7.35-7.5 (2H, m), 7.92 (1H, t, J = 5.4 Hz), 11.67 (1H, s) |
| 353 | 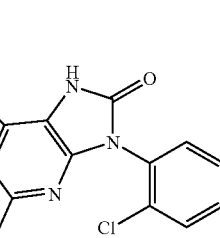 | (DMSO-d6) 3.6 (3H, s), 3.62 (2H, s), 3.81 (3H, s), 3.82 (3H, s), 3.85 (2H, d, J = 5.7 Hz), 4.04 (3H, s), 4.9-5.05 (2H, m), 6.8-7.0 (2H, m), 7.24 (1H, s), 7.35-7.5 (2H, m), 8.34 (1H, t, J = 5.7 Hz), 11.68 (1H, s) |
| 354 | 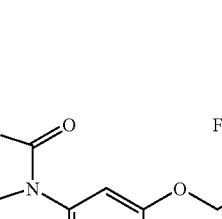 | (DMSO-d6) 3.8 (3H, s), 4.05 (3H, s), 4.57 (2H, s), 5.0-5.1 (2H, m), 6.85-6.95 (1H, m), 7.19 (1H, s), 7.33 (1H, s), 7.42 (1H, s), 7.45-7.55 (2H, m), 8.26 (1H, s), 11.76 (1H, s) |

TABLE 87
| Ex No. | Strc | (Solv) $^1$H-NMR δ ppm: |
|---|---|---|
| 355 | 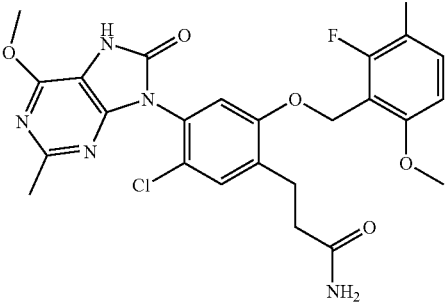 | (DMSO-d6) 2.3-2.4 (2H, m), 2.42 (3H, s), 2.65-2.8 (2H, m), 3.8 (3H, s), 4.02 (3H, s), 5.07 (2H, s), 6.78 (1H, brs), 6.85-6.95 (1H, m), 7.27 (1H, brs), 7.4-7.55 (3H, m), 11.62 (1H, brs) |
| 356 | 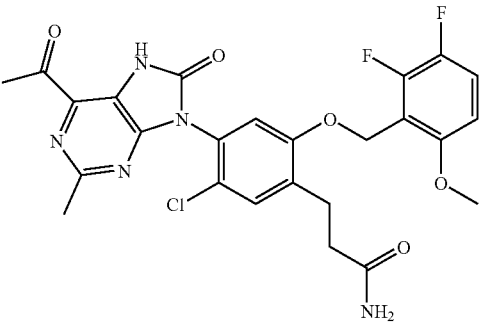 | (DMSO-d6) 2.25-2.4 (2H, m), 2.55 (3H, s), 2.6-2.8 (5H, m), 3.8 (3H, s), 5.07 (2H, s), 6.79 (1H, brs), 6.85-7.0 (1H, m), 7.28 (1H, brs), 7.4-7.55 (3H, m), 12.04 (1H, s) |
| 357 | 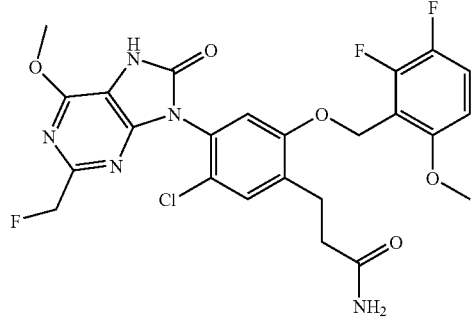 | (DMSO-d6) 2.3-2.4 (2H, m), 2.7-2.8 (2H, m), 3.8 (3H, s), 4.07 (3H, s), 5.07 (2H, s), 5.31 (2H, d, J = 46.8 Hz), 6.79 (1H, s), 6.85-6.95 (1H, m), 7.28 (1H, s), 7.4-7.55 (3H, m), 11.91 (1H, s) |
| 358 | 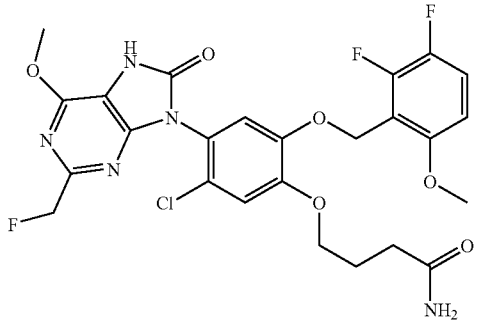 | (DMSO-d6) 1.85-1.95 (2H, m), 2.18 (2H, t, J = 7.4 Hz), 3.78 (3H, s), 4.0-4.1 (5H, m), 5.04 (2H, s), 5.3 (2H, d, J = 46.9 Hz), 6.78 (1H, s), 6.85-6.95 (1H, m), 7.25-7.35 (2H, m), 7.35-7.55 (2H, m), 11.86 (1H, s) |

TABLE 87-continued

| Ex No. | Strc | (Solv) ¹H-NMR δ ppm: |
|---|---|---|
| 359 | | (DMSO-d6) 1.85-1.95 (2H, m), 2.19 (2H, t, J = 7.5 Hz), 2.56 (3H, d, J = 4.6 Hz), 3.77 (3H, s), 4.0-4.1 (5H, m), 5.04 (2H, s), 5.3 (2H, d, J = 46.9 Hz), 6.85-6.95 (1H, m), 7.31 (1H, s), 7.35-7.55 (2H, m), 7.7-7.8 (1H, m), 11.86 (1H, s) |
| 360 | | (DMSO-d6) 1.85-2.0 (2H, m), 2.21 (2H, t, J = 7.4 Hz), 3.05-3.15 (2H, m), 3.3-3.45 (2H, m), 3.78 (3H, s), 4.0-4.1 (5H, m), 4.63 (1H, t, J = 5.6 Hz), 5.04 (2H, s), 5.3 (2H, d, J = 46.8 Hz), 6.85-6.95 (1H, m), 7.31 (1H, s), 7.35-7.55 (2H, m), 7.8-7.9 (1H, m), 11.85 (1H, s) |

TABLE 88

| Ex No. | Strc | (Solv) ¹H-NMR δ ppm: |
|---|---|---|
| 361 | | (DMSO-d6) 3.8 (3H, s), 3.84 (3H, s), 4.95-5.05 (2H, m), 6.85-6.95 (1H, m), 7.3 (1H, s), 7.45-7.55 (2H, m), 7.94 (1H, s), 8.26 (1H, s), 8.57 (1H, s), 11.84 (1H, s) |
| 362 | | (DMSO-d6) 1.4-1.65 (2H, m), 1.7-1.85 (2H, m), 2.43 (3H, s), 2.45-2.65 (2H, m), 2.7 (3H, d, J = 5.0 Hz), 3.35-3.9 (2H, m), 7.1-7.3 (4H, m), 7.65-7.75 (1H, m), 7.85-7.95 (2H, m), 7.97 (1H, d, J = 8.5 Hz), 8.15 (1H, d, J = 2.2 Hz), 11.88 (1H, s) |
| 363 | | (DMSO-d6) 1.4-1.65 (2H, m), 1.7-1.85 (2H, m), 2.35-2.65 (5H, m), 2.86 (3H, s), 2.9 (3H, s), 3.35-3.8 (2H, m), 7.1-7.25 (5H, m), 7.82 (1H, dd, J = 8.6 Hz, 2.2 Hz), 7.95 (1H, d, J = 8.6 Hz), 8.15 (1H, d, J = 2.2 Hz), 11.8 (1H, s) |

TABLE 88-continued
| Ex No. | Strc | (Solv) ¹H-NMR δ ppm: |
|---|---|---|
| 364 | 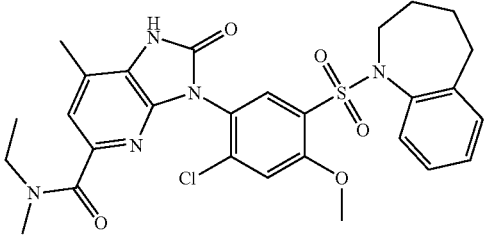 | (DMSO-d6) 0.9 (3H, t, J = 7.1 Hz), 1.5-1.7 (2H, m), 1.75-1.9 (2H, m), 2.37 (3H, s), 2.4-2.7 (2H, m), 2.7-2.95 (5H, m), 3.4-3.85 (2H, m), 4.01 (3H, s), 6.65-6.8 (1H, m), 6.95-7.1 (1H, m), 7.15-7.35 (3H, m), 7.72 (1H, s), 7.89 (1H, s), 11.7 (1H, s) |
| 365 | 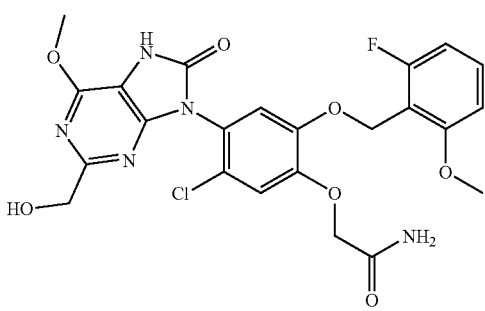 | (DMSO-d6) 3.82 (3H, s), 4.06 (3H, s), 4.4 (2H, d, J = 6.4 Hz), 4.58 (2H, s), 4.95-5.05 (2H, m), 5.2 (1H, t, J = 6.4 Hz), 6.85-7.0 (2H, m), 7.15 (1H, s), 7.3-7.5 (4H, m), 11.69 (1H, s) |
| 366 | 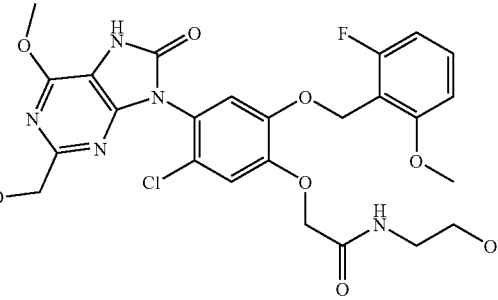 | (DMSO-d6) 3.1-3.2 (2H, m), 3.35-3.45 (2H, m), 3.82 (3H, s), 4.06 (3H, s), 4.4 (2H, d, J = 6.4 Hz), 4.61 (2H, s), 4.7 (1H, t, J = 5.4 Hz), 4.95-5.05 (2H, m), 5.2 (1H, t, J = 6.4 Hz), 6.85-7.0 (2H, m), 7.18 (1H, s), 7.4-7.5 (2H, m), 7.97 (1H, t, J = 5.6 Hz), 11.69 (1H, s) |
TABLE 89
| Ex No. | Strc | (Solv) ¹H-NMR δ ppm: |
|---|---|---|
| 367 | 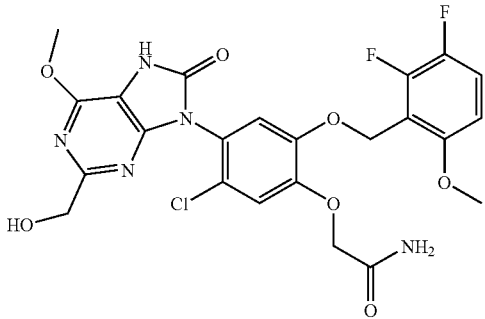 | (DMSO-d6) 3.8 (3H, s), 4.06 (3H, s), 4.4 (2H, d, J = 6.5 Hz), 4.59 (2H, s), 5.05 (2H, s), 5.2 (1H, t, J = 6.5 Hz), 6.85-6.95 (1H, m), 7.16 (1H, s), 7.3-7.55 (4H, m), 11.69 (1H, s) |

TABLE 89-continued
| Ex No. | Strc | (Solv) ¹H-NMR δ ppm: |
|---|---|---|
| 368 | 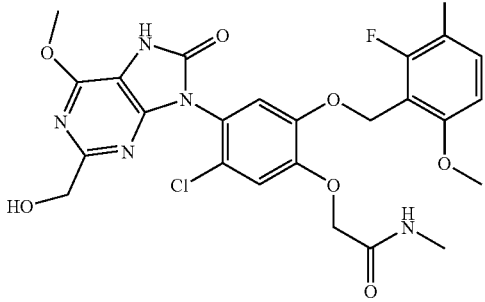 | (DMSO-d6) 2.62 (3H, d, J = 4.9 Hz), 3.8 (3H, s), 4.06 (3H, s), 4.4 (2H, d, J = 6.3 Hz), 4.6 (2H, s), 5.06 (2H, s), 5.19 (1H, t, J = 6.3 Hz), 6.85-6.95 (1H, m), 7.19 (1H, s), 7.4-7.55 (2H, m), 7.85-8.0 (1H, m), 11.69 (1H, s) |
| 369 | 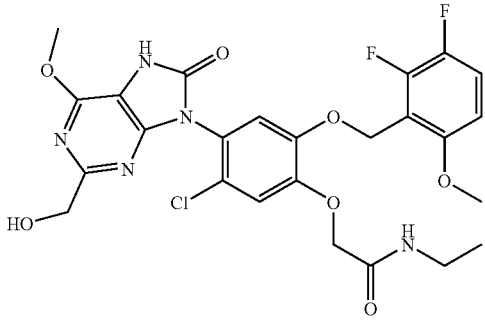 | (DMSO-d6) 1.0 (3H, t, J = 7.4 Hz), 3.05-3.2 (2H, m), 3.8 (3H, s), 4.05 (3H, s), 4.4 (2H, d, J = 6.3 Hz), 4.59 (2H, s), 5.06 (2H, s), 5.19 (1H, t, J = 6.3 Hz), 6.85-7.0 (1H, m), 7.19 (1H, s), 7.4-7.55 (2H, m), 7.9-8.0 (1H, m), 11.69 (1H, s) |
| 370 | 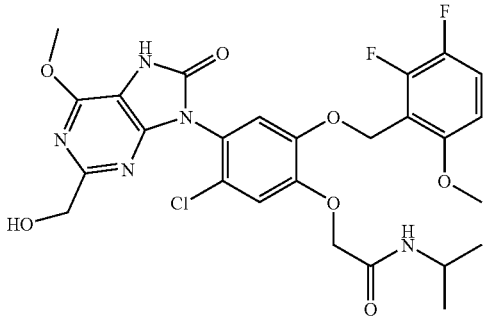 | (DMSO-d6) 1.04 (6H, d, J = 6.6 Hz), 3.75-3.95 (4H, m), 4.05 (3H, s), 4.4 (2H, d, J = 6.4 Hz), 4.57 (2H, s), 5.05 (2H, s), 5.19 (1H, t, J = 6.4 Hz), 6.85-6.95 (1H, m), 7.17 (1H, s), 7.4-7.55 (2H, m), 7.74 (1H, d, J = 7.5 Hz), 11.69 (1H, s) |
| 371 | 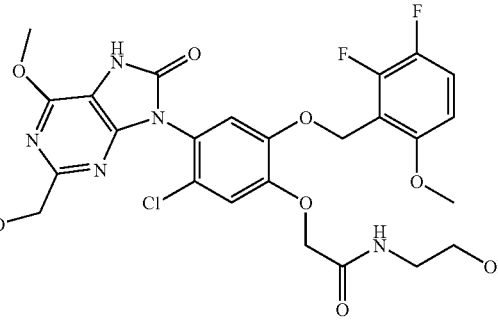 | (DMSO-d6) 3.1-3.2 (2H, m), 3.3-3.45 (2H, m), 3.8 (3H, s), 4.06 (3H, s), 4.4 (2H, d, J = 6.4 Hz), 4.62 (2H, s), 4.7 (1H, t, J = 5.5 Hz), 5.0-5.1 (2H, m), 5.2 (1H, t, J = 6.4 Hz), 6.85-6.95 (1H, m), 7.19 (1H, s), 7.4-7.55 (2H, m), 7.97 (1H, t, J = 5.6 Hz), 11.69 (1H, s) |

TABLE 89-continued
| Ex No. | Strc | (Solv) $^1$H-NMR δ ppm: |
|---|---|---|
| 372 | 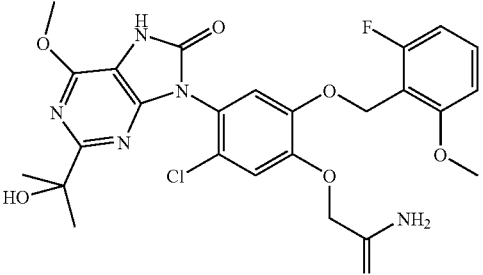 | (DMSO-d6) 1.416 (3H, s), 1.424 (3H, s), 3.82 (3H, s), 4.07 (3H, s), 4.58 (2H, s), 4.82 (1H, s), 4.95-5.1 (2H, m), 6.85-7.0 (2H, m), 7.15 (1H, s), 7.35-7.5 (4H, m), 11.7 (1H, s) |
TABLE 90
| Ex No. | Strc | (Solv) $^1$H-NMR δ ppm: |
|---|---|---|
| 373 | 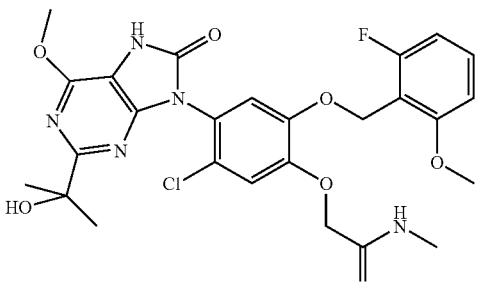 | (DMSO-d6) 1.42 (3H, s), 1.43 (3H, s), 2.62 (3H, d, J = 4.9 Hz), 3.82 (3H, s), 4.07 (3H, s), 4.59 (2H, s), 4.82 (1H, s), 4.95-5.1 (2H, m), 6.85-7.0 (2H, m), 7.18 (1H, s), 7.4-7.55 (2H, m), 7.85-8.0 (1H, m), 11.7 (1H, s) |
| 374 | 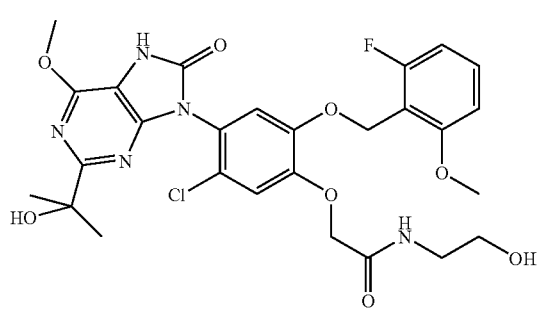 | (DMSO-d6) 1.417 (3H, s), 1.424 (3H, s), 3.1-3.2 (2H, m), 3.3-3.45 (2H, m), 3.81 (3H, s), 4.07 (3H, s), 4.61 (2H, s), 4.72 (1H, t, J = 5.3 Hz), 4.82 (1H, s), 4.95-5.1 (2H, m), 6.85-7.0 (2H, m), 7.18 (1H, s), 7.4-7.5 (2H, m), 7.98 (1H, t, J = 5.8 Hz), 11.7 (1H, s) |
| 375 | 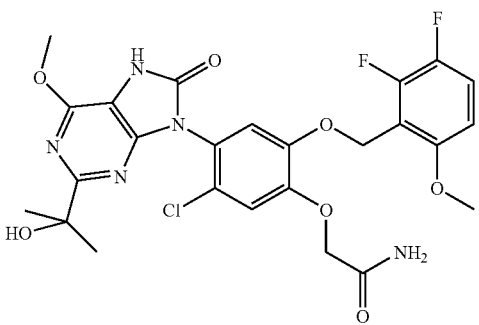 | (DMSO-d6) 1.42 (3H, s), 1.43 (3H, s), 3.8 (3H, s), 4.08 (3H, s), 4.59 (2H, s), 4.82 (1H, s), 5.0-5.1 (2H, m), 6.85-6.95 (1H, m), 7.17 (1H, s), 7.35-7.55 (4H, m), 11.7 (1H, s) |

TABLE 90-continued

| Ex No. | Strc | (Solv) $^1$H-NMR δ ppm: |
|---|---|---|
| 376 | | (DMSO-d6) 1.42 (3H, s), 1.43 (3H, s), 2.63 (3H, d, J = 4.6 Hz), 3.8 (3H, s), 4.08 (3H, s), 4.6 (2H, s), 4.81 (1H, s), 5.0-5.15 (2H, m), 6.85-6.95 (1H, m), 7.2 (1H, s), 7.4-7.55 (2H, m), 7.85-8.0 (1H, m), 11.7 (1H, s) |
| 377 | | (DMSO-d6) 1.416 (3H, s), 1.424 (3H, s), 3.1-3.25 (2H, m), 3.35-3.45 (2H, m), 3.8 (3H, s), 4.08 (3H, s), 4.62 (2H, s), 4.71 (1H, t, J = 5.4 Hz), 4.81 (1H, s), 5.0-5.1 (2H, m), 6.85-6.95 (1H, m), 7.2 (1H, s), 7.4-7.55 (2H, m), 7.98 (1H, t, J = 5.6 Hz), 11.7 (1H, s) |
| 378 | | (DMSO-d6) 3.75-3.85 (5H, m), 4.06 (3H, s), 4.68 (2H, s), 5.06 (2H, s), 5.31 (2H, d, J = 47.1 Hz), 6.85-6.95 (1H, m), 7.23 (1H, s), 7.4-7.55 (2H, m), 8.25-8.4 (1H, m), 11.88 (1H, s), 12.67 (1H, brs) |

TABLE 91

| Ex No. | Strc | (Solv) $^1$H-NMR δ ppm: |
|---|---|---|
| 379 | | (DMSO-d6) 3.63 (2H, s), 3.76 (2H, d, J = 5.7 Hz), 3.81 (3H, s), 3.82 (3H, s), 4.04 (3H, s), 4.9-5.05 (2H, m), 6.8-7.0 (2H, m), 7.24 (1H, s), 7.35-7.5 (2H, m), 8.22 (1H, t, J = 5.7Hz), 11.68 (1H, s), 12.54 (1H, brs) |

TABLE 91-continued
| Ex No. | Strc | (Solv) $^1$H-NMR δ ppm: |
|---|---|---|
| 380 | 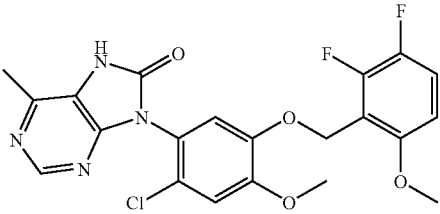 | (CDCl3) 2.58 (3H, s), 3,78 (3H, s), 3.89 (3H, s), 5.1-5.2 (2H, m), 6.55-6.65 (1H, m), 7.05-7.15 (3H, m), 8.61 (1H, s), 9.6 (1H, brs) |
| 381 | 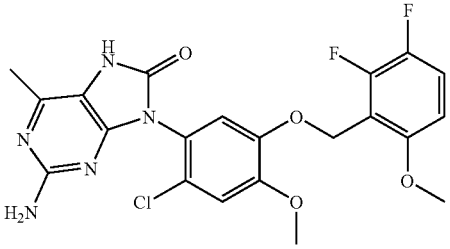 | (DMSO-d6) 2.27 (3H, s), 3.8 (3H, s), 3.81 (3H, s), 5.0 (2H, s), 6.17 (2H, s), 6.85-6.95 (1H, m), 7.23 (1H, s), 7.39 (1H, s), 7.45-7.55 (1H, m), 11.02 (1H, s) |
| 382 | 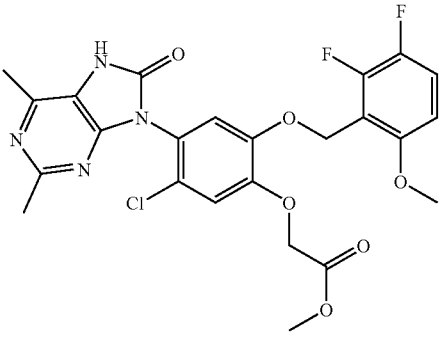 | (DMSO-d6) 2.44 (3H, s), 2.45 (3H, s), 3.7 (3H, s), 3.8 (3H, s), 4.95 (2H, s), 5.05 (2H, s), 6.85-6.95 (1H, m), 7.25 (1H, s), 7.4-7.55 (2H, m), 11.61 (1H, s) |
| 383 | 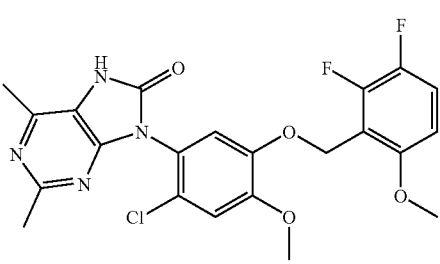 | (DMSO-d6) 2.43 (3H, s), 2.45 (3H, s), 3.8 (3H, s), 3.83 (3H, s), 5.01 (2H, s), 6.85-6.95 (1H, m), 7.27 (1H, s), 7.41 (1H, s), 7.45-7.55 (1H, m), 11.59 (1H, s) |
| 384 | 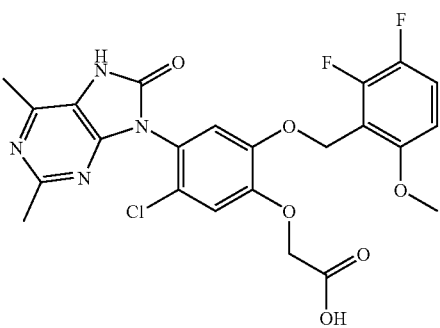 | (DMSO-d6) 2.44 (3H, s), 2.45 (3H, s), 3.8 (3H, s), 4.84 (2H, s), 5.04 (2H, s), 6.85-6.95 (1H, m), 7.17 (1H, s), 7.4-7.55 (2H, m), 11.61 (1H, s), 12.5-14.0 (1H, br) |

TABLE 92

| Ex No. | Strc | (Solv) ¹H-NMR δ ppm: |
|---|---|---|
| 385 | | (DMSO-d6) 3.79 (3H, s), 3.84 (3H, s), 4.11 (3H, s), 5.01 (2H, s), 6.85-6.95 (1H, m), 7.31 (1H, s), 7.4-7.55 (2H, m), 12.29 (1H, s) |
| 386 | | (DMSO-d6) 2.41 (3H, s), 3.87 (3H, s), 4.01 (3H, s), 5.05 (2H, s), 7.27 (1H, s), 7.3-7.5 (6H, m), 11.57 (1H, s) |
| 387 | | (DMSO-d6) 2.42 (3H, s), 3.78 (3H, s), 3.85 (3H, s), 4.01 (3H, s), 4.99 (2H, s), 6.95-7.1 (2H, m), 7.25 (1H, s), 7.3-7.4 (2H, m), 7.4-7.5 (1H, m), 11.54 (1H, s) |
| 388 | | (DMSO-d6) 2.41 (3H, s), 3.75 (3H, s), 3.87 (3H, s), 4.01 (3H, s), 5.03 (2H, s), 6.85-6.95 (1H, m), 6.95-7.05 (2H, m), 7.25-7.35 (3H, m), 11.56 (1H, s) |
| 389 | | (DMSO-d6) 2.41 (3H, s), 3.76 (3H, s), 3.85 (3H, s), 4.01 (3H, s), 4.96 (2H, s), 6.9-7.0 (2H, m), 7.25 (1H, s), 7.3-7.4 (3H, m), 11.55 (1H, s) |
| 390 | | (DMSO-d6) 2.42 (3H, s), 3.86 (3H, s), 4.02 (3H, s), 5.08 (2H, s), 7.2-7.3 (3H, m), 7.4-7.5 (2H, m), 7.55-7.65 (1H, m), 11.57 (1H, s) |

TABLE 93

| Ex No. | Strc | (Solv) $^1$H-NMR δ ppm: |
|---|---|---|
| 391 | | (DMSO-d6) 2.4 (3H, s), 3.88 (3H, s), 4.01 (3H, s), 5.09 (2H, s), 7.1-7.25 (1H, m), 7.25-7.35 (4H, m), 7.4-7.5 (1H, m), 11.56 (1H, s) |
| 392 | | (DMSO-d6) 2.41 (3H, s), 3.86 (3H, s), 4.01 (3H, s), 5.04 (2H, s), 7.15-7.25 (2H, m), 7.27 (1H, s), 7.34 (1H, s), 7.45-7.55 (2H, m), 11.56 (1H, s) |
| 393 | | (DMSO-d6) 2.31 (3H, s), 2.42 (3H, s), 3.86 (3H, s), 4.02 (3H, s), 5.03 (2H, s), 7.15-7.3 (4H, m), 7.35-7.45 (2H, m), 11.57 (1H, s) |
| 394 | | (DMSO-d6) 2.31 (3H, s), 2.41 (3H, s), 3.86 (3H, s), 4.01 (3H, s), 5.0 (2H, s), 7.1-7.3 (5H, m), 7.34 (1H, s), 11.56 (1H, s) |
| 395 | | (DMSO-d6) 2.31 (3H, s), 2.41 (3H, s), 3.86 (3H, s), 4.01 (3H, s), 4.99 (2H, s), 7.15-7.25 (2H, m), 7.26 (1H, s), 7.3-7.35 (3H, m), 11.55 (1H, s) |
| 396 | | (DMSO-d6) 3.8 (3H, s), 3.82 (3H, s), 3.99 (3H, s), 4.65-4.8 (2H, m), 4.95-5.05 (2H, m), 6.85-6.95 (1H, m), 7.26 (1H, s), 7.35-7.55 (2H, m), 11.5 (1H, s), 12.91 (1H, brs) |

TABLE 94

| Ex No. | Strc | (Solv) ¹H-NMR δ ppm: |
|---|---|---|
| 397 | | (DMSO-d6) 3.8 (3H, s), 3.804 (3H, s), 3.92 (3H, s), 4.95-5.05 (2H, m), 6.31 (2H, s), 6.85-6.95 (1H, m), 7.21 (1H, s), 7.36 (1H, s), 7.4-7.55 (1H, m), 10.94 (1H, s) |
| 398 | | (DMSO-d6) 3.8 (3H, s), 3.82 (3H, s), 3.92 (3H, s), 4.9-5.05 (2H, m), 6.32 (2H, brs), 6.8-7.0 (2H, m), 7.2 (1H, s), 7.37 (1H, s), 7.4-7.5 (1H, m), 10.94 (1H, s) |
| 399 | | (DMSO-d6) 3.8-3.85 (6H, m), 4.05 (3H, s), 4.97 (2H, s), 6.8-7.0 (2H, m), 7.27 (1H, s), 7.4-7.5 (2H, m), 11.99 (1H, s) |
| 400 | | (DMSO-d6) 2.11 (3H, s), 3.8 (3H, s), 3.82 (3H, s), 4.02 (3H, s), 4.95-5.05 (2H, m), 6.85-6.95 (1H, m), 7.25 (1H, s), 7.4-7.55 (2H, m), 10.28 (1H, s), 11.53 (1H, s) |
| 401 | | (DMSO-d6) 2.99 (6H, s), 3.79 (3H, s), 3.82 (3H, s), 3.97 (3H, s), 5.02 (2H, s), 6.85-7.0 (1H, m), 7.23 (1H, s), 7.32 (1H, s), 7.4-7.55 (1H, m), 10.99 (1H, s) |
| 402 | | (DMSO-d6) 3.8 (3H, s), 3.82 (3H, s), 4.04 (3H, s), 4.13 (2H, d, J = 6.0 Hz), 4.95-5.05 (2H, m), 5.14 (1H, t, J = 6.0 Hz), 6.85-6.95 (1H, m), 7.26 (1H, s), 7.4-7.55 (2H, m), 10.02 (1H, s), 11.58 (1H, brs) |

TABLE 95
| Ex No. | Strc | (Solv) ¹H-NMR δ ppm: |
|---|---|---|
| 403 | 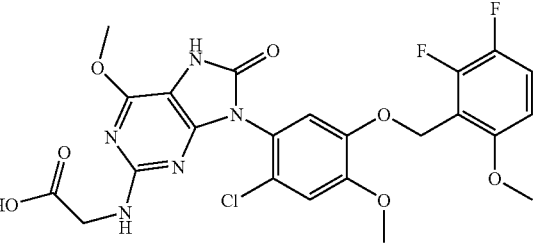 | (DMSO-d6) 3.75-3.85 (8H, m), 3.92 (3H, s), 4.95-5.05 (2H, m), 6.85-6.95 (1H, m), 7.22 (1H, s), 7.36 (1H, s), 7.4-7.55 (1H, m), 11.01 (1H, s), 12.33 (1H, brs) |
| 404 | 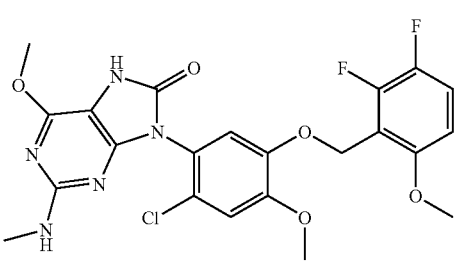 | (DMSO-d6) 2.7 (3H, d, J = 4.5 Hz), 3.8 (3H, s), 3.81 (3H, s), 3.96 (3H, s), 4.95-5.05 (2H, m), 6.75-6.95 (2H, m), 7.22 (1H, s), 7.35 (1H, s), 7.45-7.55 (1H, m), 10.94 (1H, s) |
| 405 | 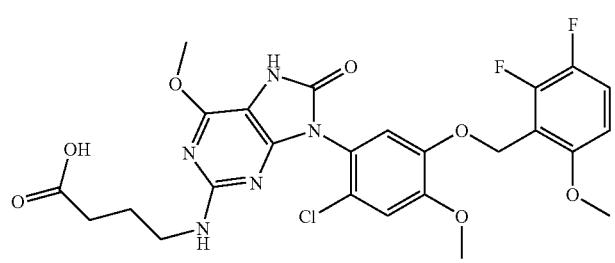 | (DMSO-d6) 1.65-1.8 (2H, m), 2.22 (2H, t, J = 7.4 Hz), 3.1-3.3 (2H, m), 3.8 (3H, s), 3.81 (3H, s), 3.95 (3H, s), 4.95-5.05 (2H, m), 6.85-7.05 (2H, m), 7.21 (1H, s), 7.36 (1H, s), 7.4-7.55 (1H, m), 10.94 (1H, s), 11.98 (1H, brs) |
| 406 | 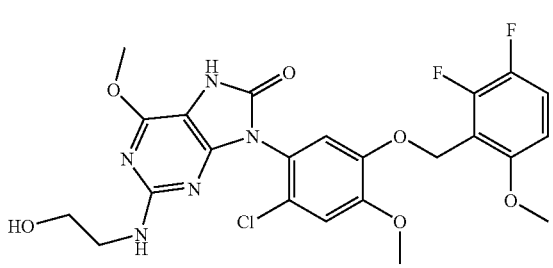 | (DMSO-d6) 3.15-3.3 (2H, m), 3.4-3.55 (2H, m), 3.8 (3H, s), 3.81 (3H, s), 3.95 (3H, s), 4.54 (1H, t, J = 5.7 Hz), 4.95-5.05 (2H, m), 6.76 (1H, brs), 6.85-6.95 (1H, m), 7.22 (1H, s), 7.35 (1H, s), 7.4-7.55 (1H, m), 10.95 (1H, s) |
| 407 | 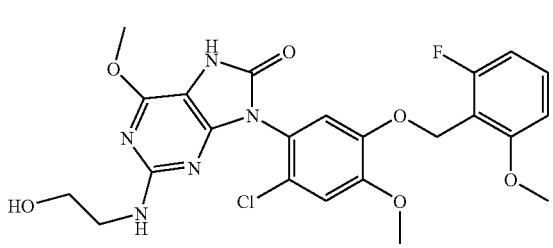 | (DMSO-d6) 3.15-3.3 (2H, m), 3.4-3.55 (2H, m), 3.8 (3H, s), 3.81 (3H, s), 3.95 (3H, s), 4.54 (1H, t, J = 5.7 Hz), 4.9-5.05 (2H, m), 6.65-7.0 (3H, m), 7.2 (1H, s), 7.35 (1H, s), 7.4-7.5 (1H, m), 10.95 (1H, s) |
| 408 | 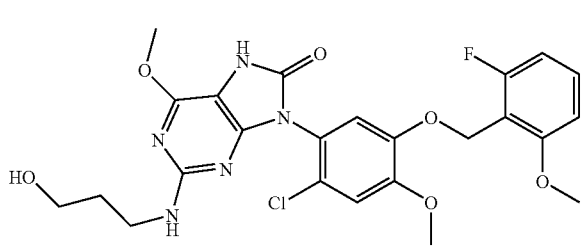 | (DMSO-d6) 1.55-1.7 (2H, m), 3.1-3.3 (2H, m), 3.35-3.5 (2H, m), 3.8 (3H, s), 3.81 (3H, s), 3.95 (3H, s), 4.36 (1H, t, J = 5.1 Hz), 4.9-5.05 (2H, m), 6.75-7.0 (3H, m), 7.2 (1H, s), 7.35 (1H, s), 7.4-7.5 (1H, m), 10.92 (1H, s) |

TABLE 96
| Ex No. | Strc | (Solv) $^1$H-NMR δ ppm: |
|---|---|---|
| 409 | 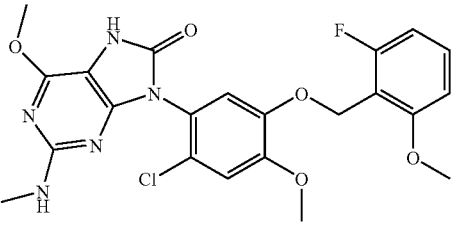 | (DMSO-d6) 2.71 (3H, d, J = 4.7 Hz), 3.8 (3H, s), 3.81 (3H, s), 3.96 (3H, s), 4.9-5.05 (2H, m), 6.75-7.0 (3H, m), 7.2 (1H, s), 7.35 (1H, s), 7.4-7.5 (1H, m), 10.94 (1H, s) |
| 410 | 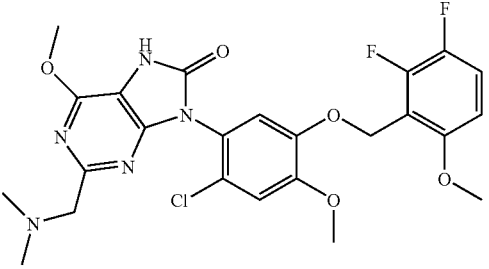 | (DMSO-d6) 2.29 (6H, brs), 3.58 (2H, brs), 3.79 (3H, s), 3.83 (3H, s), 4.05 (3H, s), 4.95-5.05 (2H, m), 6.85-6.95 (1H, m), 7.27 (1H, s), 7.4-7.55 (2H, m), 11.69 (1H, s) |
| 411 | 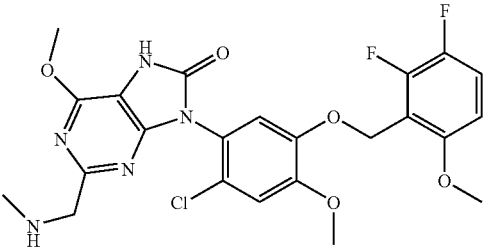 | (DMSO-d6) 2.33 (3H, s), 3.67 (2H, s), 3.79 (3H, s), 3.83 (3H, s), 4.06 (3H, s), 4.95-5.05 (2H, m), 6.85-6.95 (1H, m), 7.26 (1H, s), 7.35-7.55 (2H, m) |
| 412 | 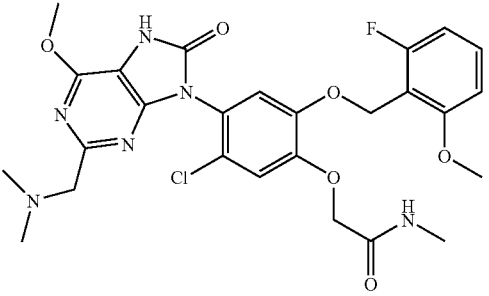 | (DMSO-d6) 2.21 (6H, s), 2.62 (3H, d, J = 4.7 Hz), 3.45 (2H, s), 3.82 (3H, s), 4.03 (3H, s), 4.58 (2H, s), 4.95-5.1 (2H, m), 6.85-7.0 (2H, m), 7.2 (1H, s), 7.4-7.5 (2H, m), 7.85-7.9 (1H, m), 11.7 (1H, brs) |
| 413 | 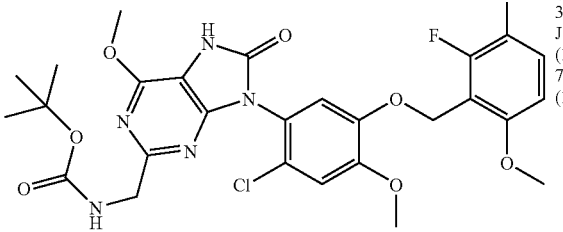 | (DMSO-d6) 1.34 (9H, s), 3.79 (3H, s), 3.82 (3H, s), 4.04 (3H, s), 4.09 (2H, d, J = 6.3 Hz), 4.95-5.05 (2H, m), 6.85-6.95 (1H, m), 7.05-7.15 (1H, m), 7.25 (1H, s), 7.38 (1H, s), 7.4-7.55 (1H, m), 11.63 (1H, s) |

TABLE 96-continued
| Ex No. | Strc | (Solv) ¹H-NMR δ ppm: |
|---|---|---|
| 414 | 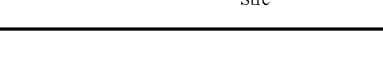 | (DMSO-d6) 3.8 (3H, s), 3.83 (3H, s), 4.12 (5H, s), 4.9-5.1 (2H, m), 6.9-7.0 (1H, m), 7.28 (1H, s), 7.4-7.55 (2H, m), 8.24 (3H, brs), 11.88 (1H, brs) |
TABLE 97
| Ex No. | Strc | (Solv) ¹H-NMR δ ppm: |
|---|---|---|
| 415 | 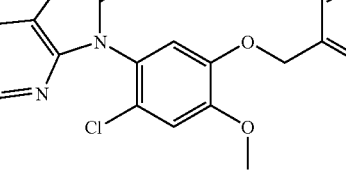 | (DMSO-d6) 3.81 (3H, s), 3.82 (3H, s), 4.06 (3H, s), 4.4 (2H, d, J = 6.2 Hz), 4.9-5.05 (2H, m), 5.13 (1H, t, J = 6.2 Hz), 6.8-7.0 (2H, m), 7.25 (1H, s), 7.35-7.5 (2H, m), 11.66 (1H, s) |
| 416 | 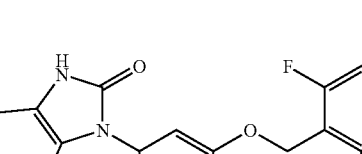 | (DMSO-d6) 3.69 (2H, s), 3.81 (3H, s), 3.82 (3H, s), 4.06 (3H, s), 4.9-5.05 (2H, m), 6.8-7.0 (2H, m), 7.25 (1H, s), 7.35-7.5 (2H, m) |
| 417 | 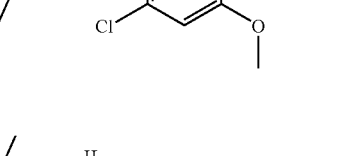 | (DMSO-d6) 1.85 (3H, s), 3.81 (3H, s), 3.82 (3H, s), 4.04 (3H, s), 4.23 (2H, d, J = 5.8 Hz), 4.9-5.05 (2H, m), 6.8-7.0 (2H, m), 7.24 (1H, s), 7.35-7.5 (2H, m), 8.25 (1H, t, J = 5.8 Hz), 11.66 (1H, s) |
| 418 | 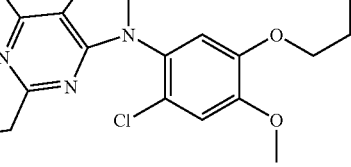 | (DMSO-d6) 2.36 (3H, s), 2.83 (3H, s), 2.95 (3H, s), 3.81 (3H, s), 4.38 (2H, d, J = 5.9 Hz), 4.95 (2H, s), 5.0 (2H, s), 5.26 (1H, t, J = 5.9 Hz), 6.8-7.05 (3H, m), 7.11 (1H, s), 7.36 (1H, s), 7.4-7.5 (1H, m), 11.36 (1H, s) |

TABLE 97-continued

| Ex No. | Strc | (Solv) $^1$H-NMR δ ppm: |
|---|---|---|
| 419 | | (DMSO-d6) 2.36 (3H, s), 3.81 (3H, s), 4.38 (2H, d, J = 6.0 Hz), 4.81 (2H, s), 4.95-5.05 (2H, m), 5.26 (1H, t, J = 6.0 Hz), 6.85-7.05 (3H, m), 7.12 (1H, s), 7.35-7.5 (2H, m), 11.37 (1H, s), 13.12 (1H, brs) |
| 420 | | (DMSO-d6) 1.2 (3H, t, J = 7.6 Hz), 2.69 (2H, q, J = 7.6 Hz), 3.79 (3H, s), 3.83 (3H, s), 4.03 (3H, s), 4.95-5.1 (2H, m), 6.85-7.0 (1H, m), 7.26 (1H, s), 7.39 (1H, s), 7.4-7.55 (1H, m), 11.56 (1H, s) |

TABLE 98

| Ex No. | Strc | (Solv) $^1$H-NMR δ ppm: |
|---|---|---|
| 421 | | (DMSO-d6) 1.2 (3H, t, J = 7.5 Hz), 2.7 (2H, q, J = 7.5 Hz), 3.69 (3H, s), 3.82 (3H, s), 4.04 (3H, s), 4.93 (2H, s), 4.95-5.05 (2H, m), 6.8-7.0 (2H, m), 7.22 (1H, s), 7.4-7.5 (2H, m), 11.58 (1H, s) |
| 422 | | (DMSO-d6) 1.15-1.25 (6H, m), 2.69 (2H, q, J = 7.6 Hz), 3.8 (3H, s), 4.03 (3H, s), 4.16 (2H, q, J = 7.1 Hz), 4.92 (2H, s), 5.05 (2H, s), 6.85-6.95 (1H, m), 7.22 (1H, s), 7.4-7.55 (2H, m), 11.58 (1H, s) |

TABLE 98-continued

| Ex No. | Strc | (Solv) ¹H-NMR δ ppm: |
|---|---|---|
| 423 | | (DMSO-d6) 2.57 (3H, s), 2.65 (3H, s), 3.69 (3H, s), 3.82 (3H, s), 4.95 (2H, s), 5.0 (2H, s), 6.85-7.0 (2H, m), 7.25 (1H, s), 7.4-7.5 (1H, m), 7.53 (1H, s), 12.01 (1H, s) |
| 424 | | (DMSO-d6) 2.68 (3H, s), 3.7 (3H, s), 3.82 (3H, s), 4.95 (2H, s), 5.0 (2H, s), 5.45 (2H, d, J = 46.9 Hz), 6.85-7.0 (2H, m), 7.27 (1H, s), 7.4-7.5 (1H, m), 7.55 (1H, s), 12.28 (1H, s) |
| 425 | | (DMSO-d6) 1.75-1.9 (2H, m), 2.43 (3H, s), 3.45-3.55 (2H, m), 3.8 (3H, s), 4.02 (3H, s), 4.12 (2H, t, J = 6.3 Hz), 4.52 (1H, t, J = 5.1 Hz), 5.0 (2H, s), 6.85-6.95 (2H, m), 7.26 (1H, s), 7.35-7.5 (2H, m), 11.59 (1H, brs) |
| 426 | | (DMSO-d6) 1.75-1.9 (2H, m), 2.07 (3H, s), 3.45-3.6 (2H, m), 3.8 (3H, s), 4.02 (3H, s), 4.05-4.15 (2H, m), 4.52 (1H, t, J = 5.3 Hz), 4.95-5.1 (4H, m), 6.8-7.0 (2H, m), 7.27 (1H, s), 7.35-7.5 (2H, m), 11.79 (1H, brs) |

TABLE 99

| Ex No. | Strc | (Solv) ¹H-NMR δ ppm: |
|---|---|---|
| 427 | | (DMSO-d6) 2.1 (3H, s), 2.64 (3H, s), 3.65-3.75 (2H, m), 3.81 (3H, s), 4.05-4.15 (2H, m), 4.87 (1H, t, J = 5.3 Hz), 4.95-5.05 (2H, m), 5.1-5.2 (2H, m), 6.85-7.0 (2H, m), 7.34 (1H, s), 7.4-7.5 (2H, m), 12.17 (1H, s) |

TABLE 99-continued

| Ex No. | Strc | (Solv) ¹H-NMR δ ppm: |
|---|---|---|
| 428 | | (DMSO-d6) 1.75-1.9 (2H, m), 2.1 (3H, s), 2.64 (3H, s), 3.45-3.55 (2H, m), 3.8 (3H, s), 4.14 (2H, t, J = 6.5 Hz), 4.52 (1H, t, J = 5.3 Hz), 4.95-5.05 (2H, m), 5.14 (2H, s), 6.8-7.0 (2H, m), 7.3 (1H, s), 7.35-7.5 (2H, m), 12.17 (1H, s) |
| 429 | | (DMSO-d6) 2.68 (3H, s), 3.65-3.75 (2H, m), 3.81 (3H, s), 4.1 (2H, t, J = 5.1 Hz), 4.89 (1H, t, J = 5.3 Hz), 4.9-5.05 (2H, m), 5.44 (2H, d, J = 46.9 Hz), 6.8-7.0 (2H, m), 7.35 (1H, s), 7.4-7.55 (2H, m), 12.28 (1H, s) |
| 430 | | (DMSO-d6) 1.75-1.9 (2H, m), 2.68 (3H, s), 3.45-3.55 (2H, m), 3.8 (3H, s), 4.14 (2H, t, J = 6.4 Hz), 4.52 (1H, t, J = 5.1 Hz), 4.9-5.05 (2H, m), 5.44 (2H, d, J = 46.8 Hz), 6.8-7.0 (2H, m), 7.31 (1H, s), 7.35-7.5 (2H, m), 12.25 (1H, s) |
| 431 | | (DMSO-d6) 2.56 (3H, s), 2.65 (3H, s), 3.65-3.75 (2H, m), 3.81 (3H, s), 4.1 (2H, t, J = 5.1 Hz), 4.89 (1H, t, J = 5.4 Hz), 4.9-5.05 (2H, m), 6.8-7.0 (2H, m), 7.33 (1H, s), 7.4-7.5 (2H, m), 12.01 (1H, s) |
| 432 | | (DMSO-d6) 1.75-1.9 (2H, m), 2.56 (3H, s), 2.65 (3H, s), 3.45-3.55 (2H, m), 3.8 (3H, s), 4.14 (2H, t, J = 6.4 Hz), 4.52 (1H, t, J = 5.3 Hz), 4.99 (2H, s), 6.8-7.0 (2H, m), 7.3 (1H, s), 7.35-7.5 (2H, m), 11.98 (1H, s) |

TABLE 99-continued

| Ex No. | Strc | (Solv) ¹H-NMR δ ppm: |
|---|---|---|
| 433 | | (DMSO-d6) 1.2 (3H, t, J = 7.6 Hz), 2.69 (2H, q, J = 7.6 Hz), 3.65-3.75 (2H, m), 3.8 (3H, s), 4.03 (3H, s), 4.05-4.15 (2H, m), 4.85 (1H, t, J = 5.3 Hz), 4.95-5.05 (2H, m), 6.8-7.0 (2H, m), 7.29 (1H, s), 7.35-7.5 (2H, m), 11.56 (1H, s) |

TABLE 100

| Ex No. | Strc | (Solv) ¹H-NMR δ ppm: |
|---|---|---|
| 434 | | (DMSO-d6) 1.19 (3H, t, J = 7.6 Hz), 2.68 (2H, q, J = 7.6 Hz), 3.65-3.75 (2H, m), 3.79 (3H, s), 4.0-4.15 (5H, m), 4.87 (1H, t, J = 5.4 Hz), 5.04 (2H, s), 6.85-6.95 (1H, m), 7.31 (1H, s), 7.37 (1H, s), 7.4-7.55 (1H, m), 11.57 (1H, s) |
| 435 | | (DMSO-d6) 1.75-1.9 (2H, m), 3.45-3.6 (2H, m), 3.8 (3H, s), 4.06 (3H, s), 4.13 (2H, t, J = 6.4 Hz), 4.4 (2H, d, J = 6.3 Hz), 4.52 (1H, t, J = 5.2 Hz), 4.95-5.05 (2H, m), 5.14 (1H, t, J = 6.3 Hz), 6.8-6.95 (2H, m), 7.27 (1H, s), 7.35-7.5 (2H, m), 11.66 (1H, s) |
| 436 | | (DMSO-d6) 1.2 (3H, t, J = 7.6 Hz), 2.65-2.75 (2H, m), 3.82 (3H, s), 4.04 (3H, s), 4.81 (2H, s), 5.0 (2H, s), 6.8-7.0 (2H, m), 7.14 (1H, s), 7.35-7.5 (2H, m), 11.58 (1H, s), 13.11 (1H, brs) |
| 437 | | (DMSO-d6) 1.2 (3H, t, J = 7.6 Hz), 2.7 (2H, q, J = 7.6 Hz), 3.8 (3H, s), 4.03 (3H, s), 4.83 (2H, s), 5.04 (2H, s), 6.9-6.95 (1H, m), 7.16 (1H, s), 7.4-7.55 (2H, m), 11.58 (1H, s), 13.12 (1H, s) |

TABLE 100-continued

| Ex No. | Strc | (Solv) ¹H-NMR δ ppm: |
|---|---|---|
| 438 | | (DMSO-d6) 2.68 (3H, s), 3.82 (3H, s), 4.83 (2H, s), 4.9-5.05 (2H, m), 5.45 (2H, d, J = 46.8 Hz), 6.8-7.0 (2H, m), 7.19 (1H, s), 7.4-7.5 (1H, m), 7.54 (1H, s), 12.27 (1H, s), 13.0-13.3 (1H, br) |
| 439 | | (DMSO-d6) 2.57 (3H, s), 2.65 (3H, s), 3.82 (3H, s), 4.82 (2H, s), 4.95-5.05 (2H, m), 6.85-7.0 (2H, m), 7,17 (1H, s), 7.4-7.5 (1H, m), 7.51 (1H, s), 12.0 (1H, s), 12.85-13.4 (1H, br) |

TABLE 101

| Ex No. | Strc | (Solv) ¹H-NMR δ ppm: |
|---|---|---|
| 440 | | (DMSO-d6) 2.68 (3H, s), 3.65-3.75 (2H, m), 3.81 (3H, s), 4.05-4.15 (2H, m), 4.52 (2H, d, J = 6.1 Hz), 4.87 (1H, t, J = 5.3 Hz), 4.95-5.05 (2H, m), 5.2-5.35 (1H, m), 6.8-7.0 (2H, m), 7.33 (1H, s), 7.4-7.5 (2H, m), 12.09 (1H, s) |
| 441 | | (DMSO-d6) 1.75-1.9 (2H, m), 2.68 (3H, s), 3.45-3.55 (2H, m), 3.8 (3H, s), 4.14 (2H, t, J = 6.4 Hz), 4.45-4.55 (3H, m), 4.95-5.05 (2H, m), 5.29 (1H, t, J = 6.2 Hz), 6.8-7.0 (2H, m), 7.3 (1H, s), 7.35-7.5 (2H, m), 12.08 (1H, s) |

TABLE 101-continued

| Ex No. | Strc | (Solv) ¹H-NMR δ ppm: |
|---|---|---|
| 442 | | (DMSO-d6) 2.68 (3H, s), 3.8 (3H, s), 4.53 (2H, d, J = 6.3 Hz), 4.84 (2H, s), 4.95-5.1 (2H, m), 5.36 (1H, t, J = 6.3 Hz), 6.85-7.0 (1H, m), 7.2 (1H, s), 7.4-7.6 (2H, m), 12.09 (1H, s), 13.0-13.5 (1H, br) |
| 443 | | (DMSO-d6) 1.2 (3H, t, J = 7.5 Hz), 2.62 (3H, d, J = 4.7 Hz), 2.65-2.75 (2H, m), 3.81 (3H, s), 4.04 (3H, s), 4.58 (2H, s), 5.03 (2H, s), 6.85-7.0 (2H, m), 7.19 (1H, s), 7.4-7.5 (2H, m), 7.85-7.95 (1H, m), 11.59 (1H, s) |
| 444 | | (DMSO-d6) 0.99 (3H, t, J = 7.1 Hz), 1.2 (3H, t, J = 7.6 Hz), 2.69 (2H, q, J = 7.6 Hz), 3.05-3.2 (2H, m), 3.82 (3H, s), 4.04 (3H, s), 4.57 (2H, s), 4.95-5.1 (2H, m), 6.8-7.0 (2H, m), 7.19 (1H, s), 7.4-7.5 (2H, m), 7.92 (1H, t, J = 5.6 Hz), 11.59 (1H, s) |
| 445 | | (DMSO-d6) 1.2 (3H, t, J = 7.6 Hz), 2.63 (3H, d, J = 4.7 Hz), 2.69 (2H, q, J = 7.6 Hz), 3.8 (3H, s), 4.03 (3H, s), 4.59 (2H, s), 5.0-5.15 (2H, m), 6.9-6.95 (1H, m), 7.2 (1H, s), 7.4-7.55 (2H, m), 7.85-7.95 (1H, m), 11.59 (1H, s) |

TABLE 102

| Ex No. | Strc | (Solv) ¹H-NMR δ ppm: |
|---|---|---|
| 446 | | (DMSO-d6) 0.99 (3H, t, J = 7.2 Hz), 2.43 (3H, s), 3.05-3.2 (2H, m), 3.82 (3H, s), 4.02 (3H, s), 4.57 (2H, s), 5.02 (2H, s), 6.85-7.0 (2H, m), 7.18 (1H, s), 7.4-7.5 (2H, m), 7.92 (1H, t, J = 5.5 Hz), 11.59 (1H, s) |
| 447 | | (DMSO-d6) 2.61 (3H, d, J = 4.5 Hz), 2.67 (3H, s), 3.81 (3H, s), 4.6 (2H, s), 4.95-5.05 (2H, m), 5.44 (2H, d, J = 47.0 Hz), 6.8-7.0 (2H, m), 7.21 (1H, s), 7.4-7.5 (1H, m), 7.56 (1H, s), 7.85-7.95 (1H, m), 12.27 (1H, s) |
| 448 | | (DMSO-d6) 1.0 (3H, t, J = 7.2 Hz), 2.68 (3H, s), 3.05-3.2 (2H, m), 3.82 (3H, s), 4.6 (2H, s), 4.95-5.1 (2H, m), 5.45 (2H, d, J = 46.9 Hz), 6.8-7.0 (2H, m), 7.22 (1H, s), 7.4-7.5 (1H, m), 7.57 (1H, s), 7.93 (1H, t, J = 5.6 Hz), 12.28 (1H, s) |
| 449 | | (DMSO-d6) 0.99 (3H, t, J = 7.0 Hz), 3.05-3.2 (2H, m), 3.82 (3H, s), 4.06 (3H, s), 4.58 (2H, s), 4.95-5.1 (2H, m), 5.31 (2H, d, J = 47.0 Hz), 6.85-7.0 (2H, m), 7.19 (1H, s), 7.4-7.55 (2H, m), 7.92 (1H, t, J = 5.5 Hz), 11.87 (1H, s) |
| 450 | | (DMSO-d6) 0.99 (3H, t, J = 7.2 Hz), 3.05-3.2 (2H, m), 3.27 (3H, s), 3.82 (3H, s), 4.05 (3H, s), 4.36 (2H, s), 4.57 (2H, s), 4.95-5.1 (2H, m), 6.8-7.0 (2H, m), 7.19 (1H, s), 7.35-7.55 (2H, m), 7.92 (1H, t, J = 5.7 Hz), 11.75 (1H, s) |

TABLE 102-continued

| Ex No. | Strc | (Solv) ¹H-NMR δ ppm: |
|---|---|---|
| 451 | | (DMSO-d6) 2.56 (3H, s), 2.62 (3H, d, J = 4.5 Hz), 2.65 (3H, s), 3.82 (3H, s), 4.6 (2H, s), 5.02 (2H, s), 6.85-7.0 (2H, m), 7.21 (1H, s), 7.4-7.5 (1H, m), 7.54 (1H, s), 7.85-7.95 (1H, m), 12.01 (1H, s) |

TABLE 103

| Ex No. | Strc | (Solv) ¹H-NMR δ ppm: |
|---|---|---|
| 452 | | (DMSO-d6) 1.0 (3H, t, J = 7.3 Hz), 2.56 (3H, s), 2.65 (3H, s), 3.05-3.2 (2H, m), 3.82 (3H, s), 4.59 (2H, s), 4.95-5.1 (2H, m), 6.8-7.0 (2H, m), 7.2 (1H, s), 7.4-7.5 (1H, m), 7.54 (1H, s), 7.93 (1H, t, J = 5.5 Hz), 12.01 (1H, s) |
| 453 | | (DMSO-d6) 0.99 (3H, t, J = 7.31 Hz), 3.05-3.15 (2H, m), 3.82 (3H, s), 4.06 (3H, s), 4.4 (2H, d, J = 6.5 Hz), 4.58 (2H, s), 4.95-5.05 (2H, m), 5.22 (1H, t, J = 6.5 Hz), 6.85-7.0 (2H, m), 7.17 (1H, s), 7.4-7.55 (2H, m), 7.96 (1H, t, J = 5.6 Hz), 11.71 (1H, s) |
| 454 | | (DMSO-d6) 2.5-2.7 (9H, m), 3.8 (3H, s), 4.61 (2H, s), 5.0-5.1 (2H, m), 6.8-7.0 (1H, m), 7.22 (1H, s), 7.35-7.6 (2H, m), 7.85-8.0 (1H, m), 12.01 (1H, s) |

TABLE 103-continued
| Ex No. | Strc | (Solv) $^1$H-NMR δ ppm: |
|---|---|---|
| 455 | 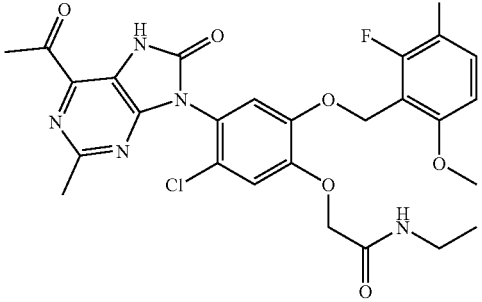 | (DMSO-d6) 1.0 (3H, t, J = 7.2 Hz), 2.56 (3H, s), 2.65 (3H, s), 3.05-3.2 (2H, m), 3.8 (3H, s), 4.6 (2H, s), 5.0-5.15 (2H, m), 6.85-7.0 (1H, m), 7.22 (1H, s), 7.4-7.6 (2H, m), 7.93 (1H, t, J = 5.2 Hz), 12.01 (1H, s) |
| 456 | 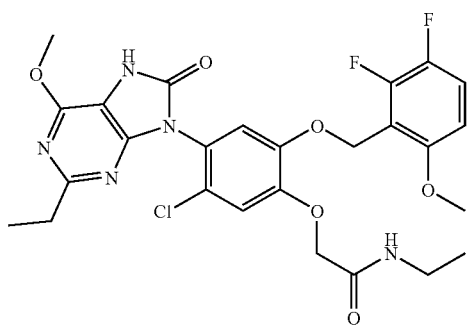 | (DMSO-d6) 1.0 (3H, t, J = 7.1 Hz), 1.2 (3H, t, J = 7.6 Hz), 2.69 (2H, q, J = 7.6 Hz), 3.05-3.2 (2H, m), 3.8 (3H, s), 4.03 (3H, s), 4.58 (2H, s), 5.0-5.15 (2H, m), 6.85-7.0 (1H, m), 7.2 (1H, s), 7.4-7.55 (2H, m), 7.92 (1H, t, J = 5.6 Hz), 11.59 (1H, s) |
| 457 | 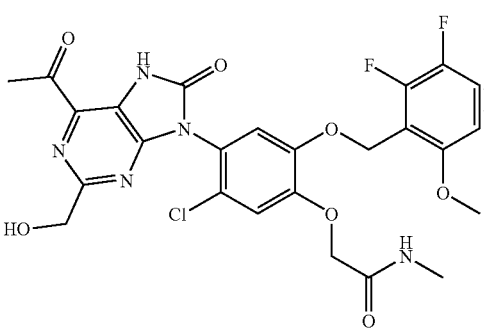 | (DMSO-d6) 2.68 (3H, d, J = 4.4 Hz), 2.68 (3H, s), 3.8 (3H, s), 4.52 (2H, d, J = 6.2 Hz), 4.62 (2H, s), 4.95-5.15 (2H, m), 5.34 (1H, t, J = 6.2 Hz), 6.85-7.0 (1H, m), 7.22 (1H, s), 7.35-7.6 (2H, m), 7.85-8.05 (1H, m), 12.1 (1H, s) |
TABLE 104
| Ex No. | Strc | (Solv) $^1$H-NMR δ ppm: |
|---|---|---|
| 458 | 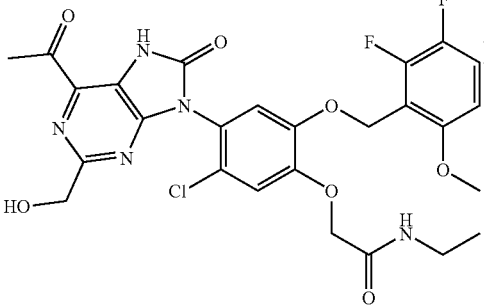 | (DMSO-d6) 1.0 (3H, t, J = 7.3 Hz), 2.68 (3H, s), 3.05-3.2 (2H, m), 3.8 (3H, s), 4.52 (2H, d, J = 6.2 Hz), 4.61 (2H, s), 4.95-5.15 (2H, m), 5.35 (1H, t, J = 6.2 Hz), 6.8-7.0 (1H, m), 7.21 (1H, s), 7.35-7.6 (2H, m), 7.85-8.05 (1H, m), 12.1 (1H, s) |

TABLE 104-continued

| Ex No. | Strc | (Solv) ¹H-NMR δ ppm: |
|---|---|---|
| 459 | | (DMSO-d6) 2.36 (3H, s), 2.62 (3H, d, J = 5.0 Hz), 3.8 (3H, s), 4.38 (2H, d, J = 5.9 Hz), 4.58 (2H, s), 4.95-5.1 (2H, m), 5.25 (1H, t, J = 5.9 Hz), 6.85-7.05 (3H, m), 7.18 (1H, s), 7.4-7.5 (2H, m), 7.85-7.95 (1H, m), 11.38 (1H, s) |
| 460 | | (DMSO-d6) 0.99 (3H, t, J = 7.1 Hz), 2.36 (3H, s), 3.05-3.2 (2H, m), 3.81 (3H, s), 4.38 (2H, d, J = 5.9 Hz), 4.57 (2H, s), 4.95-5.1 (2H, m), 5.25 (1H, t, J = 5.9 Hz), 6.85-7.05 (3H, m), 7.18 (1H, s), 7.4-7.5 (2H, m), 7.93 (1H, t, J = 5.5 Hz), 11.38 (1H, s) |
| 461 | | (DMSO-d6) 2.62 (3H, d, J = 4.5 Hz), 2.68 (3H, s), 3.82 (3H, s), 4.53 (2H, d, J = 6.4 Hz), 4.61 (2H, s), 4.95-5.1 (2H, m), 5.35 (1H, t, J = 6.4 Hz), 6.85-7.0 (2H, m), 7.21 (1H, s), 7.35-7.55 (1H, m), 7.56 (1H, s), 7.85-8.0 (1H, m), 12.1 (1H, s) |
| 462 | | (DMSO-d6) 1.0 (3H, t, J = 7.3 Hz), 2.68 (3H, s), 3.05-3.2 (2H, m), 3.82 (3H, s), 4.53 (2H, d, J = 6.2 Hz), 4.6 (2H, s), 5.01 (2H, s), 5.35 (1H, t, J = 6.2 Hz), 6.85-7.0 (2H, m), 7.2 (1H, s), 7.35-7.55 (1H, m), 7.56 (1H, s), 7.9-8.0 (1H, m), 12.1 (1H, s) |
| 463 | | (DMSO-d6) 2.36 (3H, s), 3.65-3.75 (2H, m), 3.8 (3H, s), 4.05-4.15 (2H, m), 4.38 (2H, d, J = 5.9 Hz), 4.86 (1H, t, J = 5.5 Hz), 4.95-5.05 (2H, m), 5.24 (1H, t, J = 5.9 Hz), 6.8-6.95 (2H, m), 7.0 (1H, s), 7.28 (1H, s), 7.34 (1H, s), 7.35-7.5 (1H, m), 11.36 (1H, s) |

TABLE 105

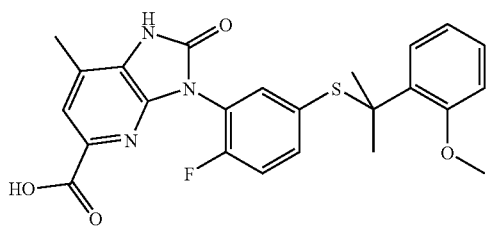

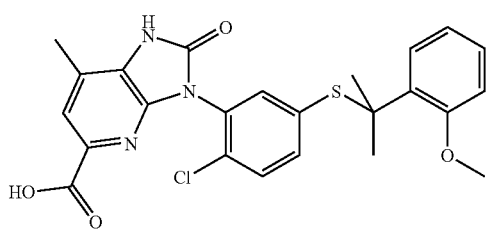

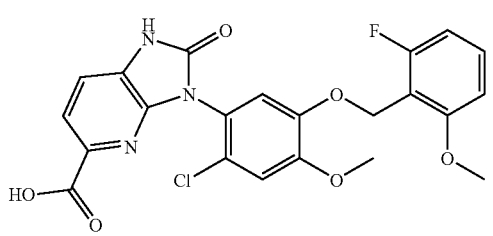

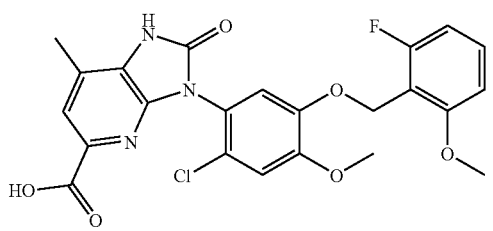

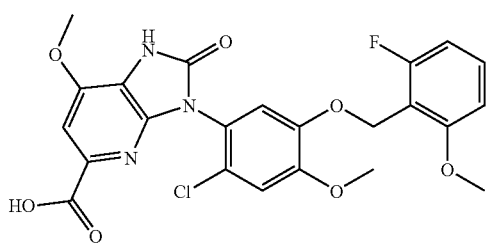

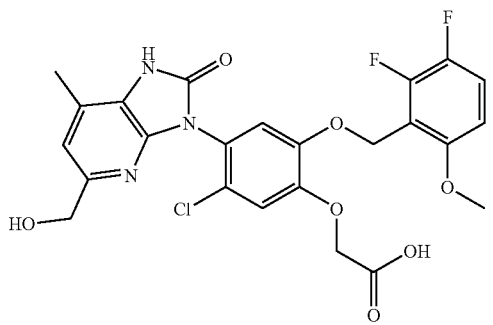

TABLE 105-continued

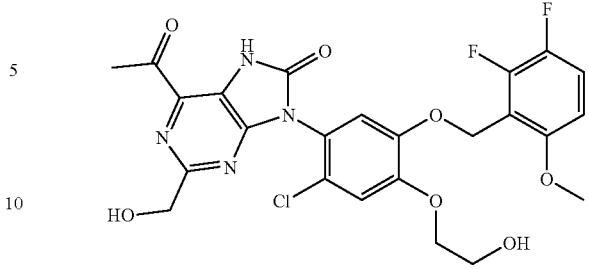

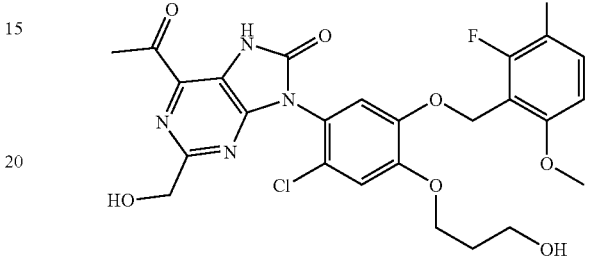

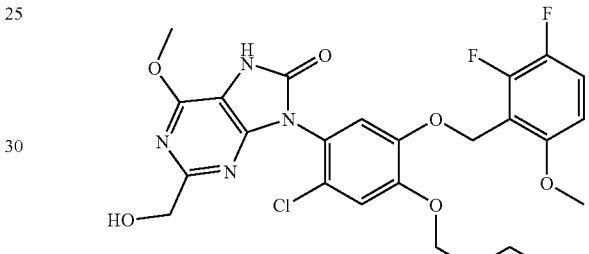

Test Example 1

1) Cloning and Construction of the Vector Expressing Human GnRH Receptor1 (GnRHR1)

Using cDNA derived from human pituitary (BECTON DICKINSON) as a template, the DNA fragment coding 45 to 1115 bp of human GnRHR1 (Accession No. L03380), which was reported by Kakar et al., was amplified by PCR method and inserted into the multi-cloning site of pcDNA3.1(+) (Invitrogen). The DNA sequence inserted was perfectly matched to the previously reported sequence.

2) Establishment of Cell Line Stably Expressing Human GnRH Receptor1 HEK293 Cells The expression vector of human GnRHR1 gene, was digested by XhoI into a linear DNA. The linear DNA was transfected into HEK293 cells by means of lipofection (Lipofectamine-2000: Invitrogen). Neomycin resistant cell lines were selected by culture in the medium containing G418 (Invitrogen) at 1 mg/mL, and then the change of calcium levels in GnRH-stimulated cells was measured by the method described below. The cell line, which showed the greatest change, was selected and designated as hGnRHR1 #1. hGnRHR1 #1 cells were cultured in the presence of G418 at 0.5 mg/mL.

3) Assay of Inhibitory Effect for the Change of Calcium Levels in GnRH-Stimulated Cells Antagonizing effect of compounds for human GnRHR1 was evaluated by depression of calcium levels in GnRH-stimulated cells. hGnRHR1#1 cells were seeded into a 96-well culture plate at a density of $1.5 \times 10^5$ cells/well and cultured for a day. After removing the culture medium, cells were washed with 200 μL per well of the washing buffer (Hanks' Balanced Salt Solutions, 20 mM N-2-hydroxyethylpiperazine-N'-2-ethanesulfonic acid, 1.3 mM calcium chloride, 0.5 mM magnesium chloride, 0.4 mM magnesium sulfate). One hundred μL of the $Ca^{2+}$ sensitive dye solution (FLIPR Calcium Assay Kit, Molecular Devices) was added to the well, and the cells were incubated for 1 hour at 37° C. in 5% $CO_2$ incubator. Then, intracellular calcium levels were determined under the following condition by using FLEX STATION (Molecular Devices). In the equipment, which was warmed to 37° C., 50 μL of test compound diluted with the measurement buffer (the washing buffer with 0.1% Albumin bovine serum) was added to the well. After 1 minute, 50 μL of 10 nM GnRH was added to the well. The drug concentration, at which 50% GnRH-stimulated intracellular calcium flux was inhibited ($IC_{50}$ value), was calculated using logit plot (Table 106).

TABLE 106

| Example No. | $IC_{50}$ (nM) |
|---|---|
| 35 | 193 |
| 39 | 27 |
| 81 | 32 |
| 93 | 20 |
| 109 | 36 |
| 128 | 24 |
| 152 | 32 |
| 160 | 99 |
| 199 | 46 |
| 251 | 54 |
| 262 | 62 |
| 274 | 15 |
| 314 | 23 |
| 341 | 32 |
| 345 | 17 |
| 346 | 38 |
| 381 | 36 |
| 452 | 19 |

INDUSTRIAL APPLICABILITY

A nitrogen-containing fused ring derivative (I) of the present invention or a prodrug thereof, or a pharmaceutically acceptable salt thereof has an excellent GnRH antagonistic activity, and thus, can be used as an agent for the prevention or treatment of sex hormone-dependent diseases by controlling the effect of gonadotropin releasing hormone and controlling the production and secretion of gonadotropin and sex hormones. Therefore, the present invention can provide an agent for the prevention or treatment of benign prostatic hypertrophy, hysteromyoma, endometriosis, metrofibroma, precocious puberty, amenorrhea, premenstrual syndrome, dysmenorrhea, polycystic ovary syndrome, lupus erythematosis, hirsutism, short stature, sleep disorders, acne, baldness, Alzheimer's disease, infertility, irritable bowel syndrome, prostatic cancer, uterine cancer, ovary cancer, breast cancer or pituitary tumor, a reproduction regulator, a contraceptive, an ovulation inducing agent or an agent for the prevention of post-operative recurrence of sex hormone-dependent cancers and the like.

The invention claimed is:
1. A nitrogen-containing fused ring derivative represented by the general formula (I):

[Chem. 1]

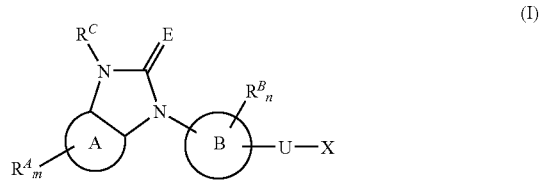

(I)

wherein ring A is a pyridine ring or a pyrimidine ring;
ring B is a benzene ring, a pyridine ring or a thiophene ring;
$R^A$ and $R^B$ independently represent a halogen atom, a cyano group, a nitro group, a lower alkyl group which may have a substituent selected from substituent group (i), a lower alkenyl group which may have a substituent selected from substituent group (i), a lower alkynyl group which may have a substituent selected from substituent group (i), a hydroxyiminomethyl group, a (lower alkyl)sulfonyl group which may have a substituent selected from substituent group (i), a (lower alkyl)sulfinyl group which may have a substituent selected from substituent group (i), —$OW^1$, —$SW^1$, —$COW^2$, —$NW^3W^4$, —$SO_2NW^3W^4$, an aryl group which may have a substituent selected from substituent group (ii), a heteroaryl group which may have a substituent selected from substituent group (ii), a cycloalkyl group which may have a substituent selected from substituent group (iii), a heterocycloalkyl group which may have a substituent selected from substituent group (iii) or a hydroxycarbamimidoyl group with the proviso that $R^B$ does not represent a hydroxycarbamimidoyl group;
$R^C$ represents a hydrogen atom;
m represents an integer number 0 to 3 with the proviso that when m is 2 or more, these $R^A$ may be the same or different from each other;
n represents an integer number 0 to 2 with the proviso that when n is 2, these $R^B$ may be the same or different from each other;
E represents an oxygen atom or a sulfur atom;
U represents a single bond;
X represents a group represented by —CO—Y, —$SO_2$—Y, —S-L-Y, —O-L-Y, —CO-L-Y, $SO_2$-L-Y, —N(Q)-L-Y, —N(Q)-CO—Y or —N(Q)-$SO_2$—Y;
in which $W^1$ represents a hydrogen atom, a lower alkyl group which may have a substituent selected from substituent group (i), an aryl group which may have a substituent selected from substituent group (ii), a heteroaryl group which may have a substituent selected from substituent group (ii), a cycloalkyl group which may have a substituent selected from substituent group (iii) or a heterocycloalkyl group which may have a substituent selected from substituent group (iii);
$W^2$ represents a hydrogen atom, a hydroxyl group, a lower alkyl group which may have a substituent selected from substituent group (i), a lower alkoxy group which may have a substituent selected from substituent group (i), —$NW^5W^6$, an aryl group which may have a substituent selected from substituent group (ii), a heteroaryl group which may have a substituent selected from substituent group (ii), a cycloalkyl group which may have a substituent selected from substituent group (iii) or a heterocycloalkyl group which may have a substituent selected from substituent group (iii);

$W^3$ and $W^4$ independently represent a hydrogen atom, a lower alkyl group which may have a substituent selected from substituent group (i), —$COW^7$, —$SO_2W^8$, an aryl group which may have a substituent selected from substituent group (ii), a heteroaryl group which may have a substituent selected from substituent group (ii), a cycloalkyl group which may have a substituent selected from substituent group (iii) or a heterocycloalkyl group which may have a substituent selected from substituent group (iii), or $W^3$ and $W^4$ optionally bind together to form a cyclic amino group which may have a substituent selected from substituent group (iii) with the neighboring nitrogen atom;

$W^5$ and $W^6$ independently represent a hydrogen atom, a lower alkyl group which may have a substituent selected from substituent group (i), a lower alkoxy group which may have a substituent selected from substituent group (i), an aryl group which may have a substituent selected from substituent group (ii), a heteroaryl group which may have a substituent selected from substituent group (ii), a cycloalkyl group which may have a substituent selected from substituent group (iii) or a heterocycloalkyl group which may have a substituent selected from substituent group (iii) with the proviso that both are not lower alkoxy groups which may have a substituent selected from substituent group (i) at the same time, or $W^5$ and $W^6$ optionally bind together to form a cyclic amino group which may have a substituent selected from substituent group (iii) with the neighboring nitrogen atom;

$W^7$ represents a hydrogen atom, a lower alkyl group which may have a substituent selected from substituent group (i), a lower alkoxy group which may have a substituent selected from substituent group (i), —$NW^9W^{10}$, an aryl group which may have a substituent selected from substituent group (ii), a heteroaryl group which may have a substituent selected from substituent group (ii), a cycloalkyl group which may have a substituent selected from substituent group (iii) or a heterocycloalkyl group which may have a substituent selected from substituent group (iii);

$W^8$ represents a lower alkyl group which may have a substitutent selected from substituent group (i), —$NW^9W^{10}$, an aryl group which may have a substituent selected from substituent group (ii), a heteroaryl group which may have a substituent selected from substituent group (ii), a cycloalkyl group which may have a substituent selected from substituent group (iii) or a heterocycloalkyl group which may have a substituent selected from substituent group (iii);

$W^9$ and $W^{10}$ independently represent a hydrogen atom, a lower alkyl group which may have a substituent selected from substituent group (i), a lower alkoxy group which may have a substituent selected from substituent group (i), an aryl group which may have a substituent selected from substituent group (ii), a heteroaryl group which may have a substituent selected from substituent group (ii), a cycloalkyl group which may have a substituent selected from substituent group (iii) or a heterocycloalkyl group which may have a substituent selected from substituent group (iii) with the proviso that both are not lower alkoxy groups which may have a substituent selected from substituent group (i) at the same time, or $W^9$ and $W^{10}$ optionally bind together to form a cyclic amino group which may have a substituent selected from substituent group (iii) with the neighboring nitrogen atom;

L represents a lower alkylene group which may have a substituent selected from substituent group (i);

Y represents a group represented by Z or —$NW^{11}W^{12}$, wherein $W^{11}$ and $W^{12}$ independently represent a hydrogen atom, a lower alkyl group which may have a substituent selected from substituent group (i) or Z with the proviso that $W^{11}$ and $W^{12}$ are not hydrogen atoms at the same time, or $W^{11}$ and $W^{12}$ optionally bind together to form a cyclic amino group which may have a substituent selected from substituent group (iii) with the neighboring nitrogen atom;

Z represents an optionally fused a cycloalkyl group which may have a substituent selected from substituent group (iii), an optionally fused heterocycloalkyl group which may have a substituent selected from substituent group (iii), an optionally fused aryl group which may have a substituent selected from substituent group (ii) or an optionally fused heteroaryl group which may have a substituent selected from substituent group (ii);

Q has the same meaning with $W^3$ and $W^4$ but independently of $W^3$ and $W^4$ and with the proviso that Q optionally forms a heteroaryl group which may have a substituent selected from substituent group (ii) or a heterocycloalkyl group which may have a substituent selected from substituent group (iii) with $R^B$;

Substituent group (i): a halogen atom, a cyano group, a (lower alkyl)sulfonyl group which may have a substituent selected from substituent group C, a (lower alkyl)sulfinyl group which may have a substituent selected from substituent group C, —$OW^{23}$, —$SW^{23}$, —$COW^{24}$, —$NW^{25}W^{26}$, —$SO_2NW^{25}W^{26}$, an aryl group which may have a substituent selected from substituent group A, a heteroaryl group which may have a substituent selected from substituent group A, a cycloalkyl group which may have a substituent selected from substituent group B and a heterocycloalkyl group which may have a substituent selected from substituent group B;

Substituent group (ii): a halogen atom, a nitro group, a cyano group, a lower alkyl group which may have a substituent selected from substituent group (i), a lower alkenyl group which may have a substituent selected from substituent group (i), a lower alkynyl group which may have a substituent selected from substituent group (i), a (lower alkyl)sulfonyl group which may have a substituent selected from substituent group (i), a (lower alkyl)sulfinyl group which may have a substituent selected from substituent group (i), —$OW^{13}$, —$SW^{13}$, —$COW^{14}$, —$NW^{15}W^{16}$, —$SO_2NW^{15}W^{16}$, an aryl group which may have a substituent selected from substituent group A, a heteroaryl group which may have a substituent selected from substituent group A, a cycloalkyl group which may have a substituent selected from substituent group B and a heterocycloalkyl group which may have a substituent selected from substituent group B;

Substituent group (iii): an oxo group, a halogen atom, a cyano group, a lower alkyl group which may have a substituent selected from substituent group (i), a lower alkenyl group which may have a substituent selected from substituent group (i), a lower alkynyl group which may have a substituent selected from substituent group (i), a (lower alkyl)sulfonyl group which may have a substituent selected from substituent group (i), a (lower alkyl)sulfinyl group which may have a substituent selected from substituent group (i), —OW$^{13}$, —SW$^{13}$, —COW$^{14}$, —NW$^{15}$W$^{16}$, —SO$_2$NW$^{15}$W$^{16}$, an aryl group which may have a substituent selected from substituent group A, a heteroaryl group which may have a substituent selected from substituent group A, a cycloalkyl group which may have a substituent selected from substituent group B and a heterocycloalkyl group which may have a substituent selected from substituent group B;

in which W$^{23}$ represents a hydrogen atom, a lower alkyl group which may have a substituent selected from substituent group C, an aryl group which may have a substituent selected from substituent group A, a heteroaryl group which may have a substituent selected from substituent group A, a cycloalkyl group which may have a substituent selected from substituent group B or a heterocycloalkyl group which may have a substituent selected from substituent group B;

W$^{24}$ represents a hydrogen atom, a hydroxyl group, a lower alkyl group which may have a substituent selected from substituent group C, a lower alkoxy group which may have a substituent selected from substituent group C, —NW$^{27}$W$^{28}$, an aryl group which may have a substituent selected from substituent group A, a heteroaryl group which may have a substituent selected from substituent group A, a cycloalkyl group which may have a substituent selected from substituent group B or a heterocycloalkyl group which may have a substituent selected from substituent group B;

W$^{25}$ and W$^{26}$ independently represent a hydrogen atom, a lower alkyl group which may have a substituent selected from substituent group C, —COW$^{29}$, —SO$_2$W$^{30}$, an aryl group which may have a substituent selected from substituent group A, a heteroaryl group which may have a substituent selected from substituent group A, a cycloalkyl group which may have a substituent selected from substituent group B or a heterocycloalkyl group which may have a substituent selected from substituent group B, or W$^{25}$ and W$^{26}$ may bind together with the neighboring nitrogen atom to form a cyclic amino group which may have a substituent selected from substituent group B;

W$^{27}$ and W$^{28}$ independently represent a hydrogen atom, a lower alkyl group which may have a substituent selected from substituent group C, a lower alkoxy group which may have a substituent selected from substituent group C, an aryl group which may have a substituent selected from substituent group A, a heteroaryl group which may have a substituent selected from substituent group A, a cycloalkyl group which may have a substituent selected from substituent group B or a heterocycloalkyl group which may have a substituent selected from substituent group B and with the proviso that W$^{27}$ and W$^{28}$ are not a lower alkoxy group which may have a substituent selected from substituent group C at the same time, or W$^{27}$ and W$^{28}$ may bind together with the neighboring nitrogen atom to form a cyclic amino group which may have a substituent selected from substituent group B;

W$^{29}$ represents a hydrogen atom, a lower alkyl group which may have a substituent selected from substituent group C, a lower alkoxy group which may have a substituent selected from substituent group C, —NW$^{31}$W$^{32}$, an aryl group which may have a substituent selected from substituent group A, a heteroaryl group which may have a substituent selected from substituent group A, a cycloalkyl group which may have a substituent selected from substituent group B or a heterocycloalkyl group which may have a substituent selected from substituent group B;

W$^{30}$ represents a lower alkyl group which may have a substituent selected from substituent group C, —NW$^{31}$W$^{32}$, an aryl group which may have a substituent selected from substituent group A, a heteroaryl group which may have a substituent selected from substituent group A, a cycloalkyl group which may have a substituent selected from substituent group B or a heterocycloalkyl group which may have a substituent selected from substituent group B;

W$^{31}$ and W$^{32}$ independently represent a hydrogen atom, a lower alkyl group which may have a substituent selected from substituent group C, a lower alkoxy group which may have a substituent selected from substituent group C, an aryl group which may have a substituent selected from substituent group A, a heteroaryl group which may have a substituent selected from substituent group A, a cycloalkyl group which may have a substituent selected from substituent group B or a heterocycloalkyl group which may have a substituent selected from substituent group B and with the proviso that W$^{31}$ and W$^{32}$ are not a lower alkoxy group which may have a substituent selected from substituent group C at the same time, or W$^{31}$ and W$^{32}$ may bind together with the neighboring nitrogen atom to form a cyclic amino group which may have a substituent selected from substituent group B;

W$^{13}$ represents a hydrogen atom, a lower alkyl group which may have a substituent selected from substituent group (i), an aryl group which may have a substituent selected from substituent group A, a heteroaryl group which may have a substituent selected from substituent group A, a cycloalkyl group which may have a substituent selected from substituent group B or a heterocycloalkyl group which may have a substituent selected from substituent group B;

W$^{14}$ represents a hydrogen atom, a hydroxyl group, a lower alkyl group which may have a substituent selected from substituent group (i), a lower alkoxy group which may have a substituent selected from substituent group (i), —NW$^{17}$W$^{18}$, an aryl group which may have a substituent selected from substituent group A, a heteroaryl group which may have a substituent selected from substituent group A, a cycloalkyl group which may have a substituent selected from substituent group B or a heterocycloalkyl group which may have a substituent selected from substituent group B;

W$^{15}$ and W$^{16}$ independently represent a hydrogen atom, a lower alkyl group which may have a substituent selected from substituent group (i), —COW$^{19}$, —SO$_2$W$^{20}$, an aryl group which may have a substituent selected from substituent group A, a heteroaryl group which may have a substituent selected from substituent group A, a cycloalkyl group which may have a substituent selected from substituent group B or a heterocycloalkyl group which may have a substituent selected from substituent group B, or W$^{15}$ and W$^{16}$ may bind together with the neighboring nitrogen atom to form a cyclic amino group which may have a substituent selected from substituent group B;

W$^{17}$ and W$^{18}$ independently represent a hydrogen atom, a lower alkyl group which may have a substituent selected from substituent group (i) a lower alkoxy group which may have a substituent selected from substituent group (i), an aryl group which may have a substituent selected from substituent group A, a heteroaryl group which may have a substituent selected from substituent group A, a cycloalkyl group which may have a substituent selected from substituent group B or a heterocycloalkyl group which may have a substituent selected from substituent group B and with the proviso that $W^{17}$ and $W^{18}$ are not a lower alkoxy group which may have a substituent selected from substituent group (i) at the same time, or $W^{17}$ and $W^{18}$ may bind together with the neighboring nitrogen atom to form a cyclic amino group which may have a substituent selected from substituent group B;

$W^{19}$ represents a hydrogen atom, a lower alkyl group which may have a substituent selected from substituent group (i), a lower alkoxy group which may have a substituent selected from substituent group (i), —$NW^{21}W^{22}$, an aryl group which may have a substituent selected from substituent group A, a heteroaryl group which may have a substituent selected from substituent group A, a cycloalkyl group which may have a substituent selected from substituent group B or a heterocycloalkyl group which may have a substituent selected from substituent group B;

$W^{20}$ represents a lower alkyl group which may have a substituent selected from substituent group (i), —$NW^{21}W^{22}$, an aryl group which may have a substituent selected from substituent group A, a heteroaryl group which may have a substituent selected from substituent group A, a cycloalkyl group which may have a substituent selected from substituent group B or a heterocycloalkyl group which may have a substituent selected from substituent group B; and $W^{21}$ and $W^{22}$ independently represent a hydrogen atom, a lower alkyl group which may have a substituent selected from substituent group (i), a lower alkoxy group which may have a substituent selected from substituent group (i), an aryl group which may have a substituent selected from substituent group A, a heteroaryl group which may have a substituent selected from substituent group A, a cycloalkyl group which may have a substituent selected from substituent group B or a heterocycloalkyl group which may have a substituent selected from substituent group B and with the proviso that $W^{21}$ and $W^{22}$ are not a lower alkoxy group which may have a substituent selected from substituent group (i) at the same time, or $W^{21}$ and $W^{22}$ may bind together with the neighboring nitrogen atom to form a cyclic amino group which may have a substituent selected from substituent group B;

Substituent group A: a halogen atom, a nitro group, a hydroxyl group, a lower alkyl group, a halo(lower alkyl) group, a lower alkoxy group, a lower alkenyl group, a lower alkynyl group, a (lower alkyl)thio group, a (lower alkyl)sulfonyl group, a (lower alkyl)sulfinyl group, a carboxy group, a (lower alkoxy)carbonyl group, a lower acyl group, a carbamoyl group, a (di)(lower alkyl)carbamoyl group, an amino group, a (di)(lower alkyl)amino group, an aryl group, a heteroaryl group, a cycloalkyl group and a heterocycloalkyl group;

Substituent group B: an oxo group, a halogen atom, a cyano group, a hydroxyl group, a lower alkyl group, a halo(lower alkyl) group, a lower alkoxy group, a lower alkenyl group, a lower alkynyl group, a (lower alkyl)thio group, a (lower alkyl)sulfonyl group, a (lower alkyl)sulfinyl group, a carboxy group, a (lower alkoxy)carbonyl group, a lower acyl group, a carbamoyl group, a (di)(lower alkyl)carbamoyl group, an amino group, a (di)(lower alkyl)amino group, an aryl group, a heteroaryl group, a cycloalkyl group and a heterocycloalkyl group;

Substituent group C: a halogen atom, a cyano group, a hydroxyl group, a lower alkoxy group, a (lower alkyl)thio group, a (lower alkyl)sulfonyl group, a (lower alkyl)sulfinyl group, a carboxy group, a (lower alkoxy)carbonyl group, a lower acyl group, a carbamoyl group, a (di)(lower alkyl)carbamoyl group, an amino group, a (di)(lower alkyl)amino group, an aryl group, a heteroaryl group, a cycloalkyl group and a heterocycloalkyl group;

or a pharmaceutically acceptable salt thereof.

2. A nitrogen-containing fused ring derivative as claimed in claim 1, wherein $R^A$ is a hydroxycarbamimidoyl group, or a prodrug thereof, or a pharmaceutically acceptable salt thereof.

3. A nitrogen-containing fused ring derivative as claimed in claim 1, wherein $R^A$ and $R^B$ independently are a halogen atom, a cyano group, a nitro group, a lower alkyl group which may have a substituent selected from substituent group (i), a lower alkenyl group which may have a substituent selected from substituent group (i), a lower alkynyl group which may have a substituent selected from substituent group (i), a hydroxyiminomethyl group, a (lower alkyl)sulfonyl group which may have a substituent selected from substituent group (i), a (lower alkyl)sulfinyl group which may have a substituent selected from substituent group (i), —$OW^1$, —$SW^1$, —$COW^2$, —$NW^3W^4$, —$SO_2NW^3W^4$, an aryl group which may have a substituent selected from substituent group (ii), a heteroaryl group which may have a substituent selected from substituent group (ii), a cycloalkyl group which may have a substituent selected from substituent group (iii) a heterocycloalkyl group which may have a substituent selected from substituent group (iii) in which $W^1$ to $W^4$ have the same meanings as defined in claim 1, or a pharmaceutically acceptable salt thereof.

4. A nitrogen-containing fused ring derivative as claimed in claim 3, wherein $R^A$ is a halogen atom, a cyano group, a lower alkyl group which may have a substituent selected from substituent group (i), a (lower alkyl)sulfonyl group which may have a substituent selected from substituent group (i), —$OW^1$, —$SW^1$, —$COW^2$, —$NW^3W^4$ or a heteroaryl group which may have a substituent selected from substituent group (ii) in which $W^1$ to $W^4$ have the same meanings as defined in claim 1, or a pharmaceutically acceptable salt thereof.

5. A nitrogen-containing fused ring derivative as claimed in claim 1, wherein ring B is any of rings represented by the formula:

[Chem. 2]

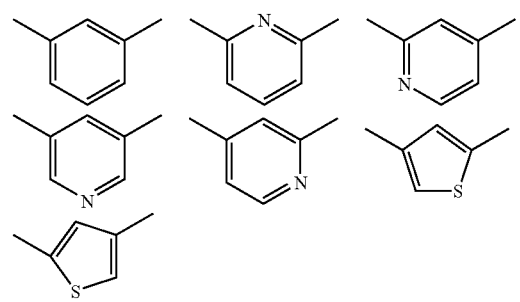

or a pharmaceutically acceptable salt thereof.

6. A nitrogen-containing fused ring derivative as claimed in claim 5, wherein n is 1 or 2 and ring B is any of rings in which $R^B$ binds to the position of ring B represented by the following formula:

[Chem. 3]

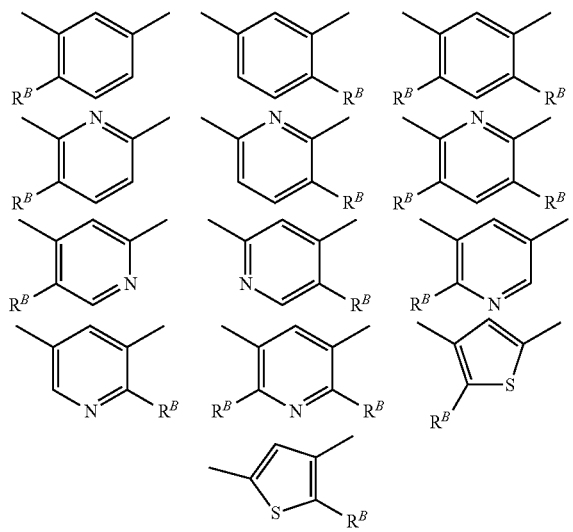

or a pharmaceutically acceptable salt thereof.

7. A nitrogen-containing fused ring derivative as claimed in claim 1, wherein X is a group represented by —CO—Y, —SO$_2$—Y, —S-L-Y, —O-L-Y, —CO-L-Y, —SO$_2$-L-Y, —N(Q)-L-Y, or N(Q)-SO$_2$—Y in which L, Y and Q have the same meanings as defined in claim 1, or a pharmaceutically acceptable salt thereof.

8. A nitrogen-containing fused ring derivative as claimed in claim 1, wherein L is a $C_{1-3}$ alkylene group, or a pharmaceutically acceptable salt thereof.

9. A nitrogen-containing fused ring derivative as claimed in claim 1, wherein Z is an optionally fused aryl group which may have a substituent selected from substituent group (ii) or an optionally fused heteroaryl group which may have a substituent selected from substituent group (ii), or a pharmaceutically acceptable salt thereof.

10. A pharmaceutical composition comprising as an active ingredient a nitrogen-containing fused ring derivative as claimed in claim 1, or a pharmaceutically acceptable salt thereof.

11. A pharmaceutical composition as claimed in claim 10, which is a gonadotropin releasing hormone antagonist.

12. A pharmaceutical composition as claimed in claim 10, which is an agent for the prevention or treatment of a sex hormone-dependent disease, a reproduction regulator, a contraceptive, an ovulation inducing agent or an agent for the prevention of post-operative recurrence of sex hormone-dependent cancers.

13. A pharmaceutical composition as claimed in claim 12, wherein the sex hormone-dependent disease is selected from the group consisting of benign prostatic hypertrophy, hysteromyoma, endometriosis, metrofibroma, precocious puberty, amenorrhea, premenstrual syndrome, dysmenorrhea, polycystic ovary syndrome, lupus erythematosis, hirsutism, short stature, sleep disorders, acne, baldness, Alzheimer's disease, infertility, irritable bowel syndrome, prostatic cancer, uterine cancer, ovary cancer, breast cancer and pituitary tumor.

14. A pharmaceutical composition as claimed in claim 10, wherein the composition is an oral formulation.

15. A pharmaceutical composition as claimed in claim 10, which comprises a combination with at least one drug selected from the group consisting of a GnRH superagonist, a chemotherapeutic agent, a peptidic GnRH antagonist, a 5α-reductase inhibitor, an α-adrenoceptor inhibitor, an aromatase inhibitor, an adrenal androgen production inhibitor and a hormonotherapeutic agent.

16. A pharmaceutical composition as claimed in claim 15, wherein the GnRH superagonist is selected from the group consisting of leuprorelin acetate, gonadorelin, buserelin, triptorelin, goserelin, nafarelin, histrelin, deslorelin, meterelin and lecirelin.

17. A pharmaceutical composition as claimed in claim 15, wherein the chemotherapeutic agent is selected from the group consisting of ifosfamide, adriamycin, peplomycin, cisplatin, cyclophosphamide, 5-FU, UFT, methotrexate, mitomycin C, mitoxantrone, paclitaxel and dotaxel.

18. A pharmaceutical composition as claimed in claim 15, wherein the peptidic GnRH antagonist is selected from the group consisting of cetrorelix, ganirelix, abarelix, ozarelix, iturelix, degarelix and teverelix.

19. A pharmaceutical composition as claimed in claim 15, wherein the 5α-reductase inhibitor is selected from the group consisting of finasteride and dutasteride.

20. A pharmaceutical composition as claimed in claim 15, wherein the α-adrenoceptor inhibitor is selected from the group consisting of tamsulosin, silodosin and urapidil.

21. A pharmaceutical composition as claimed in claim 15, wherein the aromatase inhibitor is selected from the group consisting of fadrozole, letrozole, anastrozole and formestane.

22. A pharmaceutical composition as claimed in claim 15, wherein the adrenal androgen production inhibitor is liarozole.

23. A pharmaceutical composition as claimed in claim 15, wherein the hormonotherapeutic agent is selected from the group consisting of an antiestrogenic agent, a progestational agent, an androgenic agent, an estrogeninc agent and an antiandrogenic agent.

24. A nitrogen-containing fused ring derivative as claimed in claim 1, which is selected from the group consisting of
5-Carboxy-3-[2-chloro-5-(1-methyl-1-phenylethylsulfonyl)phenyl]-1,3-dihydro-2H-imidazo[4,5-b]pyridin-2-one,
9-[2-Chloro-5-(2,3-difluoro-6-methoxybenzyloxy)-4-methoxyphenyl]-6-methoxy-7,9-dihydro-8H-purin-8-one,
3-{5-[N-Acetyl-N-(2,3-difluoro-6-methoxybenzyl)amino]-2-chlorophenyl}-5-carboxy-7-methyl-1,3-dihydro-2H-imidazo[4,5-b]pyridin-2-one,
5-Carboxy-3-[2-fluoro-5-(2,3,4,5-tetrahydro-1H-1-benzoazepin-1-ylsulfonyl)phenyl]-7-methyl-1,3-dihydro-2H-imidazo[4,5-b]pyridin-2-one,
5-Carboxy-3-{5-[1-(2-chlorophenyl)-1-methylethylthio]-2-fluoro-4-methoxyphenyl}-7-methyl-1,3-dihydro-2H-imidazo[4,5-b]pyridin-2-one,
5-Carboxy-3-{2-chloro-5-[1-(2-fluoro-6-methoxyphenyl)-1-methylethylsulfonyl]phenyl}-7-methyl-1,3-dihydro-2H-imidazo[4,5-b]pyridin-2-one,
3-[2-Chloro-5-(2,3,4,5-tetrahydro-1H-1-benzoazepin-1-ylsulfonyl)phenyl]-5-hydroxymethyl-7-methyl-1,3-dihydro-2H-imidazo[4,5-b]pyridin-2-one,
3-[2-Chloro-5-(2,3,4,5-tetrahydro-1H-1-benzoazepin-1-ylsulfonyl)phenyl]-5-hydroxycarbamimidoyl-7-methyl-1,3-dihydro-2H-imidazo[4,5-b]pyridin-2-one, 9-{2-Chloro-5-[N-(2-methoxyphenyl)-N-methylsulfamoyl]phenyl}-6-methoxy-7,9-dihydro-8H-purin-8-one, 9-[2-Chloro-5-(2-fluoro-6-methoxybenzyloxy)-4-(2-hydroxyethoxy)]-2-fluoromethyl-6-methoxy-7,9-dihydro-8H-purin-8-one, 9-{5-[6-(2-Acetylaminoethoxy)-2,3-difluorobenzyloxy]-2-chlorophenyl}-6-methoxy-7,9-dihydro-8H-purin-8-one, 9-[4-Carboxymethoxy-2-chloro-5-(2-fluoro-6-methoxybenzyloxy)phenyl]-2-hydroxymethyl-6-methoxy-7,9-dihydro-8H-purin-8-one, 9-[2-Chloro-5-(2-fluoro-6-methoxybenzyloxy)-4-methoxyphenyl]-2-(2-hydroxyethyl)-6-methoxy-7,9-dihydro-8H-purin-8-one, 2-[5-Chloro-2-(2,3-difluoro-6-methoxybenzyloxy)-4-(2-fluoromethyl-6-methoxy-7,9-dihydro-8H-purin-8-one-9-yl)phenoxy]-N-(2-hydroxyethyl)acetamide, 2-[5-Chloro-2-(2,3-difluoro-6-methoxybenzyloxy)-4-(2-difluoromethyl-6-methoxy-7,9-dihydro-8H-purin-8-one-9-yl)phenoxy]-N,N-dimethylacetamide, 2-[4-(2-Acetyl-6-methoxy-7,9-dihydro-8H-purin-8-one-9-yl)-5-chloro-2-(2,3-difluoro-6-methoxybenzyloxy)phenoxy]-N-methylacetamide, 2-Amino-9-[2-chloro-5-(2,3-difluoro-6-methoxybenzyloxy)-4-methoxyphenyl]-6-methyl-7,9-dihydro-8H-purin-8-one, 2-[4-(6-Acetyl-2-methyl-7,9-dihydro-8H-purin-8-one-9-yl)-5-chloro-2-(2-fluoro-6-methoxybenzyloxy)phenoxy]-N-methylacetamide and 2-[4-(6-Acetyl-2-methyl-7,9-dihydro-8H-purin-8-one-9-yl)-5-chloro-2-(2-fluoro-6-methoxybenzyloxy)phenoxy]-N-ethylacetamide, or a pharmaceutically acceptable salt thereof.

* * * * *

UNITED STATES PATENT AND TRADEMARK OFFICE
CERTIFICATE OF CORRECTION

PATENT NO. : 8,217,069 B2
APPLICATION NO. : 12/596313
DATED : July 10, 2012
INVENTOR(S) : Shigeru Yonekubo et al.

It is certified that error appears in the above-identified patent and that said Letters Patent is hereby corrected as shown below:

In the Specification

At columns 229 – 234: Delete TABLE 77 containing Ex Nos. 295 through 300 and TABLE 78 containing Ex Nos. 301 through 306

At column 279: Insert TABLE 77 containing Ex Nos. 295 through 300 and TABLE 78 containing Ex Nos. 301 through 306 between TABLE 76 and TABLE 79

At columns 341 – 342: Delete the structure of Ex No. 451 and insert the following structure:

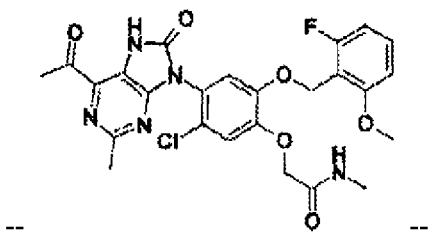

In the Claims

At column 356, lines 15-16, Claim 2: Delete the words "or a prodrug thereof".

Signed and Sealed this
Twentieth Day of August, 2013

Teresa Stanek Rea
*Acting Director of the United States Patent and Trademark Office*